United States Patent
Wu et al.

(10) Patent No.: US 10,098,885 B2
(45) Date of Patent: Oct. 16, 2018

(54) HYDROXYL PURINE COMPOUNDS AND APPLICATIONS THEREOF

(71) Applicant: GUANGDONG ZHONGSHENG PHARMACEUTICAL CO., LTD, Shilong Town Dongguan, Guangdong (CN)

(72) Inventors: Lingyun Wu, Shanghai (CN); Chaofeng Long, Shilong Town Dongguan (CN); Peng Zhang, Shanghai (CN); Xiaoxin Chen, Shilong Town Dongguan (CN); Li Zhang, Shanghai (CN); Zhuowei Liu, Shilong Town Dongguan (CN); Jian Li, Shanghai (CN); Shuhui Chen, Shanghai (CN)

(73) Assignee: GUANGDONG ZHONGSHENG PHARMACEUTICAL CO., LTD, Shilong Town Dongguan (CN)

(*) Notice: Subject to any disclaimer, the term of this patent is extended or adjusted under 35 U.S.C. 154(b) by 0 days.

(21) Appl. No.: 15/517,951

(22) PCT Filed: Sep. 22, 2015

(86) PCT No.: PCT/CN2015/090294
§ 371 (c)(1),
(2) Date: Apr. 7, 2017

(87) PCT Pub. No.: WO2016/054971
PCT Pub. Date: Apr. 14, 2016

(65) Prior Publication Data
US 2017/0326149 A1 Nov. 16, 2017

(30) Foreign Application Priority Data

Oct. 9, 2014 (CN) .......................... 2014 1 0529928
Sep. 16, 2015 (CN) .......................... 2015 1 0590904

(51) Int. Cl.
*A61K 31/522* (2006.01)
*C07D 473/04* (2006.01)
*C07D 241/10* (2006.01)
*C07D 277/20* (2006.01)
*C07D 261/06* (2006.01)

(52) U.S. Cl.
CPC .......... *A61K 31/522* (2013.01); *C07D 241/10* (2013.01); *C07D 261/06* (2013.01); *C07D 277/20* (2013.01)

(58) Field of Classification Search
None
See application file for complete search history.

(56) References Cited

U.S. PATENT DOCUMENTS

| | | | |
|---|---|---|---|
| 4,493,837 A | 1/1985 | Sugimoto et al. | |
| 4,769,379 A | 9/1988 | Leitold et al. | |
| 5,567,704 A | 10/1996 | Bianco et al. | |
| 5,780,476 A | 7/1998 | Underiner et al. | |
| 5,807,862 A | 9/1998 | Klein et al. | |
| 2005/0112069 A1 | 5/2005 | Beume et al. | |
| 2009/0215798 A1 | 8/2009 | Van Aalten et al. | |
| 2011/0053961 A1 | 3/2011 | Tung et al. | |

FOREIGN PATENT DOCUMENTS

| | | | | |
|---|---|---|---|---|
| CN | 102603737 A | 7/2012 | | |
| CN | 105566324 A | 5/2016 | | |
| EP | 0 956 855 A1 | 11/1999 | | |
| EP | 0956855 B1 | 3/2003 | | |
| FR | 2450831 A1 | 10/1980 | | |
| FR | 2450831 A1 | 10/1980 | | |
| JP | S36-021542 A | 11/1961 | | |
| JP | 3601542 B | * 12/1961 | | |
| JP | S55-118488 A | 9/1980 | | |
| JP | S61-246184 A | 11/1986 | | |
| JP | H06-509584 A | 10/1994 | | |
| JP | H09-511496 A | 11/1997 | | |
| JP | 2008-546752 A | 12/2008 | | |
| JP | 2013-503894 A | 2/2013 | | |
| WO | 9317684 A2 | 9/1993 | | |
| WO | WO-9317684 A2 | * 9/1993 | ........... | A61K 31/519 |
| WO | 9522546 A1 | 8/1995 | | |
| WO | WO-95/22546 A1 | 8/1995 | | |
| WO | 0007541 A2 | 2/2000 | | |
| WO | WO-00/07541 A2 | 2/2000 | | |
| WO | 2011028922 A1 | 3/2011 | | |
| WO | 2013013052 A1 | 1/2013 | | |
| WO | WO-2013/013052 A1 | 1/2013 | | |
| WO | WO-2013062762 A1 | * 5/2013 | ........... | C07D 473/06 |

OTHER PUBLICATIONS

Han, Ze. Tetrahedron 64 (2008) 2619-2625.*
Patani, George. Chem Rev. (1996) 96, 3147-3176.*
De Martiis, Franco/ Annali Di Chmica (1957) 47, 1232-7.*
Hirota, Kosaku. Tetrahedron Letters. 26(19) (1985) 2355-2356.*
Petit, Laurent. Chem. Commun., 2010, 46, 5148-5150.*
Australian Examination Report issued in corresponding application No. 2015330490 dated Dec. 11, 2017.
Extended European Search Report issued in corresponding application No. 15848312 dated Jun. 30, 2017.
Sinha et al., "Enhanced tumor necrosis factor suppression and cyclic adenosine monophosphate accumulation by combination of phosphodiesterase inhibitors and prost anoids," European Journal of Immunology, vol. 25, 1995, pp. 147-153.
Mar. 24, 2011 International Search Report issued in International Patent Application No. PCT/CN2015/090294.
Mar. 24, 2011 Written Opinion of the International Searching Authority issued in International Patent Application No. PCT/CN2015/090294.

(Continued)

*Primary Examiner* — Deepak R Rao
*Assistant Examiner* — Laura M Daniel
(74) *Attorney, Agent, or Firm* — Foley & Lardner LLP

(57) ABSTRACT

Hydroxyl purine compounds represented by formula (I), tautomers or pharmaceutically acceptable salts thereof, and applications thereof as PDE2 or TNF-α inhibitors.

19 Claims, No Drawings

(56) References Cited

OTHER PUBLICATIONS

Aug. 8, 2017 New Zealand First Office Action issued in New Zealand Patent Application No. 731344.
Berge et al., Pharmaceutical Salts, Journal of Pharmaceutical Sciences 66: 1-19 (1977).
Hubert Maehr et al., A Proposed New Convention for Graphic Presentation of Molecular Geometry and Topography, Journal of Chemical Education, vol. 62, No. 2, Feb. 1985.
Remington: The Science and Practice of Pharmacy, 21st Edition., Lippincott, Williams & Wilkins (2005).
Sinha et al., Enhanced tumor necrosis factor suppression and cyclic adenosine monophosphate accumulation by combination of phosphodiesterase inhibitors and prostanoids, Eur. J. Immunol, 1995, 25:147-153.
Han et al., Photochemistry synthesis. Part 1: Syntheses of xanthine derivatives by photolysis of 1-(5'-oxohexyl)-3,7-dimethyl-3,7-dihydro-1H-purine-2,6-dione(pentoxifylline): an ambident chromophore, Tetrahedron 64(2008), 2619-2625.
Masakatsu et al., Hydorxyl Purine Compound and Application Thereof Purine Compound and Application Thereof, Pharmaceutical chemistry, chemical colleagues 1995, First Edition, p. 98-99 with English translation.
A. Zlatkov et al, Synthesis, brain antihypoxic activity and cell neuroprotection of 1-substituted-3, 7-dimethylxanthines, Eur. J. Med. Chem., 2000, vol. 35, No. 10, p. 941-948.
CAS Registry No. 1012605-66-1, 2-hydroxy-3,5-bis(I-methylethyl)-, 3-(2,3,6,7-tetrahydro-3,7-dimethyl-2,6-dioxo-IH-purin-l-yl)propyl ester, benzoic acid, entered STN Apr. 7, 2008, in Chemical Library from Ambinter SARL.
CAS Registry No. 1012644-24-4,2-hydroxy-5-methoxy-, 3-(2/3/6/7-tetrahydro-3/7-dimethyl-2,6-dioxo-IH-purin-l-yl)propyl ester, benzoic acid,entered STN Apr. 7, 2008, in Chemical Library from Ambinter SARL.
CAS Registry No. 1012762-39-8, 4-chloro-2-hydroxy-,3-(2/3/6/7-tetrahydro-3/7-dimethyl-2/6-dioxo-IH-purin-l-yl)propyl ester, benzoic acid, entered STN Apr. 8, 2008, in Chemical Library from Ambinter SARL.
CAS Registry No. 1060787-72-5, 2-hydroxy-3-methoxy-, 3-(2,3,6,7-tetrahydro-3,7- dimethyl-2,6-dioxo-IH-purin-l-yl)propyl ester, benzoic acid, entered STN Oct. 13, 2008.
CAS Registry No. 1060962-04-0, 5-chloro-2-hydroxy-,3-(2/3/6/7-tetrahydro-3/7-dimethyl-2,6-dioxo-IH-purin-l-yl)propyl ester, benzoic acid, entered STN Oct. 13, 2008.
CAS Registry No. 1060966-32-6,2/3/6/7-tetrahydro-N-(3-hydroxy-2-pyridinyl)-3/7-dimethyl-2,6-dioxo-IH-purine-l-acetamide, entered STN Oct. 14, 2008.
CAS Registry No. 1061540-38-2,2-hydroxy-4-methoxy-, 3-(2,3,6,7-tetrahydro-3,7-dimethyl-2,6-dioxo-IH-purin-l-yl)propyl ester, benzoic acid, entered STN Oct. 15, 2008.
CAS Registry No. 1061929-60-9, 2-hydroxy-,3-(2/3/6/7-tetrahydro-3/7-dimethyl-2/6-dioxoIH-purin-1-yl)propyl ester, benzoic acid, entered STN Oct. 16, 2008.
CAS Registry No. 1061981-66-5, 2-hydroxy-5-methyl-,3-(2,3,6,7-tetrahydro-3,7-dimethyl-2/6-dioxo-IH-purin-l-yl)propyl ester, benzoic acid, entered STN Oct. 16, 2008.

CAS Registry No. 1320707-84-3,2/3/6/7-tetrahydro-N-[(2-hydroxyphenyl)methyl]-N/3/7-trimethyl-2,6-dioxo-IH-purine-l-acetamide, entered STN Aug. 21, 2011, in Chemical Library from FCH group.
CAS Registry No. 1321454-21-0,N45-(1,1-dioxido-2-isothiazolidinyl)-2-hydroxyphenyl1-2,3,6,7-tetrahydro-3,7-dimethyl-2,6-dioxoIH-purine-l-acetamide, entered STN Aug. 23, 2011, in Chemical Library from FCH group.
CAS Registry No. 1326165-12-1,2/3/6/7-tetrahydro-N-(2-hydroxy-4-methylphenyl)-3/7-dimethyl-2,6-dioxo-IH-purine-l-acetamide, entered STN Aug. 31, 2011, in Chemical Library from Ambinter SARL.
CAS Registry No. 1326382-53-9, N-[5-(1,1-dimethylethyl)-2-hydroxyphenyl]-2,3,6,7-tetrahydro-3,7-dimethyl-2,6-dioxo-IH-purine-l-acetamide, entered STN Sep. 1, 2011, in Chemical Library from Ambinter SARL.
CAS Registry No. 1326534-26-2,2/3/6/7-tetrahydro-N-(2-hydroxwhenyl)-3/7-dimethyl-2/6-dioxo-IH-purine-l-acetamide, entered STN Sep. 1, 2011, in Chemical Library from AmbinterSARL-.
CASRegistryNumber1390155-28-8,3,7-dihydro-1-[3-[[1-(3-hydroxwhenyl)ethyl]methylamino]propyl1-3,7- dimethyl-IH-p. urine-2,6-dione, entered STN Aug. 12, 2012, in Chemical Library from Ukrorgsyntez Ltd.
Eckert. 1965. The acylation of primary alcohols by dialkylaminoethanol ester bases. Arch Pharm, 298(6): 337-41.
Guenter Graefe et al, Synthesis of some asymmetric methylated bixanthines, Arzneimittel-Forschung, 1967, vol. 17. No. 11, p. 1459-61.
Klingler. 1977. Synthesis of bronchospasmolytically effective P-phenylethylaminoalkyl xanthines. Arzneimittel-Forschung (Drug Res), 27(1A): 4-14.
Kosaku Hirota et.al, Synthesis of Phidolopin,7-(4-Hydrox-3-Nitrobenzyl)-1, 3-Dimethylxanthine From the Bryzoan Phidolopora Pacifica, Tetrahedron Letters, 1985 vol. 26, No. 19, p. 2355-2356.
Laurent Petit et al, A radical-based approach to hydroxytetralones from unprotected phenols, Chem. Commun., 2010, vol. 46, No. 28, p. 5148-5150.
Mannich, C. and Kroll S. (1921). Phenacyl and dihydroxyphenacyl derivatives of theophylline and theobromine and of the related alcohols. Berichte der Deutschen Pharmazeutischen Gesellschaft (Reports of the German Pharmaceutical Society), 31: 291-310.
Menge HG et al, The influence of theophylline derivatives and their combinations on cerebral blood flow Arzneimittel-Forschung, 1958, vol. 8, No. 8, p. 503-507.
The First Office Action of Canadian Patent Application dated May 15, 2018.
The First Office Action of Japanese Patent Application dated May 8, 2018 with English translation.
The First Office Action of Russian Patent Application dated May 29, 2018 with English translation.
The Second Office Action of Australian Patent Application dated Apr. 17, 2018.
The Second Office Action of New Zealand Patent Application dated Apr. 5, 2018.
First Office Action dated Jul. 18, 2018 in Chinese Patent Application No. 201580054840.9. with its English translation.

* cited by examiner

HYDROXYL PURINE COMPOUNDS AND APPLICATIONS THEREOF

CROSS REFERENCE TO RELATED APPLICATIONS

The present application is a U.S. National Stage application filed under 35 U.S.C. § 371 and claims priority to International Application no. PCT/CN2015/090294, filed on Sep. 22, 2015, which in turn claims benefit of priority to Chinese Patent Application no. CN 201410529928.9, filed on Oct. 9, 2014, and Chinese Patent Application no. CN 201510590904.9, filed on Sep. 16, 2015, the disclosures of each of which are incorporated herein by reference in their entireties.

FIELD OF INVENTION

The present invention relates to a series of hydroxyl purine compounds and applications thereof as PDE2 or TNF-α inhibitors, specifically relates to a compound having a structure of formula (I), a tautomer thereof or a pharmaceutically acceptable salt thereof.

PRIOR ARTS

Phosphodiesterases (PDE) catalyzes the hydrolization of cyclic nucleotides cGMP and cAMP, and regulates various physiological responses by controlling the intramolecular concentrations of these two important second messengers. The abnormal intramolecular regulation of the cyclic nucleotides cGMP and cAMP is the cause of many diseases, there are already a number of drugs can improve and treat diseases by inhibiting the PDE activity, such as PDE5 inhibitors for pulmonary hypertension and PDE4 inhibitors for arthritis caused by psoriasis. There are eleven categories of the currently known phosphodiesterase genes, each category can be expressed in several subtypes, with a total of more than 100 PDE subtypes. Different subtypes have different structure and different tissue distribution, the activity of cyclic nucleotides cGMP and cAMP and the physiological function of regulation are also very different.

PDE2 phosphodiesterase can catalyzes the hydrolization of cyclic nucleotides cGMP and cAMP, meanwhile cAMP activity is regulated by cGMP, which plays a key role in intracellular balance of cGMP and cAMP function. PDE2 is widely expressed in human tissues, mainly distributed in the heart, central nervous system, liver, adrenal gland, endothelial cells, and platelets and so on. PDE2 is involved in regulating various physiological activity, such as learning, memory and cognitive processes of the maincenter, the maintenance of the basic rhythm of the heart, smooth muscle and endothelial cells, the maintenance of the permeability of endothelial cells, the regulation of inflammatory response. The knockout of the PDE2 gene will lead to the death of mouse embryos. Inhibition of PDE2 activity may be used for a variety of maincenter diseases, cardiovascular diseases, and controlling inflammation.

The non-selective PDE inhibitory activity of a variety of natural and synthetic purine compounds has been found very early, such as caffeine, theophylline, pentoxifylline and so on. Pentoxifylline (PDE2 activity) has been approved for clinical use in lower limbs claudication caused by peripheral vascular occlusion, the main functions of which are reducing blood viscosity, improving erythrocyte deformation, inhibiting platelet aggregation, etc. Novel high-selectivitive PDE2 inhibitors have also been reported to control the division of endothelial cells and the regeneration of blood vessels, and to improve maincenter disgnosia. However, overall, the development and application of novel selectivitive PDE2 inhibitors are still very limited, and the discovery and application of novel PDE2 inhibitors has broad prospects.

Tumor necrosis factor alpha (TNF-α) is a cytokine with multiple biological activities, which has a significant impact on the occurrence, development and prognosis of multiple diseases. TNF-α is mainly produced by monocytes and macrophage cells, which is involved in the immunomodulation and the cytokine network coordination. Under normal circumstances, TNF-α plays an important role in immune defense and immune surveillance, but in some cases it has adverse effects. Research shows that the overexpression of TNF-α can induce the expression of proinflammatory cytokines such as interleukon 1 (IL-1) and IL-6, increase the permeability of endothelial cells and up-regulate the expression of adhesion molecules and activate neutrophils and eosinophils, and induce bone synovial cells and cartilage cells to secrete acute phase substances and tissue-degrading enzymes and the like to promote the occurrence of inflammation. These pathologic reactions play a very important role in occurrence and development of many immune-mediated inflammatory diseases (IMID), such as rheumatoid arthritis (RA), psoriatic arthritis (PsA), ankylosing spondylitis (AS), inflammatory bowel disease (IBD), juvenile chronic arthritis (JCA) and vasculitis, etc. Studies have shown that TNF-α is an ideal target for above multiple IMIDs, and the use of TNF-α antagonists (TNF-α inhibitors) to neutralize excess TNF-α is an ideal way to effectively prevent chronic inflammatory diseases due to TNF-α overexpression. PDE2 regulates the expression of TNF-α according to the mechanism, therefor the level of TNF-α can be controlled by regulating the PDE2 activity, so as to control the inflammation.

Content of the Present Invention

The present invention provides a compound having a structure of formula (I), a tautomer thereof or a pharmaceutically acceptable salt thereof,

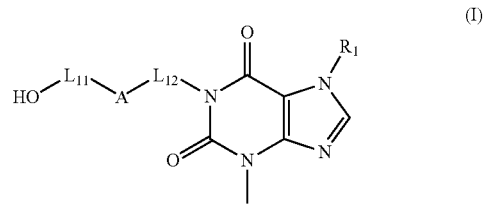

(I)

wherein,
the structural unit

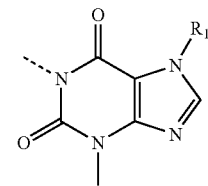

can be replaced with

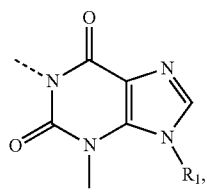

specifically replaced with

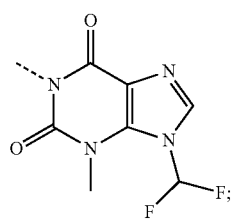

L₁₁ is selected from absence, or C(R)(R');

each of R, R' is independently selected from H, a halogen, OH, NH₂, CN, or, an optionally substituted 1- to 6-membered alkyl or heteroalkyl;

optionally, R, R' can form a 3- to 6-membered cycloalkyl, heterocyoalkyl by cyclization;

A represents absence, or is selected from cycloalkyl, heterocycloalkyl, aryl, or heteroaryl, each of which is optionally substituted;

L₁₂ is selected from an optionally substituted 1- to 6-membered alkyl or heteroalkyl;

R₁ is selected from an optionally substituted 1- to 6-membered alkyl or heteroalkyl;

"hetero" represents N, O, S, C(=O), S(=O), or S(=O)₂, the number of the heteroatom on each group is selected from 1, 2, 3 or 4.

In some embodiments of the present invention, the substituents in the R, R', A, L₁₂ and R₁ are independently selected from the halogen, OH, NH₂, CN, or, the optionally substituted 1- to 6-membered alkyl or heteroalkyl, the number of the substituent on each group is independently selected from 1, 2 or 3.

In some embodiments of the present invention, the substituents in the R, R', A, L₁₂ and R₁ are independently selected from the halogen, CF₃, CN, OH, Me, Et, n-propyl, isopropyl, cyclopropyl,

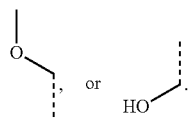

In some embodiments of the present invention, the R and R' are independently selected from H, Me, CF₃, or Et.

In some embodiments of the present invention, the L₁₁ is selected from

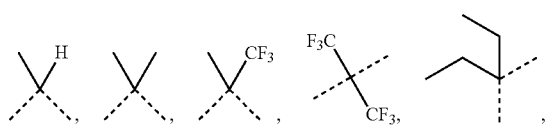

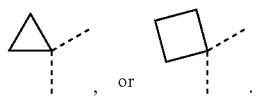

In some embodiments of the present invention, the A is selected from the 3- to 12-membered alkyl or cycloalkyl, or the 5- to 12-membered aryl or heteroaryl, each of which is optionally substituted.

In some embodiments of the present invention, the A is selected from cyclopropyl, cyclobutyl, cyclopentyl, cyclohexyl, epoxypentyl, phenyl, pyridyl, pyrazinyl, oxazolyl, isoxazolyl, thiazolyl, or bicyclo[1.1.1]pentane, or a bicyclic group, a spiro group or a fused cyclic group consisting of any two of the above groups, each of which is optionally substituted.

In some embodiments of the present invention, the A is selected from

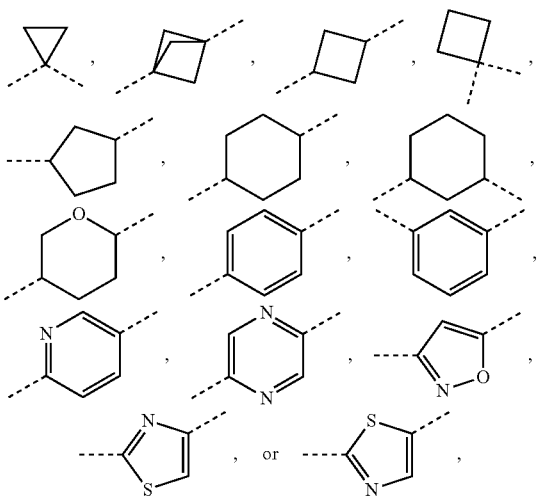

each of which is optionally substituted.

In some embodiments of the present invention, the A is selected from

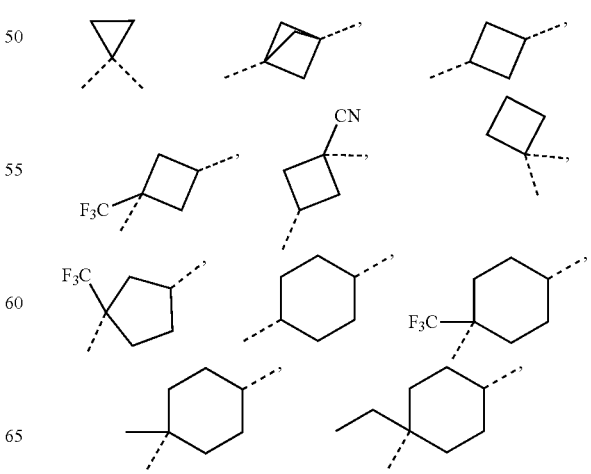

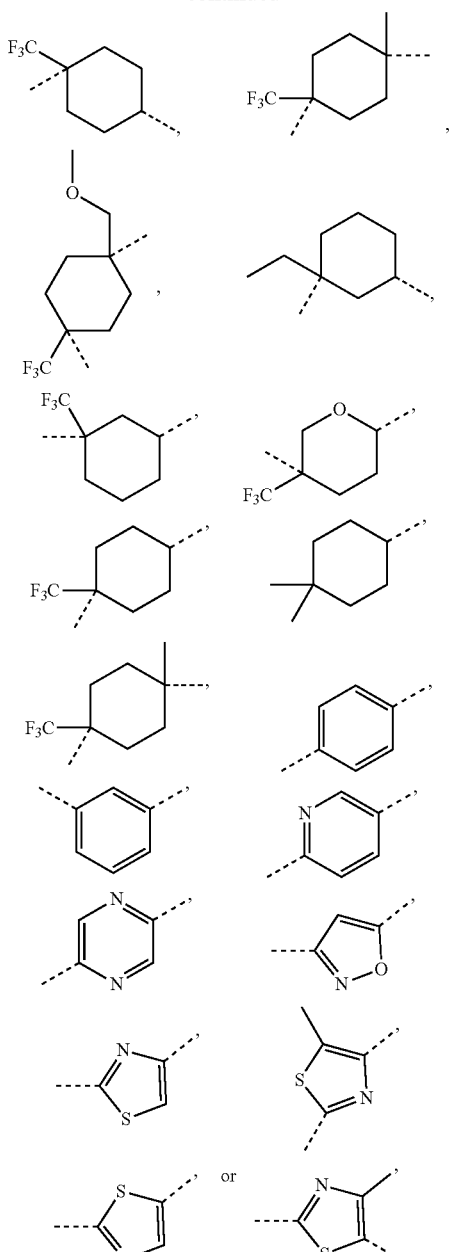
In some embodiments of the present invention, the $L_{12}$ is selected from methylene,
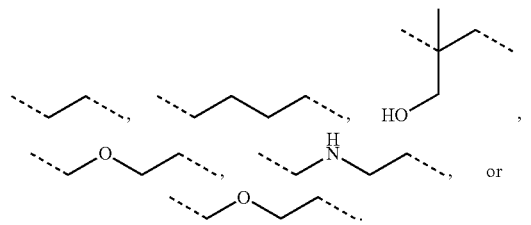
In some embodiments of the present invention, the $R_1$ is selected from Me, $CHF_2$, $CF_3$, Et, $CH_2CF_3$, isopropyl,
cyclopropyl,
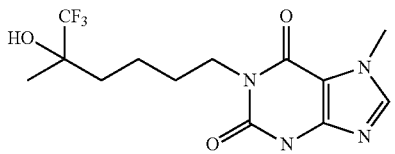
The present invention is selected from the group consisting of:
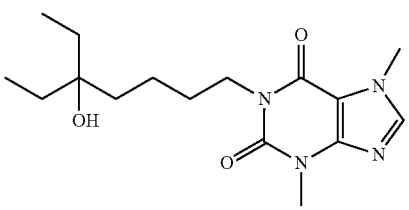
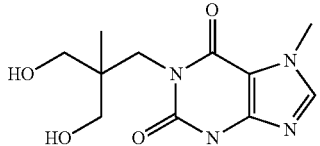
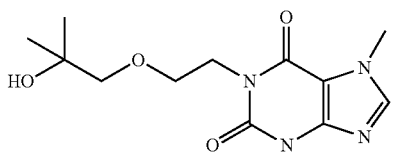
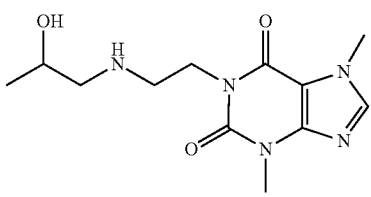

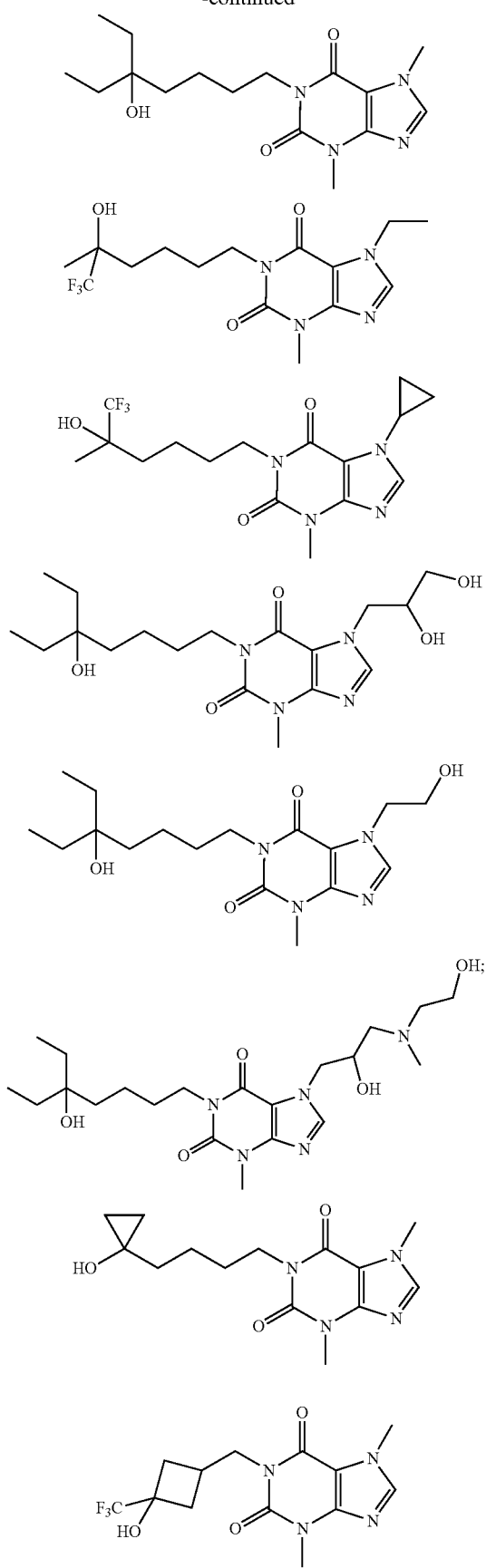
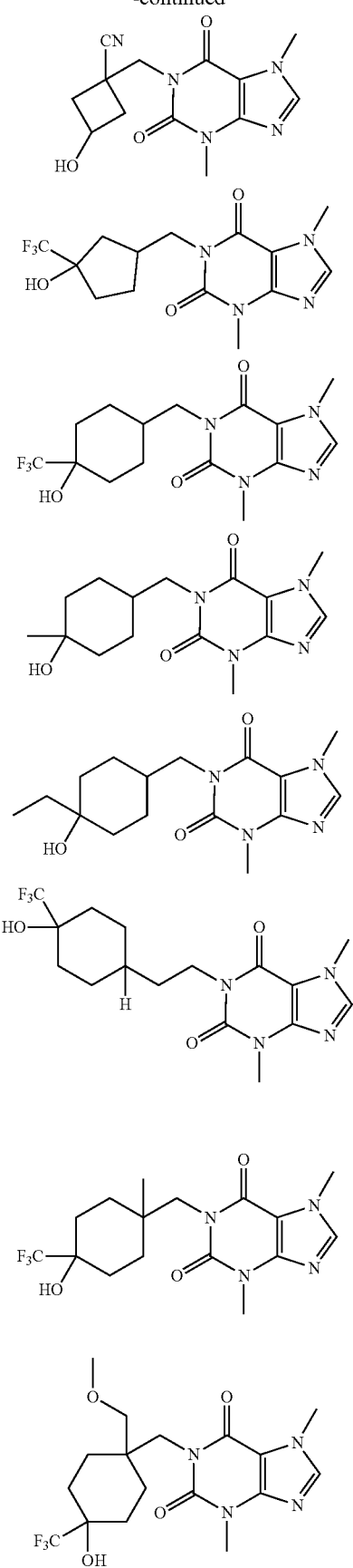

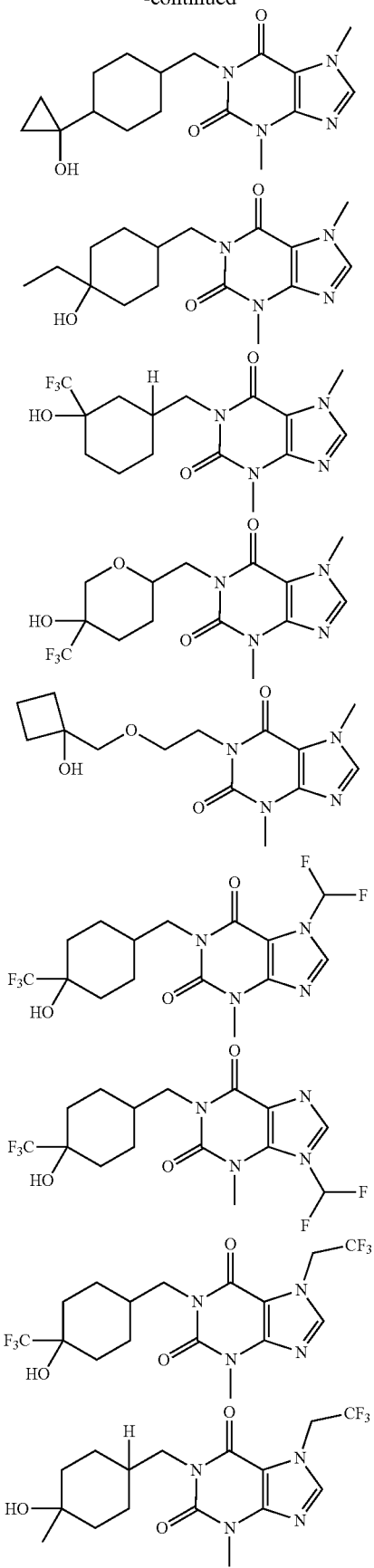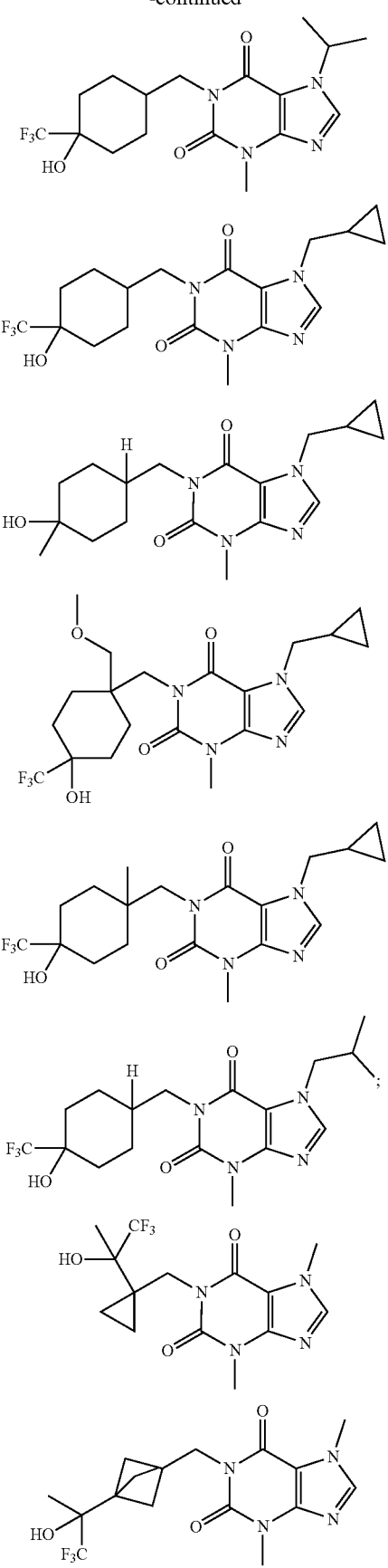

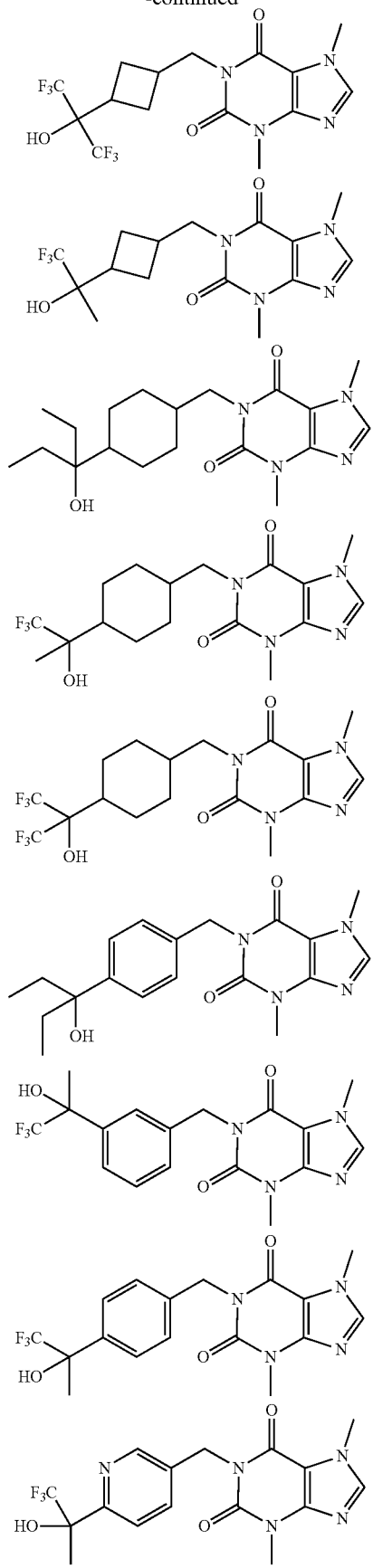
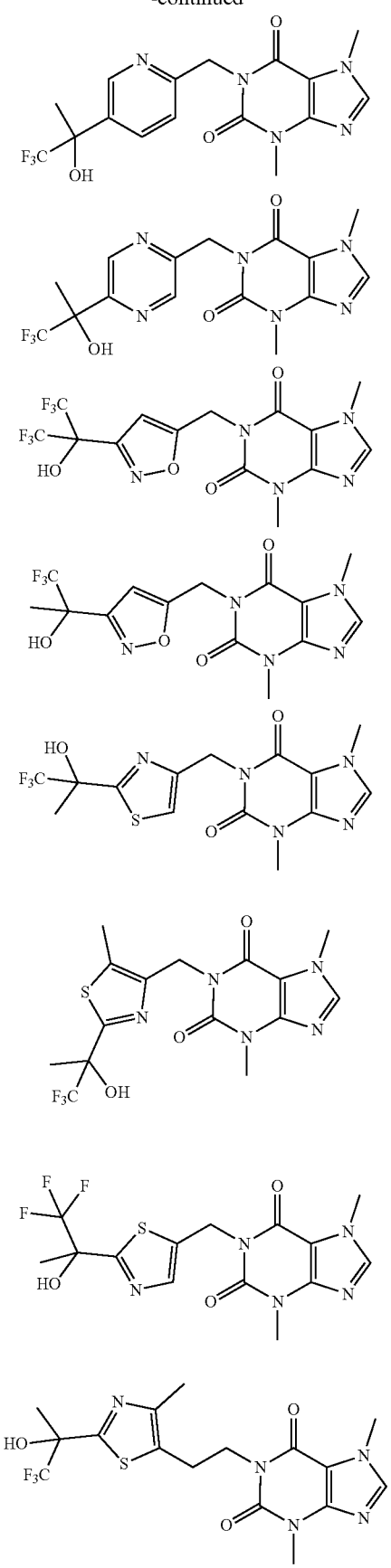

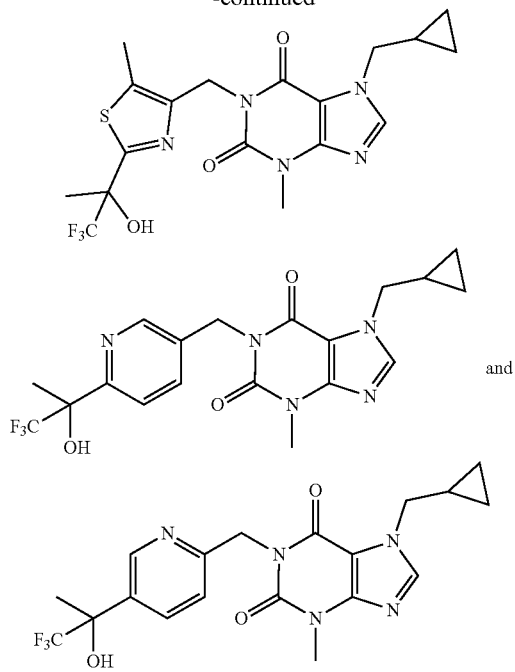
Further, the present invention is selected from the group consisting of:
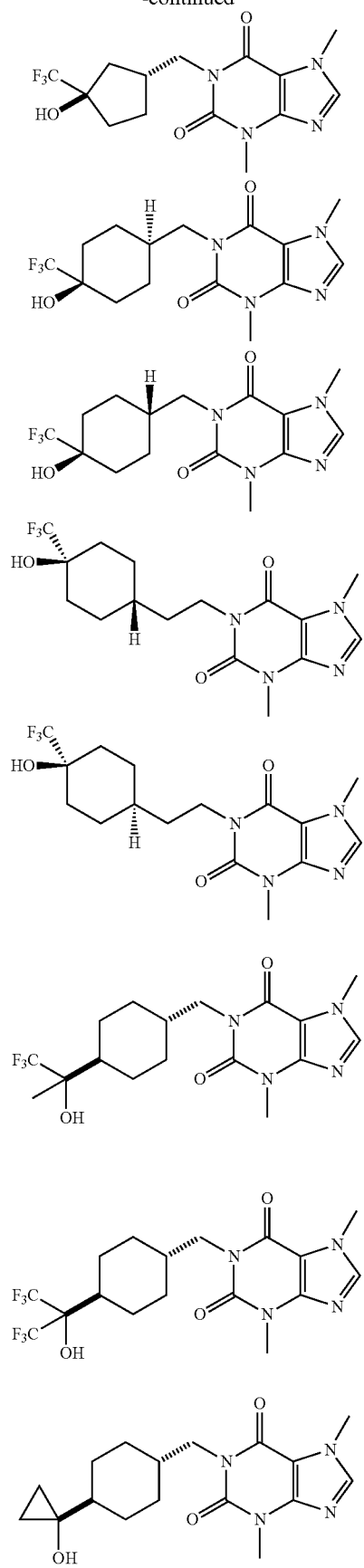

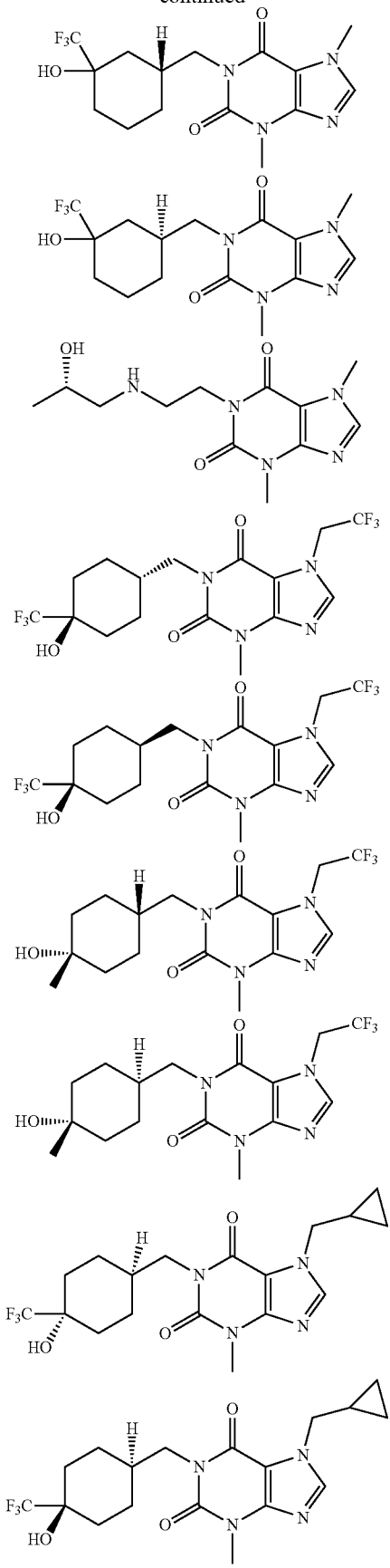
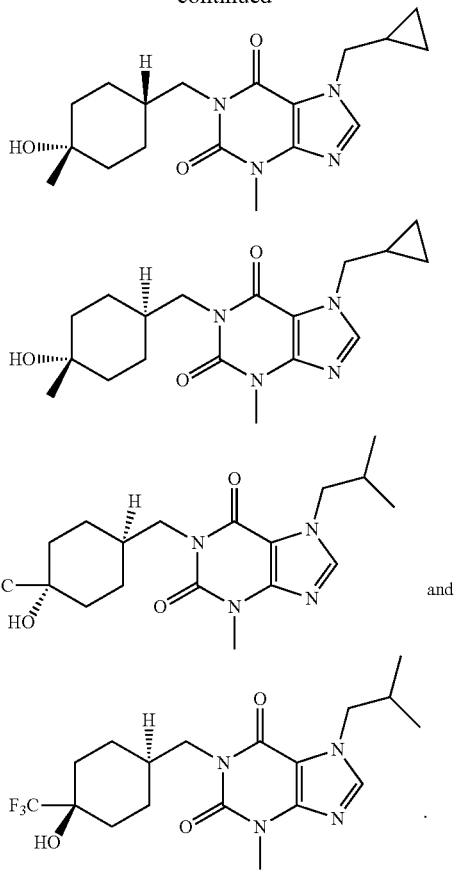

The present invention also provides an application of the compound, the tautomer thereof or the pharmaceutically acceptable salt thereof in manufacturing a PDE2 inhibitor and a TNF-α inhibitor.

Relevant Definitions

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

Herein, the term "pharmaceutically acceptable" is aimed at those compounds, materials, compositions and/or dosage forms, which are within the scope of reliable medical judgment and applicable for use in contact with human and animal tissue but without too much toxicity, irritation, allergic reactions or other problems or complications, also meet the reasonable benefit/risk ratio.

The term "pharmaceutically acceptable salt" refers to the salt of the compound of the present invention, which is prepared by the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprises that in water or an organic solvent or the mixture of water and organic solvent, reacting these compounds in forms of free acids or alkalis with stoichiometric amount of proper alkalis or acids. In general, preferably choose non-aqueous media such as ether, ethyl acetate, ethanol, isopropanol or acetonitrile and so on.

Except for the form of salt, there is a form of prodrug for the compound in the present invention. The prodrug of the compound described in the present invention is easily transformed to be the compound of the present invention via chemical changes under physiological conditions. Besides, the prodrug can be transformed to be the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention.

Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (−)- and (+)-antimers, (R)- and (S)-antimers, diastereomers, (D)-isomer, (L)-isomer, as well as racemic mixtures and other mixtures, such as enantiomers- or diastereoisomers-enriched mixtures, all of these mixtures are within the scope of the present invention. Other asymmetric carbon atoms may exist in substituents such as in an alkyl. All of these isomers and their mixtures are included within the scope of the present invention.

Optically active (R)- and (S)-isomers, (D)- and (L)-isomers can be prepared by asymmetric synthesis or chiral reagents or other conventional techniques. If an enantiomer of a compound of the present invention are wanted, asymmetric synthesis or derivatization action of the chiral auxiliaries can be employed in preparation, in which the resulting diastereomer mixtures are isolated, and the auxiliary groups are cleaved to provide the pure desired enantiomer. Or, when a molecule contains an alkaline functional group (such as amino) or an acidic functional groups (such as carboxyl), a salt of diastereomer is formed with an appropriate optical active acid or alkali, and then the pure enantiomer can be recycled after resolution on the salt of diastereomer by common methods which is known in the art. In addition, the separation of an enantiomer and a diastereomer is usually realized by the chromatographic method, the chromatography method employs a chiral stationary phase, and optionally combined with the chemical derivatization method (e.g. an amine generates a carbamate).

One or more atoms constituting the compound of the present invention may comprise an unnatural proportion of atomic isotopes. For example, the compound can be labeled by a radioactive isotope, such as tritium ($^3H$), iodine-125 ($^{125}I$) or C-14($^{14}C$). All the variations in the isotopic composition of the compound disclosed in the present invention, whether radioactive or not, are included within the scope of the present invention.

The term "a pharmaceutically acceptable carrier" refers to any formulation or carrier medium which is capable of delivering effective amount of the active substance disclosed in the present invention, does not interfere with the biological activity of the active substance, and is with no toxic side-effects on host or patient, representative carrier includes water, oil, vegetables and minerals, cream base, lotion matrix, ointment matrix etc. The matrix comprises a suspension, a viscosity increaser, transdermal enhancers etc. Their formulation are well known to the person in cosmetic or topical drug art. Other information about the carrier can refer to Remington: The Science and Practice of Pharmacy, 21st Ed., Lippincott, Williams & Wilkins (2005), the content of which is incorporated into this article as reference.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, illness or disease of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one time in the composition or structure of the compound, the definition of each occurrence is independent. Therefore, for example, if a group is substituted by 0~2 of R, the group may optionally be substituted by at most two R, and R has an independent option in each case. In addition, the combination of substituents and/or their variants is allowed only if such a combination will lead to a stable compound.

When the number of the connection group is 0, such as —(CRR)$_0$—, it indicates that the connection group is a single bond.

When one of the parameters is selected from a single bond, it indicates that the two groups which it is attached are directly connected, for example, when the L in A-L-Z represents a single bond, it indicates that the structure actually is A-Z.

When bonds of a substituent can be crossly connected to two atoms of a ring, the substituent can be bonded to arbitrary atoms in the ring. When the listed substituent does not specify through which atom it is connected to the general structure formula including the compound that is not specifically mentioned, the substituent can be bonded through any of its atoms. The combination of substituents and/or their variants is allowed only if such a combination will lead to a stable compound. For example, the structural unit

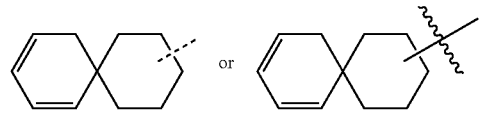

represents that the connection can occur on any atom in the cyclohexyl or cyclohexadiene.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2, 2, 2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The "alkoxy" represents that the alkyl group with a specific number of carbon atoms is connected by an oxygen bridge. The $C_{1-6}$ alkoxy includes $C_1$, $C_2$, $C_3$, $C_4$, $C_5$ and $C_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exist one or more C═C double bonds, such as vinyl and propenyl.

The term "halo" or "halogen" refers to fluorine, chlorine, bromine and iodine.

Unless otherwise specified, the term "hetero" refers to a heteroatom or a heteroatomic group (i.e. a group containing a heteroatom), including atoms except carbon (C) and hydrogen (H) and groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$ N(H)— or —S(=O) N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1-3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom and a heteroatomic group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and $S(O)_p$, p is 1 or 2). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and $S(O)_p$, p is 1 or 2). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to:acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbonyl" or its specific concept (such as alkyl, alkenyl, alkynyl, phenyl, etc.) itself or as a part of another substituent represents a linear, branched or cyclic hydrocarbonyl or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "alkyl" includes but not limited to an aliphatic hydrocarbonyl and aromatic hydrocarbonyl, the aliphatic hydrocarbonyl includes linear and cyclic structures, specifically includes but not limited to alkyl, alkenyl and alkynyl, the aromatic hydrocarbonyl includes but not limited to 6- to 12-membered aromatic hydrocarbonyl such as benzene, naphthalene and the like. In some embodiments, the term "hydrocarbonyl" refers to linear or branched groups or their combination, which can be completely saturated, monocyclic or polycyclic unsaturated, can include divalent and polyvalent groups. Examples of saturated hydrocarbonyl include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1, 4-pentadienyl), acetenyl, 1- and 3-propinyl, 3-butynyl, and more advanced homologues and isomers.

Unless otherwise specified, the term "heterohydrocarbonyl" or its specific concepts (such as heteroalkyl, heteroalkenyl, heteroalkynyl, heteroaryl, etc.) itself or the term combining with another term refers to a stable linear, branched or cyclic hydrocarbonyl or their combinations, which consists of a certain number of carbon atoms and at least one heteroatom. In some embodiments, the term "heterohydrocarbonyl" itself or the term combining with another term refers to a stable linear, branched hydrocarbonyl or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S can be located in any internal position of the heterohydrocarbonyl (including the position where hydrocarbonyl is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and "alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbonyl", "heterocyclohydrocarbonyl" or its specific concepts (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbonyl", "heterohydrocarbonyl". In addition, in terms of heterohydrocarbonyl or heterocyclohydrocarbonyl (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (preferably 1~3 rings). They fuse together or connect by a covalent linkage. The term "heteroaryl" refers to an aryl (or ring) containing 1~4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For the sake of briefness, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available, which can be used without further purification. The present invention adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluene sulfonic acid; NFSI represents N-fluorobenzenesulfonimide; NCS represents N-chlorosuccinimide; n-Bu$_4$NF represents tetrabutylammonium fluoride; iPrOH represents 2-propanol; mp represents melting point; LDA represents lithium diisopropylamide; TMSCF$_3$ represents trifluoromethyltrimethylsilane; Ti(Oi-Pr)$_4$ represents tetraisopropyl titanate; MsCl represents methanesulfonyl chloride; DMAP represents N,N-dimethyl-4-aminopyridine; TEA represents triethylamine; BnBr represents benzyl bromide; DIEA represents diisopropylethylamine; BH$_3$DMS represents borane dimethyl sulfide; DMP represents Dess-Martin periodinane; TBAF represents tetrabutylammonium fluoride; HOBT represents 1-hydroxybenzotriazole; AIBN represents 2,2'-azo bisisobutyronitrile; NBS represents N-bromosuccinimide.

Compounds are named by manual work or software ChemDraw®, commercially available compounds are named in accordance with suppliers' catalogue.

DETAILED DESCRIPTION OF THE PREFERRED EMBODIMENT

The following examples further illustrate the present invention, but the present invention is not limited thereto.

Embodiment 1

3,7-Dimethyl-1-(6,6,6-trifluoro-5-hydroxy-5-methylhexyl)-1H-purine-2,6(3H,7H)-dione

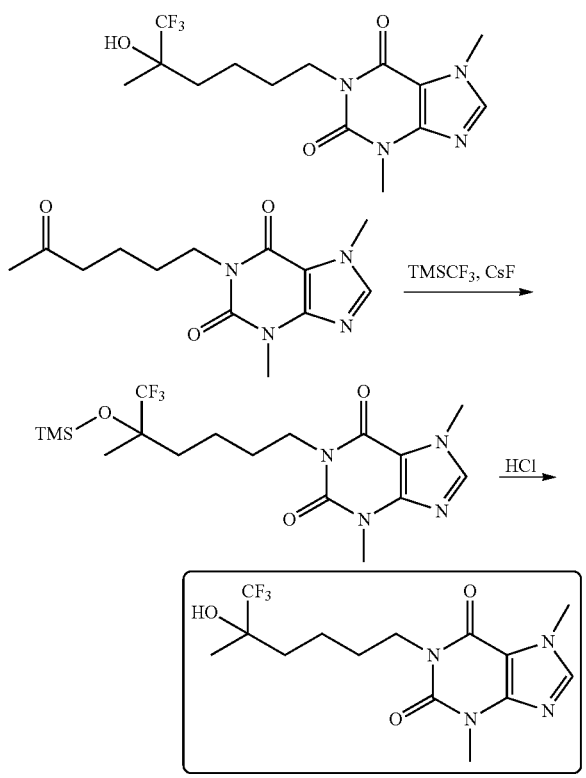

Step 1

3,7-Dimethyl-1-(6,6,6-trifluoro-5-methyl-5-(trimethylsiloxy)hexyl)-1H-purine-2,6(3H,7H)-dione 3,7-Dimethyl-1-(5-oxohexyl)-1H-purine-2,6(3H,7H)-dione (200 mg, 0.719 mmol), cesium fluoride (10.9 mg, 0.0719 mmol) were dissolved in tetrahydrofuran (2 mL), trifluoromethyltrimethylsilane (153 mg, 1.08 mmol) was added dropwise at 0° C. The reaction solution was stirred at 20° C. for 2 hours, the reaction was quenched by the addition of saturated brine (50 mL), extracted with ethyl acetate (100 mL×3). The organic phase was washed with saturated brine (100 mL×3), dried over anhydrous sodium sulfate and concentrated under reduced pressure, then dried in vacuum to deliver 3,7-dimethyl-1-(6,6,6-trifluoro-5-methyl-5-(trimethylsiloxy)hexyl)-1H-purine-2,6(3H,7H)-dione (200 mg, white solid), yield: 66%. MS-ESI: calcd. for [M+H]$^+$ 421, found 421.

Step 2

3,7-Dimethyl-1-(6,6,6-trifluoro-5-hydroxy-5-methylhexyl)-1H-purine-2,6(3H,7H)-dione 3,7-Dimethyl-1-(6,6,6-trifluoro-5-methyl-5-(trimethylsiloxy)hexyl)-1H-purine-2,6(3H,7H)-dione (200 mg, 0.476 mmol) was dissolved in tetrahydrofuran (2 mL), 1 M hydrochloric acid (0.5 mL) was added dropwise at 0° C., and then the mixture was stirred at 20° C. for 1 hour. The mixture was cooled to 0° C. and the reaction was quenched by the addition of sodium bicarbonate solution (30 mL). The mixture was extracted with ethyl acetate (100 mL×3). The organic phase was washed with saturated brine (100 mL×3), dried over anhydrous sodium sulfate and concentrated under reduced pressure. The residue was isolated and purified by preparative high performance liquid chromatography to deliver 3,7-dimethyl-1-(6,6,6-trifluoro-5-hydroxy-5-methylhexyl)-1H-purine-2,6(3H,7H)-dione (50.0 mg, white solid), yield: 30%. $^1$H NMR: (400 MHz, Methanol-d$_4$) δ 7.85 (s, 1H), 4.02-3.98 (m, 2H), 3.96 (s, 3H), 3.52 (s, 3H), 1.69-1.64 (m, 4H), 1.52-1.48 (m, 2H), 1.28 (s, 3H). MS-ESI: calcd. for [M+H]$^+$ 349, found 349.

Embodiment 2

1-(5-Hydroxy-5-methylheptyl)-3,7-dimethyl-1H-purine-2,6 (3H,7H)-dione

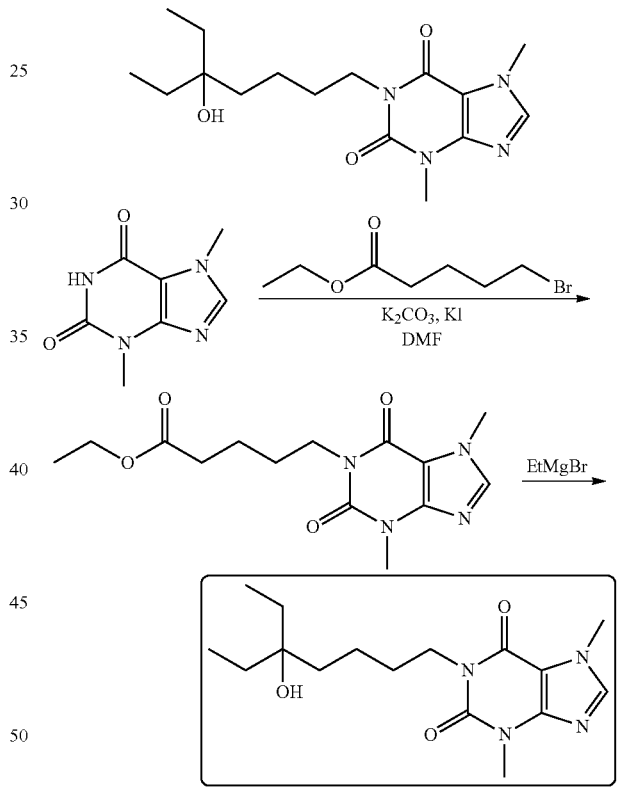

Step 1

Ethyl 5-(3,7-dimethyl-2,6-dioxo-2,3,6,7-tetrahydro-1H-purin-1-yl)pentanoate 3,7-Dimethyl-1H-purine-2,6(3H,7H)-dione (500 mg, 28.0 mmol), ethyl bromovalerate (7.51 g, 33.4 mmol), potassium carbonate (7.73 g, 56.0 mmol) and potassium iodide (500 mg, 2.80 mmol) were dissolved in N,N-dimethylformamide (62 mL). The reaction solution was heated to 110° C. and stirred for two hours. The reaction mixture was poured into water and extracted with ethyl acetate (20 mL×3). The organic phases were combined, dried over anhydrous sodium sulfate, filtered and the filtrate was concentrated to deliver ethyl 5-(3,7-dimethyl-2,6-dioxo-2,3,6,7-tetrahydro-purine-1-yl)pentanoate (5.00 g, yellow solid), yield: 50%. ¹H NMR: (400 MHz, CDCl₃) δ 7.51 (s, 1H), 4.14-4.09 (m, 2H), 4.04-4.01 (m, 2H), 3.97 (s, 3H), 3.57 (s, 3H) 2.37-2.33 (m, 2H), 1.72-1.69 (m, 4H), 1.25 (t, J=7.2 Hz, 3H).

Step 2

1-(5-Ethyl-5-hydroxyheptyl)-3,7-dimethyl-1H-purine-2,6(3H,7H)-dione

Ethyl 5-(3,7-dimethyl-2,6-dioxo-2,3,6,7-tetrahydro-purine-1-yl)pentanoate (0.500 g, 1.62 mmol) was dissolved in anhydrous tetrahydrofuran (5 mL). Under the nitrogen gas atmosphere, ethylmagnesium bromide (3 M ether solution, 3.42 mL, 9.72 mmol) was slowly added dropwise at −78° C. The reaction solution was stirred at −78° C. for 0.5 hour, slowly warmed to 0° C., and then reacted for 0.5 hour. The reaction solution was poured into water and extracted with ethyl acetate (30 mL×3). The organic phases were combined, dried over anhydrous sodium sulfate, filtered and the filtrate was concentrated under reduced pressure to deliver 1-(5-ethyl-5-hydroxyheptyl-3,7-dimethyl-1H-purine-2,6(3H,7H)-dione (0.300 g, colorless oil), yield: 57%. ¹H NMR: (400 MHz, CDCl₃) δ 7.50 (s, 1H), 4.05-4.01 (m, 2H), 3.99 (s, 3H), 3.57 (s, 3H), 1.70-1.37 (m, 10H) 0.86 (t, J=7.6 Hz, 6H). MS-ESI calcd for [M+H]⁺ 323, found 323.

Embodiment 3

1-(4-(1-Hydroxycyclopropyl)butyl)-3,7-dimethyl-1H-purine-2,6(3H,7H)-dione

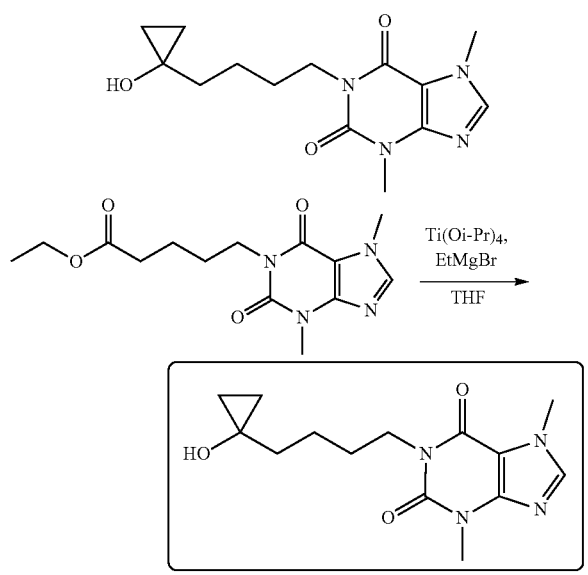

Under the nitrogen gas atmosphere, ethylmagnesium bromide (3 M ether solvent, 1.1 mL, 3.24 mmol) was added at −35° C. into a solution of ethyl 5-(3,7-dimethyl-2,6-dioxo-2,3,6,7-tetrahydro-purine-1-yl)pentanoate (500 mg, 1.62 mmol) and tetraisopropyl titanate (461 mg, 1.62 mmol) in tetrahydrofuran (10 mL). The reaction solution was slowly warmed to 25° C. and stirred for 2 hours. The reaction was quenched by the addition of water (10 mL). The insoluble substance was removed by filtration and the filtrate was extracted with ethyl acetate (20 mL×3). The organic phases were combined, dried over anhydrous sodium sulfate, filtered and the filtrate was concentrated under reduced pressure, isolated and purified by high performance liquid chromatography to deliver 1-(4-(1-hydroxycyclopropyl)butyl)-3,7-dimethyl-1H-purine-2,6(3H,7H)-dione (90.0 mg, white solid), yield: 19%. ¹H NMR: (400 MHz, Methanol-d₄) δ 7.86 (s, 1H), 4.03-3.90 (m, 5H), 3.51 (s, 3H), 1.72-1.53 (m, 6H), 0.68-0.59 (m, 2H), 0.46-0.38 (m, 2H). MS-ESI calcd. for [M+H]⁺ 293, found 293.

Embodiment 4

3,7-Dimethyl-1-((1-(1,1,1-trifluoro-2-hydroxypropan-2-yl)cyclopropyl)methyl)-1H-purine-2, 6-(3H, 7H)-dione

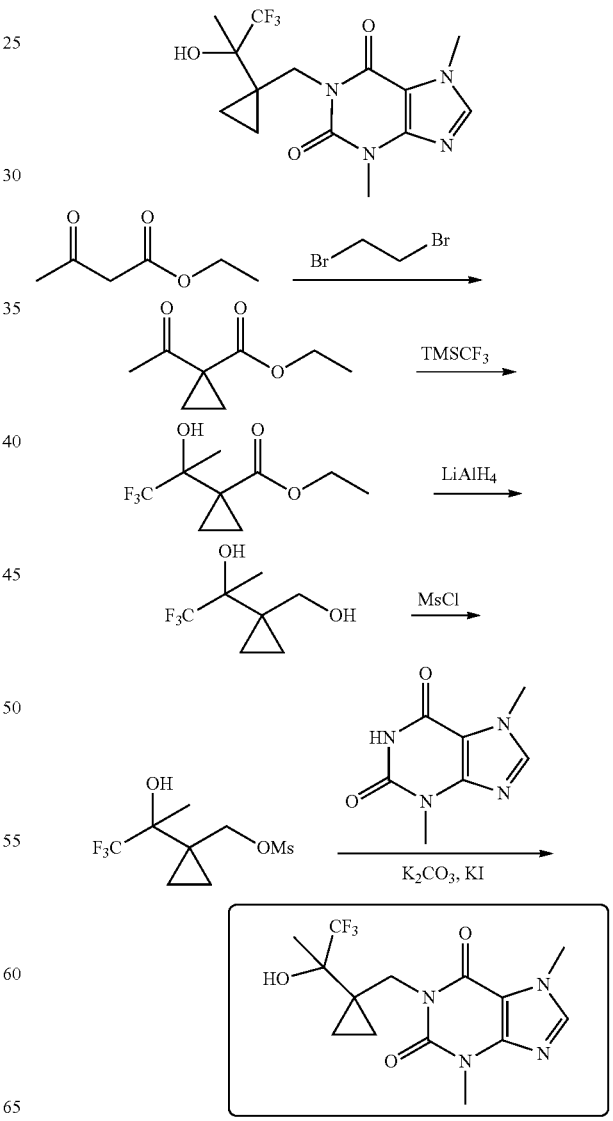

Step 1

Ethyl 1-acetylcyclopropane

Ethyl-3-oxobutanoic acid (10.0 g, 76.8 mmol) and 1,2-dibromoethane (21.7 g, 115 mmol) were dissolved in dimethylsulfoxide (300 mL), under the nitrogen gas atmosphere, potassium carbonate (42.5 g, 307 mmol) was added in portions. The reaction solution was stirred at 25° C. for 24 hours. Water (500 mL) was added, and the reaction solution was extracted with ethyl acetate (300 mL×3). The organic phases were combined, dried over anhydrous sodium sulfate, filtered, the filtrate was concentrated under reduced pressure and purified by silica gel column chromatography (10:1 petroleum ether/ethyl acetate, Rf=0.4) to deliver ethyl 1-acetylcyclopropane (6.00 g, white oil), yield: 50%. $^1$H NMR: (400 MHz, Methanol-$d_4$) δ 4.25-4.20 (m, 2H), 2.44 (s, 3H), 1.47-1.42 (m, 4H), 1.32-1.28 (m, 3H).

Step 2

1-(1,1,1-Trifluoro-2-hydroxypropan-2-yl)cyclopropanecarboxylic acid

Ethyl 1-acetylcyclopropane (2.00 g, 12.8 mmol), cesium fluoride (195 mg, 1.28 mmol) were dissolved in tetrahydrofuran (30 mL), and then trifluoromethyltrimethylsilane (3.64 g, 25.6 mmol) was added at 0° C. The reaction solution was reacted at 20° C. under the nitrogen gas atmosphere for 6 hours. Then 4 N dilute hydrochloric acid (7 mL) was added. The mixture was reacted at room temperature under the nitrogen gas atmosphere for 6 hours. The reaction was quenched by the addition of a saturated sodium bicarbonate aqueous solution (30 mL) and extracted with ethyl acetate (100 mL×3). The organic phase was dried over anhydrous sodium sulfate and filtered, the filtrate was concentrated under reduced pressure and purified by silica gel column chromatography (10:1 petroleum ether/ethyl acetate, Rf=0.4) to deliver 1-(1,1,1-trifluoro-2-hydroxypropan-2-yl)cyclopropanecarboxylic acid (1.70 g, white oil), yield: 59%. $^1$H NMR: (400 MHz, Methanol-$d_4$) δ 4.14-4.10 (m, 2H), 1.64 (s, 3H), 1.29-1.24 (m, 3H), 1.23-1.22 (m, 2H), 0.92-0.90 (M, 2H).

Step 3

1,1,1-Trifluoro-2-(1-(hydroxymethyl)cyclopropyl)propan-2-ol 1-(1,1,1-Trifluoro-2-hydroxypropan-2-yl)cyclopropanecarboxylic acid (400 mg, 1.77 mmol) was dissolved in anhydrous tetrahydrofuran (10 mL), lithium aluminum hydride (81.0 mg, 2.12 mmol) was added at 0° C. The reaction solution was warmed to 25° C. and stirred for 1 hour. The reaction was quenched by the addition of water (10 mL), extracted with ethyl acetate (50 mL×3), dried over anhydrous sodium sulfate, filtered, the filtrate was concentrated under reduced pressure and purified by silica gel column chromatography (1:1 petroleum ether/ethyl acetate, Rf=0.2) to deliver 1,1,1-trifluoro-2-(1-(hydroxymethyl)cyclopropyl)propan-2-ol (200 mg, yellow oil), yield: 61%. $^1$H NMR: (400 MHz, DMSO-$d_6$): δ 5.64 (s, 1H), 4.63-4.60 (m, 1H), 3.64-3.60 (m, 1H), 3.23-3.17 (m, 1H), 1.36 (s, 1H), 1.36 (s, 3H), 0.83-0.91 (m, 1H), 0.56-0.55 (m, 1H), 0.39-0.35 (m, 2H).

Step 4

(1-(1,1,1-Trifluoro-2-hydroxypropan-2-yl)cyclopropyl)methylmethanesulfonate 1,1,1-Trifluoro-2-(1-(hydroxymethyl)cyclopropyl)propan-2-ol (100 mg, 0.543 mmol) was dissolved in dichloromethane (5 mL), triethylamine (110 mg, 1.08 mmol) and methanesulfonyl chloride (62.2 mg, 0.543 mmol) were added at 0° C. The reaction solution was reacted at 0° C. for 2 hours. The reaction was quenched by the addition of a saturated sodium bicarbonate aqueous solution (10 mL), extracted with dichloromethane (10 mL×3), the organic phases were combined, washed with saturated sodium chloride aqueous solution (10 mL×3), dried over anhydrous sodium sulfate, filtered, and the filtrate was concentrated under reduced pressure to deliver (1-(1,1,1-trifluoro-2-hydroxypropan-2-yl)cyclopropyl)methylmethanesulfonate (80.0 mg, yellow oil), yield: 56%.

Step 5

3,7-Dimethyl-1-((1-(1,1,1-trifluoro-2-hydroxypropan-2-yl)cyclopropyl)methyl)-1H-purine-2, 6-(3H, 7H)-dione (1-(1,1,1-Trifluoro-2-hydroxypropan-2-yl)cyclopropyl)methylmethanesulfonate (80.0 mg, 0.305 mmol), 3,7-dimethyl-1H-purine-2,6-(3H,7H)-dione (54.9 mg, 0.305 mmol), potassium iodide (5.10 mg, 0.0305 mmol) and potassium carbonate (126 mg, 0.915 mmol) were dissolved in anhydrous N, N-dimethylformamide (5 mL). The reaction solution was heated to 120° C. and reacted for 2 hours. The reaction solution was cooled to 20° C., filtered, and purified by preparative high performance liquid chromatography to deliver 3,7-dimethyl-1-((1-(1,1,1-trifluoro-2-hydroxypropan-2-yl)cyclopropyl)methyl)-1H-purine-2,6-(3H, 7H)-dione (40.0 mg, white solid), yield: 38%. $^1$H NMR: (400 MHz, Methanol-$d_4$) δ 7.88 (s, 1H), 4.45 (d, J=6.8 Hz, 1H), 4.24 (d, J=6.8 Hz, 1H), 3.97 (s, 3H), 3.53 (s, 3H), 1.53 (s, 3H), 0.92-0.88 (m, 1H), 0.64-0.63 (m, 1H), 0.41-0.38 (m, 1H), 0.15-0.12 (m, 1H).

MS-ESI calcd. for [M+H]$^+$ 347, found 347.

Embodiment 5

1-(3-Hydroxy-3-(trifluoromethyl)cyclobutyl)methyl)-3,7-dimethyl-1H-purine-2,6(3H,7H)-dione

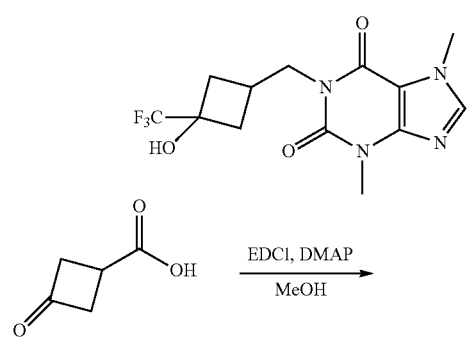

31
-continued

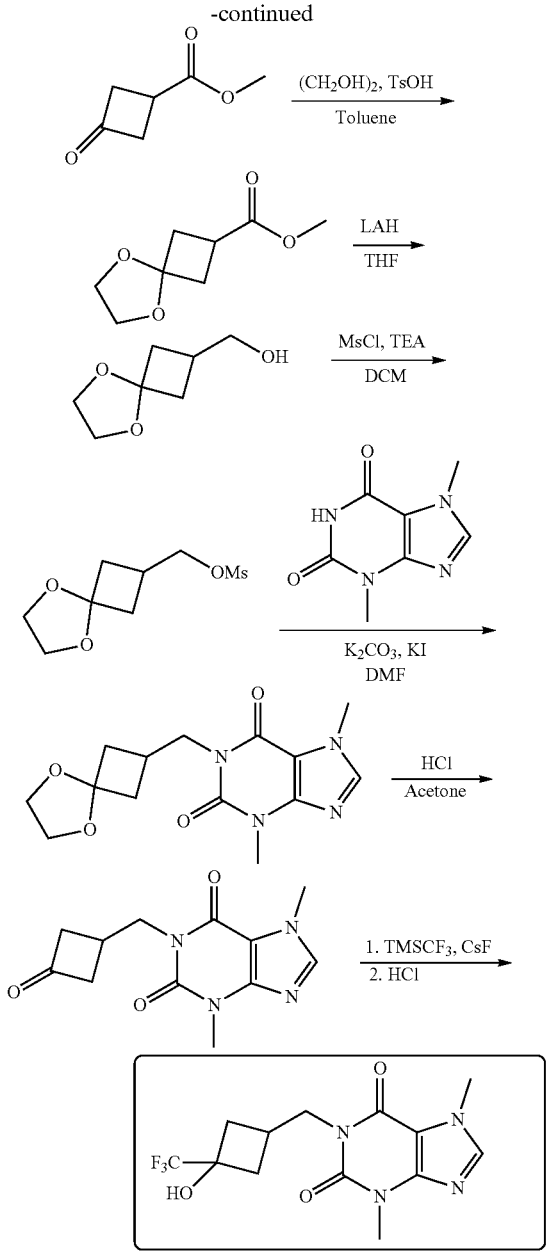

Step 1

Methyl 3-oxocyclobutanecarboxylate

3-Oxocyclobutanecarboxylic acid (25 g, 0.220 mmol), methanol (14 mL) and N,N-dimethyl-4-aminopyridine (3.00 g, 353 mmol) were dissolved in dichloromethane (500 mL), stirred at 25° C., 1-(3-dimethylaminopropyl)-3-ethylcarbodiimide hydrochloride (64.0 g, 340 mmol) was added dropwise slowly, and the mixture was stirred overnight. The reaction solution was washed successively with hydrochloric acid aqueous solution (1.5 N, 72 mL), water (150 mL×2) and saturated brine (75 mL×2). The organic phase was dried over anhydrous sodium sulfate and concentrated under reduced pressure to deliver the product methyl 3-oxocyclobutanecarboxylate (25 g, yellow liquid), yield: 89%.

32

Step 2

Methyl 5,8-dioxa spiro[3.4]octane-2-carboxylate

Methyl-3-oxocyclobutanecarboxylate (25.0 g, 195 mmol), ethylene glycol (35.0 g, 564 mmol) and p-toluenesulfonic acid (3.50 g, 20.0 mmol) were dissolved in toluene (250 mL), after equipped with a water separator, the reaction mixture was heated to reflux overnight. The reaction solution was cooled to 25° C. and washed successively with water (300 mL×2), saturated sodium bicarbonate aqueous solution (500 mL×2). The organic phase was dried over anhydrous magnesium sulfate, filtered and the filtrate was concentrated under reduced pressure to deliver methyl 5,8-dioxaspiro[3.4]octane-2-carboxylate (22.5 g, yellow liquid), yield: 90%.

Step 3

5,8-Dioxaspiro[3.4]octan-2-ylmethanol

Under the nitrogen gas atmosphere, lithium aluminum hydride (5.20 g, 136 mmol) was slowly dissolved in tetrahydrofuran (240 mL) at 0° C., and then methyl 5,8-dioxaspiro[3.4]octane-2-carboxylate (19.5 g, 113 mmol) dissolved in tetrahydrofuran (60 mL) was added dropwise. The reaction was slowly warmed to 25° C. and stirred for 3.5 hours. The reaction solution was cooled to 0° C. and water (5.20 g, 289 mmol), 15% sodium hydroxide (5.20 g, 19.5 mmol) and water (15.6 g, 867 mmol) were slowly added successively. The reaction mixture was filtered and the filter cake was washed with tetrahydrofuran (10 mL×3) and the filtrate was concentrated under reduced pressure and purified by silica gel column chromatography (1:1 petroleum ether/ethyl acetate, Rf=0.4) to deliver the product 5,8-dioxaspiro[3.4]octan-2-ylmethanol (10.0 g, yellow liquid), yield: 62%. $^1$H-NMR: (400 MHz, CDCl$_3$) δ 3.90-3.87 (m, 4H), 3.67 (d, J=6.4 Hz, 2H), 2.45-2.40 (m, 2H), 2.38-2.26 (m, 1H), 2.13-2.08 (m, 2H).

Step 4

5,8-Dioxaspiro[3.4]octan-2-ylmethyl methanesulfonate 5,8-Dioxaspiro[3.4]octan-2-ylmethanol (500 mg, 53.1 mmol) and triethylamine (896 mg, 6.90 mmol) were dissolved in dichloromethane (23 mL), methanesulfonyl chloride (1.40 g, 12.6 mmol) was slowly added at 0° C. The reaction solution was warmed to 25° C. and stirred overnight. The reaction was quenched by the addition of water (50 mL) and extracted with ethyl acetate (50 mL×3). The organic phases were combined, dried over anhydrous sodium sulfate, filtered and the filtrate was concentrated under reduced pressure to deliver the product 5,8-dioxaspiro[3,4]octan-2-ylmethyl methanesulfonate (2.30 g, yellow liquid).

MS-ESI calcd. for [M+H]$^+$ 223, found 223.

Step 5

1-(5,8-Dioxaspiro[3.4]octan-2-ylmethyl)-3,7-dimethyl-1H-purine-2,6(3H,7H)-dione 5,8-Dioxaspiro[3,4]octan-2-ylmethyl methanesulfonate (1.00 g, 4.50 mmol), 3,7-dimethyl-1H-purine-2,6(3H,7H)-dione (810 mg, 4.50 mmol), potassium carbonate (1.20 g, 13.5 mmol) and potassium iodide (75.0 mg, 0.45 mmol) were dissolved in N,N-dimethylformamide (20 mL). The reaction was heated to 130° C. and stirred for 3.5 hours. The reaction solution was filtered and the filtrate was concentrated under reduced pressure to deliver 1-(5,8-dioxaspiro [3.4]octan-2-ylmethyl)-3,7-dimethyl-1H-purine-2,6(3H, 7H)-dione (1.50 g, brown liquid), yield: 93%. MS-ESI calcd. for [M+H]$^+$ 307, found 307.

Step 6

3,7-Dimethyl-1-((4-oxocyclohexyl)methyl)-1H-purine-2,6(3H,7H)-dione 1-(5,8-Dioxaspiro[3.4]octan-2-ylmethyl)-3,7-dimethyl-1H-purine-2,6(3H,7H)-dione (1.50 g, 5.00 mmol) was dissolved in acetone (18 mL), hydrochloric acid aqueous solution (4 N, 3 mL) was added. The reaction was heated to 30° C. and stirred overnight. The reaction mixture was diluted with water, adjusted to pH neutral with saturated sodium bicarbonate aqueous solution (20 mL) and extracted with ethyl acetate (150 mL×3). The organic phases were combined, dried over anhydrous sodium sulfate, filtered and the filtrate was concentrated under reduced pressure, the resulting product was purified by silica gel column chromatography (1:1 petroleum ether/ethyl acetate, Rf=0.2) to deliver the product 3,7-dimethyl-1-((4-oxocyclohexyl)methyl)-1H-purine-2,6(3H,7H)-dione (180 mg, white solid), yield: 14%. $^1$H NMR: (400 MHz, CDCl$_3$) δ 7.49 (s, 1 H), 4.25 (d, J=7.6 Hz, 2 H), 3.95 (s, 3 H), 3.55 (s, 3 H), 3.13-2.96 (m, 4 H), 2.95-2.84 (m, 1 H). MS-ESI calcd. for [M+H]$^+$ 263, found 263.

Step 7

1-((3-Hydroxy-3-(trifluoromethyl)cyclopentyl) methyl)-3,7-dimethyl-1H-purine-2,6(3H,7H)-dione 3,7-Dimethyl-1-((3-oxocyclopentyl)methyl)-1H-purine-2,6(3H,7H)-dione (100 mg, 0.382 mmol) and cesium fluoride (11.5 mg, 0.0763 mmol) were dissolved in anhydrous tetrahydrofuran (3 mL), and trifluoromethyltrimethylsilane (95.0 mg, 0.640 mmol) was added under the nitrogen gas atmosphere. The reaction solution was slowly heated to 30° C. and stirred for 12 hours. Hydrochloric acid aqueous solution (1 N, 5 mL) was added into the reaction mixture, which was then stirred for a further 0.5 hour. The reaction solution was diluted with water (50 mL), the pH value was adjusted to 7 with saturated sodium bicarbonate aqueous solution (10 mL), concentrated under reduced pressure, and purified by preparative high performance liquid chromatography to deliver 1-((3-hydroxy-3-(trifluoromethyl)cyclopentyl)methyl)-3,7-dimethyl-1H-purine-2,6(3H,7H)-dione (80.0 mg, white solid), yield: 64%. $^1$H NMR: (400 MHz, Mehonal-d$_4$) δ 8.54 (s, 1H), 4.13-4.07 (m, 5H), 3.56 (s, 3H), 2.58-2.48 (m, 3H), 2.14-2.10 (m, 2H). MS-ESI calcd. for [M+H] 333, found 333.

Embodiment 6

1-((3,7-Dimethyl-2,6-dioxo-2,3,6,7-tetrahydro-1H-purin-1-yl)methyl)-3-hydroxycyclobutane carbonitrile

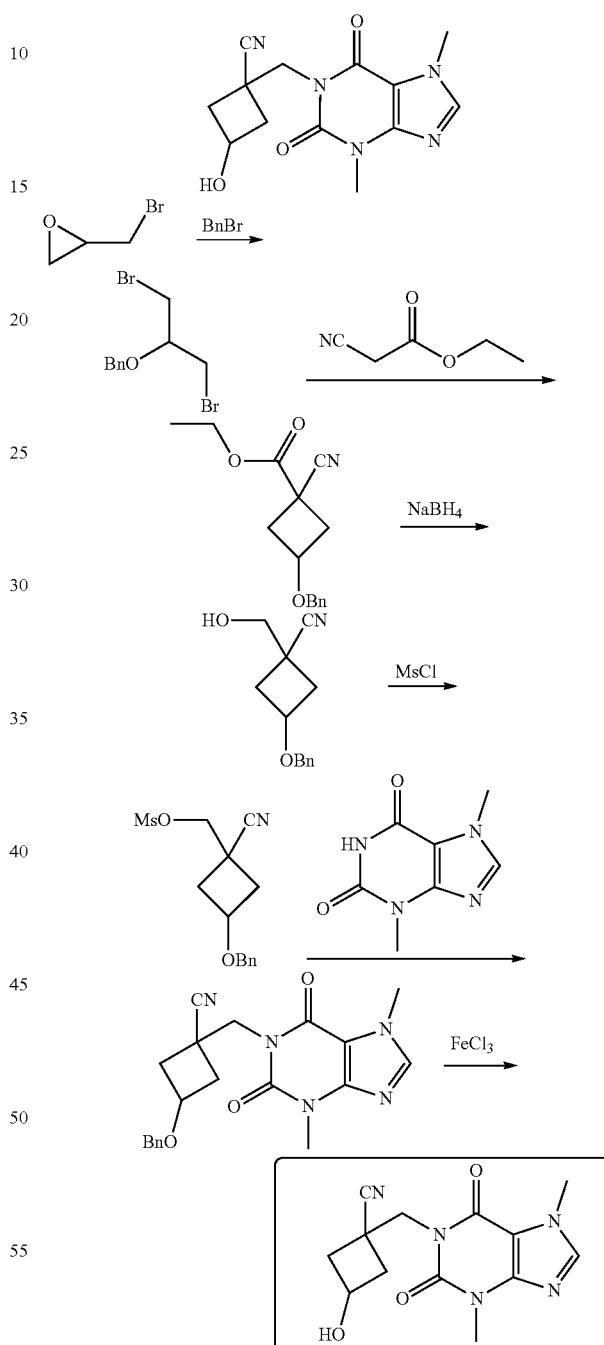

Step 1

(((1,3-Dibromopropan-2-yl)oxy)methyl)benzene 2-(Bromomethyl)oxirane (8.40 g, 61.3 mmol) was added to a solution of cuprous chloride (6.87 g, 51.1 mmol) in benzyl bromide (8.74 g, 51.1 mmol) at room temperature. The reaction was stirred at 150° C. for 11 hours. The reaction solution was cooled to room temperature, water (100 mL) was slowly added and the reaction mixture was extracted with ethyl acetate (100 mL×3). The organic phases were combined and dried over anhydrous sodium sulfate, filtered and the filtrate was concentrated under reduced pressure, the resulting product was purified by silica gel column chromatography (petroleum ether, Rf=0.6) to deliver the product (((1,3-dibromopropan-2-yl)oxy) methyl)benzene (8.60 g, yellow oil), yield: 44%. $^1$H NMR: (400 MHz, CDCl$_3$) δ 7.39-7.31 (m, 5H), 4.67 (s, 2H), 3.82-3.78 (m, 1H), 3.58 (d, J=5.2 Hz, 4H).

Step 2

Ethyl 3-(benzyloxy)-1-cyanocyclobutane carboxylate

Ethyl cyanoacetate (2.76 g, 24.3 mmol) was added slowly at room temperature to a solution of (((1,3-dibromopropan-2-yl)oxy)methyl)benzene (7.00 g, 18.2 mmol) and potassium carbonate (10.0 g, 72.7 mmol) in N, N-dimethylformamide (35 mL). The reaction was stirred at 90° C. for 4 hours. The reaction mixture was cooled to room temperature, filtered, and the solid was washed with ethyl acetate (20 mL). The resulting organic phase was washed with saturated ammonium chloride aqueous solution (20 mL×3). The organic phase was dried over anhydrous sodium sulfate, filtered and the filtrate was concentrated under reduced pressure, the resulting product was purified by silica gel column chromatography (30:1 petroleum ether/ethyl acetate, Rf=0.4) to give the product ethyl 3-(benzyloxy)-1-cyanocyclobutane carboxylate (3.80 g, colorless oil), yield: 81%. $^1$H NMR: (400 MHz, Methanol-d$_4$) δ 7.40-7.28 (m, 5H), 4.48-4.44 (m, 2H), 4.37-4.31 (m, 1H), 4.30-4.24 (m, 2H), 2.97-2.80 (m, 2H), 2.73-2.65 (m, 2H), 1.37-1.30 (m, 3H).

Step 3

3-(Benzyloxy)-1-(hydroxymethyl)cyclobutanecarbonitrile

Sodium borohydride (1.39 g, 36.6 mmol) was dissolved in tetrahydrofuran and water (20 mL:2 mL), and a solution of ethyl 3-(benzyloxy)-1-cyanocyclobutane carboxylate (3.80 g, 14.6 mmol) in tetrahydrofuran (22 mL) was slowly added dropwise at 0° C. over 20 minutes. The reaction was stirred at room temperature for 2 hours. The mixture was diluted with ethyl acetate (50 mL), washed with water (30 mL) and saturated brine (30 mL) separately, dried over anhydrous sodium sulfate, filtered and the filtrate was concentrated under reduced pressure to give the crude product 3-(benzyloxy)-1-(hydroxymethyl)cyclobutanecarbonitrile (3.70 g, colorless oil). $^1$H NMR: (400 MHz, DMSO-d$_6$) δ 7.38-7.25 (m, 5H), 5.57-5.52 (m, 1H), 4.39-4.36 (m, 2H), 4.13-4.04 (m, 1H), 3.57-3.51 (m, 2H), 2.58-2.51 (m, 1H), 2.49-2.45 (m, 1H), 2.31-2.09 (m, 2H).

Step 4

(3-(Benzyloxy)-1-cyanocyclobutyl)methyl methanesulfonate 3-(Benzyloxy)-1-(hydroxymethyl)cyclobutanecarbonitrile (3.70 g, 15.3 mmol) and triethylamine (3.10 g, 30.6 mmol) were dissolved in dichloromethane (35 mL), methanesulfonyl chloride (3.29 g, 28.7 mmol) was slowly added at 0° C. The reaction was stirred at room temperature for 4 hours, saturated ammonium chloride aqueous solution (30 mL) was added and the reaction mixture was extracted with ethyl acetate (50 mL×2), the organic phase was dried over anhydrous sodium sulfate, filtered and the filtrate was concentrated under reduced pressure to deliver the crude product (3-(benzyloxy)-1-cyanocyclobutyl)methyl methanesulfonate (4.56 g, dark brown oil). $^1$H NMR: (400 MHz, Methanol-d$_4$) δ 7.36-7.26 (m, 5H), 4.47-4.45 (m, 2H), 4.44-4.38 (m, 2H), 3.21-3.18 (m, 1H), 3.17-3.14 (m, 3H), 2.81-2.60 (m, 2H), 2.53-2.26 (m, 2H).

Step 5

3-(Benzyloxy)-1-((3,7-dimethyl-2,6-dioxo-2,3,6,7-tetrahydro-1H-purin-1-yl)methyl)cyclobutanecarbonitrile (3-(Benzyloxy)-1-cyanocyclobutyl)methyl methanesulfonate (4.50 g, 15.2 mmol), 3,7-dimethyl-1H-purine-2,6-(3H,7H)-dione (2.75 g, 15.2 mmol) and potassium iodide (1.26 g, 7.62 mmol) were dissolved in N,N-dimethylformamide (100 mL), potassium carbonate (6.32 g, 45.7 mmol) was added, the reaction mixture was heated to 120° C. and refluxed for 4 hours. The reaction mixture was cooled to room temperature, filtered, the filtrate was concentrated under reduced pressure, water (50 mL) was added and the reaction mixture was extracted with ethyl acetate (50 mL×3). The organic phases were combined, dried over anhydrous sodium sulfate, filtered and the filtrate was concentrated under reduced pressure to give the crude product 3-(benzyloxy)-1-((3,7-dimethyl-2,6-dioxo-2,3,6,7-tetrahydro-1H-purin-1-yl)methyl)cyclobutanecarbonitrile (4.60 g, yellow solid). MS-ESI calcd. for [M+H]$^+$ 380, found 380.

Step 6

1-((3,7-Dimethyl-2,6-dioxo-2,3,6,7-tetrahydro-1H-purin-1-yl)methyl)-3-hydroxycyclobutane carbonitrile 3-(Benzyloxy)-1-((3,7-dimethyl-2,6-dioxo-2,3,6,7-tetrahydro-1H-purin-1-yl)methyl)cyclobutanecarbonitrile (100 mg, 0.263 mmol) was dissolved in dichloromethane (10 mL), and ferric chloride (128 mg, 0.790 mmol) was added. The reaction was stirred at room temperature for 12 hours. Water (10 mL) was added and the mixture was extracted with dichloromethane (40 mL×3). The organic phases were combined and dried over anhydrous sodium sulfate, filtered and the filtrate was concentrated under reduced pressure, the resulting product was purified by preparative high performance liquid chromatography to deliver the product 1-((3,7-dimethyl-2,6-dioxo-2,3,6,7-tetrahydro-1H-purin-1-yl)methyl)-3-hydroxycyclobutanecarbonitrile (12.0 mg, yellow solid), yield: 16%. $^1$H NMR: (400 MHz, CDCl$_3$) δ 7.56 (s, 1H), 4.66-4.49 (m, 1H), 4.45-4.37 (m, 2H), 4.01 (s, 3H), 3.62 (s, 3H) 2.96-2.85 (m, 2H), 2.60-2.49 (m, 2H). MS-ESI calcd. for [M+H]$^+$ 290, found 290.

Embodiment 7

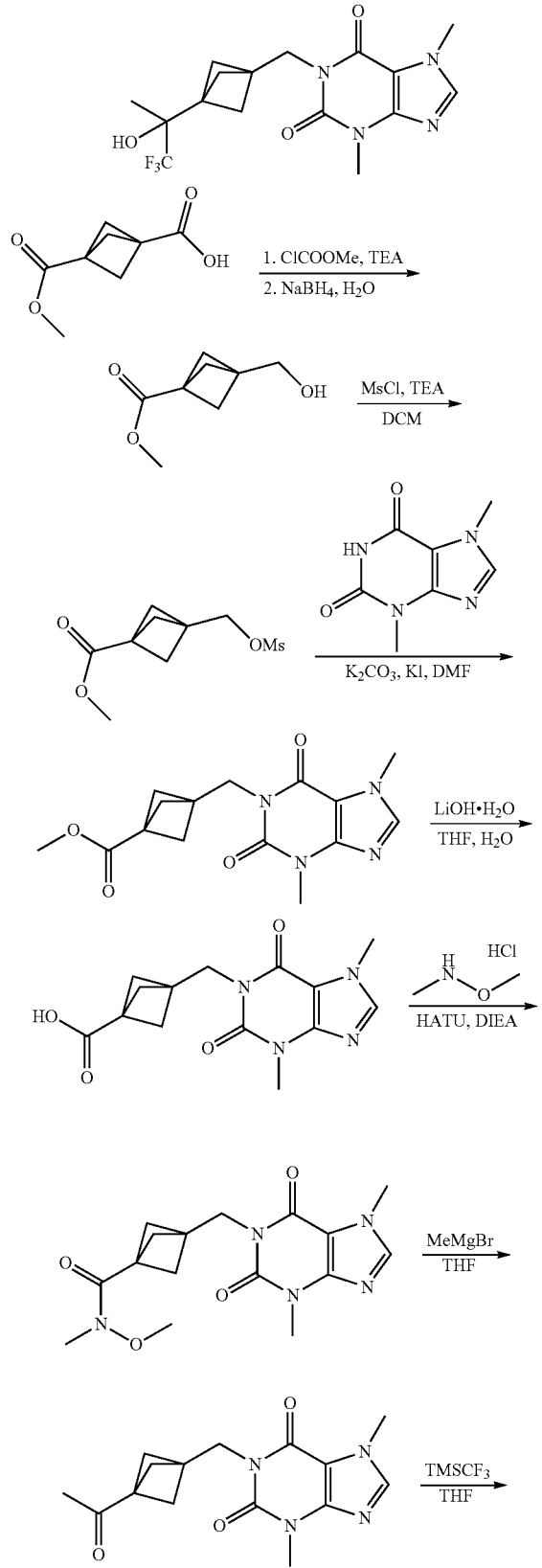

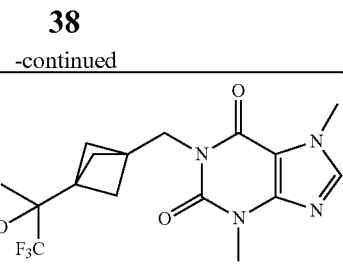

Step 1

Methyl 3-(hydroxymethyl)bicyclo[1.1.1]pentane-1-carboxylic acid methyl ester 3-(Methoxycarbonyl)bicyclo[1.1.1]pentane-1-carboxylic acid (100 mg, 0.587 mmol) and triethylamine (71.0 mg, 0.705 mmol) were dissolved in tetrahydrofuran (20 mL), methyl chloroformate (56.0 mg, 0.587 mmol) was slowly added dropwise at −10° C. The reaction solution was stirred at 0° C. for half an hour and then sodium borohydride (33.0 mg, 0.881 mmol) was added and the reaction mixture was stirred for a further 2 hours. Water (10 mL) was added to the reaction solution, which was then extracted with ethyl acetate (10 mL×3), the organic phases were combined and washed with saturated sodium chloride (10 mL×2), dried over anhydrous sodium sulfate, filtered and the filtrate was concentrated under reduced pressure to deliver methyl 3-(hydroxymethyl)bicyclo[1.1.1]pentane-1-carboxylic acid methyl ester (80.0 mg, colorless oil), yield: 87%. $^{1}$H NMR: (400 MHz, CDCl$_3$) δ 3.65 (s, 3H), 3.60 (s, 2H), 2.00 (s, 6H).

Step 2

Methyl 3-(((methylsulfonyl)oxy)methyl)bicyclo[1.1.1]pentane-1-carboxylic acid methyl ester Methyl 3-(hydroxymethyl)bicyclo[1.1.1]pentane-1-carboxylate (40.0 mg, 0.256 mmol) and triethylamine (39.0 mg, 0.384 mmol) were dissolved in dichloromethane (15 mL), methanesulfonyl chloride (35.0 mg, 0.307 mmol) was slowly added dropwise at 0° C. The reaction solution was stirred at 0° C. for 2 hours, the reaction solution was diluted with dichloromethane (10 mL), the organic phase was washed with water (10 mL×2), dried over anhydrous sodium sulfate, filtered and the filtrate was concentrated under reduced pressure to deliver methyl 3-(((methylsulfonyl)oxy)methyl)bicyclo[1.1.1]pentane-1-carboxylic acid methyl ester (50.0 mg, yellow oil), yield: 83%.

Step 3

Methyl 3-((3,7-dimethyl-2,6-dioxo-2,3,6,7-tetrahydro-1H-purin-1-yl)methyl) bicyclo[1.1.1]pentane-1-carboxylic acid methyl ester Methyl 3-(((methylsulfonyl)oxy)methyl)bicyclo[1.1.1] pentane-1-carboxylic acid methyl ester (100 mg, 0.426 mmol) and 3,7-dimethyl-1H-purine-2,6-(3H,7H)-dione (77.0 mg, 0.427 mmol) were dissolved in N,N-dimethylformamide (20 mL), potassium carbonate (88.0 mg, 0.640 mmol) and potassium iodide (8.00 mg, 0.0430 mmol) were added at room temperature. The reaction solution was stirred at 100° C. for 2 hours, the reaction solution was cooled to room temperature and concentrated, diluted with ethyl acetate (20 mL), the organic phase was washed with water (20 mL×2), dried over anhydrous sodium sulfate, filtered, the filtrate was concentrated under reduced pressure, and isolated and purified by silica gel column chromatography (1:1 petroleum ether/ethyl acetate, Rf=0.2) to deliver methyl 3-((3,7-dimethyl-2,6-dioxo-2,3,6,7-tetrahydro-1H-purin-1-yl)methyl)bicyclo[1.1.1]pentane-1-carboxylic acid methyl ester (100 mg, yellow solid), yield: 73%. $^1$H NMR: (400 MHz, CDCl$_3$) δ 7.50 (s, 3H), 3.65 (s, 3H), 3.52 (s, 3H), 1.95 (s, 6H). MS-ESI calcd. for [M+H]$^+$319, found 319.

Step 4

3-((3,7-Dimethyl-2,6-dioxo-2,3,6,7-tetrahydro-1H-purin-1-yl)methyl)bicyclo[1.1.1]pentane-1-carboxylic acid Methyl 3-((3,7-dimethyl-2,6-dioxo-2,3,6,7-tetrahydro-1H-purin-1-yl)methyl) bicyclo[1.1.1]pentane-1-carboxylic acid methyl ester (100 mg, 0.314 mmol) was dissolved in tetrahydrofuran (15 mL) and water (5 mL), lithium hydroxide (26.0 mg, 0.628 mmol) was added at room temperature. After stirring at room temperature for 2 hours, 2 N dilute hydrochloric acid (10 mL) was added to the reaction solution, the pH value was adjusted to 4, the mixture was then extracted with ethyl acetate (15 mL×3), the organic phases were combined and washed with saturated sodium chloride aqueous solution (20 mL×2), dried over anhydrous sodium sulfate, filtered and the filtrate was concentrated under reduced pressure to deliver 3-((3,7-dimethyl-2,6-dioxo-2,3,6,7-tetrahydro-1H-purin-1-yl)methyl)bicyclo[1.1.1]pentane-1-carboxylic acid (90.0 mg, white solid), yield: 94%.
MS-ESI calcd. for [M+H]$^+$ 305, found 305.

Step 5

3-((3,7-Dimethyl-2,6-dioxo-2,3,6,7-tetrahydro-1H-purin-1-yl)methyl)-N-methoxy-N-methylbicyclo[1.1.1]pentane-1-carboxamide 3-((3,7-Dimethyl-2,6-dioxo-2,3,6,7-tetrahydro-1H-purin-1-yl)methyl)bicyclo[1.1.1]pentane-1-carboxylic acid (30.0 mg, 0.0986 mmol) and N, O-dimethylhydroxylamine (10.0 mg, 0.0986 mmol) were dissolved in dichloromethane (20 mL), 2-(7-azobenzotriazole)-N,N,N',N'-tetramethyluronium hexafluorophosphate (75.0 mg, 0.197 mmol) and diisopropylethylamine (19.0 mg, 0.148 mmol) were added at room temperature. After stirring at room temperature for 12 hours, water (20 mL) was added to the reaction solution, which was then extracted with dichloromethane (20 mL×2), the organic phases were combined and washed with saturated ammonium chloride aqueous solution (20 mL×2), dried over anhydrous sodium sulfate, filtered, and the filtrate was concentrated under reduced pressure, the residue was isolated and purified by silica gel column chromatography (1:2 petroleum ether/ethyl acetate, Rf=0.2) to deliver 3-((3,7-dimethyl-2,6-dioxo-2,3,6,7-tetrahydro-1H-purin-1-yl)methyl)-N-methoxy-N-methylbicyclo[1.1.1]pentane-1-carboxamide (30.0 mg, white solid), yield: 88%.
MS-ESI calcd. for [M+H]$^+$ 348, found 348.

Step 6

1-((3-Acetylbicyclo[1.1.1]pentan-1-yl)methyl)-3,7-dimethyl-1H-purine-2,6-(3H,7H)-dione 3-((3,7-Dimethyl-2,6-dioxo-2,3,6,7-tetrahydro-1H-purin-1-yl)methyl)-N-methoxy-N-methylbicyclo[1.1.1]pentane-1-carboxamide (20.0 mg, 0.0575 mmol) was dissolved in tetrahydrofuran (20 mL), methylmagnesium bromide (3 M ether solution, 0.040 mL, 0.120 mmol) was added to the reaction solution at −78° C., after stirring for a further 30 minutes, the reaction solution was warmed to room temperature and reacted for 4 hours. Saturated ammonium chloride aqueous solution (10 mL) was added to the reaction solution at 0° C., which was then extracted with ethyl acetate (15 mL×3), the organic phases were combined and washed with saturated sodium chloride solution (20 mL×2), dried over anhydrous sodium sulfate, filtered, and the filtrate was concentrated under reduced pressure. And the residue was isolated and purified by silica gel column chromatography (1:1 petroleum ether/ethyl acetate, Rf=0.5) to deliver 1-((3-acetylbicyclo[0.1.1.1]pentan-1-yl)methyl)-3,7-dimethyl-1H-purine-2,6-(3H,7H)-dione (15.0 mg, colorless oil), yield: 86%. $^1$H NMR: (400 MHz, CDCl$_3$) δ 7.55 (s, 1H), 4.17 (s, 2H), 3.99 (s, 3H), 3.59 (s, 3H), 2.07 (s, 3H), 1.97 6H). MS-ESI calcd. for [M+H]$^+$ 303, found 303.

Step 7

3,7-Dimethyl-1-((3-(1,1,1-trifluoro-2-hydroxypropan-2-yl)bicyclo[1.1.1]pentan-1-yl)methyl)-1H-purine-2,6-(3H,7H)-dione 1-((3-Acetylbicyclo[1.1.1.1]pentan-1-yl)methyl)-3,7-dimethyl-1H-purine-2,6-(3H,7H)-dione (20.0 mg, 0.0660 mmol) and trifluoromethyltrimethylchlorosilane (19.0 mg, 0.132 mmol) were dissolved in tetrahydrofuran (15 mL), cesium fluoride (10.0 mg, 00660 mmol) was added to the reaction solution at room temperature and the reaction was stirred for a further 12 hours at room temperature. To the reaction solution was added 2 N dilute hydrochloric acid (10 mL), which was then stirred for 30 minutes, extracted with ethyl acetate (20 mL×2), the organic phases were combined and washed with saturated sodium bicarbonate aqueous solution (20 mL×2), dried over anhydrous sodium sulfate, filtered, the filtrate was concentrated under reduced pressure and purified by high performance liquid chromatography to deliver 3,7-dimethyl-1-((3-(1,1,1-trifluoro-2-hydroxypropan-2-yl)bicyclo[1.1.1.1]pentan-1-yl)methyl)-1H-purine-2, 6-(3H,7H)-dione (5.00 mg, colorless oil), yield: 20%. $^1$H NMR: (400 MHz, CDCl$_3$) δ 7.59 (s, 1H), 4.20 (s, 2H), 4.02 (s, 3H), 3.59 (s, 3H), 1.97 (s, 6H), 1.79 3H). MS-ESI calcd. for [M+H]$^+$ 373, found 373.

Embodiment 8

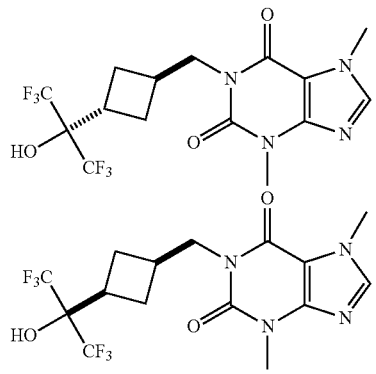

42

Embodiment 9

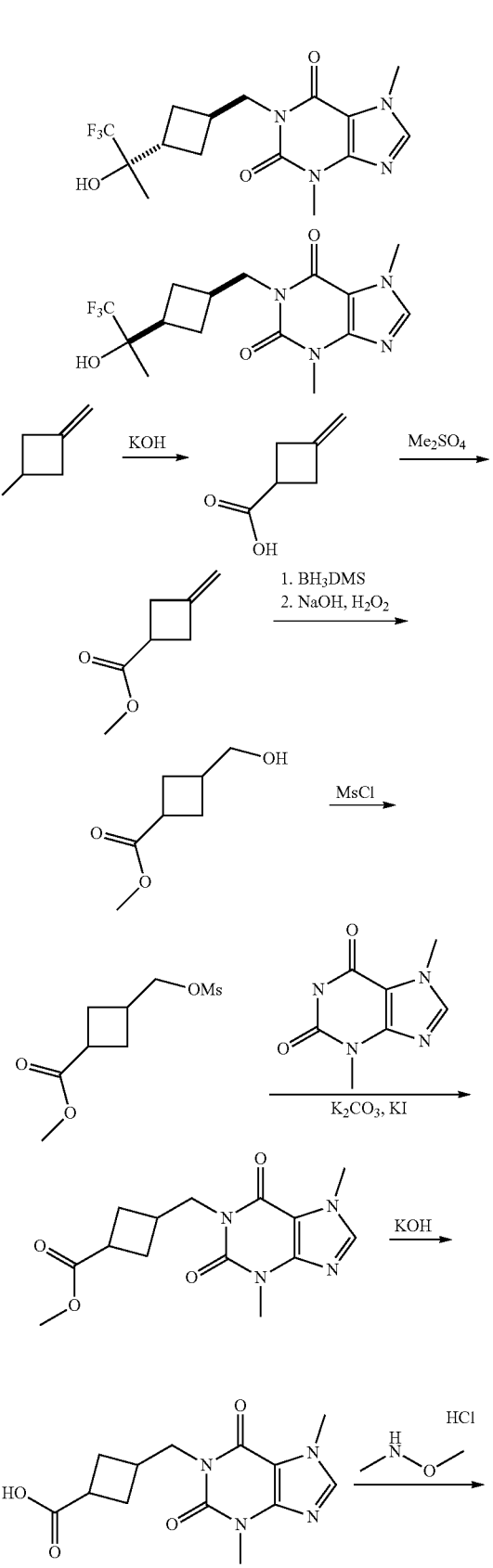

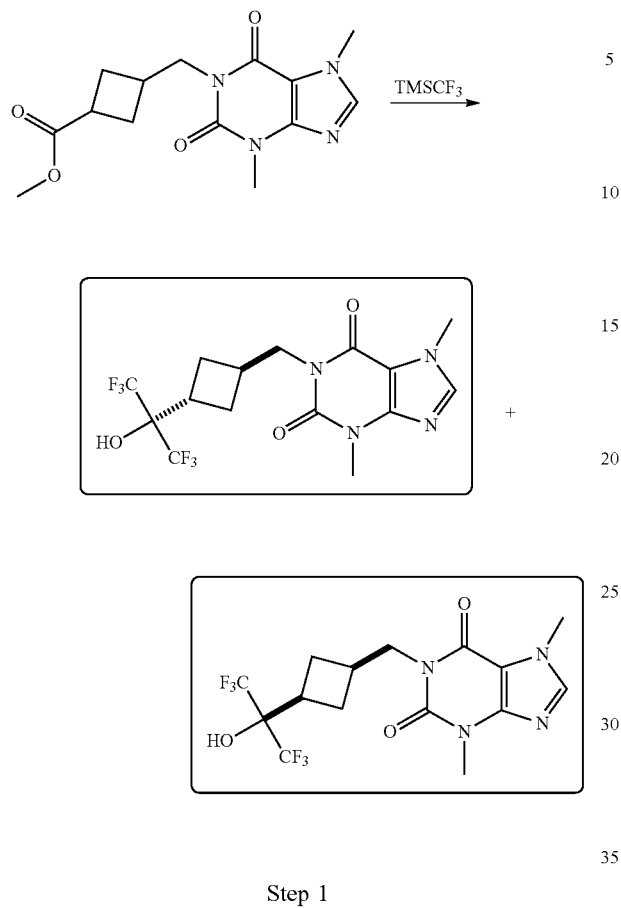

Step 1

3,7-Dimethyl-1-[[3-[2,2,2-trifluoro-1-hydroxy-1-(trifluoromethyl)ethyl]cyclobutyl]methyl]purine-2,6-dione 3,7-Dimethyl-1-[[3-(2,2,2-trifluoro-1,1-dihydroxy-ethyl)cyclobutyl]methyl]purine-2,6-dione (60.0 mg, 0.165 mmol), cesium fluoride (25.2 mg, 0.165 mmol) were dissolved in tetrahydrofuran (10 mL), trifluoromethyltrimethylchlorosilane (70.6 mg, 0.496 mmol) was added at room temperature and stirred for 12 hours. The reaction was quenched by the addition of water (20 mL). The resulting mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver product 1 (8.00 mg, yellow solid) (isomer 1, the first peak) yield: 12%. $^1$H NMR: (400 MHz, Methanol-$d_4$) δ 8.01 (s, 1H), 4.22-4.17 (m, 2H), 4.01 (s, 3H), 3.54 (s, 3H), 3.55-3.19 (m, 1H), 2.63-2.56 (m, 1H), 2.50-2.42 (m, 2H), 1.82-1.78 (m, 2H). MS-ESI calcd. for [M+H]$^+$ 415, found 415.

And product 2 (isomer 2, the second peak), yield: 6%. $^1$H NMR: (400 MHz, Methanol-$d_4$) δ 8.20 (s, 1H), 4.04-4.00 (m, 5H), 3.55 (s, 3H), 2.70-2.65 (m, 1H), 2.55-2.53 (m, 1H), 2.17-2.12 (m, 2H), 2.02-1.98 (m, 2H). MS-ESI calcd. for [M+H]$^+$ 415, found 415.

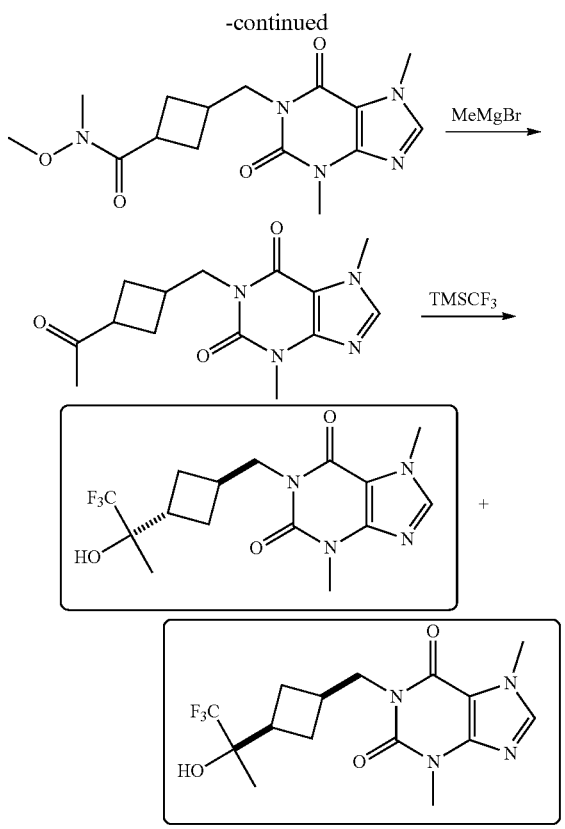

Step 1

3-Methylene cyclobutanecarboxylic acid

3-Methylene cyclobutyronitrile (10.0 g, 107 mmol) and potassium hydroxide (18.1 g, 322 mmol) were dissolved in ethanol (100 mL) and water (50 mL), after reacted at 100° C. for 2 hours, 1 N hydrochloric acid (120 mL) was added. The resulting mixture was extracted with dichloromethane (30 mL×3), dried over anhydrous sodium sulfate, filtered and the filtrate was concentrated under reduced pressure to deliver 3-methylene cyclobutanecarboxylic acid (11.0 g, yellow oil), yield: 91%. $^1$H NMR: (400 MHz, Methanol-d$_4$) δ 4.83-4.76 (m, 2H), 3.15-2.96 (m, 1H), 2.95-2.92 (m, 4H).

Step 2

Methyl-3-methylene cyclobutanecarboxylate

3-Methylene cyclobutanecarboxylic acid (11.0 g, 98.1 mmol) and potassium carbonate (27.1 g, 196 mmol) were dissolved in acetone (100 mL), dimethyl sulfate (14.8 g, 117 mmol) was added at 25° C. After reacting at 70° C. for 12 hours, the reaction was quenched by the addition of water (20 mL), extracted with dichloromethane (30 mL×3), dried over anhydrous sodium sulfate, filtered and the filtrate was concentrated under reduced pressure to deliver methyl-3-methylene cyclobutanecarboxylate (12.0 g, yellow oil), yield: 97%. $^1$H NMR: (400 MHz, Methanol-d$_4$) δ 4.83-4.79 (m, 2H), 3.96 (s, 2H), 3.68 (s, 3H), 3.17-3.15 (m, 1H), 2.95-2.92 (m, 2H).

Step 3

Methyl 3-(hydroxymethyl) cyclobutane carboxylate

Methyl-3-methylene cyclobutanecarboxylate (2.00 g, 15.8 mmol) was dissolved in tetrahydrofuran (30 mL), borane dimethyl sulfide (3.61 g, 47.5 mmol) was added dropwise at −10° C. and then reacted at −10° C. for 3 hours, 3 N sodium hydroxide aqueous solution (10 mL) and hydrogen peroxide (5 mL) were added and the reaction was continued for 1 hour, the reaction solution was quenched by the addition of saturated sodium thiosulfate aqueous solution (30 mL), extracted with dichloromethane (10 mL×3), dried over anhydrous sodium sulfate, filtered and the filtrate was concentrated under reduced pressure to deliver methyl 3-(hydroxymethyl) cyclobutane carboxylate (2.00 g, yellow oil), yield: 87%. $^1$H NMR: (400 MHz, Methanol-d$_4$) δ 3.70 (s, 3H), 3.58 (d, J=6.8 Hz, 1H), 3.49 (d, J=6.8 Hz, 1H), 3.10-3.05 (m, 1H), 2.32-2.26 (m, 3H), 2.03-1.98 (m, 2H).

Step 4

Methyl 3-(((methylsulfonyl)oxy)methyl)cyclobutane carboxylate

Methyl 3-(hydroxymethyl) cyclobutane carboxylate (1.00 g, 6.94 mmol) and triethylamine (2.11 g, 20.8 mmol) were dissolved in dichloromethane (20 mL), methanesulfonyl chloride (1.59 g, 13.9 mmol) was added at 0° C. The reaction solution was slowly warmed to room temperature and stirred for 2 hours. The reaction was quenched by the addition of sodium bicarbonate aqueous solution (50 mL). The resulting mixture was extracted with dichloromethane (10 mL×3). The organic phases were combined, washed with saturated brine, dried over anhydrous sodium sulfate, filtered and the filtrate was concentrated under reduced pressure to deliver methyl 3-(((methylsulfonyl)oxy)methyl)cyclobutane carboxylate (1.40 g, yellow oil), yield: 91%. $^1$H NMR: (400 MHz, Methanol-d$_4$) δ 4.28 (d, J=6.8 Hz, 1H), 4.19 (d, J=6.8 Hz, 1H), 3.70 (s, 3H), 3.20-3.08 (m, 4H), 2.40-2.34 (m, 3H), 2.13-2.09 (m, 2H). MS-ESI calcd. for [M+H]$^+$ 223, found 223.

Step 5

Methyl 3-[(3,7-dimethyl-2,6-dioxo-2,3,6,7-tetrahydro-1H-purin-1-yl)methyl]cyclobutanecarboxylate Ethyl 3-(((methylsulfonyl)oxy)methyl)cyclobutane carboxylate (1.40 g, 6.30 mmol), 3,7-dimethyl-1H-purine-2,6-(3H,7H)-dione (1.13 g, 6.30 mmol), potassium iodide (209 mg, 1.26 mmol) and potassium carbonate (2.61 g, 18.90 mmol) were dissolved in N,N-dimethylformamide (100 mL). The reaction solution was heated to 120° C. and stirred for 3 hours. Then the reaction mixture was cooled to room temperature, filtered, into which water (100 mL) was added, extracted with dichloromethane (10 mL×3). The organic phases were combined, washed with saturated brine, dried over anhydrous sodium sulfate, filtered and the filtrate was concentrated under reduced pressure to deliver methyl 3-[(3,7-dimethyl-2,6-dioxo-2,3,6,7-tetrahydro-1H-purin-1-yl)methyl]cyclobutanecarboxylate (1.50 g, yellow solid), yield: 78%. $^1$H NMR: (400 MHz, Methanol-d$_4$) δ 7.51 (s, 1H), 4.18-4.10 (m, 2H), 3.99 (s, 3H), 3.67 (s, 3H), 3.55 (s, 3H) 3.26-2.65 (m, 2H), 2.29-2.13 (n, 4H). MS-ESI calcd. for [M+H]$^+$ 307, found 307.

Step 6

3-[(3,7-Dimethyl-2,6-dioxo-2,3,6,7-tetrahydro-1H-purin-1-yl)methyl]cyclobutanecarboxylic acid Methyl 3-[(3,7-dimethyl-2,6-dioxo-2,3,6,7-tetrahydro-1H-purin-1-yl)methyl]cyclobutanecarboxylate (1.00 g, 3.26 mmol) and potassium hydroxide (548 mg, 9.78 mmol) were dissolved in methanol (10 mL) and water (5 mL). The reaction solution was heated to 90° C. and stirred for 3 hours. The resulting mixture was cooled to room temperature, neutralized by the addition of 1 N hydrochloric acid (20 mL) and filtered, extracted with dichloromethane (10 mL×3). The organic phases were combined, washed with saturated brine, dried over anhydrous sodium sulfate, filtered and the filtrate was concentrated under reduced pressure to deliver 3-[(3,7-dimethyl-2,6-dioxo-2,3,6,7-tetrahydro-1H-purin-1-yl)methyl]cyclobutanecarboxylic acid (800.00 mg, yellow solid), yield: 84%. MS-ESI calcd. for [M+H]$^+$ 293, found 293.

Step 7

3-[(3,7-Dimethyl-2,6-dioxo-purin-1-yl)methyl]-N-methoxy-N-methyl cyclobutanecarboxamide 3-[(3,7-Dimethyl-2,6-dioxo-2,3,6,7-tetrahydro-1H-purin-1-yl)methyl]cyclobutanecarboxylic acid (300 mg, 1.03 mmol), N,O-dimethylhydroxylamine hydrochloride (200 mg, 2.05 mmol), 1-ethyl-(3-dimethylaminopropyl)carbodiimide hydrochloride (394 mg, 2.06 mmol), 1-hydroxybenzotriazole (27.8 mg, 0.206 mmol) and triethylamine (312 mg, 3.09 mmol) were dissolved in dichloromethane (10 mL). The reaction mixture was stirred at 25° C. for 12 hours. The reaction mixture was concentrated under reduced pressure, the residue was isolated and purified by preparative TLC plate (ethyl acetate, the value of Rf=0.3) to deliver 3-[(3,7-dimethyl-2,6-dioxo-purin-1-yl)methyl]-N-methoxy-N-methylcyclobutanecarboxamide (200 mg, yellow solid), yield: 58%. MS-ESI calcd. for [M+H]$^+$ 336, found 336.

Step 8

1-[(3-Acetylcyclobutyl)methyl]-3,7-dimethylpurine-2,6-dione

3-[(3,7-Dimethyl-2,6-dioxo-purin-1-yl)methyl]-N-methoxy-N-methylcyclobutanecarboxamide (300 mg, 0.894 mmol) was dissolved in tetrahydrofuran (10 mL). Methylmagnesium bromide (3 M ether solution, 1.49 mL, 4.47 mmol) was added dropwise at 0° C. and stirred for 3 hours. The reaction solution was quenched by the addition of saturated ammonium chloride aqueous solution (20 mL) and extracted with dichloromethane (10 mL×3). The organic phases were combined, washed with saturated brine, dried over anhydrous sodium sulfate, filtered, the filtrate was concentrated under reduced pressure, the residue was isolated and purified by preparative TLC plate (ethyl acetate, the value of Rf=0.5) to deliver 1-[(3-acetylcyclobutyl)methyl]-3,7-dimethylpurine-2,6-dione (200 mg, yellow solid), yield: 77%.

MS-ESI calcd. for [M+H]$^+$ 291, found 291.

Step 9

1-[(3-Acetylcyclobutyl)methyl]-3,7-dimethylpurine-2,6-dione (250 mg, 0.861 mmol), cesium fluoride (130 mg, 0.861 mmol) were dissolved in tetrahydrofuran (10 mL), trimethyl-trifluoromethyl-silane (244 mg, 1.72 mmol) was added at room temperature and stirred for 12 hours. The reaction was quenched by the addition of water (20 mL). The resulting mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver product 1 (65.0 mg, yellow solid) (isomer 1, the first peak), yield: 20%. $^1$H NMR: (400 MHz, Methanol-d$_4$) δ 8.21 (s, 1H), 4.23 (d, J=7.6 Hz, 2H), 4.03 (s, 3H), 3.55 (s, 3H), 3.26-3.19 (m, 2H), 2.63-2.56 (m, 2H), 2.55-2.42 (m, 2H), 1.82-1.78 (m, 3H). MS-ESI calcd. for [M+H]$^+$ 361, found 361.

Product 2 (isomer 2, the second peak), yield: 22%. $^1$H NMR: (400 MHz, Methanol-d$_4$) δ 8.05 (s, 1H), 4.01-3.99 (m, 5H), 4.03 (s, 3H), 3.54 (s, 3H), 2.71-2.66 (m, 1H), 2.55-2.54 (m, 1H), 2.17-2.12 (m, 2H), 2.02-1.98 (m, 2H). MS-ESI calcd. for [M+H]$^+$ 361, found 361.

Embodiment 10

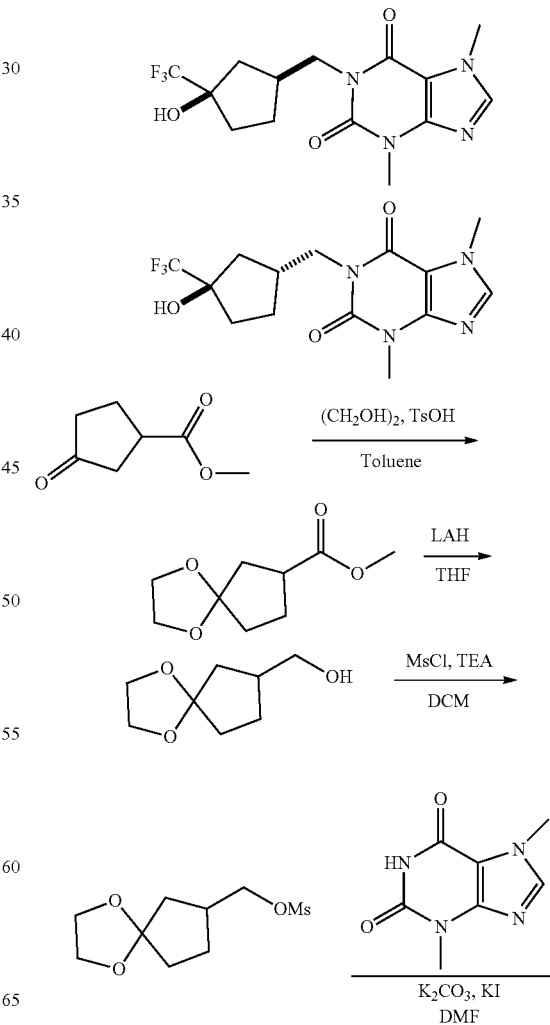

-continued

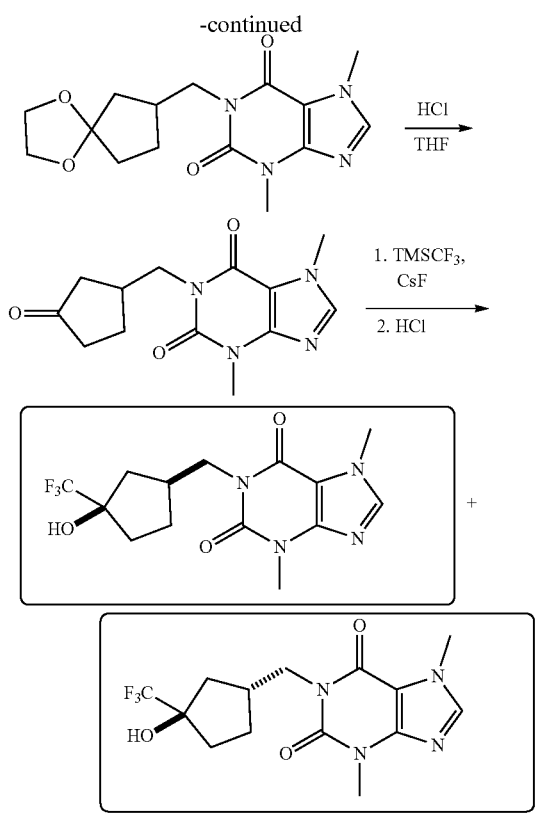

Step 1

Methyl 1,4-dioxaspiro[4.4]nonane-7-carboxylate

Methyl 3-oxocyclopentanecarboxylate (16.0 g, 110 mmol), p-toluenesulfonic acid (14.0 g, 220 mmol) and ethylene glycol (969 mg, 5.60 mmol) were dissolved in anhydrous toluene (160 mL), after equipped with a water separator, the reaction mixture was heated to reflux for 4 hours. The reaction was quenched by the addition of water (200 mL), extracted with ethyl acetate, and the organic phases were combined. The combined organic phase was washed successively with water (200 mL×2), saturated sodium chloride aqueous solution (200 mL×2), dried over anhydrous magnesium sulfate and filtered. The filtrate was concentrated under reduced pressure and purified by silica gel column chromatography (5:1 petroleum ether/ethyl acetate, Rf=0.3) to deliver methyl 1,4-dioxaspiro[4.4] nonane-7-carboxylate (6.20 g, yellow oil), yield: 29%. $^1$H NMR: (400 MHz, CDCl$_3$) δ 3.93-3.89 (m, 4H), 3.69 (s, 3H), 2.91-2.89 (m, 1H), 2.11-1.82 (m, 6H). MS-ESI calcd. for [M+H]$^+$ 187, found 187.

Step 2

(1,4-Dioxaspiro [4.4] nonan-7-yl)-methanol

Methyl 1,4-dioxaspiro[4.4]nonane-7-carboxylate (1.00 g, 10.7 mmol) was dissolved in anhydrous tetrahydrofuran (30 mL), under the nitrogen gas atmosphere, lithium aluminum hydride (531 mg, 13.9 mmol) was slowly added at −10° C. The reaction solution was slowly warmed to 25° C. and stirred for 3 hours. Water (0.5 mL), 15% sodium hydroxide solution (0.5 mL) and water (1.5 mL) were added successively to the reaction solution. The insoluble substance was removed by filtration and the filtrate was concentrated under reduced pressure to deliver (1,4-dioxaspiro[4.4]nonane-7-yl)-methanol (1.5 mg, yellow oil), yield: 88%. $^1$H NMR: (400 MHz, CDCl$_3$) δ 3.94-3.89 (m, 4H), 3.58-3.57 (m, 2H), 2.31-1.48 (m, 7H). MS-ESI calcd. for [M+H]$^+$ 159, found 159.

Step 3

1,4-Dioxaspiro[4.4]nonan-7-ylmethyl methanesulfonate (1,4-Dioxaspiro[4.4]nonane-7-yl)-methanol (500 mg, 53.1 mmol) and triethylamine (800 mg, 7.92 mmol) were dissolved in anhydrous dichloromethane (5 mL), under the nitrogen gas atmosphere, methanesulfonyl chloride (433 mg, 3.80 mmol) was slowly added at 0° C. The reaction solution was warmed to 25° C. and stirred for 2 hours. The reaction was quenched by the addition of water (40 mL) and extracted with ethyl acetate. The organic phases were combined, washed successively with water (20 mL×2), saturated sodium chloride aqueous solution (50 mL×2), dried over anhydrous magnesium sulfate, filtered and the filtrate was concentrated under reduced pressure to deliver 1,4-dioxaspiro[4.4]nonan-7-ylmethyl methanesulfonate (800 mg, yellow oil). MS-ESI calcd. for [M+H]$^+$ 237, found 237.

Step 4

(1,4-Dioxaspiro[4.4]nonan-7-ylmethyl)-3,7-dimethyl-1H-purine-2,6(3H,7H)-dione 1,4-Dioxaspiro[4.4]nonan-7-ylmethyl methanesulfonate (300 mg, 1.27 mmol) was dissolved in anhydrous N,N-dimethylformamide (10 mL), under the nitrogen gas atmosphere, potassium carbonate (350 mg, 2.54 mmol), potassium iodide (21.0 mg, 0.130 mmol), 2,6-hydroxy-3,7-dimethylpurine (275 mg, 1.52 mmol) were added at 25° C. The reaction solution was heated to 130° C. and stirred for 3 hours. The reaction solution was cooled to 25° C., quenched by the addition of water (40 mL), and extracted with ethyl acetate (30 mL×2). The organic phases were combined, washed with saturated sodium chloride aqueous solution (100 mL×2), dried over anhydrous magnesium sulfate, filtered and the filtrate was concentrated under reduced pressure to deliver (1,4-dioxaspiro[4.4]nonan-7-ylmethyl)-3,7-dimethyl-1H-purine-2,6(3H,7H)-dione (200 mg, white solid), yield: 45%. MS-ESI calcd. for [M+H]$^+$ 321, found 321.

Step 5

3,7-Dimethyl-1-(3-oxocyclopentylmethyl)-1H-purine-2,6(3H,7H)-dione (1,4-dioxaspiro[4.4]nonan-7-ylmethyl)-3,7-dimethyl-1H-purine-2,6(3H,7H)-dione (200 mg, 0.620 mmol) was dissolved in anhydrous tetrahydrofuran (5 mL), under the nitrogen gas atmosphere, conc. hydrochloric acid (3 mL) was added at 25° C. The reaction solution was stirred at 25° C. for 1 hour. The mixture was diluted with water (60 mL) and the reaction was extracted with ethyl acetate (20 mL×3). The organic phases were combined, washed with saturated sodium chloride aqueous solution (100 mL×2), dried over anhydrous magnesium sulfate, filtered, the filtrate was concentrated under reduced pressure and purified by silica gel column chromatography (1:1 petroleum ether/ethyl acetate, Rf=0.3) to deliver 3,7-dimethyl-1-(3-oxocyclopentylmethyl)-1H-purine-2,6(3H,7H)-dione (100 mg, yellow oil), yield: 57%. MS-ESI calcd. for [M+H]+ 277, found 277.

Step 6

1,3-trans-1-((3-Hydroxy-3-(trifluoromethyl)cyclopentyl)methyl)-3,7-dimethyl-1H-purine-2,6 (3H, 7H)-dione 1,3-cis-1-((3-Hydroxy-3-(trifluoromethyl)cyclopentyl)methyl)-3,7-dimethyl-1H-purine-2,6(3H,7H)-dione 3,7-Dimethyl-1-((3-oxocyclopentyl)methyl)-1H-purine-2,6(3H,7H)-dione (100 mg, 0.362 mmol) and cesium fluoride (11.0 mg, 0.0725 mmol) were dissolved in anhydrous tetrahydrofuran (3 mL), under the nitrogen gas atmosphere, trifluoromethyltrimethylsilane (95.0 mg, 0.640 mmol) was added. The reaction solution was slowly heated to 30° C. and stirred for 12 hours. To the reaction solution was added hydrochloric acid aqueous solution (1 N, 5 mL), and the reaction was stirred for a further 0.5 hour at 30° C. The reaction solution was diluted with water (50 mL) and the pH value was adjusted to 7 with saturated sodium bicarbonate aqueous solution (10 mL) and extracted with ethyl acetate (30 mL×2). The organic phases were combined, dried over anhydrous sodium sulfate, filtered, and the filtrate was concentrated under reduced pressure and purified by preparative high performance liquid chromatography to give two isomeric products.

Product 1 (isomer 1, the first peak) (40.0 mg, white solid), yield: 32%. 1H NMR: (400 MHz, Methanol-d4) δ 7.68 (s, 1H), 4.13-4.08 (m, 2H), 4.05 (s, 3H), 3.61 (s, 3H), 2.80-2.78 (m, 1H), 2.40-2.24 (m, 1H), 2.04-2.03 (m, 1H), 2.01-1.87 (m, 2H), 1.84-1.76 (m, 1H), 1.62-1.60 (m, 1H). MS-ESI calcd. for [M+H]+ 347, found 347.

Product 2 (isomer 2, the second peak) (20.0 mg, white solid), yield: 16%. 1H NMR: (400 MHz, Methanol-d4) δ 7.62 (s, 1H), 4.22-4.18 (m, 1H), 4.05-4.04 (m, 1H), 4.00 (s, 3H), 3.63 (s, 3H), 2.65-2.63 (m, 1H), 2.09-2.01 (m, 4H), 1.70-1.68 (m, 1H), 1.67-1.65 (m, 1H). MS-ESI calcd. for [M+H]+ 347, found 347.

Embodiment 11

1-((4-Hydroxy-4-(trifluoromethyl)cyclohexyl)methyl)-3,7-dimethyl-1H-purine-2,6(3H, 7H)-dione

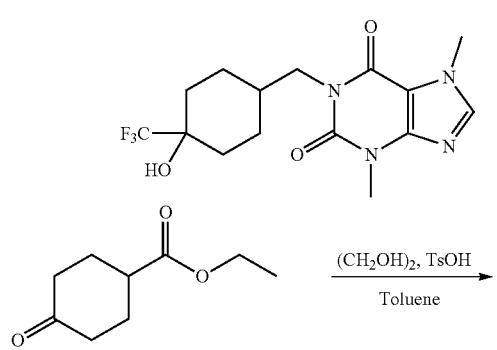

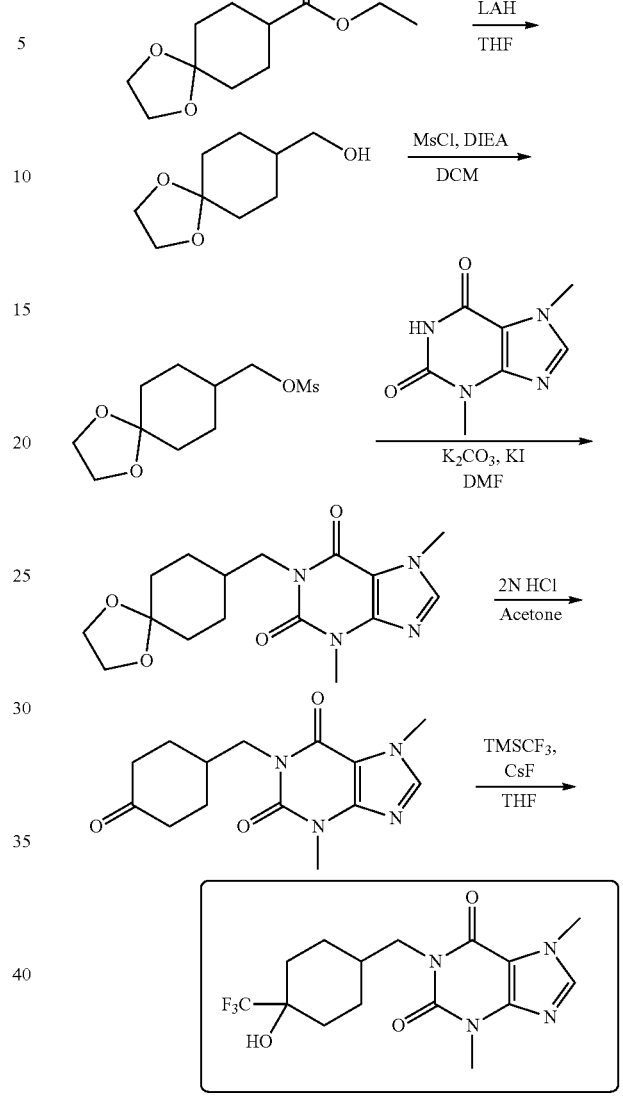

Step 1

Ethyl 1,4-dioxaspiro[4.5]decane-8-carboxylate

Ethyl 4-oxocyclohexanecarboxylate (30.0 g, 176 mmol), ethylene glycol (22.0 g, 353 mmol) and p-toluenesulfonic acid (304 mg, 1.70 mmol) were dissolved in toluene (315 mL), after equipped with a water separator, the reaction mixture was heated to reflux overnight. The reaction mixture was cooled to 25° C. and washed successively with water (300 mL×2), saturated sodium bicarbonate aqueous solution (500 mL×2), the organic phase was dried over anhydrous magnesium sulfate, filtered and the filtrate was concentrated under reduced pressure, purified by silica gel column chromatography (1:1 petroleum ether/ethyl acetate, Rf=0.3) to deliver the product ethyl 1,4-dioxaspiro[4.5]decane-8-carboxylate (37.2 g, yellow liquid), yield: 99%. MS-ESI calcd. for [M+H]+ 215, found 215.

Step 2

1,4-Dioxaspiro[4.5]decan-8-ylmethanol

Under the nitrogen gas atmosphere, lithium aluminum hydride (2.30 g, 61.0 mmol) was slowly added into tetrahydrofuran (60 mL) at 0° C., a solution of ethyl 1,4-dioxaspiro[4.5]decane-8-carboxylate (10.0 g, 42.0 mmol) in tetrahydrofuran (40 mL) was added dropwise. The reaction was slowly warmed to 25° C. and stirred for 3.5 hours. The reaction solution was cooled to 0° C. and water (2.3 g, 127 mmol), 15% sodium hydroxide (2.3 g, 8.60 mmol) and water (6.9 g, 383 mmol) were slowly added successively. The resulting mixture was filtered and the filter cake was washed with tetrahydrofuran (50 mL×3), the organic phases were combined, dried over anhydrous sodium sulfate, filtered and the filtrate was concentrated under reduced pressure to deliver the product 1,4-dioxaspiro[4.5]decan-8-ylmethanol (6.22 g, yellow liquid), yield: 89%. MS-ESI calcd. for [M+H]$^+$ 173, found 173.

Step 3

1,4-Dioxaspiro[4.5]decan-8-ylmethyl methanesulfonate 1,4-Dioxaspiro[4.5]decan-8-ylmethanol (2.00 g, 12.0 mmol) and diisopropylethylamine (3.10 g, 24.0 mmol) were dissolved in dichloromethane (40 mL), methanesulfonyl chloride (3.90 g, 30.0 mmol) was slowly added at 0° C. The reaction solution was warmed to 25° C. and stirred overnight. The reaction was quenched by the addition of a saturated ammonium chloride aqueous solution (100 mL) and extracted with ethyl acetate (200 mL×3). The organic phases were combined, dried over anhydrous magnesium sulfate and filtered, the filtrate was concentrated under reduced pressure and purified by silica gel column chromatography (3:1 petroleum ether/ethyl acetate, Rf=0.4) to deliver the product 1,4-dioxaspiro[4.5]decan-8-ylmethyl methanesulfonate (1.80 g, yellow liquid), yield: 60%. MS-ESI calcd. for [M+H]$^+$ 251, found 251.

Step 4

1-(1,4-Dioxaspiro[4.5]decan-8-ylmethyl)-3,7-dimethyl-1H-purine-2,6(3H,7H)-dione 1,4-Dioxaspiro[4.5]decan-8-ylmethyl methanesulfonate (1.50 g, 6.00 mmol), 3,7-dimethyl-1H-purine-2,6-(3H,7H)-dione (1.00 g, 6.00 mmol), potassium carbonate (2.50 g, 18.0 mmol), potassium iodide (100 mg, 0.600 mmol) were dissolved in N,N-dimethylformamide (20 mL), the reaction solution was heated to 130° C. and stirred for 3 hours. The reaction solution was cooled to 25° C., quenched with saturated brine (100 mL) and extracted with ethyl acetate (500 mL×3). The organic phases were combined, dried over anhydrous magnesium sulfate, filtered, the filtrate was concentrated under reduced pressure, and purified by silica gel column chromatography (1:1 petroleum ether/ethyl acetate, Rf=0.3) to deliver the product 1-(1,4-dioxaspiro[4.5]decan-8-ylmethyl)-3,7-dimethyl-1H-purine-2,6(3H,7H)-dione (1.75 g, white solid), yield: 63%. MS-ESI calcd. for [M+H]$^+$ 335, found 335.

Step 5

3,7-Dimethyl-1-((4-oxocyclohexyl)methyl)-1H-purine-2,6(3H,7H)-dione 1-(1,4-Dioxaspiro[4.5]decan-8-ylmethyl)-3,7-dimethyl-1H-purine-2,6(3H,7H)-dione (1.50 g, 4.50 mmol) was dissolved in acetone (15 mL), and hydrochloric acid aqueous solution (2 N, 2.5 mL) was added. The reaction was stirred overnight at 25° C., quenched by the addition of water (50 mL) and extracted with ethyl acetate (50 mL×3). The organic phases were combined, dried over anhydrous sodium sulfate, filtered and the filtrate was concentrated under reduced pressure and purified by silica gel column chromatography (1:3 petroleum ether/ethyl acetate, Rf=0.4) to deliver the product 3,7-dimethyl-1-((4-oxocyclohexyl)methyl)-1H-purine-2,6(3H,7H)-dione (1.02 g, white solid), yield: 78%. MS-ESI calcd. for [M+H]$^+$ 291, found 291.

Step 6

1-((4-Hydroxy-4-(trifluoromethyl)cyclohexyl)methyl)-3,7-dimethyl-1H-purine-2,6(3H,7H)-dione 3,7-Dimethyl-1-((4-oxocyclohexyl)methyl)-1H-purine-2,6(3H,7H)-dione (100 mg, 0.330 mmol) and cesium fluoride (60.0 mg, 0.350 mmol) were dissolved in tetrahydrofuran (5 mL), under the nitrogen gas atmosphere, trifluoromethyltrimethylsilane (75.0 mg, 0.500 mmol) was slowly added. The reaction solution was stirred at 30° C. for 3 hours. The reaction solution was cooled to 25° C., into which hydrochloric acid aqueous solution (4 N, 3 mL) was added, then stirred at 25° C. for half an hour, the pH value of the resulting mixture was adjusted to 7, and diluted with water and extracted with ethyl acetate (20 mL×3). The organic phases were combined, dried over anhydrous sodium sulfate, filtered, concentrated under reduced pressure, and the residue was purified by preparative high performance liquid chromatography to deliver the product 1-((4-hydroxy-4-(trifluoromethyl)cyclohexyl)methyl)-3,7-dimethyl-1H-purine-2,6(3H,7H)-di one (24.0 mg, white solid), yield: 39%.

$^1$H NMR: (400 MHz, Methanol-d$_4$) δ 7.86 (s, 1H), 4.04 (d, J=7.2 Hz, 1H), 3.97 (s, 3H), 3.89 (d, J=7.6 Hz, 1H), 3.53 (s, 3H), 2.06-1.97 (m, 2H), 1.88-1.77 (m, 3H), 1.62-1.43 (m, 4H). MS-ESI calcd. for [M+H]$^+$ 361, found 361.

Embodiment 12

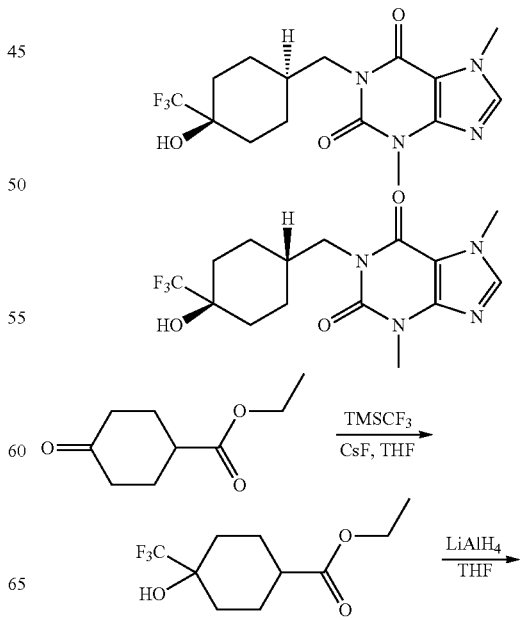

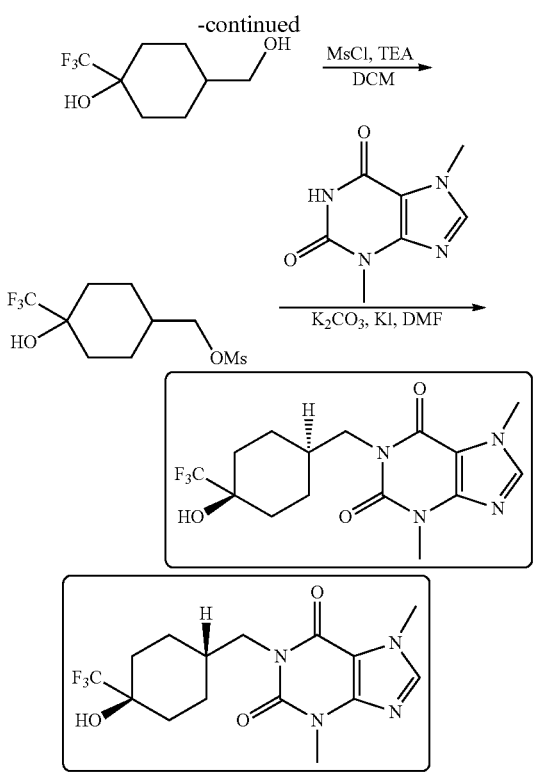

Step 1

Ethyl 4-hydroxy-4-(trifluoromethyl)cyclohexanecarboxylate

Ethyl 4-oxocyclohexanecarboxylate (10.0 g, 58.7 mmol) was dissolved in tetrahydrofuran (100 mL), trifluoromethyltrimethylsilane (12.5 g, 88.1 mmol) and cesium fluoride (8.92 g, 58.7 mmol) were added at room temperature. The reaction solution was stirred at room temperature for 12 hours, tetrabutylammonium fluoride (9.27 g, 29.4 mmol) was added, after stirring at room temperature for 30 minutes, ethyl acetate (80 mL) was added to dilute the reaction solution, the organic phase was washed with saturated sodium bicarbonate aqueous solution (50 mL×2), dried over anhydrous sodium sulfate, filtered and concentrated, the residue was isolated and purified by silica gel column chromatography (10:1 petroleum ether/ethyl acetate, Rf=0.5) to deliver ethyl 4-hydroxy-4-(trifluoromethyl)cyclohexanecarboxylate (12.0 g, colorless oil), yield: 85%. $^1$H NMR: (400 MHz, Methanol-$d_4$) δ 4.20-4.12 (m, 2H), 2.03-1.86 (m, 9H), 1.29-1.25 (m, 3H).
MS-ESI calcd. for [M+H]$^+$ 241, found 241.

Step 2

4-(Hydroxymethyl)-1-(trifluoromethyl)cyclohexanol

Ethyl 4-hydroxy-4-(trifluoromethyl)cyclohexanecarboxylate (12.00 g, 49.9 mmol) was dissolved in tetrahydrofuran (20 mL), lithium aluminum hydride (3.79 g, 100 mmol) was added at 0° C. and reacted for 2 hours. The reaction was quenched by the addition of water (30 mL). The resulting mixture was extracted with (50 mL×3), dried over anhydrous sodium sulfate, filtered and the filtrate was concentrated under reduced pressure, the residue was purified by silica gel column chromatography (1:1 petroleum ether/ethyl acetate, Rf=0.2) to deliver 4-(hydroxymethyl)-1-(trifluoromethyl)cyclohexanol (9.00 g, colorless oil), yield: 91%. $^1$H NMR: (400 MHz, Methanol-$d_4$) δ 3.58-3.40 (m, 2H), 1.90-1.40 (m, 9H).

Step 3

(4-Hydroxy-4-(trifluoromethyl)cyclohexyl)methyl methanesulfonate 4-(Hydroxymethyl)-1-(trifluoromethyl)cyclohexanol (11.0 g, 55.5 mmol) and triethylamine (1.18 g, 11.6 mmol) were dissolved in dichloromethane (80 mL) and methanesulfonyl chloride (14.4 g, 125 mmol) was added at 0° C. The reaction solution was stirred at room temperature for 2 hours, diluted with dichloromethane (60 mL), washed with saturated sodium bicarbonate aqueous solution (50 mL×2), dried over anhydrous sodium sulfate, filtered and the filtrate was concentrated under reduced pressure, the residue was isolated and purified by silica gel column chromatography (4:1 petroleum ether/ethyl acetate, Rf=0.5) to deliver (4-hydroxy-4-(trifluoromethyl)cyclohexyl)methyl methanesulfonate (13.00 g, colorless oil), yield: 85%. $^1$H NMR: (400 MHz, Methanol-$d_4$) δ 4.25-4.01 (m, 2H), 3.10-3.07 (m, 3H), 2.03-1.24 (m, 9H).

Step 4

1-(((1S,4S)-4-Hydroxy-4-(trifluoromethyl)cyclohexyl)methyl)-3,7-dimethyl-1H-purine-2,6(3H,7H)-dione (4-Hydroxy-4-(trifluoromethyl)cyclohexyl)methyl methanesulfonate (10.0 g, 36.2 mmol) was dissolved in N,N-dimethylformamide (100 mL), and 3,7-dimethyl-1H-purine-2,6(3H,7H)-dione (6.52 g, 36.2 mmol), potassium carbonate (7.50 g, 54.3 mmol) and potassium iodide (184 mg, 1.11 mmol) were added into the reaction solution at room temperature. The reaction solution was heated to 100° C. and reacted for 5 hours, the reaction solution was concentrated and diluted with ethyl acetate (100 mL), the organic phase was washed with saturated sodium bicarbonate aqueous solution (50 mL×2), dried over anhydrous sodium sulfate, filtered, the filtrate was concentrated under reduced pressure and separated by preparative SFC to deliver product 1 (2.5 g, white solid) (isomer 1, the first peak), yield: 19%. The separation conditions: column: Chiralpak AD-3 150×4.6 mm, I.D: 3 um, mobile phase: ethanol (0.05% diethylamine) in $CO_2$ from 5% to 40% at 2.5 mL/min, wavelength: 220 nm. $^1$H NMR: (400 MHz, Methanol-$d_4$) δ 7.88 (s, 1H), 4.02 (d, J=7.6 Hz, 2H), 3.98 (s, 3H), 3.53 (s, 3H), 2.16-2.02 (m, 1H), 1.99-1.98 (m, 2H), 1.87-1.80 (m, 2H), 1.60-1.49 (m, 2H), 1.48-1.46 (m, 2H). MS-ESI calcd. for [M+H]$^+$ 361, found 361.

Product 2 (2.40 g, white solid) (isomer 2, the second peak), yield: 19%. $^1$H NMR: (400 MHz, CDCl$_3$) δ7.88 (s, 1H), 3.99 (s, 3H), 3.90 (d, J=7.6 Hz, 2H), 3.54 (s, 3H), 1.84-1.81 (m, 3H), 1.58-1.46 (m, 6H). MS-ESI calcd. for [M+H]$^+$ 361, found 361.

Embodiment 13

1-((4-Hydroxy-4-methylcyclohexyl)methyl)-3,7-dimethyl-1H-purine-2,6(3H,7H)-dione

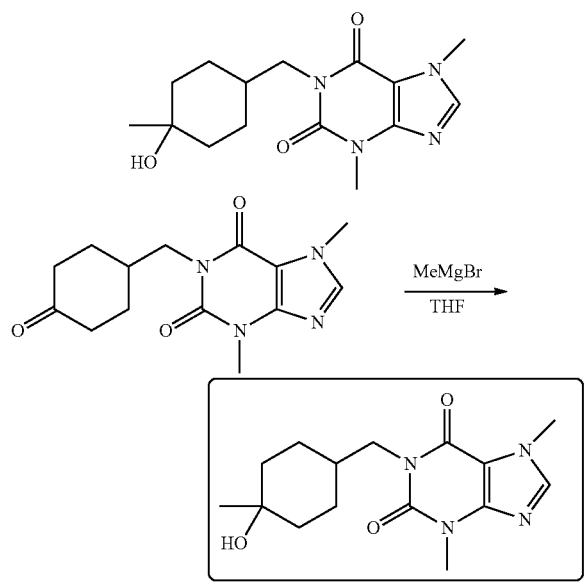

3,7-Dimethyl-1-((4-oxocyclohexyl)methyl)-1H-purine-2,6(3H,7H)-dione (50.0 mg, 0.170 mmol) was dissolved in tetrahydrofuran (2 mL). Under the nitrogen gas atmosphere, methyl Grignard reagent (3 M ether solvent, 0.4 mL, 1.20 mmol) was slowly added at −78° C. The reaction solution was stirred at −78° C. for 0.5 hour and slowly warmed to 0° C. and stirred for a further 0.5 hour. The reaction was quenched by the addition of a saturated ammonium chloride aqueous solution, the pH value of which was adjusted to 7. The resulting mixture was extracted with ethyl acetate, dried over anhydrous sodium sulfate and filtered. The filtrate was concentrated under reduced pressure and purified by preparative high performance liquid chromatography to deliver the product 1-((4-hydroxy-4-methylcyclohexyl)methyl)-3,7-dimethyl-1H-purine-2,6(3H,7H)-dione (8.0 mg, white solid), yield: 16%. $^1$H NMR: (400 MHz, Methanol-$d_4$) δ 7.86 (s, 1H), 3.97 (s, 3H), 3.88 (d, J=7.6 Hz, 2H), 3.52 (s, 3H), 1.85-1.78 (m, 1H), 1.73-1.57 (m, 3H), 1.46-1.33 (m, 2H), 1.32-1.15 (m, 6H). MS-ESI calcd. for [M+H−H$_2$O]$^+$ 289, found 289.

Embodiment 14

1-((4-Ethyl-4-hydroxycyclohexyl)methyl)-3,7-dimethyl-1H-purine-2,6(3H,7H)-dione

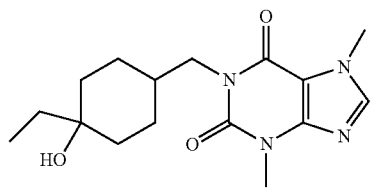

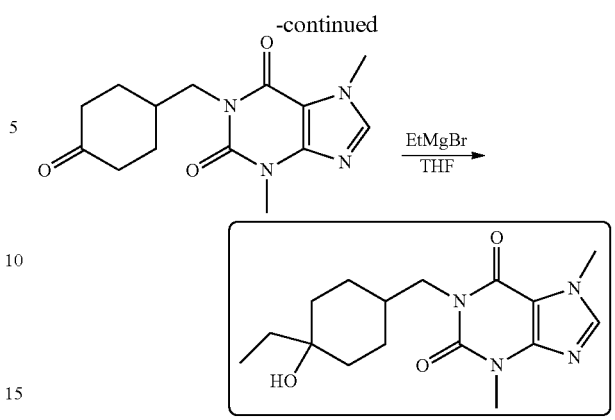

3,7-Dimethyl-1-((4-oxocyclohexyl)methyl)-1H-purine-2,6(3H,7H)-dione (50.0 mg, 0.170 mmol) was dissolved in tetrahydrofuran (2 mL). Under the nitrogen gas atmosphere, ethyl Grignard reagent (3 M in ether solvent, 0.4 mL, 1.20 mmol) was slowly added at −78° C. The reaction solution was stirred at −78° C. for 0.5 hour and slowly warmed to 0° C. and stirred for a further 0.5 hour. The reaction was quenched by the addition of a saturated ammonium chloride aqueous solution, the pH value of which was adjusted to 7. Then the resulting mixture was extracted with ethyl acetate, dried over anhydrous sodium sulfate and filtered. The filtrate was concentrated under reduced pressure and purified by preparative high performance liquid chromatography to deliver the product 1-((4-ethyl-4-hydroxycyclohexyl)methyl)-3,7-dimethyl-1H-purine-2,6(3H,7H)-dione (42.0 mg, white solid), yield: 77%. $^1$H NMR: (400 MHz, Methanol-$d_4$) δ 7.86 (s, 1H), 3.97 (s, 3H), 3.88 (d, J=7.6 Hz, 2H), 3.54-3.50 (m, 3H), 1.93-1.80 (m, 1H), 1.76-1.72 (m, 2H), 1.66-1.51 (m, 3H), 1.38-1.28 (m, 3H), 1.27-1.13 (m, 2H), 0.89 (t, J=7.2 Hz, 3H). MS-ESI calcd. for [M+H−H$_2$O]$^+$ 303, found 303.

Embodiment 15

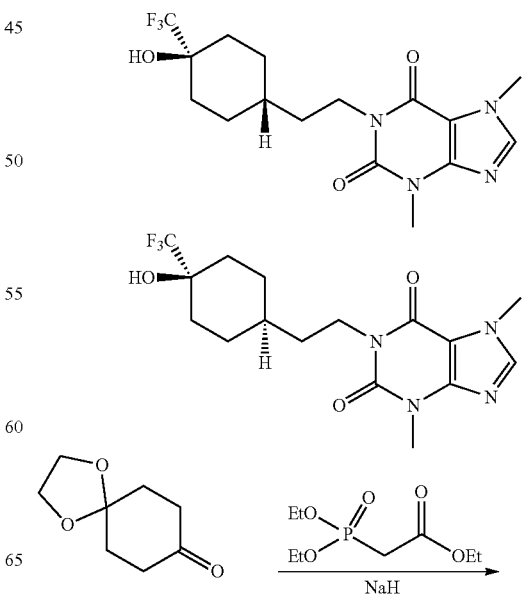

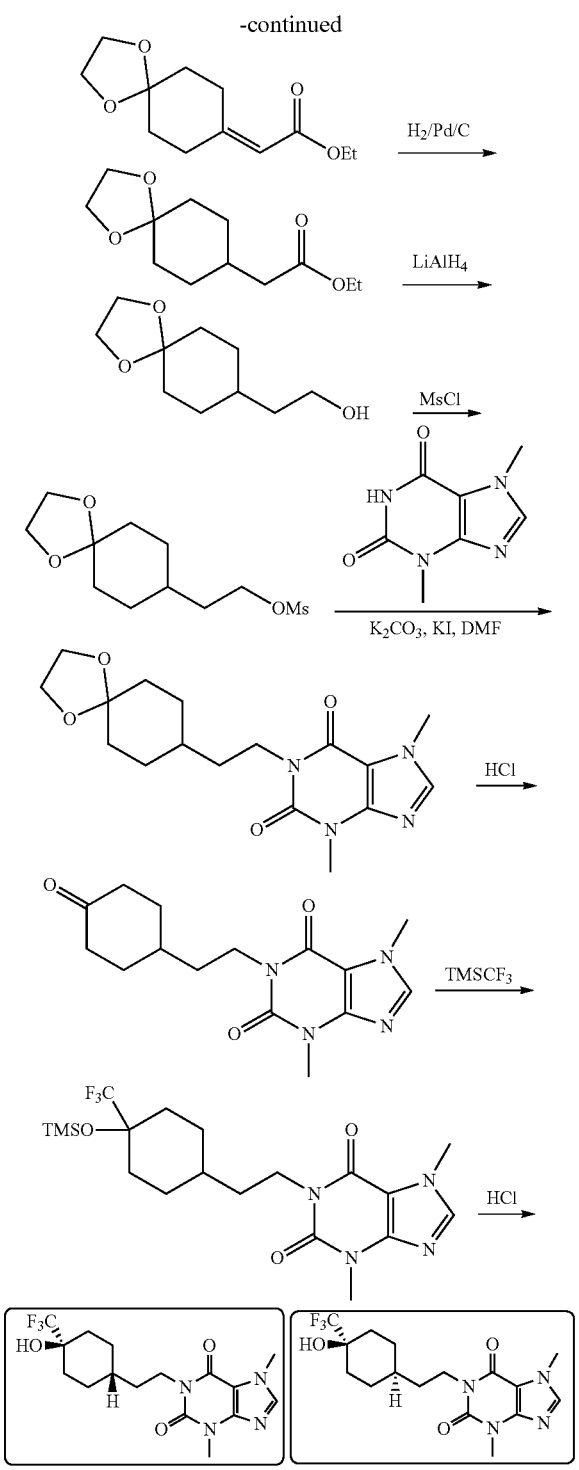

Step 1

Ethyl 2-(1,4-dioxaspiro[4.5]decan-8-ylidene) acetate

Triethyl phosphonoacetate (12.2 g, 54.4 mmol) was dissolved in tetrahydrofuran (100 mL), sodium hydride (1.92 g, 48.0 mmol) was added in portions at 0° C., the reaction was stirred under the nitrogen gas atmosphere for 30 minutes. A solution of 1,4-cyclohexanedione monoethylene acetal (5.00 g, 32.0 mmol) dissolved in tetrahydrofuran (15 mL) was added dropwise to the reaction solution at 0° C., and the reaction was stirred at 25° C. for 3 hours. The reaction was quenched by the addition of water (25 mL) and extracted with dichloromethane (20 mL×3). The organic phases were combined, washed with saturated brine (20 mL), dried over anhydrous sodium sulfate and concentrated under reduced pressure, the residue was purified by silica gel column chromatography (5:1 petroleum ether/ethyl acetate, Rf=0.3) to deliver ethyl 2-(1,4-dioxaspiro[4.5]decan-8-ylidene)acetate (6.30 g, colorless oil), yield: 93%. $^1$H NMR: (400 MHz, CDCl$_3$) δ 5.67 (s, 1H), 4.15 (q, J=7.2 Hz, 2H), 3.98 (s, 4H), 3.00 (t, J=6.4 Hz, 2H), 2.38 (t, J=6.4 Hz, 2H), 1.84-1.68 (m, 4H), 1.28 (t, J=7.2 Hz, 3H). MS-ESI calcd. for [M+H]$^+$ 227, found 227.

Step 2

Ethyl 2-(1,4-dioxaspiro[4.5]decan-8-yl)acetate

Eethyl 2-(1,4-dioxaspiro[4.5]decan-8-ylidene)acetate (3.80 g, 17.9 mmol) was dissolved in methanol (50 mL), dry palladium on carbon (palladium 10%, water 1%, 400 mg) was added, the reaction was reacted under hydrogen gas atmosphere (50 psi) for 18 hours at room temperature. The reaction solution was filtered and the filtrate was concentrated under reduced pressure to deliver ethyl 2-(1,4-dioxaspiro[4.5]decan-8-yl)acetate (3.50 g, colorless oil), yield: 91%.

$^1$H-NMR: (400 MHz, CDCl$_3$) δ 4.12 (q, J=7.2 Hz, 2H), 3.93 (s, 4H), 2.22 (d, J=7.2 Hz, 2H), 1.90-1.64 (m, 5H), 1.63-1.48 (m, 2H), 1.40-1.16 (m, 5H). MS-ESI calcd. for [M+H]$^+$ 229, found 229.

Step 3

2-(1,4-Dioxaspiro[4.5]decan-8-yl)ethanol

Ethyl 2-(1,4-dioxaspiro[4.5]decan-8-yl)acetate (1.00 g, 4.38 mmol) was dissolved in tetrahydrofuran (20 mL), lithium aluminum hydride (216 mg, 5.69 mmol) was added in portions at 0° C. and stirred for 18 hours under the nitrogen gas atmosphere. The reaction solution was cooled to 0° C., water (0.2 mL), 15% sodium hydroxide aqueous solution (0.2 mL) and water (0.6 mL) were slowly added successively. The reaction mixture was filtered and the filtrate was concentrated under reduced pressure to deliver the product 2-(1,4-dioxaspiro[4.5]decan-8-yl)ethanol (780 mg, yellow oil), yield: 96%.

$^1$H NMR: (400 MHz, CDCl$_3$) δ 3.94 (s, 4H), 3.69 (t, J=6.4 Hz, 2H), 1.79-1.65 (m, 4H), 1.59-1.38 (m, 5H), 1.34-1.17 (m, 2H). MS-ESI calcd. for [M+H]$^+$ 187, found 187.

Step 4

2-(1,4-Dioxaspiro[4.5]decan-8-yl)ethyl methanesulfonate 2-(1,4-Dioxaspiro[4.5]decan-8-yl)ethanol (400 mg, 2.15 mmol) and triethylamine (435 mg, 4.30 mmol) were dissolved in dichloromethane (10 mL), methanesulfonyl chloride (369 mg, 3.23 mmol) was slowly added at 0° C. The reaction solution was stirred at 0° C. for 4 hours. The reaction was quenched by the addition of water (10 mL) and extracted with dichloromethane (30 mL×2). The organic phases were combined, washed with saturated sodium bicarbonate aqueous solution (50 mL), dried over anhydrous sodium sulfate, filtered and the filtrate was concentrated under reduced pressure to deliver 2-(1,4-dioxaspiro[4.5]decan-8-yl) ethyl methanesulfonate (500 mg crude, yellow oil).

¹H NMR: (400 MHz, CDCl₃) δ 4.28 (t, J=6.4 Hz, 2H), 3.94 (s, 4H), 3.01 (s, 3H), 1.76-1.63 (m, 6H), 1.60-1.43 (m, 3H), 1.37-1.21 (m, 2H). MS-ESI calcd. for [M+H]⁺ 265, found 265.

Step 5

1-(2-(1,4-Dioxaspiro[4.5]decan-8-yl)ethyl)-3,7-dimethyl-1H-purine-2,6(3H,7H)-dione 3,7-Dimethyl-1H-purine-2,6-(3H,7H)-dione (204 mg, 1.13 mmol) was dissolved in N,N-dimethylformamide (15 mL), 2-(1,4-dioxaspiro[4.5]decan-8-yl)ethyl methanesulfonate (300 mg, 1.13 mmol), potassium carbonate (312 mg, 2.26 mmol) and potassium iodide (225 mg, 1.36 mmol) were added. The reaction solution was heated to 120° C. and stirred for 3 hours. The reaction mixture was concentrated under reduced pressure, and the residue was purified by silica gel column chromatography (1:1 petroleum ether/ethyl acetate, Rf=0.2) to deliver 1-(2-(1,4-dioxaspiro[4.5]decan-8-yl)ethyl)-3,7-dimethyl-1H-purine-2,6(3H,7H)-dione (190 mg, white solid), yield: 48%.

¹H NMR: (400 MHz, CDCl₃) δ 7.50 (s, 1H), 4.09-4.03 (m, 2H), 4.02 (s, 3H), 3.99 (s, 4H), 3.57 (s, 1H), 1.90-1.70 (m, 5H), 1.68-1.47 (m, 6H), 1.45-1.31 (m, 2H). MS-ESI calcd. for [M+H]⁺ 349, found 349.

Step 6

3,7-Dimethyl-1-(2-(4-oxocyclohexyl)ethyl)-1H-purine-2,6(3H,7H)-dione 1-(2-(1,4-Dioxaspiro[4.5]decan-8-yl)ethyl)-3,7-dimethyl-1H-purine-2,6(3H,7H)-dione (190 mg, 545 μmol) was dissolved in tetrahydrofuran (3 mL) and conc. hydrochloric acid (1 mL) was added. The reaction solution was stirred at room temperature for 18 hours. The reaction solution was concentrated under reduced pressure and the pH value of the aqueous phase was neutralized to 7 with saturated sodium bicarbonate aqueous solution and extracted with ethyl acetate (20 mL×2). The organic phases were combined, washed with saturated brine (10 mL), dried over anhydrous sodium sulfate, filtered, concentrated under reduced pressure, and the residue was purified by silica gel column chromatography (ethyl acetate, Rf=0.3) to deliver 3,7-dimethyl-1-(2-(4-oxocyclohexyl)ethyl)-1H-purine-2,6(3H,7H)-dione (150 mg, colorless oil), yield: 90%.

MS-ESI calcd. for [M+H]⁺ 305, found 305.

Step 7

3,7-Dimethyl-1-(2-(4-(trifluoromethyl)-4-((trimethylsilyl)oxy)cyclohexyl)ethyl)-1-purine-2,6 (3H,7H)-dione 3,7-Dimethyl-1-(2-(4-oxocyclohexyl)ethyl)purine-2,6-dione (145 mg, 0.476 mmol) and cesium fluoride (7.2 mg, 0.0476 mmol) were dissolved in tetrahydrofuran (10 mL), trifluoromethyltrimethylsilane (203 mg, 1.43 mmol) was slowly added under the nitrogen gas atmosphere. The reaction solution was stirred at 25° C. for 18 hours. The reaction solution was diluted with water (20 mL) and extracted with ethyl acetate (15 mL×2). The organic phases were combined, washed with saturated brine (10 mL), dried over anhydrous sodium sulfate, filtered, the filtrate was concentrated under reduced pressure to deliver 3,7-dimethyl-1-(2-(4-(trifluoromethyl)-4-((trimethylsilyl)oxy)cyclohexyl)ethyl)-1-purine-2,6(3H,7H)-dione (170 mg, colorless liquid), yield: 80%.

MS-ESI calcd. for [M+H]⁺ 447, found 447.

Step 8

3,7-Dimethyl-1-[2-[4-(trifluoromethyl)-4-trimethylsilyloxy-cyclohexyl]ethyl]purine-2,6-dione (160 mg, 0.358 mmol) was dissolved in tetrahydrofuran (3 mL) and conc. hydrochloric acid (12 M, 0.107 mL) was added. The reaction solution was stirred at 25° C. for 18 hours. The reaction mixture was diluted with water, the pH value of which was adjusted to 7 with a saturated sodium bicarbonate aqueous solution (10 mL), extracted with ethyl acetate (10 mL×2). The organic phases were combined, dried over anhydrous sodium sulfate, filtered, concentrated under reduced pressure and the residue was purified by preparative high performance liquid chromatography to deliver product 1 (40.0 mg, white solid) (isomer 1, the first peak), yield: 27%. ¹H NMR: (400 MHz, CDCl₃) δ 8.01 (s, 1H), 4.09-3.94 (m, 5H), 3.53 (s, 3H), 1.97-1.79 (m, 4H), 1.76-1.62 (m, 3H), 1.61-1.45 (m, 4H). MS-ESI calcd. for [M+H]⁺ 375, found 375.

And product 2 (15.0 mg, white solid) (isomer 2, the second peak), yield: 10%. ¹H-NMR: (400 MHz, CDCl₃) δ 8.01 (s, 1H), 4.09-3.95 (m, 5H), 3.53 (s, 3H), 1.87-1.68 (m, 4H), 1.64-1.48 (m, 4H), 1.46-1.25 (m, 3H). MS-ESI calcd. for [M+H]⁺ 375, found 375.

Embodiment 16

1-((4-Hydroxy-1-methyl-4-(trifluoromethyl)cyclohexyl)methyl)-3,7-dimethyl-1H-purine-2,6(3H,7H)-dione

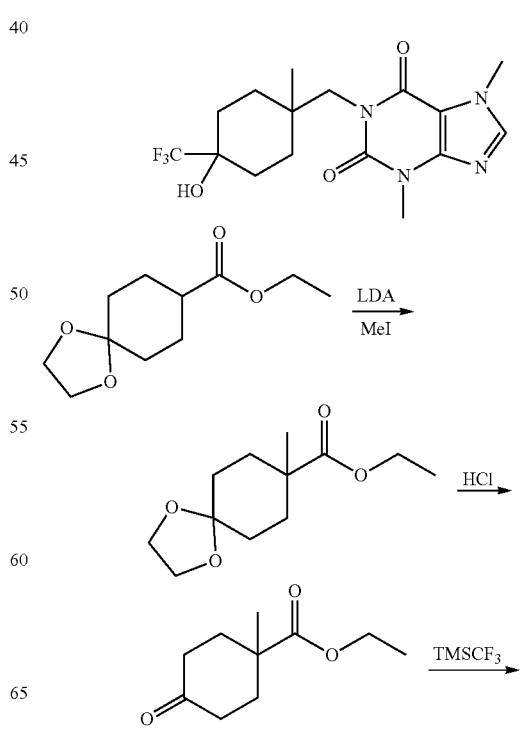

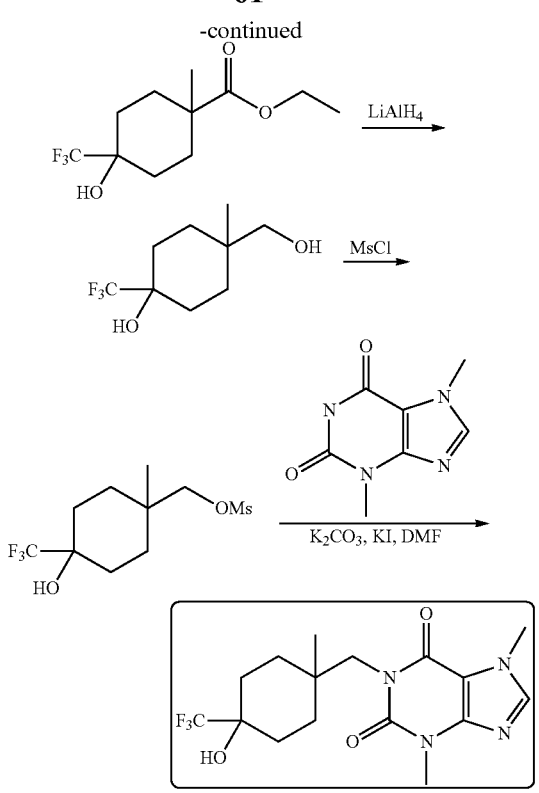

Step 1

Ethyl-8-methyl-1,4-dioxaspiro[4.5]decane-8-carboxylate

Ethyl 1,4-dioxaspiro[4.5]decane-8-carboxylic acid ethyl ester (5.00 g, 23.3 mmol) was dissolved in anhydrous tetrahydrofuran (100 mL), under the nitrogen gas atmosphere, a solution of lithium diisopropylamide (2 M tetrahydrofuran solution, 14.0 mL, 28.0 mmol) was slowly added dropwise at −78° C., the reaction solution was stirred at −78° C. for 1 hour. Iodomethane (6.62 g, 46.7 mmol) was slowly added and the reaction mixture was stirred for a further 1 hour. The reaction was quenched by the addition of water (100 mL). The reaction mixture was extracted with ethyl acetate (100 mL×3) and the organic phases were combined, dried over anhydrous sodium sulfate, filtered and the filtrate was concentrated under reduced pressure, the residue was purified by silica gel column chromatography (10:1 petroleum ether/ethyl acetate, Rf=0.4) to deliver ethyl-8-methyl-1,4-dioxaspiro[4.5]decane-8-carboxylate (5.00 g, yellow oil), yield: 94%.

$^1$H NMR: (400 MHz, Methanol-$d_4$) δ 4.16-4.10 (m, 2H), 3.93-3.86 (m, 4H), 2.13-2.06 (m, 2H), 1.61-1.48 (m, 6H), 1.25-1.22 (m, 3H), 1.15 (s, 3H).

Step 2

Ethyl-1-methyl-4-oxocyclohexanecarboxylate

Ethyl-8-methyl-1,4-dioxaspiro[4.5]decane-8-carboxylate (5.00 g, 21.9 mmol) was dissolved in tetrahydrofuran (50 mL), and 1 N hydrochloric acid aqueous solution (20 mL) was added dropwise at 0° C., and then stirred at 20° C. for 1 hour. The mixture was cooled to 0° C. and the reaction was quenched by the addition of a sodium bicarbonate aqueous solution (50 mL). The mixture was extracted with ethyl acetate (100 mL×3). The organic phase was washed with saturated brine (100 mL×3), dried over anhydrous sodium sulfate and concentrated under reduced pressure. The residue was purified by silica gel column chromatography (10:1 petroleum ether/ethyl acetate, Rf=0.4) to deliver ethyl-1-methyl-4-oxocyclohexanecarboxylate (3.00 g, colorless oil), yield 74%. $^1$H NMR: (400 MHz, Methanol-$d_4$) δ 4.26-4.11 (m, 2H), 2.46-2.29 (m, 5H), 1.74-1.55 (m, 3H), 1.33-1.26 (m, 6H).

Step 3

Ethyl 4-hydroxy-1-methyl-4-(trifluoromethyl) cyclohexanecarboxylate

Ethyl-1-methyl-4-oxocyclohexanecarboxylate (3.00 g, 16.3 mmol), cesium fluoride (247 mg, 1.63 mmol) was dissolved in tetrahydrofuran (50 mL) and then trifluoromethyltrimethylsilane (4.63 g, 35.3 mmol) was added at 0° C. Under the nitrogen gas atmosphere, the reaction solution was reacted at 20° C. for 6 hours. Then 4 N hydrochloric acid aqueous solution (4 mL) was added. Under the nitrogen gas atmosphere, the mixture was reacted at room temperature for 6 hours. The reaction was quenched with saturated sodium bicarbonate aqueous solution (30 mL) and extracted with ethyl acetate (100 mL×3), the organic phase was dried over anhydrous sodium sulfate and filtered, the filtrate was concentrated under reduced pressure and the residue was purified by silica gel column chromatography (10:1 petroleum ether/ethyl acetate, Rf=0.3) to deliver ethyl 4-hydroxy-1-methyl-4-(trifluoromethyl)cyclohexanecarboxylate (3.00 g, colorless oil), yield: 73%. $^1$H NMR: (400 MHz, Methanol-$d_4$) δ 4.20-4.12 (m, 2H), 2.03-1.31 (m, 8H), 1.29-1.23 (m, 6H).

Step 4

4-(Hydroxymethyl)-4-methyl-1-(trifluoromethyl) cyclohexanol

Ethyl-4-hydroxy-1-methyl-4-(trifluoromethyl)cyclohexanecarboxylate (3.00 g, 11.8 mmol) was dissolved in anhydrous tetrahydrofuran (50 mL), lithium aluminium hydride (896 mg, 23.6 mmol) was added at 0° C. The reaction solution was warmed to 25° C. and stirred for 1 hour. The reaction was quenched by the addition of water (20 mL), extracted with ethyl acetate (50 mL×3), dried over anhydrous sodium sulfate, filtered, the filtrate was concentrated under reduced pressure and the residue was purified by silica gel column chromatography (3:1 petroleum ether/ethyl acetate, Rf=0.2) to deliver 4-(hydroxymethyl)-4-methyl-1-(trifluoromethyl)cyclohexanol (2.00 g, colorless oil), yield: 80%. $^1$H NMR: (400 MHz, Methanol-$d_4$) δ 3.25 (s, 2H), 1.76-1.64 (m, 6H), 1.29-1.26 (m, 2H), 0.93-0.91 (m, 3H).

Step 5

(4-Hydroxy-1-methyl-4-(trifluoromethyl)cyclohexyl) methyl methanesulfonate 4-(Hydroxymethyl)-4-methyl-1-(trifluoromethyl)cyclohexanol (2.00 g, 9.42 mmol) was dissolved in dichloromethane (30 mL), triethylamine (953 mg, 9.42 mmol) and methanesulfonyl chloride (1.08 g, 9.42 mmol) were added at 0° C. The reaction solution was reacted at 0° C. for 2 hours. The reaction was quenched by the addition of a saturated sodium bicarbonate aqueous solution (10 mL), extracted with dichloromethane (50 mL×3), the organic phases were combined, dried over anhydrous sodium sulfate, filtered and the filtrate was concentrated under reduced pressure to deliver (4-hydroxy-1-methyl-4-(trifluoromethyl)cyclohexyl)methyl methanesulfonate (2.00 g, yellow oil), yield 73%.

Step 6

1-((4-Hydroxy-1-methyl-4-(trifluoromethyl)cyclohexyl)methyl)-3,7-dimethyl-TH-purine-2,6(3H,7H)-dione (4-Hydroxy-1-methyl-4-(trifluoromethyl)cyclohexyl) methyl methanesulfonate (100 mg, 0.344 mmol), 3,7-dimethyl-1H-purine-2,6(3H,7H)-dione (62.1 mg, 0.344 mmol), potassium iodide (5.70 mg, 0.0344 mmol) and potassium carbonate (47.6 mg, 0.344 mmol) were dissolved in anhydrous N,N-dimethylformamide (5 mL). The reaction solution was heated to 150° C. by microwave and reacted for 4 hours. The reaction solution was cooled to 20° C., filtered, purified by preparative high performance liquid chromatography to deliver 1-((4-hydroxy-1-methyl-4-(trifluoromethyl) cyclohexyl)methyl)-3,7-dimethyl-1H-purine-2,6(3H,7H)-dione (3.0 mg, white solid), yield: 2%. $^1$H NMR: (400 MHz, Methanol-$d_4$) δ 7.88 (s, 1H), 3.98 (s, 3H), 3.96 (s, 2H), 3.54 (s, 3H), 1.81-1.64 (m, 6H), 1.63-1.34 (m, 2H), 1.00 (s, 3H). MS-ESI calcd. for [M+H]$^+$ 375, found 375.

Embodiment 17

1-((4-Hydroxy-1-methyl-4-(trifluoromethyl)cyclohexyl)methyl)-3,7-dimethyl-1H-purine-2,6(3H,7H)-dione

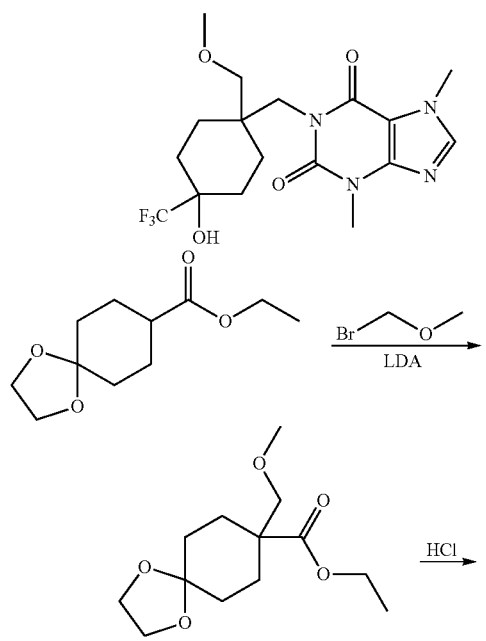

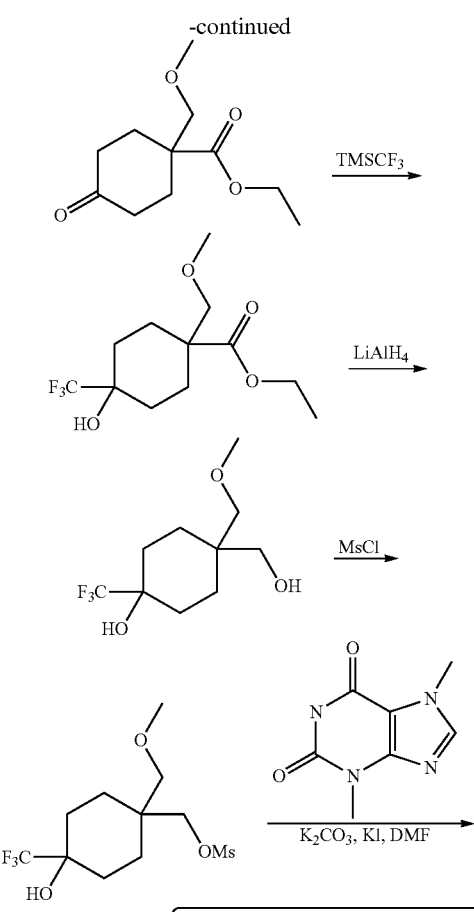

Step 1

Ethyl 8-(methoxymethyl)-1,4-dioxaspiro[4.5]decane-8-carboxylate

Ethyl 1,4-dioxaspiro[4.5]decane-8-carboxylate (5.00 g, 23.3 mmol) was dissolved in anhydrous tetrahydrofuran (100 mL), under the nitrogen gas atmosphere, a solution of lithium diisopropylamide (2 M n-hexane solution, 14.0 mL, 28.0 mmol) was slowly added dropwise at −78° C., and the reaction was stirred at −78° C. for 1 hour. Methoxybromomethane (5.83 g, 46.7 mmol) was slowly added and the reaction mixture was stirred for a further 1 hour. The reaction was quenched by the addition of water (100 mL). The reaction mixture was extracted with ethyl acetate (100 mL×3) and the organic phases were combined, dried over anhydrous sodium sulfate, filtered and the filtrate was concentrated under reduced pressure, the residue was purified by silica gel column chromatography (10:1 petroleum ether/ ethyl acetate, Rf=0.3) to deliver ethyl 8-(methoxymethyl)-1,4-dioxaspiro[4.5]decane-8-carboxylate (5.00 g, yellow oil), yield: 83%. ¹H NMR: (400 MHz, Methanol-d₄) δ 4.18 (q, J=6.8 Hz, 2H), 3.94 (s, 4H), 3.55 (s, 2H), 3.33 (s, 3H), 2.14-2.12 (m, 2H), 1.65-1.57 (m, 6H), 1.26 (t, J=6.8 Hz, 3H).

Step 2

Ethyl 1-(methoxymethyl)-4-oxocyclohexanecarboxylate

Ethyl 8-(methoxymethyl)-1,4-dioxaspiro[4.5]decane-8-carboxylate (5.00 g, 19.4 mmol) was dissolved in tetrahydrofuran (50 mL), 1 N dilute hydrochloric acid (10 mL) was added dropwise at 0° C. and stirred at 20° C. for 1 hour. The mixture was cooled to 0° C. and quenched by the addition of a sodium bicarbonate aqueous solution (50 mL). The mixture was extracted with ethyl acetate (100 mL×3). The organic phase was washed with saturated brine (100 mL×3), dried over anhydrous sodium sulfate and concentrated under reduced pressure. The residue was purified by silica gel column chromatography (10:1 petroleum ether/ethyl acetate, Rf=0.4) to deliver ethyl 1-(methoxymethyl)-4-oxo-cyclohexanecarboxylate (3.00 g, white oil), yield: 73%. ¹H NMR: (400 MHz, Methanol-d₄) δ 4.25 (q, J=6.8 Hz, 2H), 3.52 (s, 2H), 3.34 (s, 3H), 2.52-2.30 (m, 6H), 1.82-1.78 (m, 2H), 1.30 (t, J=6.8 Hz, 3H).

Step 3

Ethyl 4-hydroxy-1-(methoxymethyl)-4-(trifluoromethyl)cyclohexanecarboxylate

Ethyl 1-(methoxymethyl)-4-oxocyclohexanecarboxylate (3.00 g, 14.0 mmol), cesium fluoride (243 mg, 1.40 mmol) was dissolved in tetrahydrofuran (50 mL) and then trifluoromethyltrimethylsilane (3.98 g, 28.0 mmol) was added at 0° C. Under the nitrogen gas atmosphere, the reaction solution was reacted at 20° C. for 6 hours. Then 4 N dilute hydrochloric acid (7 mL) was added. Under the nitrogen gas atmosphere, the mixture was reacted at room temperature for 6 hours. The reaction was quenched with saturated sodium bicarbonate aqueous solution (30 mL) and extracted with ethyl acetate (100 mL×3), the organic phase was dried over anhydrous sodium sulfate and filtered, the filtrate was concentrated under reduced pressure and purified by silica gel column chromatography (10:1 petroleum ether/ethyl acetate, Rf=0.4) to deliver ethyl 4-hydroxy-1-(methoxymethyl)-4-(trifluoromethyl) cyclohexanecarboxylate (1.7 g, colorless oil), yield: 43%. ¹H NMR: (400 MHz, Methanol-d₄) 4.18-4.09 (m, 2H), 3.61 (s, 2H), 3.33 (s, 3H), 1.84-1.71 (m, 8H), 1.28-1.25 (m, 3H).

Step 4

4-(Hydroxymethyl)-4-(methoxymethyl)-1-(trifluoromethyl)cyclohexanol

Ethyl 4-hydroxy-1-(methoxymethyl)-4-(trifluoromethyl) cyclohexane carboxylate (1.50 g, 5.28 mmol) was dissolved in anhydrous tetrahydrofuran (50 mL), lithium aluminum hydride (220 mg, 5.81 mmol) was added at 0° C. The reaction solution was heated to 25° C. and stirred for 1 hour. The reaction was quenched by the addition of water (20 mL), extracted with ethyl acetate (50 mL×3), dried over anhydrous sodium sulfate, filtered, the filtrate was concentrated under reduced pressure, and the residue was purified by silica gel column chromatography (1:1 petroleum ether/ ethyl acetate, Rf=0.2) to deliver 4-(hydroxymethyl)-4-(methoxymethyl)-1-(trifluoromethyl) cyclohexanol (1.20 g, colorless oil), yield: 84%. ¹H NMR: (400 MHz, Methanol-d₄) δ 3.33-3.32 (m, 7H), 1.67-1.63 (m, 4H), 1.52-1.48 (m, 4H).

Step 5

(4-Hydroxy-1-methyl-4-(trifluoromethyl)cyclohexyl) methyl methanesulfonate 4-(Hydroxymethyl)-4-(methoxymethyl)-1-(trifluoromethyl)cyclohexanol (1.20 g, 4.95 mmol) was dissolved in dichloromethane (20 mL), triethylamine (851 mg, 9.91 mmol) and methanesulfonyl chloride (851 mg, 7.43 mmol) were added at 0° C. The reaction solution was reacted at 0° C. for 2 hours. The reaction was quenched by the addition of the saturated sodium bicarbonate aqueous solution (10 mL), extracted with dichloromethane (50 mL×3), the organic phases were combined, washed with saturated sodium chloride solution (50 mL×3), dried over anhydrous sodium sulfate, filtered and the filtrate was concentrated under reduced pressure to deliver (4-hydroxy-1-methyl-4-(trifluoromethyl)cyclohexyl)methyl methanesulfonate (1.30 g, yellow oil), yield: 92%.

Step 6

1-((4-Hydroxy-1-methyl-4-(trifluoromethyl)cyclohexyl)methyl)-3,7-dimethyl-1H-purine-2,6(3H,7H)-dione (4-Hydroxy-1-methyl-4-(trifluoromethyl)cyclohexyl) methyl methanesulfonate (300 mg, 1.05 mmol), 3,7-dimethyl-1H-purine-2,6(3H,7H)-dione (189 mg, 1.05 mmol), potassium iodide (17.4 mg, 0.105 mmol) and potassium carbonate (435 mg, 3.15 mmol) were dissolved in anhydrous N,N-dimethylformamide (5 mL). The reaction solution was heated to 150° C. by microwave and reacted for 2 hours. The reaction solution was cooled to 20° C., filtered, purified by preparative high performance liquid chromatography to deliver 1-((4-hydroxy-1-methyl-4-(trifluoromethyl)cyclohexyl)methyl)-3,7-dimethyl-1H-purine-2,6(3H,7H)-dione (12.0 mg, white solid), yield: 3%. ¹H NMR: (400 MHz, Methanol-d₄) δ 7.87 (s, 1H), 4.06 (s, 2H), 3.83 (s, 3H), 3.98 (s, 3H), 3.53 (s, 2H), 3.42 (s, 3H), 1.69-1.58 (m, 8H). MS-ESI calcd. for [M+H]⁺ 405, found 405.

Embodiment 18

1-((4-(3-Hydroxypentan-3-yl)-cyclohexyl)methyl)-3, 7-dimethyl-1H-purine-2,6(3H,7H)-dione

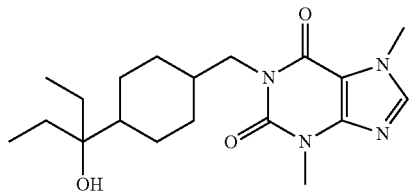

-continued

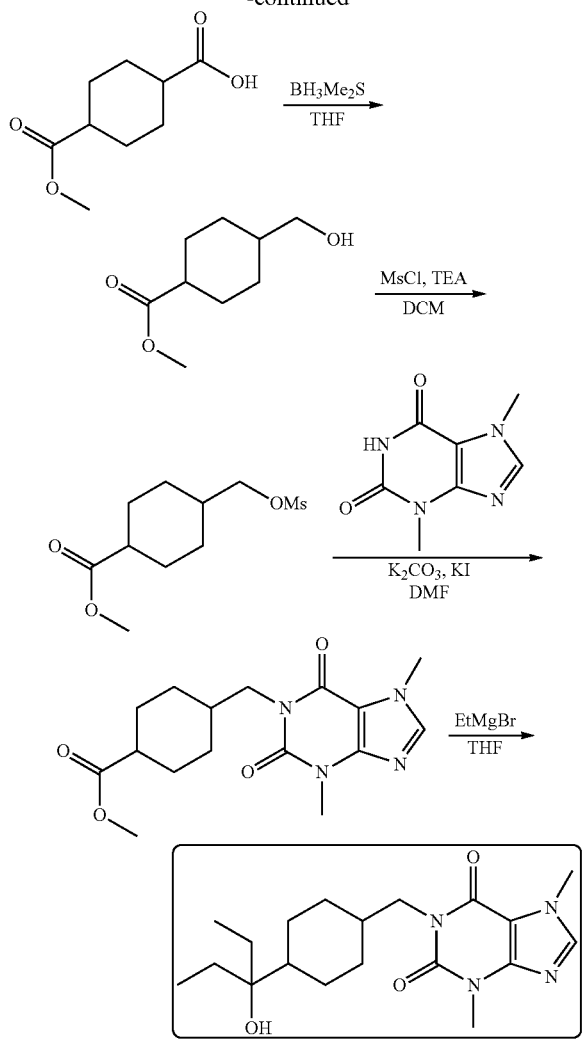

Step 1

Methyl 4-(hydroxymethyl)cyclohexane carboxylate 4-(Methoxycarbonyl)cyclohexanecarboxylic acid (1.20 g, 6.45 mmol) was dissolved in anhydrous tetrahydrofuran (20 mL), under the nitrogen gas atmosphere borane dimethyl sulfide (10 M, 1.0 mL, 10.3 mmol) was slowly added dropwise at 0° C., the reaction solution was stirred at 0° C. for 0.5 hour, slowly warmed to 25° C. and then stirred for a further 1 hour. The reaction was quenched by the addition of water (40 mL) and the reaction solution was extracted with ethyl acetate. The organic phases were combined, washed successively with water and saturated sodium chloride aqueous solution, dried over anhydrous magnesium sulfate, filtered and the filtrate was concentrated under reduced pressure to deliver methyl 4-(hydroxymethyl) cyclohexanecarboxylate (1.00 g, white solid), yield: 91%. $^1$H NMR: (400 MHz, CDCl$_3$) δ 3.67 (s, 3H), 3.48-3.46 (m, 2H), 2.26-2.25 (m, 1H), 2.05-2.01 (m, 2H), 1.89-1.85 (m, 2H), 1.47-1.43 (m, 2H), 1.31 (s, 1H), 1.01-0.98 (m, 2H). MS-ESI calcd. for [M+H]$^+$ 173, found 173.

Step 2

Methyl 4-(((methylsulfonyl)oxy)methyl)cyclohexanecarboxylate

Methyl 4-(hydroxymethyl)cyclohexanecarboxylate (900 mg, 5.20 mmol) and triethylamine (1.58 g, 15.6 mmol) were dissolved in anhydrous dichloromethane (5 mL), under the nitrogen gas atmosphere, methanesulfonyl chloride (720 mg, 6.30 mmol) was added at 0° C. The reaction solution was warmed to 25° C. and stirred for 2 hours. The reaction was quenched by the addition of water (60 mL) and the reaction solution was extracted with ethyl acetate. The organic phases were combined, washed successively with water and saturated sodium chloride aqueous solution, dried over anhydrous magnesium sulfate, filtered, and the filtrate was concentrated under reduced pressure, the residue was purified by preparative TLC plate (3:1 petroleum ether/ethyl acetate, Rf=0.5) to deliver methyl 4-(((methylsulfonyl)oxy) methyl)cyclohexanecarboxylate (1.00 g, white solid), yield: 91%. $^1$H NMR: (400 MHz, CDCl$_3$) δ 3.67 (s, 3H), 3.48-3.46 (m, 2H), 3.01 (s, 3H), 2.26-2.25 (m, 1H), 2.05-2.01 (m, 2H), 1.89-1.85 (m, 2H), 1.47-1.43 (m, 2H), 1.31 (s, 1H), 1.01-0.98 (m, 2H). MS-ESI calcd. for [M+H]$^+$ 251, found 251.

Step 3

Methyl 4-((3,7-Dimethyl-2,6-dioxo-2,3,6,7-tetrahydro-1H-purin-1-yl)methyl)cyclohexanecarboxylate Methyl 4-(((methylsulfonyl)oxy)methyl)cyclohexanecarboxylate (350 mg, 2.32 mmol) was dissolved in 5 mL anhydrous N,N-dimethylformamide, under the nitrogen gas atmosphere, potassium carbonate (640 mg, 4.64 mmol), potassium iodide (38.0 mg, 0.230 mmol) and 2,6-hydroxy-3,7-dimethylpurine (501 mg, 2.80 mmol) were added at 25° C. The reaction solution was stirred at 130° C. for 3 hours. 40 mL water was added into the reaction solution, which was extracted with ethyl acetate, the organic phases were combined, washed successively with water and saturated sodium chloride aqueous solution, dried over anhydrous magnesium sulfate, filtered, and the filtrate was concentrated under reduced pressure, the residue was purified by preparative TLC plate to deliver the product Methyl 4-((3,7-dimethyl-2,6-dioxo-2,3,6,7-tetrahydro-1H-purin-1-yl)methyl)cyclohexanecarboxylate (400 mg, white solid), yield: 52%. MS-ESI calcd. for [M+H]$^+$ 335, found 335.

Step 4

1-((4-(3-Hydroxypentan-3-yl)-cyclohexyl)methyl)-3,7-dimethyl-1H-purine-2,6(3H,7H)-dione Methyl 4-((3,7-dimethyl-2,6-dioxo-2,3,6,7-tetrahydro-1H-purin-1-yl)methyl)cyclohexanecarboxylate (100 mg, 0.30 mmol) was dissolved in 5 mL anhydrous tetrahydrofuran, under the nitrogen gas atmosphere, ethyl magnesium bromide solution (3 M solution in ether, 1 mL, 3.00 mmol) was slowly added dropwise at −65° C. and the reaction was stirred at −65 C for 2 hours. The reaction solution was added with water (40 mL) and extracted with ethyl acetate, the organic phases were combined, washed with saturated sodium chloride aqueous solution (50 mL), dried over anhydrous magnesium sulfate, filtered and the filtrate was concentrated under reduced pressure, the residue was purified by preparative high performance liquid chromatography to deliver the product 1-((4-(3-hydroxypentan-3-yl)-cyclohexyl)methyl)-3,7-dimethyl-1H-purine-2,6(3H,7H)-dione (20.0 mg, white solid), yield: 19%. $^1$H NMR: (400 MHz, CDCl$_3$) δ 7.52 (s, 1H), 4.00 (s, 3H), 3.90-3.88 (m, 2H), 3.59 (s, 3H), 1.80-1.74 (m, 6H)-1.45 (m, 4H), 1.11-1.10 (m, 4H), 0.86-0.82 (m, 6H). MS ESI calcd. for [M+H]$^+$ 363, found 363.

Embodiment 19

3,7-Dimethyl-1-[[trans-4-(2,2,2-trifluoro-1-hydroxy-1-methyl-ethyl)cyclohexyl]methyl]purine-2,6-dione

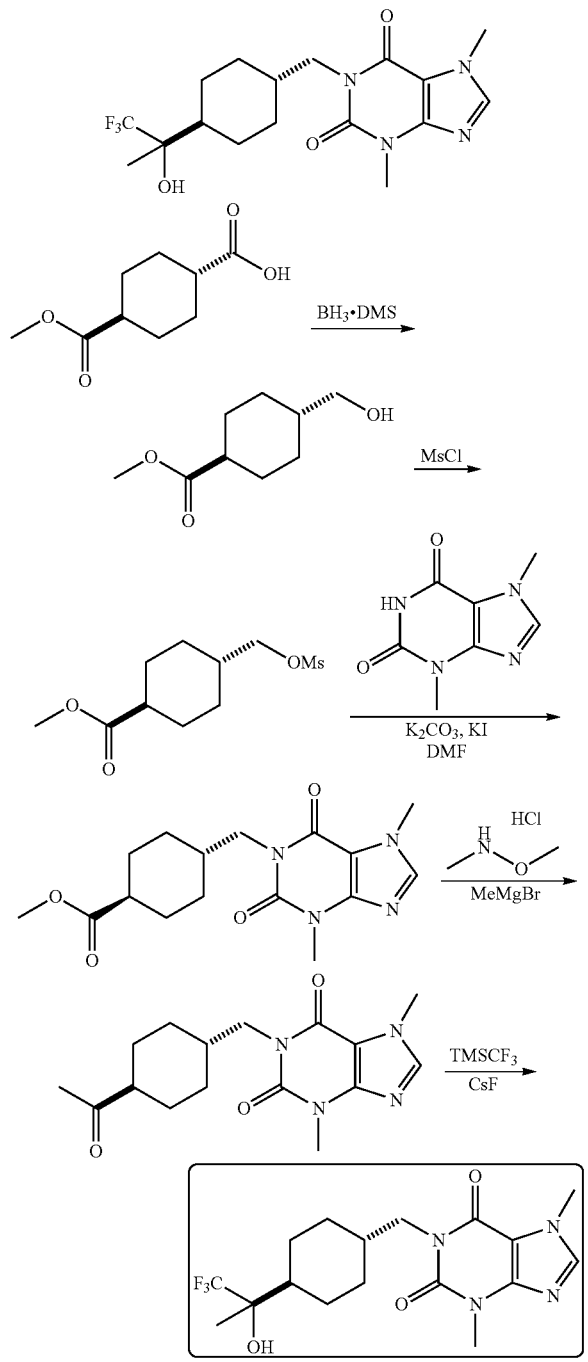

Step 1

Methyl trans-4-hydroxymethylcyclohexanecarboxylate trans-Cyclohexane-1,4-dicarboxylic acid monomethyl ester (5.00 g, 26.8 mmol) was dissolved in tetrahydrofuran (100 mL), borane dimethyl sulfide (3.06 g, 40.3 mmol) was added at 0° C. and the reaction mixture was reacted at room temperature for 2 hours. The reaction was quenched by the addition of the saturated methanol (50 mL). After concentration, water (50 mL) was added into the mixture, which was then extracted with ethyl acetate (10 mL×3), dried over anhydrous sodium sulfate, filtered and the filtrate was concentrated under reduced pressure to deliver methyl trans-4-hydroxymethylcyclohexanecarboxylate (4.00 g, yellow oil), yield: 87%. $^1$H NMR: (400 MHz, Methanol-d$_4$) δ 3.67 (s, 3H), 3.43-3.38 (m, 2H), 2.31-2.54 (m, 1H), 2.03-1.98 (m, 2H), 1.90-1.82 (m, 2H), 1.45-1.38 (m, 3H), 1.03-0.99 (m, 2H). MS-ESI calcd. for [M+H]$^+$173, found 173.

Step 2 trans-Methyl 4-(((methylsulfonyl)oxy)methyl)cyclohexanecarboxylate

Methyl trans-4-hydroxymethylcyclohexanecarboxylate (3.00 g, 23.2 mmol) and triethylamine (7.05 g, 69.6 mmol) were dissolved in dichloromethane (50 mL), and methanesulfonyl chloride (7.98 g, 69.6 mmol) was added at 0° C. The reaction solution was slowly warmed to room temperature and stirred for 2 hours. The reaction was quenched by the addition of sodium bicarbonate aqueous solution (50 mL). The resulting mixture was extracted with dichloromethane (20 mL×3). The organic phases were combined, washed with saturated brine (30 mL), dried over anhydrous sodium sulfate, filtered, and the filtrate was concentrated under reduced pressure to deliver trans-methyl 4-(((methylsulfonyl)oxy)methyl)cyclohexanecarboxylate (5.80 g, yellow oil), yield: 99%. $^1$H NMR: (400 MHz, Methanol-d$_4$) δ 4.10-4.03 (m, 2H), 3.65 (s, 3H), 3.07 (s, 3H), 2.42-2.31 (m, 1H), 2.10-2.03 (m 2H), 1.90-1.82 (m, 2H), 1.75-1.66 (m, 1H), 1.48-1.42 (m, 2H), 1.21-1.10 (m, 2H). MS-ESI calcd. for [M+H]$^+$ 251, found 251.

Step 3 trans-Methyl 4-((3,7-dimethyl-2,6-dioxo-purin-1-yl)methyl)cyclohexanecarboxylate trans-Methyl 4-(((methylsulfonyl)oxy)methyl)cyclohexanecarboxylate (1.00 g, 4.00 mmol), 3,7-dimethyl-1H-purine-2,6(3H,7H)-dione (719 mg, 4.00 mmol), potassium iodide (66.0 mg, 0.397 mmol) and potassium carbonate (1.10 g, 7.96 mmol) were dissolved in N,N-dimethylformamide (10 mL). The reaction solution was heated to 120° C. and stirred for 3 hours. The reaction mixture was cooled to room temperature, filtered, and the filtrate was concentrated under reduced pressure. The residue was purified by silica gel column chromatography (ethyl acetate, Rf=0.1) to deliver trans-methyl 4-((3,7-dimethyl-2,6-dioxo-purin-1-yl)methyl)cyclohexanecarboxylate (800 mg, yellow solid), yield: 60%. $^1$H NMR: (400 MHz, Methanol-d$_4$) δ 7.88 (s, 1H), 3.98 (s, 3H), 3.90-3.82 (m, 2H), 3.72 (s, 3H), 3.51 (s, 3H) 2.33-2.25 (m, 1H), 2.03-1.98 (m, 2H), 1.80-1.74 (m, 3H), 1.42-1.36 (m, 2H), 1.21-1.10 (m, 2H). MS-ESI calcd. for [M+H]$^+$ 335, found 335.

71

Step 4

1-(trans-4-Acetylcyclohexylmethyl)-3,7-dimethyl-1H-purine-2,6(3H,7H)-dione trans-Methyl 4-((3,7-dimethyl-2,6-dioxo-purin-1-yl)methyl)cyclohexanecarboxylic acid (300 mg, 0.897 mmol) and O,N-dimethylhydroxylamine hydrochloride (114 mg, 1.17 mmol) were dissolved in tetrahydrofuran (25 mL), methylmagnesium bromide (3 M ether solution, 1.50 mL, 4.50 mmol) was added at 0° C. The reaction solution was warmed to room temperature slowly and stirred for 12 hours. The reaction was quenched by the addition of saturated ammonium chloride aqueous solution (10 mL). The resulting mixture was extracted with ethyl acetate (10 mL×3). The organic phases were combined, washed with saturated brine (30 mL), dried over anhydrous sodium sulfate, filtered and the filtrate was concentrated under reduced pressure. The residue was purified by preparative TLC plate (ethyl acetate, Rf=0.4) to deliver 1-(trans-4-acetylcyclohexylmethyl)-3,7-dimethyl-1H-purine-2,6(3H,7H)-dione (80.0 mg, yellow oil), yield: 29%. $^1$H NMR: (400 MHz, Methanol-$d_4$) δ 7.88 (s, 1H), 3.98 (s, 3H), 3.92-3.84 (m, 2H), 3.55 (s, 3H), 2.42-2.33 (m, 1H), 2.15 (s, 3H), 1.98-1.88 (m, 2H), 1.85-1.75 (m, 3H), 1.32-1.10 (m, 4H). MS-ESI calcd. for [M+H]$^+$ 319, found 319.

Step 5

3,7-Dimethyl-1-[[trans-4-(2,2,2-trifluoro-1-hydroxy-1-methyl-ethyl)cyclohexyl]methyl]-1H-purine-2,6(3H,7H)-dione

1-(trans-4-Acetylcyclohexylmethyl)-3,7-dimethyl-3,7-dihydro-purine-2,6-dione (80.0 mg, 0.251 mmol), cesium fluoride (11.5 mg, 0.753 mmol) were dissolved in tetrahydrofuran (10 mL), trimethyl-trifluoromethyl-silane (71.6 mg, 0.502 mmol) was added at room temperature and stirred for 12 hours. 1 N hydrochloric acid (10 mL) was added into the reaction solution, which was then stirred at room temperature for 1 hour, the reaction was quenched by the addition of saturated sodium bicarbonate aqueous solution (50 mL). The resulting mixture was extracted with ethyl acetate (10 mL×3). The organic phases were combined, washed with saturated brine (30 mL), dried over anhydrous sodium sulfate, filtered and the filtrate was concentrated under reduced pressure. And the residue was purified by preparative high performance liquid chromatography to deliver 3,7-dimethyl-1-[[trans-4-(2,2,2-trifluoro-1-hydroxy-1-methyl-ethyl)cyclohexyl]methyl]-1H-purine-2,6(3H,7H)-dione (35.0 mg, yellow solid), yield: 70%. $^1$H NMR: (400 MHz, Methanol-$d_4$) δ 7.88 (s, 1H), 3.98 (s, 3H), 3.88 (d, J=6.8 Hz, 2H), 3.53 (s, 3H), 1.96-1.67 (m, 6H), 1.22 (s, 3H), 1.15-1.06 (m, 4H). MS-ESI calcd. for [M+H]$^+$ 389, found 389.

72

Embodiment 20

3,7-Dimethyl-1-[trans-4-(2,2,2-trifluoro-1-hydroxy-1-trifluoromethyl-ethyl)cyclohexylmethyl]-3,7-dihydro-purine-2,6-dione

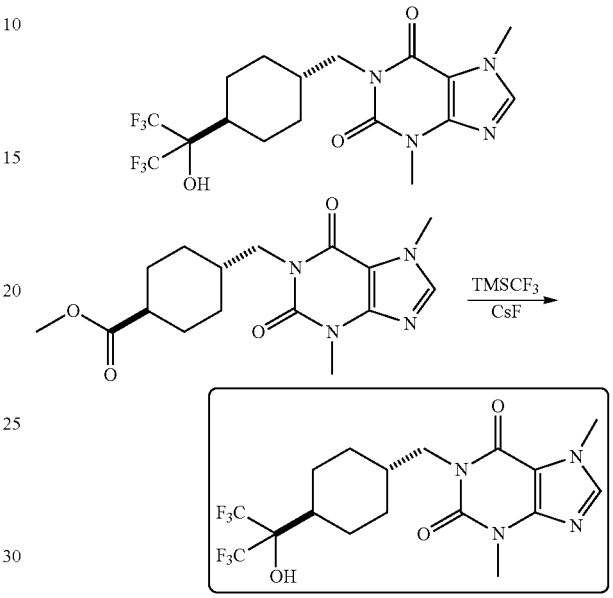

Step 1

3,7-Dimethyl-1-[trans-4-(2,2,2-trifluoro-1-hydroxy-1-trifluoromethyl-ethyl)cyclohexylmethyl]-3,7-dihydro-purine-2,6-dione trans-Methyl 4-((3,7-dimethyl-2,6-dioxo-purin-1-yl)methyl)cyclohexane carboxylate (200 mg, 0.598 mmol), cesium fluoride (45.4 mg, 0.299 mmol) were dissolved in tetrahydrofuran (10 mL), trimethyl-trifluoromethyl-silane (340 mg, 2.39 mmol) was added at room temperature and stirred for 12 hours. 1 N hydrochloric acid (10 mL) was added into the reaction solution, which was then stirred at room temperature for 1 hour, the reaction was quenched by the addition of saturated sodium bicarbonate aqueous solution (50 mL). The resulting mixture was extracted with ethyl acetate (10 mL×3). The organic phases were combined, washed with saturated brine (20 mL), dried over anhydrous sodium sulfate, filtered and the filtrate was concentrated under reduced pressure. And the residue was purified by preparative high performance liquid chromatography to deliver 3,7-dimethyl-1-[trans-4-(2,2,2-trifluoro-1-hydroxy-1-trifluoromethyl-ethyl)cyclohexylmethyl]-3,7-dihydro-purine-2,6-dione (35.0 mg, yellow solid), yield: 41%.

$^1$H NMR: (400 MHz, Methanol-$d_4$) δ 7.88 (s, 1H), 3.98 (s, 3H), 3.88 (d, J=6.8 Hz, 2H), 3.53 (s, 3H), 2.08-1.79 (m, 6H), 1.30-1.24 (m, 2H), 1.11-1.08 (m, 2H). MS-ESI calcd. for [M+H]$^+$ 443, found 443.

Embodiment 21

1-[[trans-4-(1-hydroxycyclopropyl)cyclohexyl]methyl]-3,7-dimethylpurine-2,6-dione

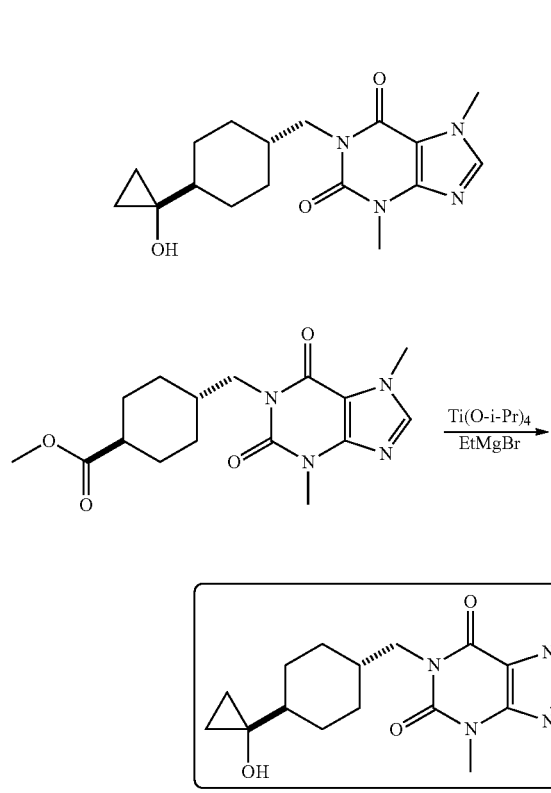

Step 1

1-[[trans-4-(1-Hydroxycyclopropyl)cyclohexyl]methyl]-3,7-dimethylpurine-2,6-dione trans-Methyl 4-[(3,7-dimethyl-2,6-dioxo-purin-1-yl)methyl]cyclohexane carboxylate (200 mg, 0.598 mmol), tetraisopropyl titanate (340 mg, 1.20 mmol) was dissolved in tetrahydrofuran (10 mL), ethylmagnesium bromide (3 M ether solution, 0.39 mL, 1.17 mmol) was added at room temperature and stirred for 12 hours. The reaction was quenched by the addition of saturated ammonium chloride aqueous solution (50 mL). The resulting mixture was extracted with ethyl acetate (10 mL×3). The organic phases were combined, washed with saturated brine (30 mL), dried over anhydrous sodium sulfate, filtered and the filtrate was concentrated under reduced pressure. The residue was purified by preparative high performance liquid chromatography to deliver 1-[[trans-4-(1-hydroxycyclopropyl)cyclohexyl]methyl]-3,7-dimethylpurine-2,6-dione (70.0 mg, yellow solid), yield: 35%.

$^1$H NMR: (400 MHz, Methanol-$d_4$) δ 7.87 (s, 1H), 3.98 (s, 3H), 3.88 (d, J=6.8 Hz, 2H), 3.53 (s, 3H), 1.79-1.71 (m, 5H), 1.29-1.07 (m, 5H), 0.60-0.57 (m, 2H), 0.42-0.39 (m, 2H). MS-ESI calcd. for [M+H]$^+$ 333, found 333.

Embodiment 22

1-(2-(3-Ethyl-3-hydroxycyclohexyl)ethyl)-3,7-dimethyl-1H-purine-2,6(3H,7H)-dione

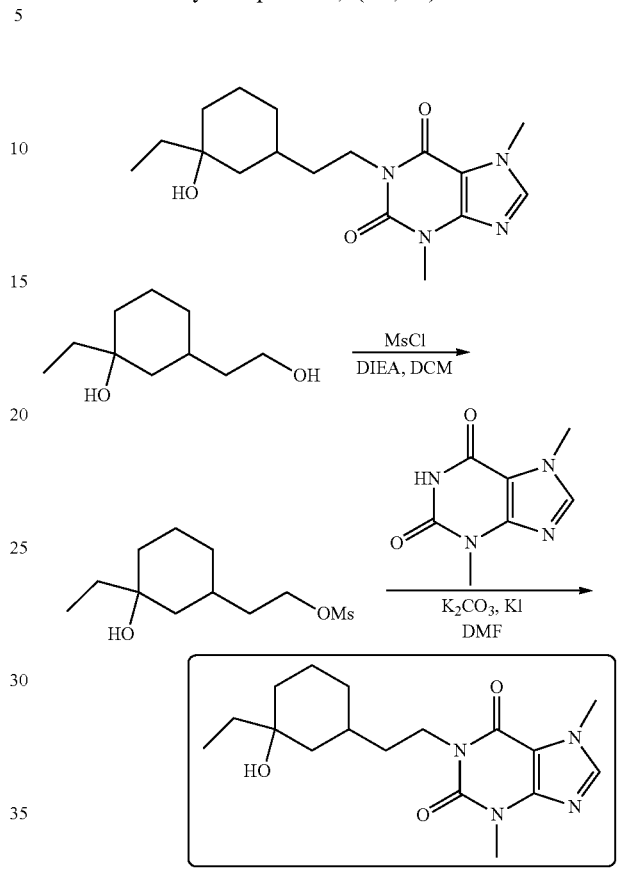

Step 1

2-(3-Ethyl-3-hydroxycyclohexyl)ethyl methanesulfonate

1-Ethyl-3-(2-hydroxyethyl)cyclohexanol (450 mg, 2.61 mmol) and diisopropylethylamine (500 mg, 3.92 mmol) were dissolved in dichloromethane (10 mL), and methanesulfonyl chloride (600 mg, 5.40 mmol) was slowly added at 0° C. The reaction solution was stirred at 0° C. for 0.5 hour. The reaction was quenched by the addition of water and extracted with ethyl acetate (20 mL×3). The organic phases were combined, dried over anhydrous sodium sulfate, filtered and the filtrate was concentrated under reduced pressure and the residue was purified by silica gel column chromatography (10:1 petroleum ether/ethyl acetate, Rf=0.4) to deliver the product 2-(3-ethyl-3-hydroxycyclohexyl)ethyl methanesulfonate (450 mg, yellow oil), yield: 69%. MS-ESI calcd. [M+H]$^+$ 251, found 251.

Step 2

1-(2-(3-Ethyl-3-hydroxycyclohexyl)ethyl)-3,7-dimethyl-1H-purine-2,6(3H,7H)-dione 2-(3-Ethyl-3-hydroxycyclohexyl)ethyl methanesulfonate (200 mg, 0.790 mmol), 3,7-dimethyl-1H-purine-2,6(3H,7H)-dione (144 mg, 0.790 mmol) and potassium carbonate (220 mg, 1.60 mmol), potassium iodide (13.1 mg, 0.0790 mmol) were dissolved in N,N-dimethylformamide (3 mL). The reaction solution was heated to 130° C. and stirred for 3 hours. The reaction solution was cooled to 25° C., into which saturated brine was added, and then extracted with ethyl acetate (40 mL×3). The organic phases were combined, dried over anhydrous sodium sulfate, filtered, the filtrate was concentrated under reduced pressure, the residue was isolated and purified by preparative high performance liquid chromatography to deliver the product 1-(2-(3-ethyl-3-hydroxycyclohexyl)ethyl)-3,7-dimethyl-1H-purine-2,6 (3H,7H)-dione (70.0 mg, white solid), yield: 26%. $^1$H NMR: (400 MHz, Methanol-d$_4$) δ 7.86 (s, 1H), 4.09-3.94 (m, 5H), 3.52 (s, 3H), 1.88-1.84 (m, 1H), 1.80-1.40 (m, 10H), 1.26-1.16 (m, 1H), 1.02-0.95 (m, 1H), 0.91 (t, J=7.2 Hz, 3H). MS-ESI calcd. for [M+H-18]$^+$ 317, found 317.

Embodiment 23

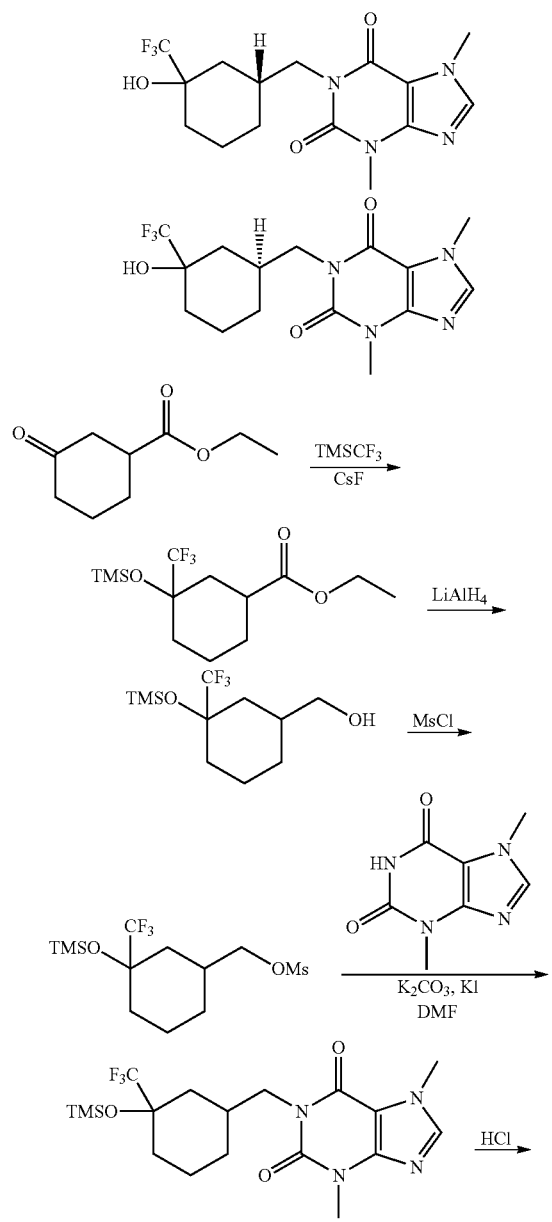

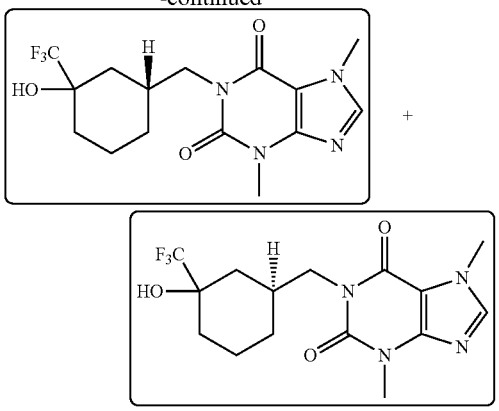

Step 1

Ethyl 3-trifluoromethyl-3-trimethylsilyloxy-cyclohexanecarboxylate

Ethyl-3-oxocyclohexanecarboxylate (1.00 g, 5.88 mmol), cesium fluoride (446 mg, 2.94 mmol) were dissolved in tetrahydrofuran (30 mL), trimethyl-trifluoromethyl-silane (1.67 g, 11.7 mmol) was added at room temperature and stirred for 12 hours. The reaction was quenched by the addition of water (20 mL). The resulting mixture extracted with ethyl acetate (20 mL×3). The organic phases were combined, washed with saturated brine (60 mL), dried over anhydrous sodium sulfate, filtered and the filtrate was concentrated under reduced pressure to deliver ethyl 3-trifluoromethyl-3-trimethylsiloxy-cyclohexanecarboxylate (1.40 g, yellow oil), yield: 76%. MS-ESI calcd. for [M+H]$^+$ 313, found 313.

Step 2

(3-Ttrifluoromethyl-3-trimethylsilanyloxycyclohexyl) methanol

Ethyl 3-trifluoromethyl-3-trimethylsilyloxy-cyclohexanecarboxylate (1.00 g, 3.20 mmol) was dissolved in tetrahydrofuran (10 mL), and lithium tetrahydropyran (243 mg, 6.40 mmol) was added at 0° C. for 1 hour. The reaction was quenched by the addition of water (10 mL). The resulting mixture was extracted with ethyl acetate (20 mL×3), dried over anhydrous sodium sulfate, filtered and the filtrate was concentrated under reduced pressure to deliver (3-trifluoromethyl-3-trimethylsilanyloxycyclohexyl) methanol (800 mg, colorless oil), yield 92%. MS-ESI calcd. for [M+H]$^+$ 271, found 271.

Step 3

[3-(Trifluoromethyl)-3-trimethylsilyloxycyclohexyl) methyl methanesulfonate (3-Ttrifluoromethyl-3-trimethylsilanyloxycyclohexyl) methanol (850 mg, 3.14 mmol) and triethylamine (953 mg, 9.42 mmol) were dissolved in dichloromethane (15 mL), methanesulfonyl chloride (719 mg, 6.28 mmol) was added at 0° C. The reaction solution was slowly warmed to room temperature and stirred for 2 hours. The reaction was quenched by the addition of sodium bicarbonate aqueous solution (10 mL). The resulting mixture was extracted with dichloromethane (20 mL×3). The organic phases were combined, washed with saturated brine (20 mL), dried over anhydrous sodium sulfate, filtered and the filtrate was concentrated under reduced pressure to deliver [3-(trifluoromethyl)-3-trimethylsilyloxycyclohexyl)methyl methanesulfonate (900 mg, yellow oil), yield: 82%. ¹H NMR: (400 MHz, Methanol-d₄) δ 4.36-4.32 (m, 1H), 4.17-4.13 (m, 1H), 3.08 (s, 3H), 2.12-1.60 (m, 9H), 0.16 (s, 9H). MS-ESI calcd. for [M+H]⁺ 349, found 349.

Step 4

3,7-Dimethyl-1-[[3-(trifluoromethyl)-3-trimethylsilyloxy-cyclohexyl]methyl]purine-2,6-dione

[3-(Trifluoromethyl)-3-trimethylsilyloxycyclohexyl) methyl methanesulfonate (200 mg, 0.573 mmol), 3,7-dimethyl-1H-purine-2,6(3H,7H)-dione (103 mg, 0.574 mmol), potassium iodide (28.6 mg, 0.172 mmol) and potassium carbonate (374 mg, 1.15 mmol) were dissolved in N,N-dimethylformamide (30 mL). The reaction solution was heated to 120° C. and stirred for 3 hours. The reaction mixture was cooled to room temperature, filtered, the filtrate was concentrated under reduced pressure, the residue was purified by preparative high performance liquid chromatography to deliver 3,7-dimethyl-1-[[3-(trifluoromethyl)-3-trimethylsilyloxy-cyclohexyl]methyl]purine-2,6-dione (150 mg, yellow solid), yield: 60%.

MS-ESI calcd. for [M+H]⁺ 433, found 433.

Step 5

3,7-Dimethyl-1-[[3-(trifluoromethyl)-3-trimethylsilyloxy-cyclohexyl]methyl]purine-2,6-dione (200 mg, 0.462 mmol) was dissolved in tetrahydrofuran (10 mL), 1 N hydrochloric acid (10 mL) was added and the resulting mixture was stirred at room temperature for 1 hour, the reaction was quenched by the addition of saturated sodium bicarbonate aqueous solution (50 mL). The reaction mixture was extracted with ethyl acetate (20 mL×3). The organic phases were combined, washed with saturated brine, dried over anhydrous sodium sulfate, filtered and the filtrate was concentrated under reduced pressure. The residue was purified by preparative high performance liquid chromatography to deliver product 1 (10.0 mg, yellow solid) (isomer 1, the first peak), yield: 6%. ¹H NMR: (400 MHz, Methanol-d₄) δ 7.87 (s, 1H), 3.97 (s, 3H), 3.89-3.83 (m, 2H), 3.52 (s, 3H), 2.23-2.22 (m, 1H), 1.76-1.07 (m, 8H). MS-ESI calcd. for [M+H]⁺ 361, found 361.

Product 2 (85.0 mg, yellow solid) (isomer 2, the second peak), yield: 51%. ¹H NMR: (400 MHz, Methanol-d₄) δ 7.87 (s, 1H), 4.31-4.26 (m, 1H), 3.99-3.95 (m, 4H), 3.55 (s, 3H), 2.26-1.88 (m, 3H), 1.79-1.47 (m, 6H). MS-ESI calcd. for [M+H]⁺ 361, found 361.

Embodiment 24

1-((5-Hydroxy-5-(trifluoromethyl)tetrahydro-2H-pyran-2-yl)-3,7-dimethyl-1H-purine-2,6(3H,7H)-dione

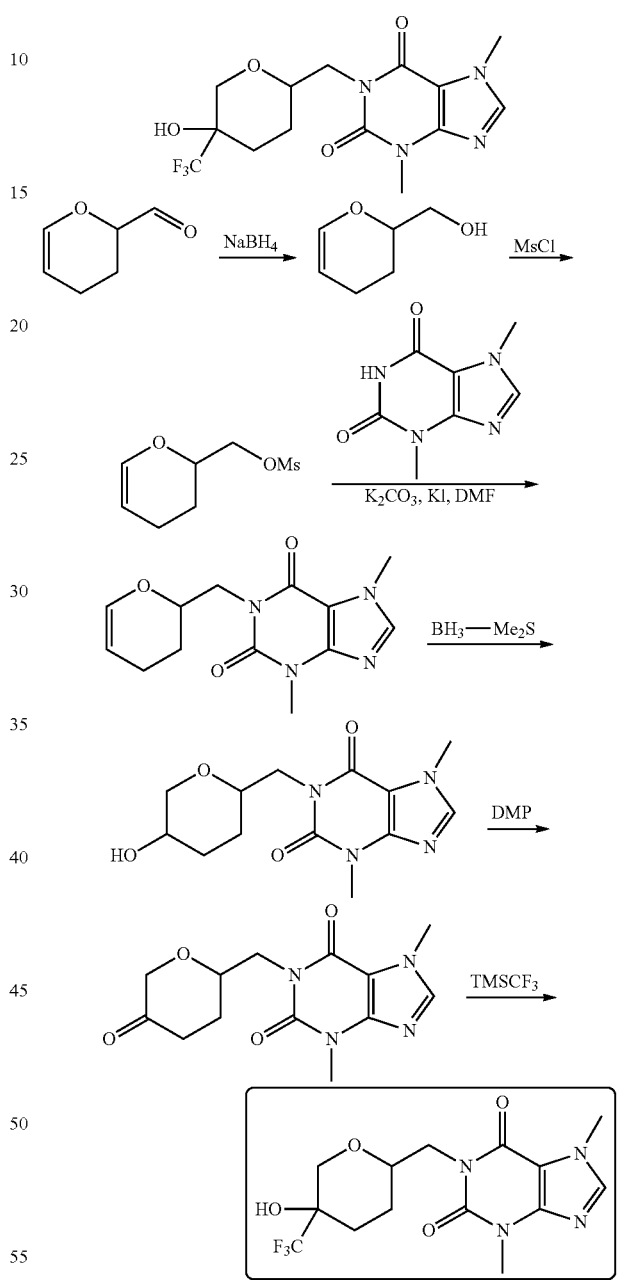

Step 1

(3,4-Dihydro-2H-pyran-2-yl) methanol 3,4-Dihydro-2H-pyran-2-carbaldehyde (3.00 g, 26.7 mmol) was dissolved in methanol (20 mL), sodium borohydride (2.02 g, 53.5 mmol) was added at 0° C. for 2 hours. The reaction was quenched by the addition of saturated ammonium chloride aqueous solution (30 mL). The resulting mixture was extracted with dichloromethane (20 mL×3), dried over anhydrous sodium sulfate, filtered and the filtrate was concentrated under reduced pressure to deliver (3,4-dihydro-2H-pyran-2-yl) methanol (1.50 g, yellow oil), yield: 49%. $^1$H-NMR: (400 MHz, Methanol-$d_4$) δ 6.40 (d, J=6.0 Hz, 1H), 4.71-4.68 (m, 1H), 3.86-3.83 (m, 1H), 3.82-3.61 (m, 2H), 2.13-2.12 (m, 1H), 2.10-2.08 (m, 1H), 2.02-2.01 (m, 1H), 1.68-1.63 (m, 1H).

Step 2

(3,4-Dihydro-2H-pyran-2-yl) methyl methanesulfonate (3,4-Dihydro-2H-pyran-2-yl) methanol (1.50 g, 13.1 mmol) and triethylamine (2.66 g, 26.3 mmol) were dissolved in dichloromethane (20 mL), and methanesulfonyl chloride (3.01 g, 26.3 mmol) was added at 0° C. The reaction solution was slowly warmed to room temperature and stirred for 2 hours. The reaction was quenched by the addition of sodium bicarbonate aqueous solution (10 mL). The resulting mixture was extracted with dichloromethane (20 mL×3). The organic phases were combined, washed with saturated brine, dried over anhydrous sodium sulfate, filtered and the filtrate was concentrated under reduced pressure to deliver (3,4-dihydro-2H-pyran-2-yl) methylmethanesulfonate (1.70 g, yellow oil), yield: 67%. MS-ESI calcd. for [M+H]$^+$ 193, found 193.

Step 3

1-((3,4-Dihydro-2H-pyran-2-yl)methyl)-3,7-dimethyl-1H-purine-2,6-(3H,7H)-dione (3,4-Dihydro-2H-pyran-2-yl)methylmethanesulfonate (1.70 g, 8.84 mmol), 3,7-dimethyl-1H-purine-2,6-dione (1.59 g, 8.84 mmol), potassium iodide (146 mg, 0.884 mmol) and potassium carbonate (2.44 g, 17.7 mmol) were dissolved in N,N-dimethylformamide (50 mL). The reaction solution was heated to 120° C. and stirred for 3 hours. The reaction mixture was cooled to room temperature, filtered, and the filtrate was concentrated under reduced pressure, the residue was purified by silica gel column chromatography (ethyl acetate, Rf=0.4) to deliver 1-((3,4-dihydro-2H-pyran-2-yl)methyl)-3,7-dimethyl-1H-purine-2,6-(3H,7H)-dione (1.30 g, yellow solid), yield: 53%. MS-ESI calcd. for [M+H]$^+$ 277, found 277.

Step 4

1-((5-Hydroxytetrahydro-2H-pyran-2-yl)methyl)-3,7-dimethyl-1H-purine-2,6-(3H,7H)-dione 1-((3,4-Dihydro-2H-pyran-2-yl)methyl)-3,7-dimethyl-1H-purine-2,6-(3H,7H)-dione (600 mg, 2.17 mmol) was dissolved in tetrahydrofuran (30 mL), and borane dimethyl sulfide (825 mg, 10.7 mmol) was added at 0° C. The reaction solution was slowly warmed to room temperature and stirred for 12 hours. 3 N Sodium hydroxide aqueous solution (30 mL) and hydrogen peroxide (10 mL) were added and the reaction was continued for 1 hour. The reaction was quenched by the addition of methanol (10 mL), washed with sodium thiosulfate aqueous solution (30 mL) and extracted with dichloromethane (10 mL×3). The organic phases were combined, washed with saturated brine, dried over anhydrous sodium sulfate, filtered and the filtrate was concentrated under reduced pressure. And the residue was purified by preparative TLC plate (20:1 dichloromethane/methanol, Rf=0.3) 1-((5-hydroxytetrahydro-2H-pyran-2-yl)methyl)-3,7-dimethyl-1H-purine-2,6-(3H,7H)-dione (130 mg, yellow oil), yield: 20%. $^1$H NMR: (400 MHz, Methanol-$d_4$) δ 7.88 (s, 1H), 4.25-4.23 (m, 1H), 4.20 (s, 3H), 3.98-3.67 (m, 5H), 3.54 (s, 3H), 2.10-1.77 (m, 2H), 1.49-1.31 (m, 2H). MS-ESI calcd. for [M+H]$^+$ 295, found 295.

Step 5

3,7-Dimethyl-1-((5-oxotetrahydro-2H-pyran-2-yl)methyl)-1H-purine-2,6-(3H,7H)-dione 1-((5-Hydroxytetrahydro-2H-pyran-2-yl)methyl)-3,7-dimethyl-1H-purine-2,6-(3H,7H)-dione (130 mg, 0.441 mmol) was dissolved in dichloromethane (10 mL), Dess-Martin periodinane (138 mg, 1.33 mmol) was added, and then reacted at 25° C. for 3 hours. The reaction was quenched by the addition of saturated sodium thiosulfate aqueous solution (20 mL), the resulting mixture was extracted with dichloromethane (10 mL×3), the organic phases were combined, washed with saturated brine, dried over anhydrous sodium sulfate, filtered and the filtrate was concentrated under reduced pressure. The residue was purified by preparative TLC plate (20:1 dichloromethane/methanol, Rf=0.4) to deliver 3,7-dimethyl-1-((5-oxotetrahydro-2H-pyran-2-yl)methyl)-1H-purine-2,6-(3H,7H)-dione (60.0 mg, yellow solid), yield: 47%. MS-ESI calcd. for [M+H]$^+$ 293, found 293.

Step 6

1-((5-Hydroxy-5-(trifluoromethyl)tetrahydro-2H-pyran-2-yl)-3,7-dimethyl-1H-purine-2,6-(3 H,7H)-dione 3,7-Dimethyl-1-((5-oxotetrahydro-2H-pyran-2-yl) methyl)-1H-purine-2,6-(3H,7H)-dione (60.0 mg, 0.205 mmol), cesium fluoride (6.24 mg, 0.0411 mmol) were dissolved in tetrahydrofuran (10 mL), trimethyl trifluoromethylsilane (87.5 mg, 0.615 mmol) was added at room temperature and stirred for 5 hours. 1 N hydrochloric acid (10 mL) was added and stirred at room temperature for 1 hour. The reaction was quenched by the addition of saturated sodium bicarbonate aqueous solution (50 mL). The resulting mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver 1-((5-hydroxy-5-(trifluoromethyl)tetrahydro-2H-pyran-2-yl)-3,7-dimethyl-1H-purine-2,6-(3H, 7H)-dione (15.0 mg, yellow solid), yield: 30%. $^1$H NMR: (400 MHz, Methanol-$d_4$) δ 8.28 (s, 1H), 4.39-4.10 (m, 2H), 4.05 (s, 3H), 3.93-3.89 (m, 2H), 3.55 (s, 3H), 3.32-3.27 (m, 1H), 1.89-1.65 (m, 4H). MS-ESI calcd. for [M+H]$^+$ 363, found 363.

Embodiment 25

1-(4-(3-Hydroxypentan-3-yl)benzyl)-3,7-dimethyl-1H-purine-2,6(3H,7H)-dione

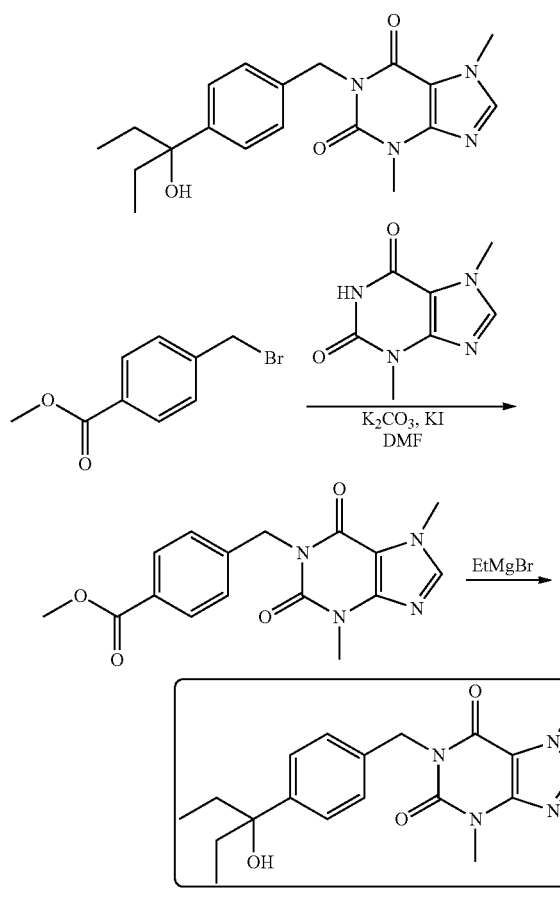

Step 1

Methyl 4-((3,7-dimethyl-2,6-dioxo-2,3,6,7-tetrahydro-1H-purin-1-yl)methyl)benzoate Under the nitrogen gas atmosphere, 3,7-dimethyl-1H-purine-2,6(3H, 7H)-dione (180 mg, 1.00 mmol), methyl 4-(bromomethyl)benzoate (251 mg, 1.10 mmol), potassium iodide (55.0 mg, 0.33 mmol) and potassium carbonate (179 mg, 1.30 mmol) were dissolved in anhydrous N,N-dimethylformamide (4 mL) at 25° C., and then heated to 110° C. and stirred for 3 hours. After cooling to 25° C., the reaction mixture was diluted with water and extract with ethyl acetate (30 mL×2). The organic phases were combined, dried over anhydrous sodium sulfate, filtered and the filtrate was concentrated under reduced pressure, the residue was purified by chromatography on silica gel column (1:1 petroleum ether/ethyl acetate, Rf 0.3) to deliver methyl 4-((3,7-dimethyl-2,6-dioxo-2,3,6,7-tetrahydro-1H-purin-1-yl)methyl) benzoate (300 mg, white solid), yield: 91%. MS-ESI calcd. for [M+H]$^+$ 329, found 329.

Step 2

1-(4-(3-Hydroxypentan-3-yl)benzyl)-3,7-dimethyl-1H-purine-2,6(3H,7H)-dione

Methyl 4-((3,7-dimethyl-2,6-dioxo-2,3,6,7-tetrahydro-1H-purin-1-yl)methyl) benzoate (200 mg, 0.610 mmol) was dissolved in anhydrous tetrahydrofuran (3 mL). Under the nitrogen gas atmosphere, ethylmagnesium bromide (3 M ether solution, 1.2 mL, 3.60 mmol) was added dropwise at −78° C. The reaction solution was stirred at this temperature for 0.5 hour and spontaneously warmed to 25° C. and continued for 1 hour, and the reaction was continued for 1 hour. Saturated ammonium chloride aqueous solution (5 mL) was added and the resulting mixture was extracted with ethyl acetate (30 mL×2). The organic phases were combined, dried over anhydrous sodium sulfate, filtered and the filtrate was concentrated under reduced pressure, the residue was purified by preparative TLC plate (1:3 petroleum ether/ethyl acetate, Rf=0.3) to deliver 1-(4-(3-hydroxypentan-3-yl)benzyl)-3,7-dimethyl-1H-purine-2,6(3H,7H)-dione (190 mg, white solid), yield: 87%. $^1$H NMR: (400 MHz, Methanol-d$_4$) δ 7.85 (s, 1H), 7.32 (d, J=8.0 Hz, 2H), 7.28 (d, J=8.0 Hz, 2H), 5.25 (s, 2H), 3.96 (s, 3H), 3.52 (s, 3H), 1.82-1.72 (m, 4H), 0.69 (t, J=7.2 Hz, 6H). MS-ESI calcd. for [M+H]$^+$ 357, found 357.

Embodiment 26

3,7-dimethyl-1-(3-(1,1,1-trifluoro-2-hydroxypropan-2-yl)benzyl)-1H-purine-2,6-(3H,7H)-dione

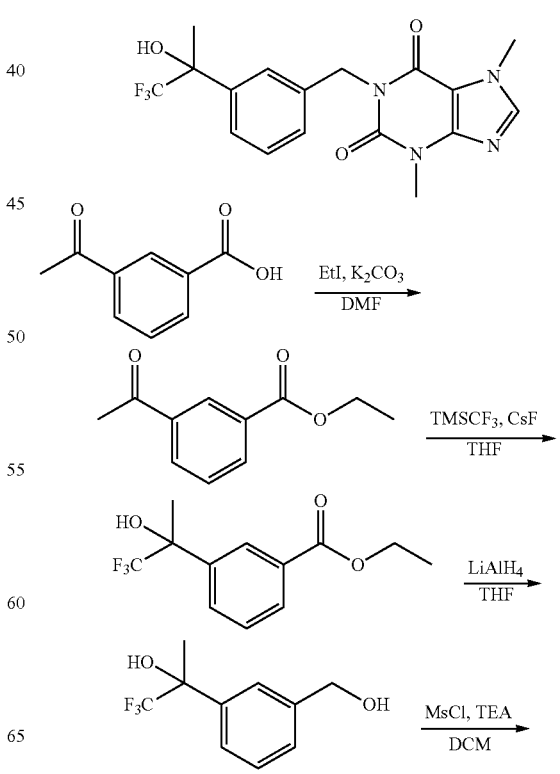

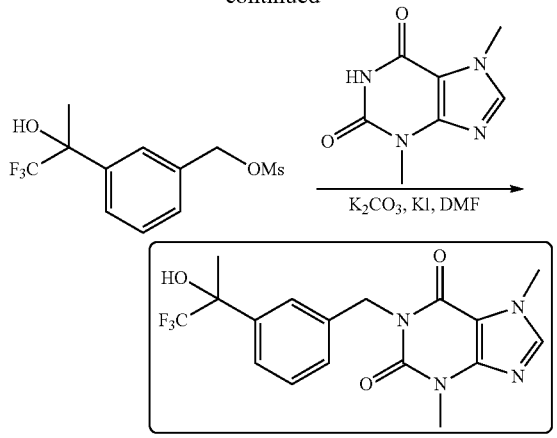

Step 1

Ethyl 3-acetylbenzoate

3-Acetylbenzoic acid (500 mg, 3.05 mmol) was dissolved in N,N-dimethylformamide (20 mL), ethyl iodide (475 mg, 3.05 mmol) and potassium carbonate (632 mg, 4.57 mmol) were added at room temperature, after stirring at room temperature for 2 hours, the reaction solution was concentrated and diluted with ethyl acetate (30 mL), the organic phase was washed with water (20 mL×2), dried over anhydrous sodium sulfate, filtered and the filtrate was concentrated under reduced pressure, the residue was isolated and purified by silica gel column chromatography (5:1 petroleum ether/ethyl acetate, Rf=0.5) to deliver ethyl 3-acetylbenzoate (530 mg, white solid), yield: 90%. $^1$H NMR (400 MHz, CDCl$_3$) δ 8.60 (s, 1H), 8.24 (d, J=7.6 Hz, 1H), 8.15 (d, J=7.6 Hz, 1H), 7.56 (t, J=7.6 Hz, 1H), 4.41 (q, J=7.2 Hz, 2H), 2.66 (s, 3H), 1.42 (t, J=7.2 Hz, 3H). MS-ESI calcd. for [M+H]$^+$ 193, found 193.

Step 2

Ethyl 3-(1,1,1-trifluoro-2-hydroxypropan-2-yl)benzoate

Ethyl 3-acetylbenzoate (500 mg, 2.60 mmol) was dissolved in tetrahydrofuran (20 mL), trifluoromethyltrimethylsilane (370 mg, 2.60 mmol) and cesium fluoride (79.0 mg, 0.520 mmol) were added at room temperature. The reaction solution was stirred at room temperature for 12 hours, diluted with ethyl acetate (30 mL), the organic phase was washed with water (20 mL×2), dried with anhydrous sodium sulfate, filtered and the filtrate was concentrated under reduced pressure, the residue was isolated and purified by silica gel column chromatography (2:1 petroleum ether/ethyl acetate, Rf=0.5) to deliver ethyl 3-(1,1,1-trifluoro-2-hydroxypropan-2-yl) benzoate (600 mg, yellow solid), yield: 88%. $^1$H NMR: (400 MHz, CDCl$_3$) δ 8.26 (s, 1H), 8.05 (d, J=7.6 Hz, 1H), 7.80 (d, J=7.6 Hz, 1H), 7.48 (t, J=7.6 Hz, 1H), 4.39 (q, J=7.2 Hz, 2H), 1.82 (s, 3H), 1.40 (t, J=7.2 Hz, 3H). MS-ESI calcd. for [M+H]$^+$ 263, found 263.

Step 3

1,1,1-Trifluoro-2-(3-hydroxymethyl)phenyl)propan-2-ol

Ethyl 3-(1,1,1-trifluoro-2-hydroxypropan-2-yl)benzoate (500 mg, 1.91 mmol) was dissolved in tetrahydrofuran (20 mL), and lithium aluminum hydride (108 mg, 2.87 mmol) was added to the reaction solution at 0° C., the mixture was stirred at room temperature for 2 hours, water (0.1 mL), 15% sodium hydroxide (0.1 mL) and water (0.3 mL) were added separately to the reaction solution and stirred for 20 minutes. The reaction solution was diluted with ethyl acetate (30 mL) and the organic phase was washed with water (20 mL×2), dried over anhydrous sodium sulfate, filtered and the filtrate was concentrated under reduced pressure to deliver 1,1,1-trifluoro-2-(3-hydroxymethyl)phenyl)propan-2-ol (400 mg, yellow solid), yield: 95%.

$^1$H-NMR: (400 MHz, CDCl$_3$) δ 7.62 (s, 1H), 8.05 (d, J=7.6 Hz, 1H), 7.41-7.37 (m, 2H), 4.73 (s, 2H), 1.80). MS-ESI calcd. for [M+H]$^+$ 221, found 221.

Step 4

3-(1,1,1-Trifluoro-2-hydroxypropan-2-yl)benzyl methanesulfonate 1,1,1-Trifluoro-2-(3-hydroxymethyl)phenyl)propan-2-ol (400 mg, 1.82 mmol) and triethylamine (275 mg, 2.72 mmol) were dissolved in dichloromethane (20 mL), methanesulfonyl chloride (250 mg, 2.18 mmol) was added to the reaction solution at 0° C., stirred for 2 hours. The reaction solution was diluted by dichloromethane (30 mL), and the organic phase was washed with water (20 mL×2), dried over anhydrous sodium sulfate, filtered and the filtrate was concentrated under reduced pressure to deliver 3-(1,1,1-trifluoro-2-hydroxypropan-2-yl)benzyl methanesulfonate (500 mg, yellow oil), yield: 92%.

MS-ESI calcd. for [M+H]$^+$ 299, found 299.

Step 5

3,7-Dimethyl-1-(3-(1,1,1-trifluoro-2-hydroxypropan-2-yl)benzyl)-1H-purine-2,6-(3H,7H)-dione 3-(1,1,1-Trifluoro-2-hydroxypropan-2-yl)benzyl methanesulfonate (100 mg, 0.335 mmol) and 3,7-dimethyl-1H-purine-2,6-(3H, 7H)-dione (60.0 mg, 0.335 mmol) were dissolved in N,N-dimethylformamide (20 mL), potassium carbonate (70.0 mg, 0.502 mmol) and potassium iodide (6.00 mg, 0.0335 mmol) were added at room temperature, after stirring at 100° C. for 2 hours, the reaction mixture was cooled and concentrated, diluted with ethyl acetate (30 mL), the organic phase was washed with water (20 mL×2), dried over anhydrous sodium sulfate, filtered, and the filtrate was concentrated under reduced pressure. The residue was purified by high performance liquid chromatography to deliver 3,7-dimethyl-1-(3-(1,1,1-trifluoro-2-hydroxypropan-2-yl)benzyl)-1H-purine-2,6-(3H,7H)-dione (30.0 mg, white solid), yield: 23%. $^1$H NMR: (400 MHz, CDCl$_3$) δ 7.90 (s, 1H), 7.70 (s, 1H), 7.49 (d, J=7.6 Hz, 1H), 7.38-7.32 (m, 2H), 5.21 (s, 2H), 4.00 (s, 3H), 3.55 (s, 3H), 1.71 (s, 3H). MS-ESI calcd. for [M+H]$^+$ 383, found 383.

Embodiment 27

3,7-Dimethyl-1-(4-(1,1,1-trifluoro-2-hydroxypropan-2-yl)phenyl)-1H-purine-2,6(3H,7H)-dione

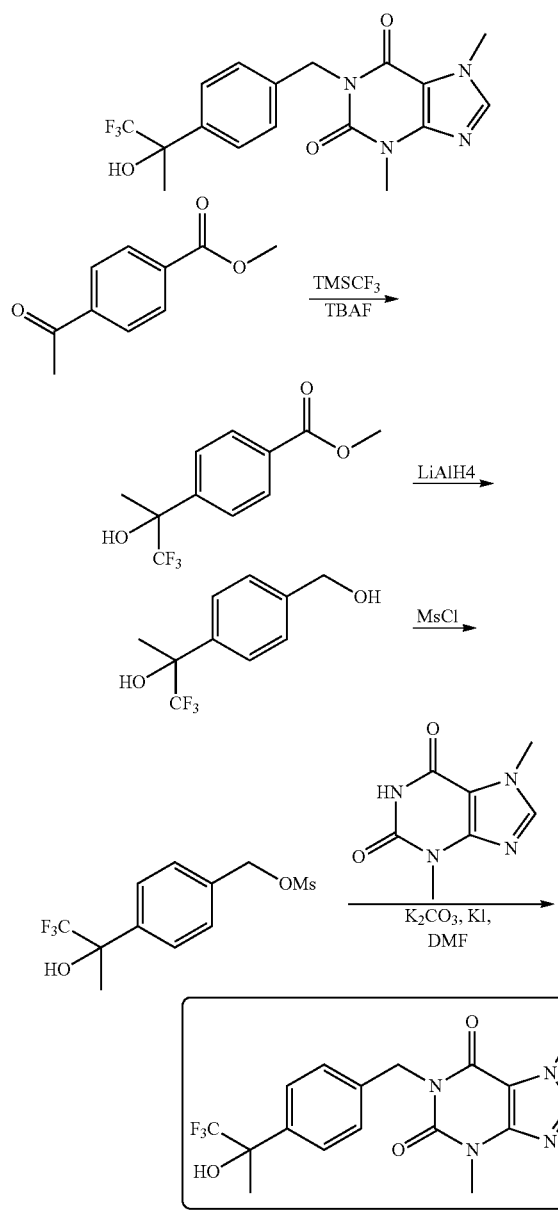

Step 1

Methyl 4-(1,1,1-trifluoro-2-hydroxypropan-2-yl)benzoate

Under the nitrogen gas atmosphere, methyl 4-acetylbenzoate (10.0 g, 56.1 mmol) and trimethyl(trifluoromethyl)silane (16.0 g, 112 mmol) were dissolved in anhydrous tetrahydrofuran (150 mL) at 0° C., tetrabutylammonium fluoride (22.0 g, 84.2 mmol) was slowly added. The reaction was slowly warmed to room temperature and stirred overnight. The reaction was quenched by the addition of water (50 mL). The resulting mixture was extracted with ethyl acetate (50 mL×3). The organic phases were combined, washed successively with saturated sodium bicarbonate aqueous solution and saturated brine, dried over anhydrous sodium sulfate, filtered and the filtrate was concentrated under reduced pressure to deliver the product methyl 4-(1,1,1-trifluoro-2-hydroxypropan-2-yl)benzoate (7.00 g, yellow liquid), yield: 50%. $^1$H NMR: (400 MHz, CDCl$_3$) δ 8.04 (d, J=8.0 Hz, 2H), 7.68 (d, J=8.0 Hz, 2H), 3.92 (s, 3H), 3.27 (s, 1H), 1.80 (s, 3H). MS-ESI calcd. for [M+H]$^+$ 249, found 249.

Step 2

1,1,1-Trifluoro-2-(4-(hydroxymethyl)phenyl)propan-2-ol

Under the nitrogen gas atmosphere, lithium aluminum hydride (1.61 g, 42.3 mmol) was slowly added to a solution of methyl 4-(1,1,1-trifluoro-2-hydroxypropan-2-yl)benzoate (7.00 g, 28.2 mmol) in tetrahydrofuran (150 mL). The reaction solution was stirred at 0° C. for 3 hours. Water (1.60 mL), 15% sodium hydroxide solution (1.60 mL) and water (4.80 mL) were slowly added successively at 0° C. Filtered and the filtrate was concentrated under reduced pressure to deliver 1,1,1-trifluoro-2-(4-(hydroxymethyl)phenyl)propan-2-ol (2.40 g, yellow liquid), yield: 93%. $^1$H-NMR: (400 MHz, CDCl$_3$) δ 7.55 (d, J=8.0 Hz, 2H), 7.34 (d, J=8.0 Hz, 2H), 4.66 (s, 2H), 3.37 (s, 1H) (S, 1H), 1.75 (s, 3H). MS-ESI calcd. for [M+H]$^+$ 221, found 221.

Step 3

4-(1,1,1-Trifluoro-2-hydroxypropan-2-yl)phenyl methanesulfonate 1,1,1-Trifluoro-2-(4-(hydroxymethyl)phenyl)propan-2-ol (5.80 g, 26.3 mmol) and diisopropylethylamine (10.2 g, 79.0 mmol) were dissolved in dichloromethane (80 mL), methanesulfonyl chloride (4.53 g, 39.5 mmol) was slowly added at 0° C. The reaction solution was stirred at 0° C. for 0.5 hour. The reaction was quenched by the addition of saturated ammonium chloride aqueous solution (50 mL) and extracted with dichloromethane (20 mL×3). The organic phases were combined, washed with saturated sodium bicarbonate aqueous solution (50 mL), dried over anhydrous sodium sulfate, filtered, the filtrate was concentrated under reduced pressure and purified by silica gel column chromatography (5:1 petroleum ether/ethyl acetate, Rf=0.4) to deliver the product 4-(1,1,1-trifluoro-2-hydroxypropan-2-yl) phenyl methanesulfonate (3.45 g, yellow oil), yield: 44%. $^1$H NMR: (400 MHz, CDCl$_3$) δ 7.66 (d, J=8.0 Hz, 2H), 7.46 (d, J=8.0 Hz, 2H), 5.26 (s, 2H), 2.96 (s, 3H), 2.84 (s, 1H), 1.80 (s, 3H). MS-ESI calcd. for [M+H]$^+$ 299, found 299.

Step 4

3,7-Dimethyl-1-(4-(1,1,1-trifluoro-2-hydroxypropan-2-yl)phenyl)-1H-purine-2,6(3H,7H)-dione 4-(1,1,1-Trifluoro-2-hydroxypropan-2-yl)phenyl methanesulfonate (1.95 g, 10.8 mmol), 3,7-dimethyl-1H-purine-2,6(3H,7H)-dione (652 mg, 3.62 mmol), potassium carbonate (2.99 g, 21.6 mmol) and potassium iodide (180 mg, 1.08 mmol) were dissolved in N,N-dimethylformamide (30 mL). The reaction solution was heated to 130° C. and stirred for 3 hours. The reaction solution was cooled to room temperature, saturated brine (20 mL) was added and extracted with ethyl acetate (100 mL×3). The organic phases were combined, dried over anhydrous sodium sulfate, filtered, and the filtrate was concentrated under reduced pressure, isolated and purified by silica gel column chromatography (1:2 petroleum ether/ethyl acetate, Rf=0.3) to deliver the product 3,7-dimethyl-1-(4-(1,1,1-trifluoro-2-hydroxypropan-2-yl)phenyl)-1H-purine-2,6(3H,7H)-dione (1.27 g, white solid), yield: 31%. $^1$H NMR: (400 MHz, CDCl$_3$) δ 7.57-7.55 (m, 5H), 5.20 (s, 2H), 3.99 (s, 3H), 3.58 (s, 3H), 2.60 (s, 1H), 1.74 (s, 3H). MS-ESI calcd. for [M+H]$^+$ 383, found 383.

Embodiment 28

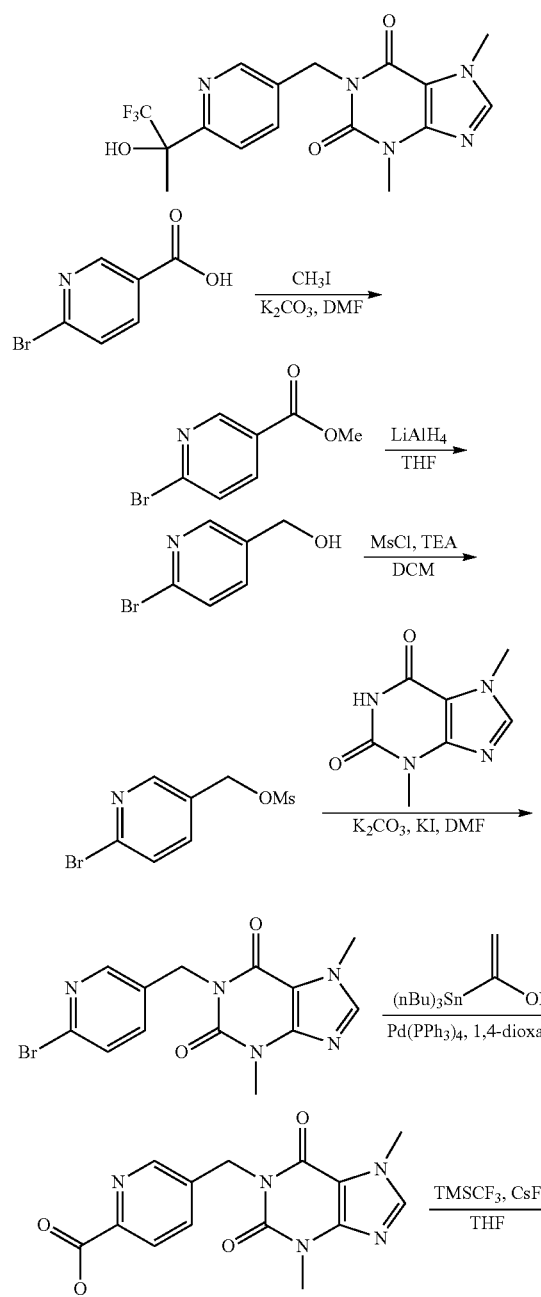

-continued

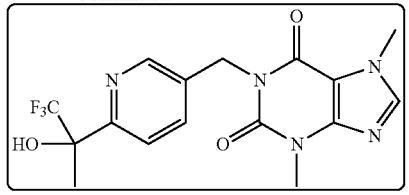

Step 1

Methyl 6-bromonicotinate

6-Bromonicotinic acid (1.00 g, 4.95 mmol) was dissolved in N,N-dimethylformamide (30 mL), iodomethane (0.703 g, 4.95 mmol) and potassium carbonate (1.03 g, 7.43 mmol) were added. The reaction solution was stirred at 20° C. for 12 hours. The reaction solution was diluted with water (100 mL) and extracted with ethyl acetate (30 mL×3), the organic phase was dried over anhydrous sodium sulfate and filtered, the filtrate was concentrated under reduced pressure, the residue was isolated and purified by silica gel column chromatography (2:1 petroleum ether/ethyl acetate, Rf=0.5) to deliver methyl 6-bromonicotinate (1.00 g, white solid), yield: 94%. MS-ESI calcd. for [M+H]$^+$ 216 and 218, found 216 and 218.

Step 2

(6-Bromopyridin-3-yl) methanol

Methyl 6-bromonicotinate (1.00 g, 4.63 mmol) was dissolved in tetrahydrofuran (20 mL), and lithium aluminum hydride (351 mg, 9.26 mmol) was added at 0° C. and reacted for 1 hour. The reaction was quenched by the addition of water (10 mL). The mixture was extracted with ethyl acetate (20 mL×3), dried over anhydrous sodium sulfate, filtered and the filtrate was concentrated under reduced pressure, the residue was isolated and purified by silica gel column chromatography (1:1 petroleum ether/ethyl acetate, Rf=0.3) to deliver (6-bromopyridin-3-yl) methanol (600 mg, yellow oil), yield: 69%. MS-ESI calcd. for [M+H]$^+$ 188 and 190, found 188 and 190.

Step 3

(6-Bromopyridin-3-yl)methyl methanesulfonate (6-Bromopyridin-3-yl)methanol (1.00 g, 5.32 mmol) and triethylamine (1.18 g, 11.6 mmol) were dissolved in dichloromethane (20 mL) and methanesulfonyl chloride (1.38 g, 12.0 mmol) was added at 0° C. The reaction solution was stirred at room temperature for 2 hours, diluted with dichloromethane (20 mL), washed with saturated sodium bicarbonate aqueous solution (30 mL×2), dried over anhydrous sodium sulfate, filtered and the filtrate was concentrated under reduced pressure, the residue was isolated and purified by silica gel column chromatography (4:1 petroleum ether/ethyl acetate, Rf=0.5) to deliver (6-bromopyridin-3-yl)methyl methanesulfonate (1.20 g, colorless oil), yield: 85%. MS-ESI calcd. for [M+H]$^+$ 266 and 268, found 266 and 268.

Step 4

1-((6-Bromopyridin-3-yl)methyl)-3,7-dimethyl-1H-purine-2,6(3H,7H)-dione (6-Bromopyridin-3-yl)methyl methanesulfonate (500 mg, 1.88 mmol) was dissolved in N,N-dimethylformamide (20 mL), 3,7-dimethyl-1H-purine-2,6(3H,7H)-dione (338 mg, 1.88 mmol), potassium carbonate (389 mg, 2.82 mmol) and potassium iodide (184 mg, 1.11 mmol) were added into the reaction solution at room temperature. The reaction solution was heated to 100° C. and reacted for 2 hours, then diluted with ethyl acetate (20 mL) and the organic phase was washed with saturated sodium bicarbonate aqueous solution (20 mL×2), dried over anhydrous sodium sulfate, filtered and the filtrate was concentrated under reduced pressure, the residue was isolated and purified by silica gel column chromatography (1:1 petroleum ether/ethyl acetate, Rf=0.3) to deliver 1-((6-bromopyridin-3-yl)methyl)-3,7-dimethyl-1H-purine-2,6(3H,7H)-dione (300 mg, yellow solid), yield: 46%. MS-ESI calcd. for [M+H]+ 350 and 352, found 350 and 352.

Step 5

1-((6-Acetylpyridin-3-yl)methyl)-3,7-dimethyl-1H-purine-2,6(3H,7H)-dione 1-((6-Bromopyridin-3-yl)methyl)-3,7-dimethyl-1H-purine-2,6(3H,7H)-dione (2.00 g, 5.71 mmol) was dissolved in 1,4-dioxane (50 mL), tributyl(1-ethoxyvinyl) stannane (8.25 g, 22.8 mmol) and tetrakis(triphenylphosphine)palladium (329 mg, 0.285 mmol) were added into the reaction solution at room temperature. The reaction solution was heated to 120° C. and stirred for 2 hours. The reaction solution was cooled to room temperature, diluted with ethyl acetate (70 mL), washed with saturated sodium bicarbonate aqueous solution (20 mL) (30 mL×2), dried over anhydrous sodium sulfate, filtered, concentrated, the residue was isolated and purified by silica gel column chromatography (3:1 petroleum ether/ethyl acetate, Rf=0.3) to deliver 1-((6-acetylpyridin-3-yl)methyl)-3,7-dimethyl-1H-purine-2,6(3H,7H)-dione (1.00 g, yellow solid), yield: 56%. $^1$H NMR: (400 MHz, CDCl$_3$) δ 8.83 (s, 1H), 8.00-7.98 (m, 1H), 7.95-7.93 (m, 1H), 7.54 (s, 1H), 5.27 (s, 2H) 4.01 (s, 3H), 3.59 (s, 3H), 2.71 (s, 3H). MS-ESI calcd. for [M+H]+ 314, found 314.

Step 6

3,7-Dimethyl-1-((6-(1,1,1-trifluoro-2-hydroxypropan-2-yl)pyridin-3-yl)-1H-purine-2,6(3H,7H)-dione 1-((6-Acetylpyridin-3-yl)methyl)-3,7-dimethyl-1H-purine-2,6(3H,7H)-dione (150 mg, 0.478 mmol) was dissolved in tetrahydrofuran (30 mL), trifluoromethyltrimethylsilane (102 mg, 0.718 mmol) and cesium fluoride (73.0 mg, 0.478 mmol) were added at room temperature. The reaction solution was stirred at room temperature for 12 hours, tetrabutylammonium fluoride (50.0 mg, 0.207 mmol) was added, after stirring at room temperature for 30 minutes, the reaction mixture was diluted by ethyl acetate (20 mL) and the organic phase was washed with saturated sodium bicarbonate aqueous solution (20 mL×2), dried over anhydrous sodium sulfate, filtered and the filtrate was concentrated under reduced pressure and the residue was purified by high performance liquid chromatography to deliver 3,7-dimethyl-1-((6-(1,1,1-trifluoro-2-hydroxypropan-2-yl)pyridin-3-yl)-1H-purine-2,6(3H,7H)-dione (50 mg, white solid), yield: 27%. $^1$H NMR: (400 MHz, CDCl$_3$) δ 8.76 (s, 1H), 7.99 (d, J=8.0 Hz, 1H), 7.53 (s, 1H), 7.44 (d, J=8.0 Hz, 1H) 5.23 (s, 2H), 3.99 (s, 3H), 3.58 (s, 3H), 1.68 (s, 3H). MS-ESI calcd. for [M+H]+ 384, found 384.

Embodiment 29

3,7-Dimethyl-1-(([[5-(2,2,2-trifluoro-1-hydroxy-1-methyl-ethyl)-2-pyridyl]methyl]-dione

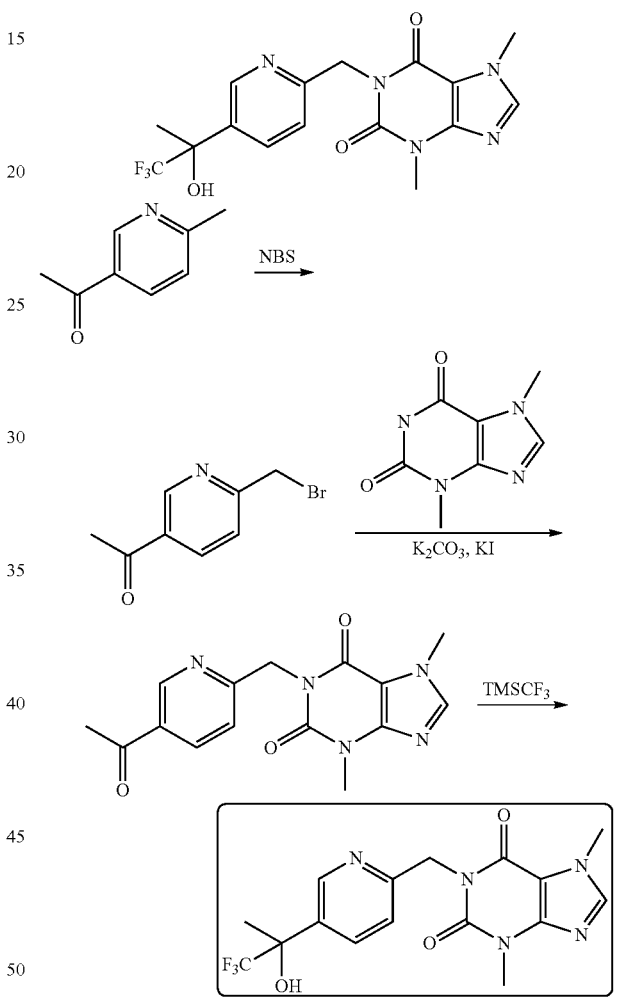

Step 1

1-(6-(Bromomethyl)-3-pyridyl)ethanone 1-(6-Methyl-3-pyridyl)ethanone (500 mg, 3.70 mmol), N-bromosuccinimide (658 mg, 3.70 mmol), azodiisobutyronitrile (182 mg, 1.11 mmol) were dissolved in carbon tetrachloride (20 mL), which was reacted at 90° C. for 12 hours. The reaction was quenched by the addition of saturated sodium thiosulfate aqueous solution (30 mL). The mixture was extracted with dichloromethane (10 mL×3), dried over anhydrous sodium sulfate, filtered and the filtrate was concentrated under reduced pressure to deliver 1-[6-

(bromomethyl)-3-pyridyl]ethanone (125 mg, yellow oil), yield: 16%. MS-ESI calcd. for [M+H]+ 214, 216, found 214,216.

Step 2

1-((5-Acetyl-2-pyridyl)methyl)-3,7-dimethylpurine-2,6-dione 1-(6-(Bromomethyl)-3-pyridyl)ethanone (100 mg, 0.467 mmol), 3,7-dimethylpurine-2,6-dione (84.2 mg, 0.467 mmol), potassium iodide (7.70 mg, 0.0467 mmol) and potassium carbonate (194 mg, 1.40 mmol) were dissolved in N,N-dimethylformamide (10 mL). The reaction solution was heated to 120° C. and stirred for 3 hours. The reaction mixture was cooled to room temperature, filtered and the filtrate was concentrated under reduced pressure, the residue was isolated and purified by preparative TLC plate (ethyl acetate, Rf=0.3) to deliver 1-((5-acetyl-2-pyridyl)methyl)-3,7-dimethylpurine-2,6-dione (50.0 mg, yellow solid), yield: 34%. MS-ESI calcd. for [M+H]+ 314, found 314.

Step 3

3,7-Dimethyl-1-[[5-(2,2,2-trifluoro-1-hydroxy-1-methyl-ethyl)-2-pyridyl]methyl]purine-2,6-dione 1-((5-Acetyl-2-pyridyl)methyl)-3,7-dimethylpurine-2,6-dione (50.0 mg, 0.159 mmol), cesium fluoride (24.2 mg, 0.159 mmol) were dissolved in tetrahydrofuran (10 mL), trimethyl-trifluoromethyl-silane (113 mg, 0.798 mmol) was added at room temperature and stirred for 12 hours. The reaction was quenched by the addition of water (20 mL). The resulting mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver 3,7-dimethyl-1-[[5-(2,2,2-trifluoro-1-hydroxy-1-methyl-ethyl)-2-pyridyl]methyl]purine-2,6-dione (10.0 mg, yellow solid), yield: 16%. 1H NMR: (400 MHz, Methanol-d4) δ 8.96 (s, 1H), 8.75 (d, J=8.0 Hz, 1H), 8.06 (d, J=8.0 Hz, 1H), 7.97 (s, 1H), 5.55 (s, 2H), 4.00 (s, 3H), 3.57 (s, 3H), 1.86 (s, 3H). MS-ESI calcd. for [M+H]+ 384, found 384.

Embodiment 30

3,7-Dimethyl-1-((5-(1,1,1-trifluoro-2-hydroxypropan-2-yl)pyrazin-2-yl)-purine-2,6(3H,7H)-dione

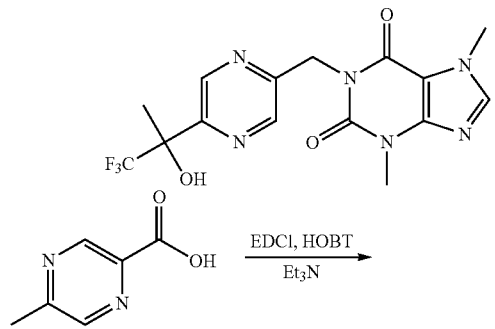

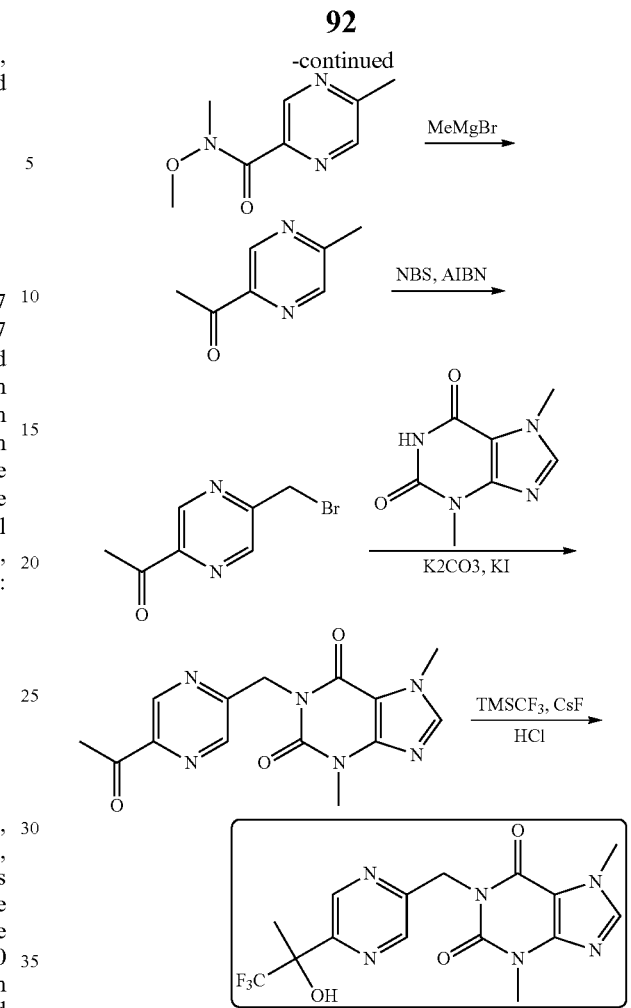

Step 1

N-Methoxy-N,5-dimethylpyrazine-2-carboxamide

5-Methylpyrazine-2-carboxylic acid (2.00 g, 14.5 mmol), 1-hydroxybenzotriazole (391 mg, 2.90 mmol), 1-(3-dimethylaminopropyl)-3-ethylcarbodiimide hydrochloride (1.69 g, 17.4 mmol) were dissolved in anhydrous dichloromethane (10 mL) and trichloromethane (30 mL), under the nitrogen gas atmosphere, triethylamine (1.76 g, 17.4 mmol) was slowly added at 0° C. and the reaction mixture was stirred at 25° C. for 12 hours. The reaction was quenched by the addition of water (50 mL). The resulting mixture was extracted with ethyl acetate (50 mL×3) and the organic phases were combined, dried over anhydrous sodium sulfate, filtered and the filtrate was concentrated under reduced pressure, the residue was purified by silica gel column chromatography (20:1 petroleum ether/ethyl acetate, Rf=0.1) to deliver the N-methoxy-N,5-dimethylpyrazine-2-carboxamide (2.00 g, yellow oil), yield: 76%. 1H NMR: (400 MHz, CDCl3) δ 8.80 (s, 1H), 8.45 (s, 1H), 3.73 (s, 3H), 3.40 (s, 3H), 2.61 (s, 3H).

Step 2

1-(5-Methylpyrazin-2-yl)ethanone

N-methoxy-N,5-dimethylpyrazine-2-carboxamide (1.50 g, 8.28 mmol) was dissolved in tetrahydrofuran (30 mL), methylmagnesium bromide (3 M ether solution, 13.3 mL, 39.9 mmol) was added at 0° C., followed by stirring at 25° C. for 1 hour. The mixture was cooled to 0° C. and the reaction was quenched by the addition of water (10 mL). The mixture was extracted with ethyl acetate (30 mL×3), dried over anhydrous sodium sulfate and concentrated under reduced pressure. The residue was purified by silica gel column chromatography (20:1 petroleum ether/ethyl acetate, Rf=0.2) to deliver 1-(5-methylpyrazin-2-yl)ethanone (700 mg, yellow oil), yield: 62%. MS-ESI calcd. for [M+H]+ 137, found 137.

Step 3

1-(5-(Bromomethyl)pyrazin-2-yl)ethanone 1-(5-Methylpyrazin-2-yl)ethanone (700 mg, 5.14 mmol) was dissolved in carbon tetrachloride (20 mL), and then azobisisobutyronitrile (169 mg, 1.03 mmol) and N-bromosuccinimide (1.14 g, 6.43 mmol) were added. The reaction solution was reacted at 100° C. under the nitrogen gas atmosphere for 5 hours. The reaction mixture was directly filtered and concentrated under reduced pressure, the residue was purified by silica gel column chromatography (20:1 petroleum ether/ethyl acetate, Rf=0.5) to deliver 1-(5-(bromomethyl)pyrazine-2-yl)ethanone (300 mg, yellow oil), yield: 27%. MS-ESI calcd. for [M+H]+ 215 and 217, found 215 and 217.

Step 4

1-((5-Acetylpyrazin-2-yl)methyl)-3,7-dimethyl-1H-purine-2,6(3H,7H)-dione 1-(5-(bromomethyl)pyrazin-2-yl)ethanone (300 mg, 1.40 mmol), 3,7-dimethyl-1H-purine-2,6(3H,7H)-dione (251 mg, 1.40 mmol), potassium iodide (23.2 mg, 0.140 mmol) and potassium carbonate (578 mg, 4.19 mmol) were dissolved in anhydrous N,N-dimethylformamide (20 mL). The reaction solution was heated to 120° C. and reacted for 3 hours. The reaction solution was cooled to 20° C., filtered, and the filtrate was concentrated under reduced pressure, the residue was purified by silica gel column chromatography (ethyl acetate, Rf=0.3) to deliver 1-((5-acetylpyrazin-2-yl)methyl)-3,7-dimethyl-1H-purine-2,6(3H, 7H)-dione (300 mg, yellow solid), yield: 68%. MS ESI calcd. for [M+H]+ 315, found 315.

Step 5

3,7-Dimethyl-1-((5-(1,1,1-trifluoro-2-hydroxypropan-2-yl)pyrazin-2-yl)-1H-purine-2,6(3H, 7H)-dione 1-((5-Acetylpyrazin-2-yl)methyl)-3,7-dimethyl-1H-purine-2,6(3H,7H)-dione (300 mg, 0.954 mmol), cesium fluoride (14.5 mg, 0.0954 mmol) were dissolved in anhydrous tetrahydrofuran (10 mL). Then trimethylsilyl trifluoromethyl (407 mg, 2.86 mmol) was added. Under the nitrogen gas atmosphere, the reaction solution was reacted at 25° C. for 2 hours. Then hydrochloric acid (4 N, 4 mL) was added. Under the nitrogen gas atmosphere, the mixture was reacted at room temperature for 1 hour. The reaction was quenched by the addition of saturated sodium bicarbonate aqueous solution (10 mL), the resulting mixture was extracted with ethyl acetate (10×3 mL), the organic phase was dried over anhydrous sodium sulfate, filtered, and the filtrate was concentrated under reduced pressure, the residue was purified by silica gel column chromatography (1:1 petroleum ether/ethyl acetate, Rf=0.3) to deliver 3,7-dimethyl-1-((5-(1,1,1-trifluoro-2-hydroxypropan-2-yl)pyrazin-2-yl)-1H-purine-2,6(3H, 7H)-dione (100 mg, white solid), yield: 40%. 1H NMR: (400 MHz, Methanol-d4) δ 8.85 (s, 1H), 8.65 (s, 1H), 7.92 (s, 1H), 5.40 (s, 2H), 3.99 (s, 3H), 3.56 (s, 3H), 1.78 (s, 3H). MS ESI calcd. for [M+H]+ 385, found 385.

Embodiment 31

1-((3-(1,1,1,3,3,3-Hexafluoro-2-hydroxypropan-2-yl)isoxazol-5-yl)-3,7-dimethyl-1H-purine-2,6(3H, 7H)-dione

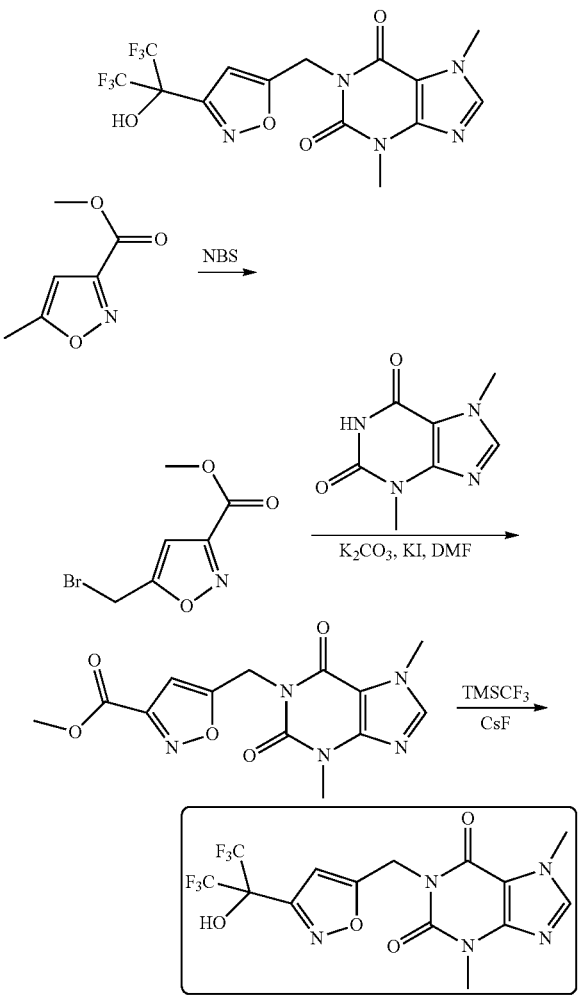

Step 1

Methyl 5-(bromomethyl)isoxazole-3-carboxylate

Methyl 5-methylisoxazole-3-carboxylic acid ethyl ester (5.00 g, 35.4 mmol), N-bromosuccinimide (6.31 g, 35.4 mmol), benzoyl peroxide (858 mg, 3.54 mmol) were dissolved in carbon tetrachloride (20 mL), which was then reacted at 80° C. for 12 hours. The reaction was quenched by the addition of saturated sodium thiosulfate aqueous solution (30 mL). The mixture was extracted with dichloromethane (20 mL×3), dried over anhydrous sodium sulfate, filtered, and the filtrate was concentrated under reduced pressure, the residue was purified by silica gel column chromatography (3:1 petroleum ether/ethyl acetate, Rf=0.5) to deliver methyl 5-(bromomethyl)isoxazole-3-carboxylic acid ethyl ester (2.00 g, yellow oil), yield: 26%. $^1$H NMR: (400 MHz, Methanol-$d_4$) δ 6.88 (s, 1H), 4.73 (s, 2H), 3.97 (s, 3H). MS-ESI calcd. for [M+H]$^+$ 220, 222, found 220, 222.

Step 2

Methyl 5-((3,7-dimethyl-2,6-dioxo-2,3,6,7-tetrahydro-1H-purin-1-yl)methyl)carboxylate Ethyl 5-(bromomethyl) isoxazole-3-carboxylate (2.00 g, 9.09 mmol), 3,7-dimethyl-1H-purine-2,6-(3H,7H)-dione (1.64 g, 9.09 mmol), potassium iodide (151 mg, 0.909 mmol) and potassium carbonate (2.51 g, 18.2 mmol) were dissolved in N,N-dimethylformamide (50 mL). The reaction solution was heated to 120° C. and stirred for 3 hours. Then the reaction mixture was cooled to room temperature, filtered, and the filtrate was concentrated under reduced pressure, the residue was isolated and purified by silica gel column chromatography (ethyl acetate, Rf=0.4) to deliver methyl 5-((3,7-dimethyl-2,6-dioxo-2,3,6,7-tetrahydro-1H-purin-1-yl)methyl) carboxylate (1.70 g, yellow solid), yield: 59%. $^1$H NMR: (400 MHz, Methanol-$d_4$) δ 8.06 (s, 1H), 6.82 (s, 1H), 5.22 (s, 2H), 3.87 (s, 3H), 3.83 (s, 3H), 3.45 (s, 3H). MS-ESI calcd. for [M+H]$^+$ 320, found 320.

Step 3

1-((3-(1,1,1,3,3,3-Hexafluoro-2-hydroxypropan-2-yl)isoxazol-5-yl)-3,7-dimethyl-1H-purine-2,6(3H,7H)-dione Methyl 5-((3,7-dimethyl-2,6-dioxo-2,3,6,7-tetrahydro-1H-purin-1-yl)methyl) carboxylate (200 mg, 0.626 mmol), cesium fluoride (95.0 mg, 0.626 mmol) were dissolved in tetrahydrofuran (10 mL), trimethyl trifluoromethylsilane (445 mg, 3.13 mmol) was added at room temperature and the resulting mixture was stirred for 12 hours. 1 N hydrochloric acid (10 mL) was added and the resulting mixture was stirred at room temperature for 1 hour. The reaction was quenched by the addition of saturated sodium bicarbonate aqueous solution (50 mL). The mixture was extracted with ethyl acetate (10 mL×3). The organic phases were combined, washed with saturated brine (30 mL), dried over anhydrous sodium sulfate, filtered and the filtrate was concentrated under reduced pressure. The residue was purified by preparative high performance liquid chromatography to deliver 1-((3-(1,1,1,3,3,3-hexafluoro-2-hydroxypropan-2-yl)isoxazol-5-yl)-3,7-dimethyl-1H-purine-2,6(3H,7H)-dione (10.0 mg, yellow solid), yield: 4%. $^1$H NMR: (400 MHz, Methanol-$d_4$) δ 7.95 (s, 1H), 6.52 (s, 1H), 5.37 (s, 2H), 4.00 (s, 3H), 3.57 (s, 3H). MS-ESI calcd. for [M+H]$^+$ 428, found 428.

Embodiment 32

3,7-Dimethyl-1-((3-(1,1,1-trifluoro-2-hydroxypropan-2-yl)isoxazol-5-yl)-1H-purine-2,6-(3H, 7H)-dione

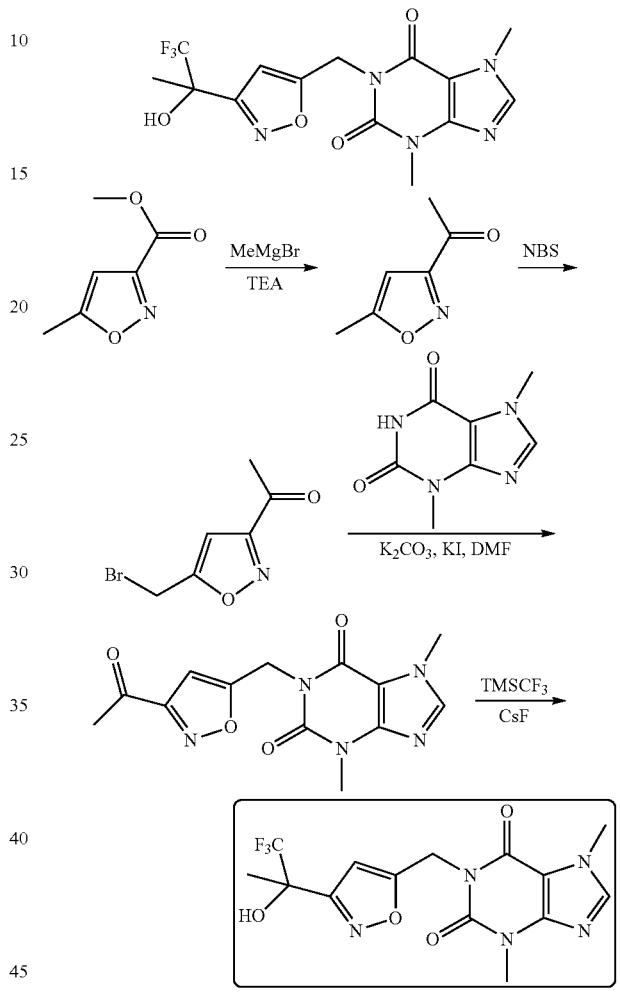

Step 1

1-(5-Methylisoxazol-3-yl)ethanone

Methyl 5-methylisoxazole-3-carboxylate (5.00 g, 35.4 mmol) and triethylamine (21.5 g, 213 mmol) were dissolved in tetrahydrofuran (80 mL), methylmagnesium bromide (3 M ether solution, 35 mL, 105 mmol) was added at 0° C., the resulting mixture was reacted for 3 hours. The reaction was quenched by the addition of saturated ammonium chloride aqueous solution (30 mL). The mixture was extracted with ethyl acetate (30 mL×3), dried over anhydrous sodium sulfate, filtered, and the filtrate was concentrated under reduced pressure, the residue was purified by silica gel column chromatography (3:1 petroleum ether/ethyl acetate, Rf=0.7) to deliver 1-(5-methylisoxazol-3-yl)ethanone (1.00 g, yellow oil), yield: 23%. $^1$H NMR: (400 MHz, Methanol-$d_4$) δ 6.39 (s, 1H), 2.58 (s, 3H), 2.49 (s, 3H). MS-ESI calcd. for [M+H]$^+$ 126, found 126.

Step 2

1-(5-(Bromomethyl)isoxazol-3-yl)ethanone 1-(5-Methylisoxazol-3-yl)ethanone (100 mg, 0.799 mmol), N-bromosuccinimide (142 mg, 0.799 mmol), benzoyl peroxide (19.3 mg, 0.0800 mmol) were dissolved in carbon tetrachloride (10 mL), which was then reacted at 90° C. for 12 hours. The reaction was quenched by the addition of saturated sodium thiosulfate solution (30 mL). The mixture was extracted with dichloromethane (10 mL×3), dried over anhydrous sodium sulfate, filtered and the filtrate was concentrated under reduced pressure to deliver 1-(5-(bromomethyl)isoxazol-3-yl)ethanone (150 mg, yellow oil), yield: 93%. MS-ESI calcd/for [M+H]$^+$ 204 and 206, found 204 and 206.

Step 3

1-((3-Acetylisoxazol-5-yl)methyl)-3,7-dimethyl-1H-purine-2,6-(3H,7H)-dione 1-(5-(Bromomethyl)isoxazol-3-yl)ethanone (150 mg, 0.735 mmol), 3,7-dimethyl-1H-purine-2,6-(3H,7H)-dione (132 mg, 0.735 mmol), potassium iodide (61.0 mg, 0.367 mmol) and potassium carbonate (305 mg, 2.21 mmol) were dissolved in N,N-dimethylformamide (10 mL). The reaction solution was heated to 120° C. and stirred for 3 hours. The reaction mixture was cooled to room temperature, filtered, the filtrate was concentrated under reduced pressure, the residue was isolated and purified by preparative TLC plate (ethyl acetate, Rf=0.3) to deliver 1-((3-acetylisoxazol-5-yl)methyl)-3,7-dimethyl-1H-purine-2,6-(3H,7H)-dione (50.0 mg, yellow solid), yield: 22%. MS-ESI calcd. for [M+H]$^+$ 304, found 304.

Step 4

3,7-Dimethyl-1-((3-(1,1,1-trifluoro-2-hydroxypropan-2-yl)isoxazol-5-yl)-1H-purine-2,6-(3H, 7H)-dione 1-[(3-Acetylisoxazol-5-yl)methyl]-3,7-dimethyl-purine-2,6-(3H,7H)-dione (50.0 mg, 0.164 mmol), cesium fluoride (25.0 mg, 0.164 mmol) was dissolved in tetrahydrofuran (10 mL), trimethyl trifluoromethylsilane (70.3 mg, 0.494 mmol) was added at room temperature and the resulting mixture was stirred for 12 hours. 1 N hydrochloric acid (10 mL) was added in and the resulting mixture was stirred at room temperature for 1 hour, the reaction was quenched by the addition of saturated sodium bicarbonate aqueous solution (50 mL). The mixture was then extracted with ethyl acetate (10 mL×3). The organic phases were combined, washed with saturated brine, dried over anhydrous sodium sulfate, filtered and the filtrate was concentrated under reduced pressure. And the residue was purified by preparative high performance liquid chromatography to deliver 3,7-dimethyl-1-((3-(1,1,1-trifluoro-2-hydroxypropan-2-yl)isoxazol-5-yl)-1H-purine-2,6-(3H, 7H)-dione (22.0 mg, yellow solid), yield: 36%. $^1$H NMR: (400 MHz, Methanol-d$_4$) δ 7.98 (s, 1H), 6.48 (s, 1H), 5.33 (s, 2H), 4.01 (s, 3H), 3.57 (s, 3H), 1.71 (s, 3H). MS-ESI calcd. for [M+H]$^+$ 374, found 374.

Step 33

3,7-Dimethyl-1-((2-(1,1,1-trifluoro-2-hydroxypropan-2-yl)thiazol-4-yl)methyl)-1H-purine-2, 6-(3H, 7H)-dione

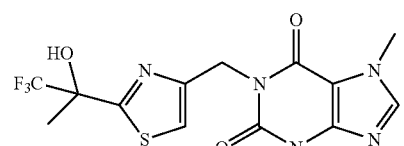

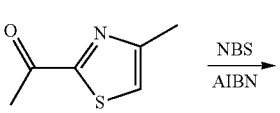

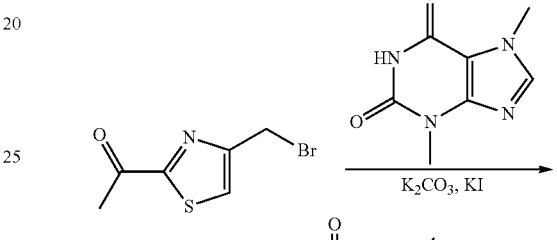

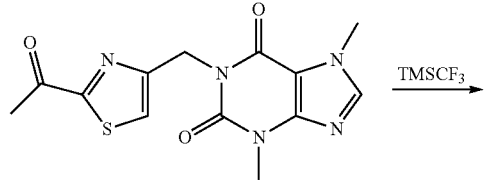

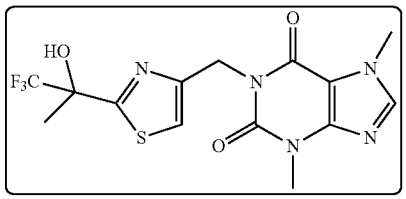

Step 1

1-(4-(Bromomethyl)thiazol-2-yl)ethanone 1-(4-Methylthiazol-2-yl)ethanone (200 mg, 1.42 mmol), N-bromosuccinimide (252 mg, 1.42 mmol), and azobisisobutyronitrile (46.6 mg, 0.284 mmol) were dissolved in carbon tetrachloride (20 mL), which was then reacted at 80° C. for 12 hours. The reaction was quenched by the addition of saturated sodium thiosulfate aqueous solution (30 mL). The mixture was extracted with dichloromethane (10 mL×3), dried over anhydrous sodium sulfate, filtered and the filtrate was concentrated under reduced pressure to deliver 1-(4-(bromomethyl)thiazol-2-yl)ethanone (200 mg, yellow oil), yield: 64%. $^1$H NMR: (400 MHz, Methanol-d$_4$) δ 7.97 (s, 1H), 4.73 (s, 2H), 2.66 (s, 3H). MS-ESI calcd. for [M+H]$^+$ 220, 222, found 220, 222.

Step 2

1-((2-Acetylthiazol-4-yl)methyl)-3,7-dimethyl-1H-purine-2,6-(3H, 7H)-dione 1-(4-(Bromomethyl)thiazol-2-yl)ethanone (100 mg, 0.454 mmol), 3,7-dimethyl-1H-purine-2,6-(3H,7H)-dione (81.9 mg, 0.454 mmol), potassium iodide (7.50 mg, 0.0454 mmol) and potassium carbonate (125 mg, 0.908 mmol) were dissolved in N,N-dimethylformamide (10 mL). The reaction solution was heated to 120° C. and stirred for 3 hours, then cooled to room temperature, filtered, and the filtrate was concentrated under reduced pressure and purified by preparative TLC plate (ethyl acetate, Rf=0.3) to deliver 1-((2-acetylthiazol-4-yl)methyl)-3,7-dimethyl-1H-purine-2,6-(3H,7H)-dione (80.0 mg, yellow solid), yield: 55%. $^1$H NMR: (400 MHz, Methanol-$d_4$) δ 7.92 (s, 1H), 7.73 (s, IH), 5.38 (s, 2H), 4.00 (s, 3H), 3.57 (s, 3H) 2.64 (s, 3H). MS-ESI calcd. for [M+H]$^+$ 320, found 320.

Step 3

3,7-Dimethyl-1-((2-(1,1,1-trifluoro-2-hydroxypropan-2-yl)thiazol-4-yl)-methyl-1H-purine-2, 6-(3H, 7H)-dione 1-((2-Acetylthiazol-4-yl)methyl)-3,7-dimethyl-1H-purine-2,6-(3H,7H)-dione (200 mg, 0.626 mmol), cesium fluoride (95.0 mg, 0.626 mmol) were dissolved in tetrahydrofuran (10 mL), trimethyl-trifluoromethyl-silane (267 mg, 1.88 mmol) was added at room temperature and stirred for 12 hours. The reaction was quenched by the addition of water (20 mL), the resulting mixture was extracted with ethyl acetate (10 mL×3). The organic phases were combined, washed with saturated brine, dried over anhydrous sodium sulfate, filtered and the filtrate was concentrated under reduced pressure. And the residue was purified by preparative high performance liquid chromatography to deliver 3,7-dimethyl-1-((2-(1,1,1-trifluoro-2-hydroxypropan-2-yl)thiazol-4-yl)-methyl-1H-purine-2,6-(3H,7H)-dione (100 mg, yellow solid), yield: 41%. $^1$H NMR: (400 MHz, Methanol-$d_4$) δ 8.10 (s, 1H), 7.33 (s, 1H), 5.32 (s, 2H), 4.03 (s, 3H), 3.57 (s, 3H), 1.80 (s, 3H). MS-ESI calcd. for [M+H]$^+$ 390, found 390.

Embodiment 34

3,7-Dimethyl-1-((5-methyl-2-(1,1,1-trifluoro-2-hydroxypropan-2-yl)thiazol-4-yl)-methyl-1H-purine-2, 6-(3H,7H)-dione

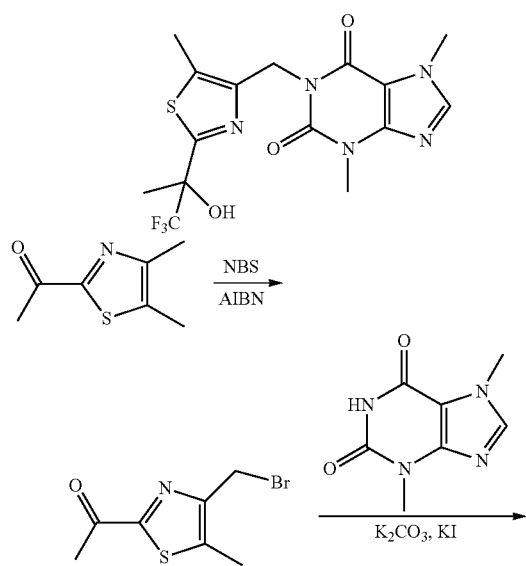

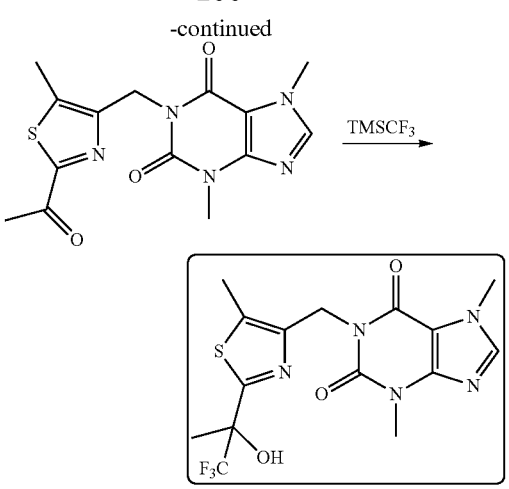

Step 1

1-(4-(Bromomethyl)-5-methylthiazol-2-yl)ethanone 1-(4,5-Dimethylpyridin-2-yl)ethanone (200 mg, 1.29 mmol), N-bromosuccinimide (229 mg, 1.29 mmol), azobisisobutyronitrile (21.1 mg, 0.129 mmol) were dissolved in carbon tetrachloride (10 mL), which was then reacted at 80° C. for 12 hours. The reaction was quenched by the addition of saturated sodium thiosulfate aqueous solution (30 mL). The mixture was extracted with dichloromethane (10 mL×3), dried over anhydrous sodium sulfate, filtered and the filtrate was concentrated under reduced pressure to deliver 1-(4-(bromomethyl)-5-methylthiazol-2-yl)ethanone (200 mg, yellow oil), yield: 66%. $^1$H NMR: (400 MHz, Methanol-$d_4$) δ 4.88 (s, 2H), 2.65 (s, 3H), 2.47 (s, 3H). MS-ESI calcd. for [M+H]$^+$ 234, 236, found 234, 236.

Step 2

1-((2-Acetyl-5-methylthiazol-4-yl)methyl)-3,7-dimethyl-1H-purine-2,6-(3H,7H)-dione 1-(4-(Bromomethyl)-5-methylthiazol-2-yl)ethanone (500 mg, 0.854 mmol), 3,7-dimethyl-1H-purine-2,6-(3H,7H)-dione (154 mg, 0.854 mmol), potassium iodide (14.0 mg, 0.0854 mmol) and potassium carbonate (354 mg, 2.56 mmol) were dissolved in N,N-dimethylformamide (10 mL). The reaction solution was heated to 120° C. and stirred for 3 hours. Then the reaction mixture was cooled to room temperature, filtered and the filtrate was concentrated under reduced pressure, the residue was isolated and purified by preparative TLC plate (ethyl acetate, Rf=0.3) to deliver 1-((2-acetyl-5-methylthiazol-4-yl)methyl)-3,7-dimethyl-1H-purine-2,6-(3H,7H)-dione (200 mg, yellow solid), yield: 70%. $^1$H NMR: (400 MHz, Methanol-$d_4$) δ 7.90 (s, 1H), 5.35 (s, 2H), 4.00 (s, 3H), 3.55 (s, 3H), 2.66 (s, 3H), 2.61 (s, 3H). MS-ESI calcd. for [M+H]$^+$ 334, found 334.

Step 3

3,7-Dimethyl-1-((5-methyl-2-(1,1,1-trifluoro-2-hydroxypropan-2-yl)thiazol-4-yl)methyl)-1H-purine-2, 6-(3H,7H)-dione 1-((2-Acetyl-5-methylthiazol-4-yl)methyl)-3,7-dimethyl-1H-purine-2,6-(3H,7H)-dione (80.0 mg, 0.240 mmol), cesium fluoride (18.2 mg, 0.120 mmol) was dissolved in tetrahydrofuran (10 mL), trimethyl-trifluoromethyl-silane (102 mg, 0.720 mmol) was added at room temperature and stirred for 12 hours. The reaction was quenched by the addition of water (20 mL), extracted with ethyl acetate (10 mL×3). The organic phases were combined, washed with saturated brine, dried over anhydrous sodium sulfate, filtered and the filtrate was concentrated under reduced pressure. And the residue was purified by preparative high performance liquid chromatography to deliver 3,7-dimethyl-1-((5-methyl-2-(1,1,1-trifluoro-2-hydroxypropan-2-yl)thiazol-4-yl)methyl)-1H-purine-2,6-(3H,7H)-dione (35.0 mg, yellow solid), yield: 36%. $^1$H NMR: (400 MHz, Methanol-$d_4$) δ 8.27 (s, 1H), 5.36 (s, 2H), 4.06 (s, 3H), 3.57 (s, 3H), 2.73 (s, 3H), 1.90 (s, 3H). MS-ESI calcd. for [M+H]$^+$ 404, found 404.

Embodiment 35

3,7-Dimethyl-1-((2-(1,1,1-trifluoro-2-hydroxypropan-2-yl)methyl)-1H-purine-2, 6-(3H, 7H)-dione

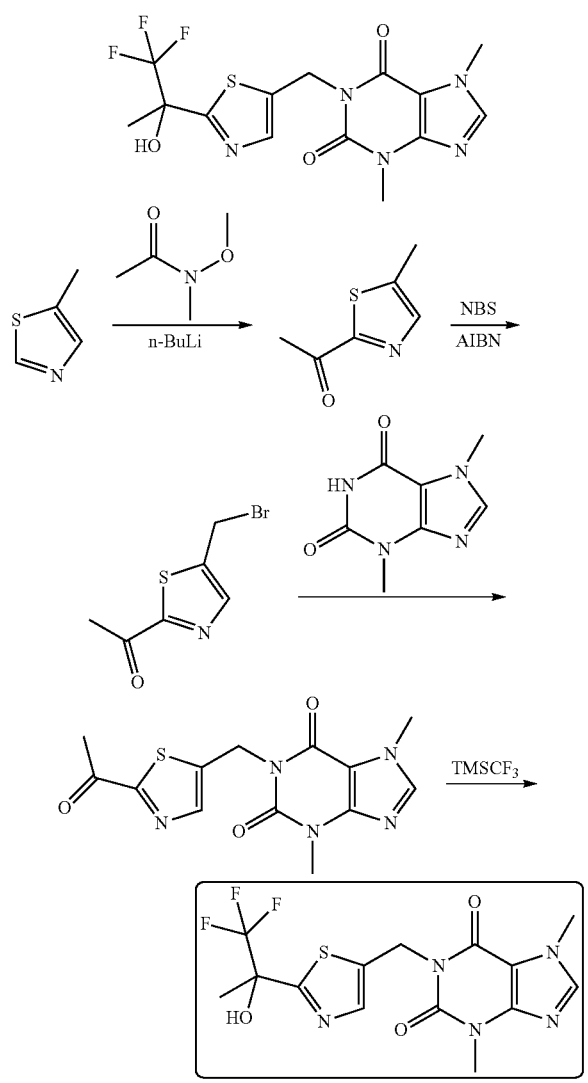

Step 1

1-(5-Methylthiazol-2-yl)ethyl cyclohexanone

5-Methylthiazole (2.00 g, 20.2 mmol) was dissolved in tetrahydrofuran (50 mL), under the nitrogen gas atmosphere, n-butyllithium (2.5 M tetrahydrofuran solution, 9.68 mL, 24.2 mmol) was slowly added dropwise at −78° C. The reaction was stirred at −78° C. for 0.5 hour and a solution of N-methoxy-N-methylacetamide (2.50 g, 24.2 mmol) in tetrahydrofuran (1 mL) was slowly added dropwise. The reaction solution was warmed to 0° C. and stirred for 1.5 hours. Water (10 mL) was slowly added into the reaction solution at 0° C. and the resulting mixture was extracted with ethyl acetate (30 mL×3). The organic phases were combined, dried over anhydrous sodium sulphate, filtered and distilled under reduced pressure. The resulting product was purified by high performance preparative plates (1:1 petroleum ether/ethyl acetate, Rf=0.7) to deliver the product 1-(5-methylthiazol-2-yl)ethyl cyclohexanone (1.45 g, yellow solid), yield: 51%. $^1$H NMR: (400 MHz, Methanol-$d_4$) δ 7.73 (s, 1H), 2.61 (s, 3H), 2.57 (s, 3H). MS-ESI calcd. for [M+H]$^+$ 142, found 142.

Step 2

1-(5-(Bromomethyl)thiazol-2-yl)ethyl cyclohexanone 1-(5-Methylthiazol-2-yl)ethyl cyclohexanone (200 mg, 1.42 mmol) and azoisobutyronitrile (2.33 mg, 0.0142 mmol) were dissolved in chloroform (5 mL), bromosuccinimide (252 mg, 1.42 mmol) was added at room temperature. The reaction was heated to 78° C. and stirred for 16 hours. The reaction solution was cooled to room temperature, water (30 mL) was slowly added and the resulting mixture was extracted with chloroform (30 mL×3). The organic phases were combined and dried over anhydrous sodium sulphate, filtered and the filtrate was concentrated under reduced pressure to give the crude product 1-(5-(bromomethyl)thiazol-2-yl)ethyl cyclohexanone (290 mg, yellow oil). MS-ESI calcd. for [M+H]$^+$ 220 and 222, found 220 and 222.

Step 3

1-((2-Acetylthiazol-5-yl)methyl)-3,7-dimethyl-1H-purine-2,6-(3H,7H)-dione 1-(5-(Bromomethyl)thiazol-2-yl)ethyl cyclohexanone (290 mg, 1.05 mmol), 3,7-dimethyl-1H-purine-2,6-(3H,7H)-dione (284 mg, 1.58 mmol) and potassium iodide (17.5 mg, 0.105 mmol) were dissolved in N,N-dimethylformamide (5 mL), potassium carbonate (437 mg, 3.16 mmol) was added and the resulting mixture was reacted at 130° C. for 2.5 hours. The reaction solution was cooled to room temperature, filtered and the filtrate was concentrated under reduced pressure, the resulting product was purified by a highly performance preparative plate (ethyl acetate, Rf=0.4) to deliver the product 1-((2-acetylthiazol-5-yl)methyl)-3,7-dimethyl-1H-purine-2,6-(3H,7H)-dione (292 mg, yellow solid), yield: 87%. MS-ESI calcd. for [M+H]$^+$ 320, found 320.

Step 4

3,7-Dimethyl-1-((2-(1,1,1-trifluoro-2-hydroxypropan-2-yl)thiazol-5-yl)methyl)-1H-purine-2, 6-(3H, 7H)-dione 1-((2-Acetylthiazol-5-yl)methyl)-3,7-dimethyl-1H-purine-2,6-(3H,7H)-dione (280 mg, 0.438 mmol) and cesium fluoride (6.66 mg, 0.0438 mmol) were dissolved in tetrahydrofuran (6 mL), under the nitrogen gas atmosphere, trifluoromethyltrimethylsilane (75.0 mg, 0.500 mmol) was added slowly. The reaction mixture was stirred at 25° C. for 1.5 hours. After adding 4 N hydrochloric acid aqueous solution (0.2 mL) and stirring for half an hour at room temperature, the pH value of the reaction mixture was adjusted to 7 with saturated sodium bicarbonate aqueous solution (10 mL), water (20 mL) was added and the mixture was extracted with ethyl acetate (50 mL×3), the organic phase was dried over anhydrous sodium sulfate and concentrated under reduced pressure, the crude product was purified by preparative high performance liquid chromatography to deliver the product 3,7-dimethyl-1-((2-(1,1,1-trifluoro-2-hydroxypropan-2-yl)thiazol-5-yl)methyl)-1H-purine-2,6-(3H,7H)-dione (32.0 mg, white solid), yield: 19%. $^1$H NMR: (400 MHz, Methanol-$d_4$) δ7.89 (s, 1H), 7.82 (s, 1H), 5.35 (s, 2H), 4.00 (s, 3H), 3.56 (s, 3H), 1.76 (s, 3H). MS-ESI calcd. for [M+H]$^+$ 390, found 390.

Embodiment 36

3,7-Dimethyl-1-(2-(4-methyl-2-(1,1,1-trifluoro-2-hydroxypropan-2-yl)thiazol-5-yl)ethyl)-1H-purine-2,6-(3H,7H)-dione

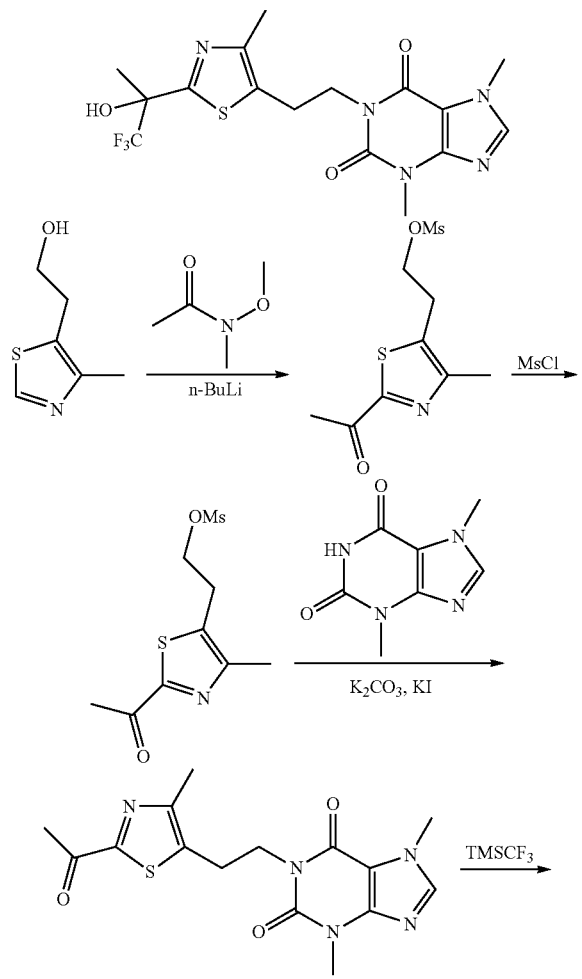

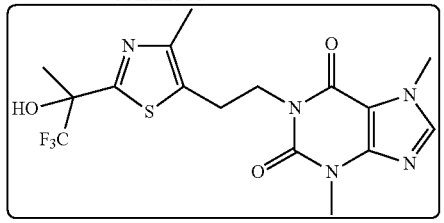

Step 1

1-(5-(2-Hydroxyethyl)-4-methylthiazol-2-yl) ethanone 2-(4-Methylthiazol-5-yl)ethanol (500 mg, 3.49 mmol) was dissolved in tetrahydrofuran (100 mL), n-butyllithium (3 M n-hexane solution, 2.33 mL, 6.98 mmol) was added at −78° C., after reacting for half an hour N-methoxy-N-methyl-acetamide (432 mg, 4.19 mmol) was added into the reaction mixture, the stirring was continued for 3 hours. The reaction was quenched by the addition of saturated ammonium chloride aqueous solution (50 mL), extracted with ethyl acetate (10 mL×3), dried over anhydrous sodium sulfate, filtered, and the filtrate was concentrated under reduced pressure, the residue was isolated and purified by silica gel column chromatography (5:1 petroleum ether/ethyl acetate, Rf=0.1) to deliver 1-(5-(2-hydroxyethyl)-4-methylthiazol-2-yl)ethanone (200 mg, yellow oil), yield: 31%. $^1$H NMR: (400 MHz, CDCl$_3$) δ 3.78 (t, J=6.4 Hz, 2H), 3.18 (t, J=6.4 Hz, 2H), 2.67 (s, 3H), 2.47 (s, 3H). MS-ESI calcd. for [M+H]$^+$ 186, found 186.

Step 2

2-(2-Acetyl-4-methyl-thiazol-5-yl)ethyl methanesulfonate 1-(5-(2-Hydroxyethyl)-4-methylthiazol-2-yl)ethanone (120 mg, 0.647 mmol) and triethylamine (196 mg, 1.94 mmol) were dissolved in dichloromethane (10 mL), methanesulfonyl chloride (148 mg, 1.30 mmol) was added at 0° C. The reaction solution was slowly warmed to room temperature and stirred for 2 hours. The reaction was quenched by the addition of sodium bicarbonate aqueous solution (50 mL), extracted with dichloromethane (10 mL×3). The organic phases were combined, washed with saturated brine, dried over anhydrous sodium sulfate, filtered and the filtrate was concentrated under reduced pressure, the residue was isolated and purified by preparative TLC plate (1:1 petroleum ether/ethyl acetate, Rf=0.5) to deliver 2-(2-acetyl-4-methyl-thiazol-5-yl)ethyl methanesulfonate (150 mg, yellow oil), yield: 88%. $^1$H-NMR (400 MHz, CDCl$_3$) δ 4.41 (t, J=6.4 Hz, 2H), 3.27 (t, J=6.4 Hz, 2H), 3.01 (s, 3H), 2.67 (s, 3H), 2.46 (s, 3H). MS-ESI calcd. for [M+H]$^+$ 264, found 264.

Step 3

1-(2-(2-Acetyl-4-methylthiazol-5-yl)ethyl)-3,7-dimethyl-1H-purine-2,6-(3H,7H)-dione 2-(2-Acetyl-4-methyl-thiazol-5-yl)ethyl methanesulfonate (150 mg, 0.569 mmol), 3,7-dimethyl-1H-purine-2,6-(3H,7H)-dione (102 mg, 0.569 mmol), potassium iodide (18.9 mg, 0.114 mmol) and potassium carbonate (236 mg, 1.71 mmol) were dissolved in N,N-dimethylformamide (10 mL). The reaction solution was heated to 120° C. and stirred for 3 hours. Then the mixture was cooled to room temperature, filtered, and the filtrate was concentrated under reduced pressure. And the residue was isolated and purified by preparative TLC plate (ethyl acetate, Rf=0.5) to deliver 1-(2-(2-acetyl-4-methylthiazol-5-yl)ethyl)-3,7-dimethyl-1H-purine-2,6-(3H,7H)-dione (30.0 mg, yellow solid), yield: 15%. MS-ESI calcd. for [M+H]$^+$ 348, found 348.

Step 4

3,7-Dimethyl-1-(2-(4-methyl-2-(1-trifluoro-2,1,1-trifluoro-2-hydroxypropan-2-yl)thiazol-5-yl)ethyl)-1H-purine-2,6-(3H,7H)-dione 1-(2-(2-Acetyl-4-methylthiazol-5-yl)ethyl)-3,7-dimethyl-1H-purine-2,6-(3H,7H)-dione (40.0 mg, 0.115 mmol), cesium fluoride (17.5 mg, 0.115 mmol) were dissolved in tetrahydrofuran (10 mL), trimethyl trifluoromethylsilane (49.0 mg, 0.345 mmol) was added at room temperature and the resulting mixture was stirred for 12 hours. The reaction was quenched by the addition of water (20 mL), the resulting mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver 3,7-dimethyl-1-(2-(4-methyl-2-(1,1,1-trifluoro-2-hydroxypropan-2-yl)thiazol-5-yl)thiazol-5-yl)ethyl-1H-purine-2,6-(3H,7H)-dione (15.0 mg, yellow solid), yield: 31%. $^1$H NMR: (400 MHz, Methanol-d$_4$) δ 8.37 (s, 1H), 4.25 (t, J=6.4 Hz, 2H), 4.01 (s, 3H), 3.54 (s, 3H), 3.26 (t, J=6.4 Hz, 2H), 2.50 (s, 3H), 1.90 (s, 3H). MS-ESI calcd. for [M+H]$^+$ 418, found 418.

Embodiment 37

1-(3-Hydroxy-2-(hydroxymethyl)-2-methylpropyl)-3,7-dimethyl-1H-purine-2,6-(3H,7H)-dione

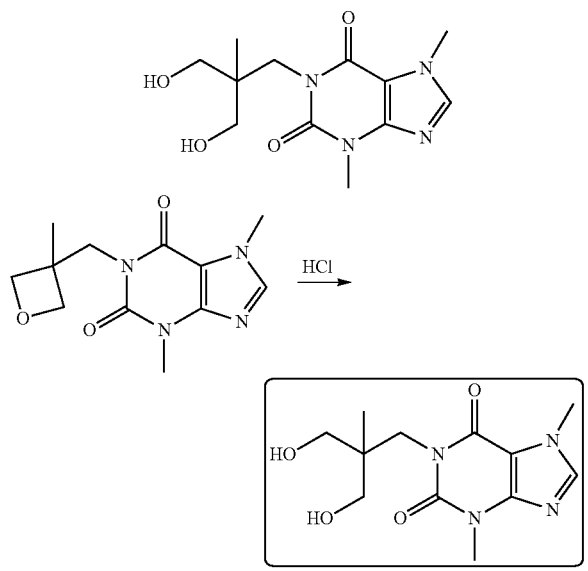

3,7-Dimethyl-1-((3-methyloxetan-3-yl)methyl) 1H-purine-2,6(3H,7H)-dione (20.0 mg, 0.0757 mmol) was dissolved in 0.16% hydrochloric acid (0.5 mL) and the reaction was stirred at room temperature for 6 hours, the pH value of which was adjusted to 7 with saturated sodium bicarbonate aqueous solution and the residue was purified by high performance liquid chromatography to deliver 1-(3-hydroxy-2-(hydroxymethyl)-2-methylpropyl)-3,7-dimethyl-1H-purine-2,6-(3H,7H)-dione (12.0 mg, white solid), yield: 56%. $^1$H NMR: (400 MHz, CDCl$_3$) δ 7.58 (s, 1H), 4.25-3.94 (m, 7H), 3.62 (s, 3H), 3.35-3.26 (m, 2H), 3.25-3.14 (m, 2H), 1.01 (s, 3H). MS-ESI calcd. for [M+H]$^+$ 283, found 283.

Embodiment 38

1-(2-(2-Hydroxy-2-methylcyclopropyl)ethyl)-3,7-dimethyl-1H-purine-2,6(3H,7H)-dione

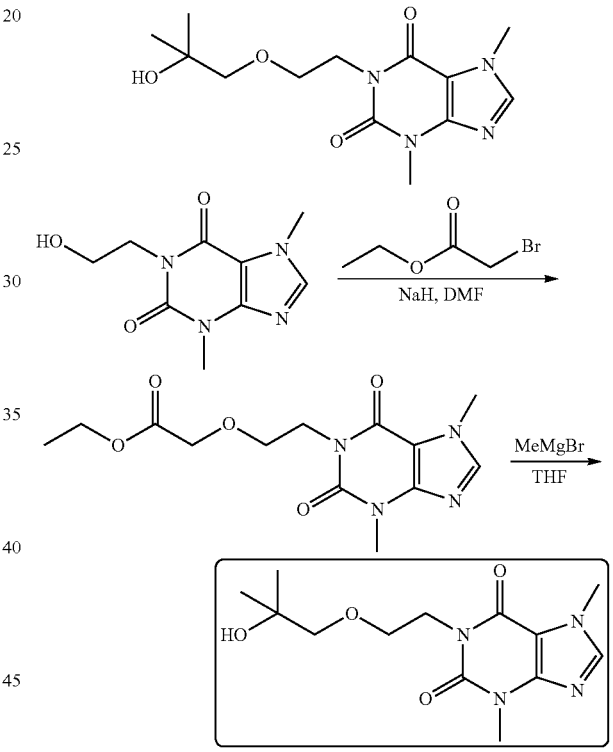

Step 1

Ethyl 2-(2-(3,7-Dimethyl-2,6-dioxo-2,3,6,7-tetrahydro-1H-purin-1-yl)ethoxy)acetate 1-(2-Hydroxyethyl)-3,7-dimethyl-1H-purine-2,6(3H,7H)-dione (100 mg, 0.446 mmol) was added to a solution of sodium hydride (21.0 mg, 0.890 mmol) in N,N-dimethylformamide (10 mL) at room temperature, the reaction solution was stirred at 25° C. for 1 hour. Ethyl 2-bromoacetate (149 mg, 0.890 mmol) was added then. The reaction solution was stirred for a further 16 hours. The insoluble substance was removed by filtration, and the filtrate was concentrated under reduced pressure, the residue was isolated and purified by preparative high performance liquid chromatography to deliver ethyl 2-(2-(3,7-dimethyl-2,6-dioxo-2,3,6,7-tetrahydro-1H-purin-1-yl)ethoxy)acetate (60.0 mg, white solid), yield: 43%.

MS-ESI calcd. for [M+H]$^+$ 311, found 311.

Step 2

1-(2-(2-Hydroxy-2-methylcyclopropyl)ethyl)-3,7-dimethyl-1H-purine-2,6(3H,7H)-dione Methyl magnesium bromide solution (3 M tetrahydrofuran solution, 0.43 mL, 1.29 mmol) was slowly added dropwise to a solution of ethyl 2-(2-(3,7-dimethyl-2,6-dioxo-2,3,6,7-tetrahydro-1H-purin-1-yl)ethoxy)acetate in tetrahydrofuran (5 mL) at −78° C. The reaction solution was stirred at −78° C. for 2 hours. The reaction was quenched by the addition of saturated ammonium chloride aqueous solution (20 mL). The mixture was extracted with ethyl acetate (20 mL×3). The organic phases were combined and concentrated under reduced pressure, the residue was isolated and purified by preparative high performance liquid chromatography to deliver 1-(2-(2-hydroxy-2-methylcyclopropyl)ethyl)-3,7-dimethyl-1H-purine-2,6(3H,7H)-dione (40.0 mg, colorless oil), yield: 42%. $^1$H NMR: (400 MHz, Methanol-d$_4$) δ 7.88 (s, 1H), 4.23 (t, J=5.8 Hz, 2H), 3.98 (s, 3H), 3.72 (t, J=5.8 Hz, 2H), 3.53 (s, 3H), 3.32 (s, 2H), 1.13 (s, 6H). MS-ESI calcd. for [M+H]$^+$ 296, found 296.

Embodiment 39

1-(2-((1-Hydroxycyclobutyl)methoxy)ethyl)-3,7-dimethyl-1H-purine-2,6(3H,7H)-dione

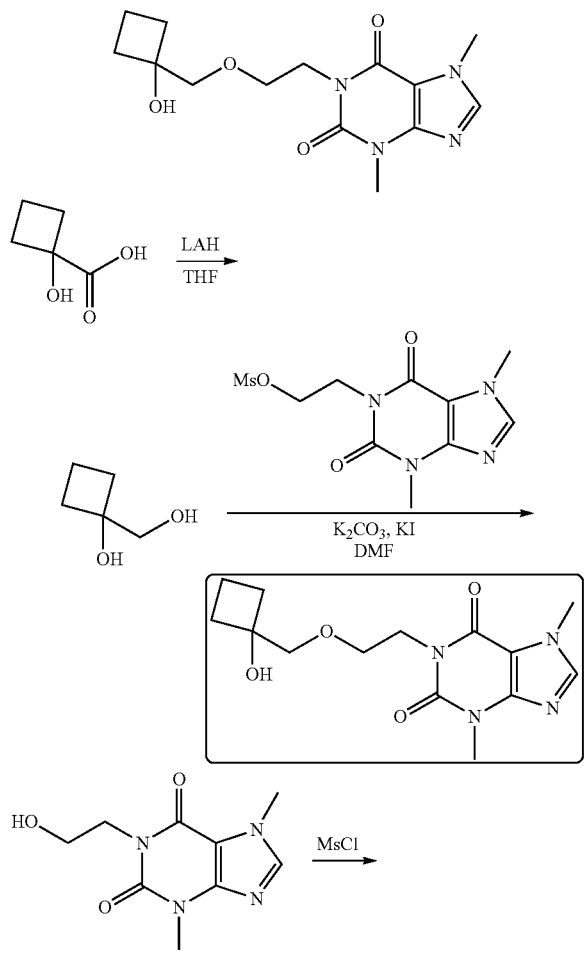

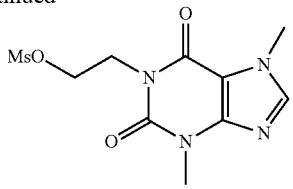

Step 1

1-(Hydroxymethyl)cyclobutanol

A solution of 1-hydroxycyclobutanoic acid (1.16 g, 10.0 mmol) in tetrahydrofuran (10 mL) was added dropwise to a solution of lithium aluminum hydride (1.52 g, 40.0 mmol) in tetrahydrofuran (30 mL) at 25° C. The reaction solution was heated to reflux for 1 hour. The reaction solution was cooled to 25° C., quenched by the addition of water (20 mL), extracted with ethyl acetate (50 mL×3), the organic phase was dried over anhydrous sodium sulfate, filtered and the filtrate was concentrated under reduced pressure to deliver 1-(hydroxymethyl)cyclobutanol (0.800 g, colorless oil), yield: 80%.

Step 2

2-(3,7-Dimethyl-2,6-dioxo-2,3,6,7-tetrahydro-1H-purin-1-yl)ethyl methanesulfonate Triethylamine (600 mg, 6.00 mmol) and methanesulfonyl chloride (342 mg, 3.00 mmol) were added to a solution of 1-(2-hydroxyethyl)-3,7-dimethyl-1H-purine-2,6(3H,7H)-dione (448 mg, 2.00 mmol) in dichloromethane (25 mL). The reaction solution was stirred at 0° C. for 0.5 hour. The reaction was quenched by the addition of saturated sodium bicarbonate aqueous solution (30 mL) and extracted with dichloromethane (20 mL×3). The organic phase was washed with saturated brine (20 mL×3), dried over anhydrous sodium sulfate, filtered and concentrated under reduced pressure to deliver 2-(3,7-dimethyl-2,6-dioxo-2,3,6,7-tetrahydro-1H-purin-1-yl)ethyl methanesulfonate (650 mg, yellow oil), yield 100%.

Step 3

1-(2-((1-Hydroxycyclobutyl)methoxy)ethyl)-3,7-dimethyl-1H-purine-2,6(3H,7H)-dione Potassium carbonate (414 mg, 3.00 mmol) and potassium iodide (16.0 mg, 0.100 mmol) were added to a solution of a mixture of 1-(hydroxymethyl)cyclobutanol (102 mg, 1.00 mmol) and 2-(3,7-dimethyl-2,6-dioxo-2,3,6,7-tetrahydro-1H-purin-1-yl)ethyl methanesulfonate (450 mg, 1.50 mmol) in N,N-dimethylformamide (5 mL). The reaction was heated to 60° C. and stirred overnight. Then the reaction mixture was slowly cooled to room temperature, quenched by the addition of water (20 mL). The mixture was extracted with ethyl acetate (20 mL×3) and the organic phase was washed with saturated brine (20 mL×3) and dried over anhydrous sodium sulfate, filtered and the filtrate was concentrated under reduced pressure and the residue was purified by preparative high performance liquid chromatography to deliver 1-(2-((1-hydroxycyclobutyl)methoxy)ethyl)-3,7-dimethyl-1H-purine-2,6(3H,7H)-dione (50.0 mg, white solid), yield: 16%. $^1$H NMR: (400 MHz, Methanol-$d_4$) δ 7.88 (s, 1H), 4.57-4.59 (m, 2H), 4.21-4.24 (m, 2H), 3.98 (s, 3H), 3.80 (s, 2H), 3.54 (s, 3H), 2.07-1.95 (m, 4H), 1.52-1.54 (m, 2H). MS-ESI calcd. for [M+H]$^+$ 309, found 309.

Embodiment 40

(S)-1-(2-((2-Hydroxypropyl)amino)ethyl)-3,7-dimethyl-1H-purine-2,6(3H,7H)-dione

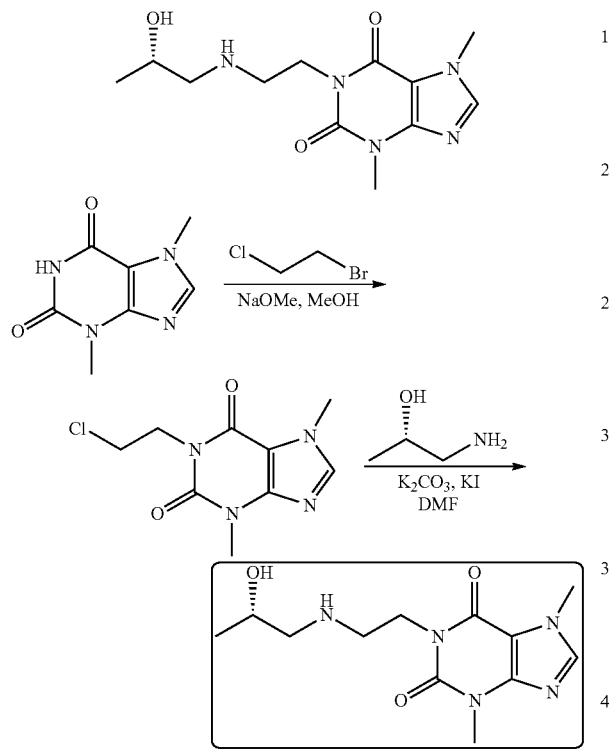

Step 1

1-(3-Chloropropyl)-3,7-dimethyl-1H-purine-2,6(3H, 7H)-dione 3,7-Dimethyl-1H-purine-2,6(3H,7H)-dione (1.00 g, 5.56 mmol) was dissolved in methanol (20 mL), 30% sodium methoxide (9.64 g, 49.9 mmol) was added and the reaction was refluxed for 1 hour. Then 1-bromo-2-chloroethane (47.2 g, 299 mmol) was added and the reaction was stirred for a further 16 hours. The reaction was quenched by the addition of water (30 mL), extracted with dichloromethane (20 mL×3), the organic phase was washed with saturated brine (20 mL×3), dried over anhydrous sodium sulfate, filtered and the filtrate was concentrated under reduced pressure, the residue was isolated and purified by column chromatography (1:2 petroleum ether/ethyl acetate) to deliver 1-(3-chloropropyl)-3,7-dimethyl-1H-purine-2,6(3H,7H)-dione (230 mg, white solid), yield: 17%. $^1$H NMR: (400 MHz, CDCl$_3$) δ 7.50 (s, 1H), 4.36 (t, J=6.4 Hz, 2H), 3.97 (s, 3H), 3.75 (t, J=6.4 Hz, 2H), 3.56 (s, 3H).

Step 2

(S)-1-(2-((2-Hydroxypropyl)amino)ethyl)-3,7-dimethyl-1H-purine-2,6(3H,7H)-dione

Potassium carbonate (138 mg, 1.03 mmol) and potassium iodide (86.3 mg, 0.517 mmol) were added to a solution of a mixture of 1-(3-chloropropyl)-3,7-dimethyl-1H-purine-2,6 (3H,7H)-dione (62.4 mg, 0.826 mmol) and (S)-1-aminopropan-2-ol (50.0 mg, 0.207 mmol) in acetonitrile (2 mL) at 25° C. The reaction solution was stirred at 90° C. for 4 hours. The reaction was quenched by addition of water (10 mL) and extracted with ethyl acetate (20 mL×3). The organic phase was washed with saturated brine (20 mL×3), dried over anhydrous sodium sulfate and concentrated under reduced pressure. The residue was isolated and purified by preparative high performance liquid chromatography to deliver (S)-1-(2-((2-hydroxypropyl)amino)ethyl)-3,7-dimethyl-1H-purine-2,6(3H,7H)-dione (10.0 mg, white solid), yield: 17%. $^1$H NMR: (400 MHz, Methanol-$d_4$) δ 7.86 (s, 1H), 4.16 (t, J=6.4 Hz, 2H), 3.97 (s, 3H), 3.84 (m, 1H), 3.56 (s, 3H), 3.93 (m, 2H), 2.64 (m, 2H), 1.14 (d, J=6.4 Hz, 3H). MS-ESI calcd. for [M+H]$^+$ 282, found 282.

Embodiment 41

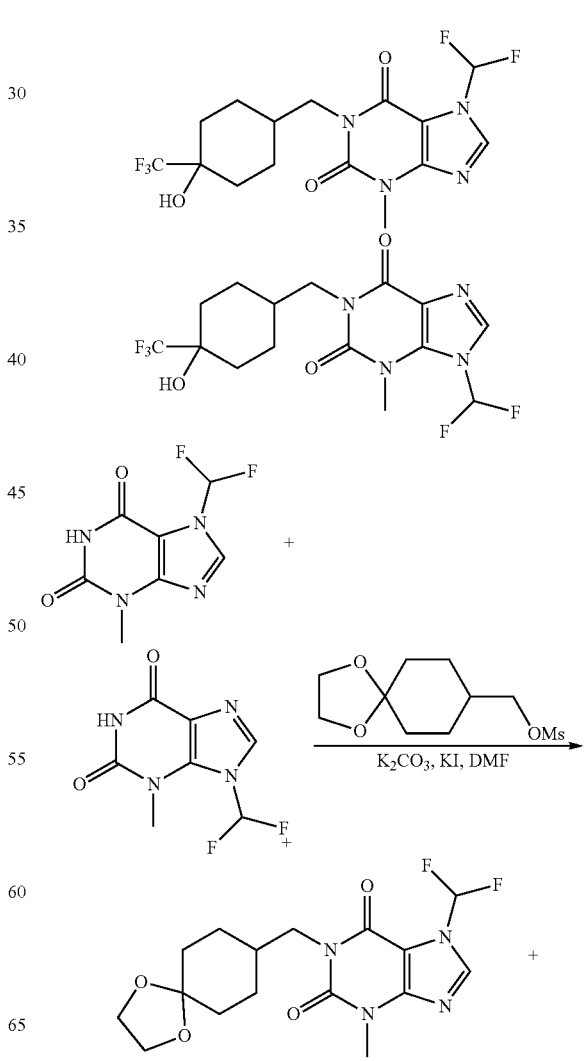

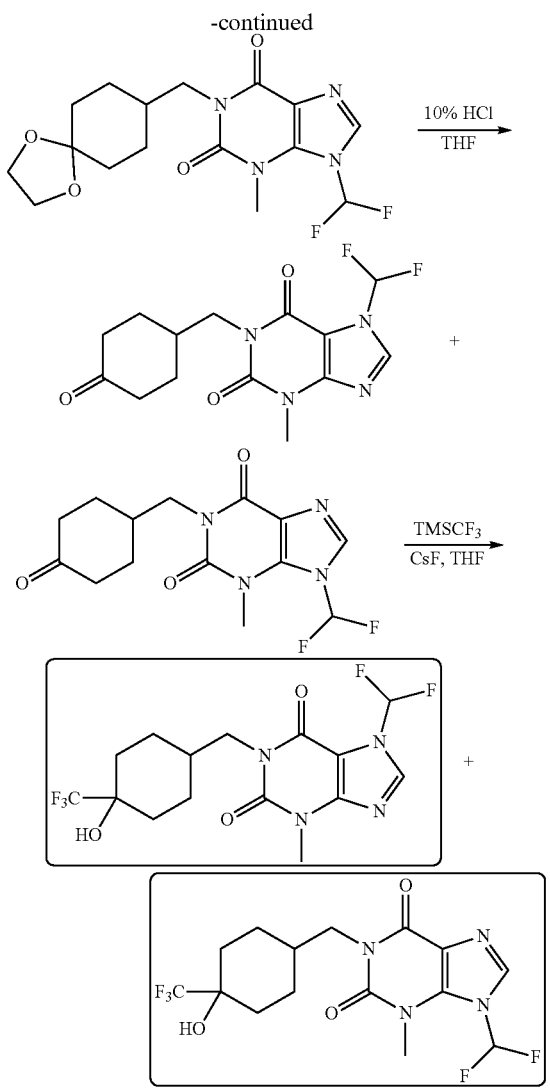

Step 1

1-(1,4-Dioxaspiro[4.5]decan-8-ylmethyl)-7-(difluoromethyl)-3-methyl-1H-purine-2,6(3H,7H)-dione 1-(1,4-Dioxaspiro[4.5]decan-8-ylmethyl)-9-(difluoromethyl)-3-methyl-1H-purine-2,6(3H,7H)-dione A mixture of 7-(difluoromethyl)-3-methyl-1H-purine-2,6(3H,7H)-dione and 9-(difluoromethyl)-3-methyl-2,6(3H,7H)-dione (200 mg, 0.930 mmol) was dissolved in N,N-dimethylformamide (20 mL), 1,4-dioxaspiro[4.5]decan-8-ylmethyl methanesulfonate (245 mg, 1.10 mmol), potassium iodide (183 mg, 1.10 mmol) and potassium carbonate (303 mg, 2.20 mmol) were added to the reaction solution at room temperature. The reaction solution was heated to 100° C. and stirred for 2 hours. The reaction solution was diluted with ethyl acetate (30 mL) and the organic phase was washed with water (20 mL×2), dried over anhydrous sodium sulfate and concentrated to deliver a mixture of 1-(1,4-dioxaspiro[4.5]decan-8-ylmethyl)-7-(difluoromethyl)-3-methyl-1H-purine-2,6(3H,7H)-dione and 1-(1,4-dioxaspiro[4.5]decan-8-ylmethyl)-9-(difluoromethyl)-3-methyl-1H-purine-2,6(3H,7H)-dione (234 mg, yellow oil), yield: 68%.

MS-ESI calcd. for [M+H]$^+$ 371, found 371.

Step 2

7-(Difluoromethyl)-3-methyl-1-((4-oxocyclohexyl)methyl)-1H-purine-2,6(3H,7H)-dione 9-(Difluoromethyl)-3-methyl-1-((4-oxocyclohexyl)methyl)-1H-purine-2,6(3H,7H)-dione A mixture of 1-(1,4-dioxaspiro[4.5]decan-8-ylmethyl)-7-(difluoromethyl)-3-methyl-1H-purine-2,6(3H,7H)-dione and 1-(1,4-dioxaspiro[4.5]decan-8-ylmethyl)-9-(difluoromethyl)-3-methyl-1H-purine-2,6(3H,7H)-dione (230 mg, 0.750 mmol) was dissolved in tetrahydrofuran (15 mL), 10% hydrochloric acid (5 mL) was added at room temperature and the reaction was heated to 50° C. for 1 hour. The reaction mixture was cooled to room temperature, ethyl acetate (20 mL) was added and the organic phase was washed with saturated sodium bicarbonate aqueous solution (20 mL×2), dried over anhydrous sodium sulfate, filtered, and the filtrate was concentrated under reduced pressure, the residue was isolated and purified by silica gel column chromatography (2:1 petroleum ether/ethyl acetate, Rf=0.3) to deliver a mixture of 7-(difluoromethyl)-3-methyl-1-((4-oxocyclohexyl)methyl)-1H-purine-2,6(3H,7H)-dione and 9-(difluoromethyl)-3-methyl-1-((4-oxocyclohexyl)methyl)-1H-purine-2,6(3H,7H)-dione (200 mg, white solid), yield: 81%.

MS-ESI calcd. for [M+H]$^+$ 327, found 327.

Step 3

7-(Difluoromethyl)-1-(4-hydroxy-4-(trifluoromethyl)cyclohexyl)methyl)-3-methyl-1H-purine-2,6(3H,7H)-dione 9-(Difluoromethyl)-1-(4-hydroxy-4-(trifluoromethyl)cyclohexyl)methyl)-3-methyl-1H-purine-2,6(3H,7H)-dione A mixture of 7-(difluoromethyl)-3-methyl-1-((4-oxocyclohexyl)methyl)-1H-purine-2,6(3H,7H)-dione and 9-(difluoromethyl)-3-methyl-1-((4-oxocyclohexyl)methyl)-1H-purine-2,6(3H,7H)-dione (168 mg, 0.515 mmol) was dissolved in tetrahydrofuran (30 mL), trifluoromethyltrimethylsilane (109 mg, 0.773 mmol) and cesium fluoride (15.7 mg, 0.103 mmol) were added at room temperature. The reaction solution was stirred at room temperature for 12 hours, tetrabutylammonium fluoride (50.0 mg, 0.207 mmol) was added and the resulting mixture was stirred at room temperature for 30 minutes, then was diluted by ethyl acetate (20 mL) and the organic phase was washed with saturated sodium bicarbonate aqueous solution (20 mL×2), dried over anhydrous sodium sulfate, filtered, and the filtrate was concentrated under reduced pressure and the residue was purified by high performance liquid chromatography to deliver 7-(difluoromethyl)-1-(4-hydroxy-4-(trifluoromethyl)cyclohexyl)methyl)-3-methyl-1H-purine-2,6(3H,7H)-dione (54 mg, white solid), yield: 23%. $^1$H NMR: (400 MHz, Methanol-$d_4$) δ 8.46 (s, 1H), 7.89-7.74 (m, 1H), 4.06 (d, J=7.2 Hz, 2H), 3.59 (s, 3H), 2.19-2.17 (m, 1H), 2.05-1.99 (m, 2H), 1.88-1.81 (m, 2H), 1.61-1.58 (m, 2H), 1.51-1.47 (m, 2H). MS-ESI calcd. for [M+H]$^+$ 397, found 397.

And 9-(difluoromethyl)-1-(4-hydroxy-4-(trifluoromethyl)cyclohexyl)methyl)-3-methyl-1H-purine-2,6(3H,7H)-dione (12 mg, white solid), yield: 10%. $^1$H NMR: (400 MHz, Methanol-$d_4$) δ 8.49 (s, 1H), 7.93-7.89 (m, 1H), 4.07 (d, J=7.2 Hz, 2H), 3.59 (s, 3H), 2.20-2.19 (m, 1H), 2.05-1.99 (m, 2H), 1.88-1.85 (m, 2H), 1.61-1.58 (m, 2H), 1.51-1.48 (m, 2H). MS-ESI calcd. for [M+H]+ 397, found 397.

Embodiment 42

7-Ethyl-1-(5-ethyl-5-hydroxyheptyl)-3-methyl-1H-purine-2,6(3H,7H)-dione

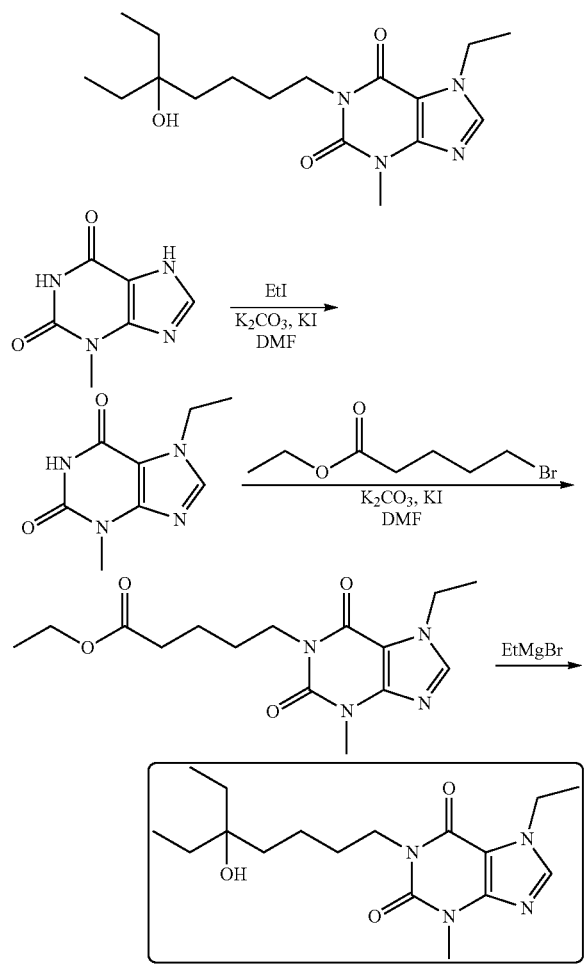

Step 1

7-Ethyl-3-methyl-1H-purine-2,6(3H,7H)-dione

3-Methyl-1H-purine-2,6(3H,7H)-dione (500 mg, 3.00 mmol), potassium carbonate (414 mg, 3.00 mmol) and potassium iodide (4.0 mg, 0.300 mmol) were dissolved in N,N-dimethylformamide (15 mL). The reaction solution was heated to 80° C. for half an hour. Ethyl iodide (470 mg, 4.50 mmol) was added. The reaction was continued for 5 hours. The reaction was quenched by pouring the reaction solution into sodium hydroxide aqueous solution (50 mL) and extracted with ethyl acetate (20 mL×3). The pH value of the aqueous phase was adjusted to 7 with 1 N dilute hydrochloric acid (10 mL), then the mixture was filtered, the filter cake was dried to deliver 7-ethyl-3-methyl-1H-purine-2,6(3H,7H)-dione (500 mg, pale yellow solid), yield: 86%.

$^1$H NMR: (400 MHz, DMSO-$d_6$): δ 8.05 (s, 1H), 4.25-4.19 (m, 2H), 3.34 (s, 3H), 1.37 (t, J=7.2 Hz, 3H). MS-ESI calcd. for [M+H]+ 195, found 195.

Step 2

Ethyl 5-(7-ethyl-3-methyl-2,6-dioxo-2,3,6,7-tetrahydro-1H-purin-1-yl)valate

7-Ethyl-3-methyl-1H-purine-2,6(3H,7H)-dione (0.300 g, 1.55 mmol), ethyl bromovalerate (480 mg, 2.32 mmol), potassium carbonate (430 mg, 3.10 mmol) and potassium iodide (26.0 mg, 0.155 mmol) were dissolved in N,N-dimethylformamide (4 mL). The reaction solution was heated to 110° C. for 2 hours. The reaction was quenched by pouring the reaction solution into water (20 mL) and the mixture was extracted with ethyl acetate (20 mL×3). The organic phases were combined, dried over anhydrous sodium sulfate, filtered and concentrated under reduced pressure to deliver ethyl 5-(7-ethyl-3-methyl-2,6-dioxo-2,3,6,7-tetrahydro-1H-purin-1-yl)valate (320 mg, yellow solid), yield: 62%. MS-ESI calcd. for [M+H]+ 323, found 323.

Step 3

7-Ethyl-1-(5-ethyl-5-hydroxyheptyl)-3-methyl-1H-purine-2,6(3H,7H)-dione

Ethyl 5-(7-ethyl-3-methyl-2,6-dioxo-2,3,6,7-tetrahydro-1H-purin-1-yl) valate (0.100 g, 0.310 mmol) was dissolved in anhydrous tetrahydrofuran (10 mL) and ethyl magnesium bromide (3 M tetrahydrofuran solution, 0.62 mL, 1.86 mmol) was slowly added dropwise at −78° C. The reaction solution was reacted at −78° C. for 0.5 hour and slowly warmed to 0° C. and reacted for 0.5 hour. After the reaction was complete, the reaction solution was poured into water (20 mL) and extracted with ethyl acetate (30 mL×3). The organic phase was dried over anhydrous sodium sulfate, filtered, concentrated under reduced pressure and the residue was purified by silica gel column chromatography to deliver 7-ethyl-1-(5-ethyl-5-hydroxyheptyl)-3-methyl-1H-purine-2,6(3H,7H)-dione (30.0 mg, colorless oil), yield: 30%.

$^1$H NMR: (400 MHz, CDCl$_3$): δ 7.56 (s, 1H), 4.37-4.32 (m, 2H), 4.05 (t, J=7.2 Hz, 2H), 3.60 (s, 3H), 1.68-1.37 (m, 13H), 0.86 (t, J=7.2 Hz, 6H). MS-ESI calcd. for [M+H]+337, found 337.

Embodiment 43

7-Ethyl-3-methyl-1-(6,6,6-trifluoro-5-hydroxy-5-methylhexyl)-1H-purine-2,6(3H,7H)-dione

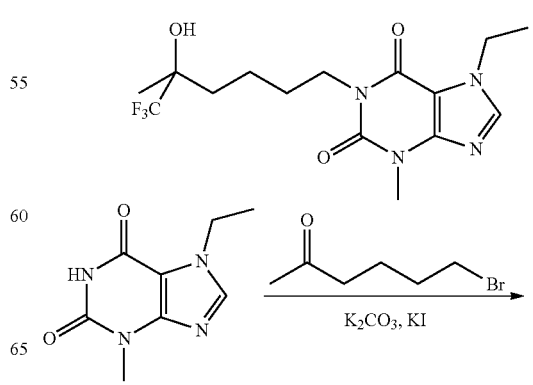

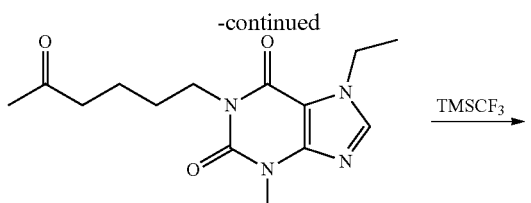
-continued

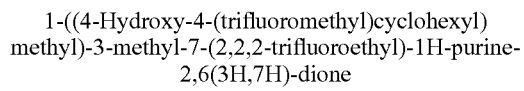

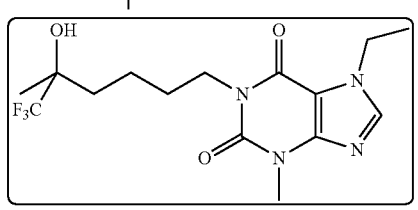

Step 1

7-Ethyl-3-methyl-1-(5-oxohexyl)-1H-purine-2,6(3H,7H)-dione

7-Ethyl-3-methyl-1H-purine-2,6(3H,7H)-dione (0.100 g, 0.515 mmol), 6-chloro-2-pentanone (90.0 mg, 0.670 mmol), potassium carbonate (140 mg, 1.03 mmol) and potassium iodide (8.5 mg, 0.0155 mmol) were dissolved in DMF (2 mL), the resulting reaction mixture was heated to 110° C. for two hours. The reaction mixture was poured into water and extracted with ethyl acetate (20 mL×3). The organic phases were combined, dried, filtered, concentrated and washed with t-butyl methyl ether, the solid was dried to deliver the target compound 7-ethyl-3-methyl-1-(5-oxohexyl)-1H-purine-2,6(3H,7H)-dione (100 mg, white solid), yield: 70%. MS-ESI calcd. for [M+H]$^+$ 293, found 293.

Step 2

7-Ethyl-3-methyl-1-(6,6,6-trifluoro-5-hydroxy-5-methylhexyl)-1H-purine-2,6(3H,7H)-dione 7-Ethyl-3-methyl-1-(5-oxohexyl)-1H-purine-2,6(3H,7H)-dione (100 mg, 0.340 mmol) was dissolved in 1 mL tetrahydrofuran, trifluoromethyltrimethylsilane (53.0 mg, 0.370 mmol) and cesium fluoride (10.0 mg, 0.0340 mmol) were added successively, and reacted at 30° C. for 3 hours. The reaction solution was poured into dilute hydrochloric acid (10%, 10 mL) and stirred for half an hour. Then the mixture was extracted with ethyl acetate (20 mL×3). The organic phases were combined, dried, concentrated and the residue was purified by preparative column to deliver the target compound 7-ethyl-3-methyl-1-(6,6,6-trifluoro-5-hydroxy-5-methylhexyl)-1H-purine-2,6(3H,7H)-dione (20.0 mg, white solid), yield: 79%. $^1$H NMR: (400 MHz, CDCl$_3$): δ 7.95 (s, 1H), 4.39-4.33 (m, 2H), 4.04-4.00 (m, 2H), 3.53 (s, 3H), 1.71-1.64 (m, 4H), 1.50-1.46 (m, 5H), 1.28 (s, 3H). MS-ESI calcd. for [M+H]$^+$ 363, found 363.

Embodiment 44

1-((4-Hydroxy-4-(trifluoromethyl)cyclohexyl)methyl)-3-methyl-7-(2,2,2-trifluoroethyl)-1H-purine-2,6(3H,7H)-dione

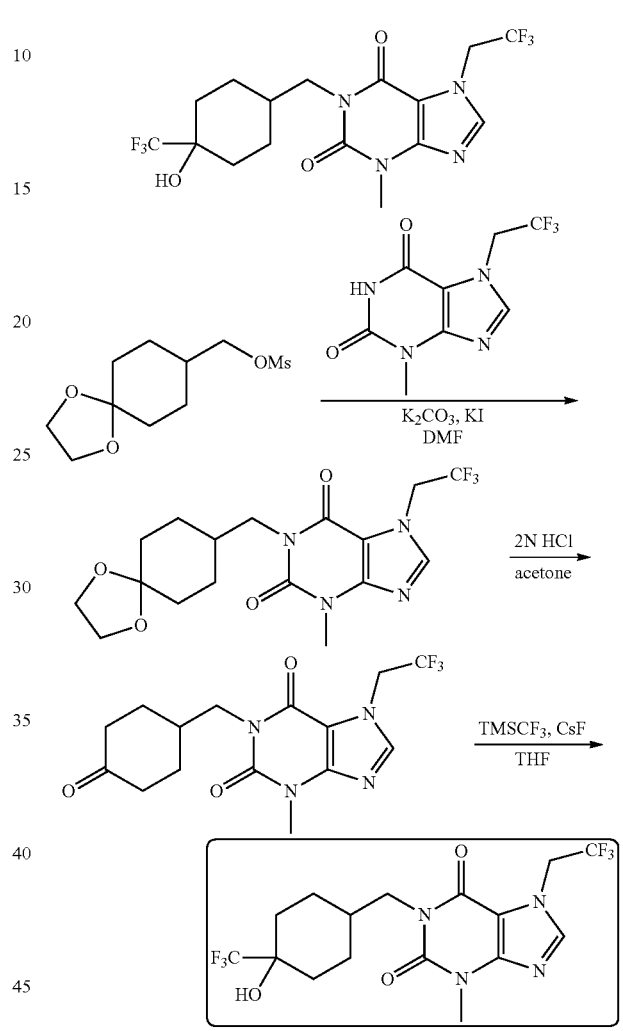

Step 1

1-(1,4-Dioxaspiro[4.5]decan-8-ylmethyl)-3-methyl-7-(2,2,2-trifluoroethyl)-1H-purine-2,6(3H,7H)-dione 1,4-Dioxaspiro[4.5]decan-8-ylmethyl methanesulfonate (200 mg, 0.800 mmol), 3-methyl-7-(2,2,2-trifluoroethyl)-1H-purine-2,6(3H,7H)-dione (200 g, 0.800 mmol) and potassium carbonate (334 mg, 2.42 mmol), potassium iodide (14.0 mg, 0.0800 mmol) were dissolved in N,N-dimethylformamide (3 mL), the reaction solution was heated to 130° C. and stirred for 3.5 hours. The reaction solution was directly filtered and the filtrate was concentrated under reduced pressure to obtain a crude product 1-(1,4-dioxaspiro[4.5]decan-8-ylmethyl)-3-methyl-7-(2,2,2-trifluoroethyl)-1H-purine-2,6(3H, 7H)-dione. MS-ESI calcd. for [M+H]$^+$ 403, found 403.

Step 2

3-Methyl-1-((4-oxocyclohexyl)methyl)-7-(2,2,2-trifluoroethyl)-1H-purine-2,6(3H,7H)-dione 1-(1,4-Dioxaspiro[4.5]decan-8-ylmethyl)-3-methyl-7-(2,2,2-trifluoroethyl)-1H-purine-2,6(3H,7H)-dione (2.50 g, 6.00 mmol) was dissolved in acetone (18 mL) and hydrochloric acid aqueous solution (4 N, 2.5 mL) was added. The reaction was stirred at 30° C. overnight, water (50 mL) was added and the resulting mixture was extracted with ethyl acetate (20 mL×3). The organic phases were combined, dried over anhydrous sodium sulfate, filtered and the filtrate was concentrated under reduced pressure and purified by silica gel column chromatography (1:3 petroleum ether/ethyl acetate, Rf=0.3) to deliver the product 3-methyl-1-((4-oxocyclohexyl)methyl)-7-(2,2,2-trifluoroethyl)-1H-purine-2,6(3H,7H)-dione (220 mg, white solid), yield: 11%. $^1$H NMR: (400 MHz, CDCl$_3$) δ 7.68 (s, 1H), 5.08-4.99 (m, 2H), 4.00 (d, J=7.0 Hz, 2H), 3.61 (s, 3H), 2.46-2.24 (m, 5H), 2.04-1.96 (m, 2H), 1.63-1.56 (m, 2H). MS-ESI calcd. for [M+H]$^+$ 359, found 359.

Step 3

1-((4-Hydroxy-4-(trifluoromethyl)cyclohexyl)methyl)-3-methyl-7-(2,2,2-trifluoroethyl)-1H-purine-2,6(3H,7H)-dione 3-Methyl-1-((4-oxocyclohexyl)methyl)-7-(2,2,2-trifluoroethyl)-1H-purine-2,6(3H,7H)-dione (128 mg, 0.360 mmol) and cesium fluoride (6.0 mg, 0.0360 mmol) were dissolved in tetrahydrofuran (3 mL). Under the nitrogen gas atmosphere, trifluoromethyltrimethylsilane (77.0 mg, 0.540 mmol) was slowly added. The reaction solution was stirred at 30° C. for 3 hours. The reaction solution was cooled to room temperature, 4 N hydrochloric acid aqueous solution (2.5 mL) was added, and the resulting mixture was stirred at 25° C. for half an hour, the pH value of which was adjusted to 7, the mixture was diluted with water and extracted with ethyl acetate (20 mL×3). The organic phases were combined, dried over anhydrous sodium sulfate, filtered, concentrated under reduced pressure, and the residue was purified by preparative high performance liquid chromatography to deliver the product 1-((4-hydroxy-4-(trifluoromethyl)cyclohexyl)methyl)-3-methyl-7-(2,2,2-trifluoroethyl)-1H-purine-2,6(3H,7H)-dione (14.0 mg, white solid), yield: 10%. $^1$H NMR: (400 MHz, CDCl$_3$) δ 8.09 (s, 1H), 5.27-5.20 (m, 2H), 4.08-3.91 (m, 2H), 3.58 (s, 3H), 2.07-1.98 (m, 2H), 1.89-1.80 (m, 2H), 1.62-1.46 (m, 5H). MS-ESI calcd. for [M+H]$^+$ 429, found 429.

Embodiment 45

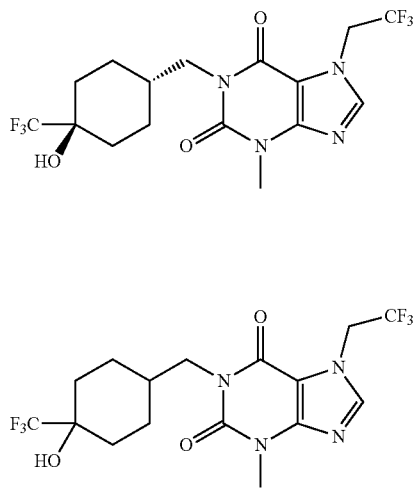

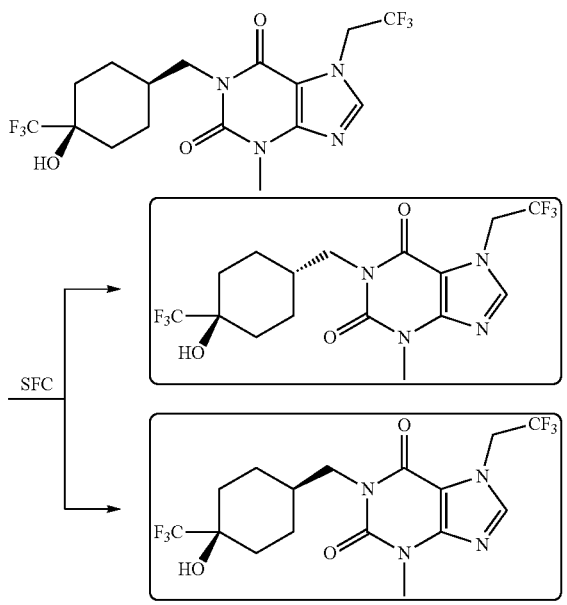

1-((4-Hydroxy-4-(trifluoromethyl)cyclohexyl)methyl)-3-methyl-7-(2,2,2-trifluoroethyl)-1H-purine-2,6(3H,7H)-dione (500 mg, 1.17 mmol) were separated by preparative SFC to deliver two isomers. Separation conditions: Column: AD 250 mm×30 mm, 10 m; Mobile phase: A: Supercritical carbon dioxide, B: Ethanol (0.05% ammonia), A:B=550:45; Flow rate: 80 mL/min; Wavelength: 220 nm.

Product 1 (isomer 1, the first peak) (300 mg, white solid), yield: 90%. $^1$H NMR: (400 MHz, DMSO-d$_6$) δ 8.23 (s, 1H), 5.64 (s, 1H), 5.31-5.24 (m, 2H), 3.89 (d, J=3.6 Hz, 2H), 3.43 (s, 3H), 2.06-2.05 (m, 1H), 1.87-1.81 (m, 2H), 1.73-1.61 (m, 2H), 1.49-1.45 (m, 2H), 1.33-1.31 (m, 2H). MS ESI calcd. for [M+H]$^+$ 429, found 429.

Product 2 (isomer 2, the second peak) (150 mg, white solid), yield: 90%. $^1$H NMR: (400 MHz, DMSO-d$_6$) δ 8.22 (s, 1H), 5.63 (s, 1H), 5.29-5.23 (m, 2H), 3.74 (d, J=3.6 Hz, 2H), 3.42 (s, 3H), 1.68-1.66 (m, 3H), 1.45-1.31 (m, 6H). MS ESI calcd. for [M+H]$^+$ 429, found 429.

Embodiment 46

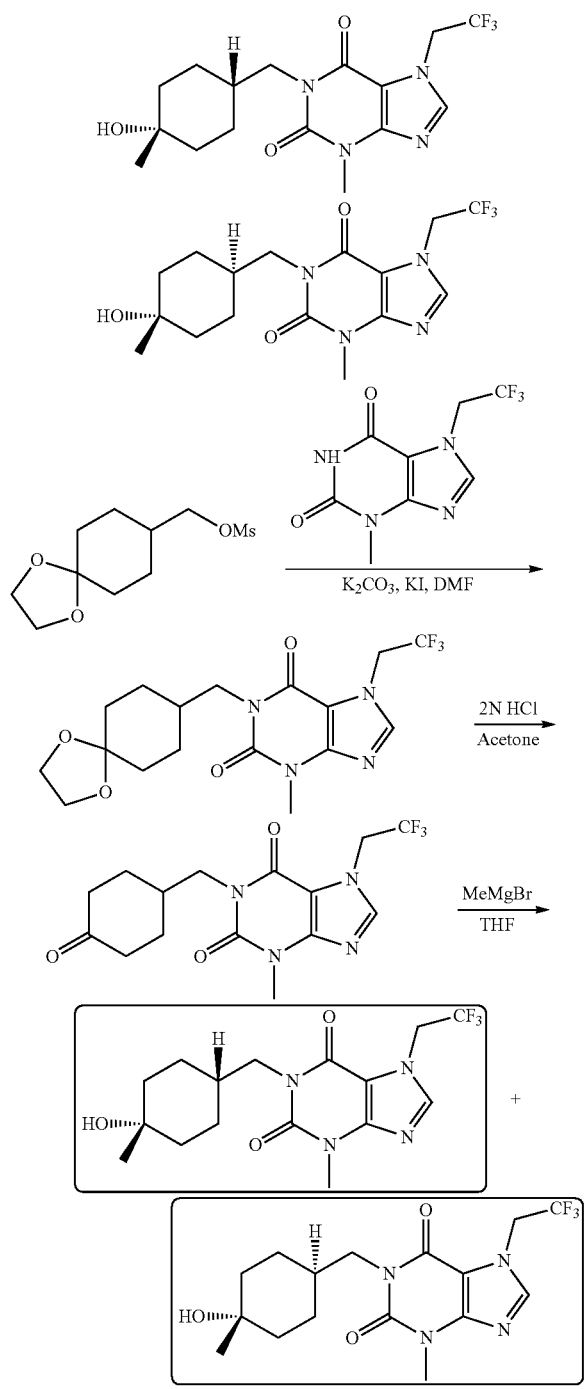

Step 1

1-(1,4-Dioxaspiro[4.5]decan-8-ylmethyl)-3-methyl-7-(2,2,2-trifluoroethyl)-1H-purine-2,6(3H,7H)-dione 1,4-Dioxaspiro[4,5]decan-8-ylmethyl methanesulfonate (603 mg, 2.41 mmol), 3-methyl-7-(2,2,2-trifluoroethyl)-1H-purine-2,6-(3H,7H)-dione (500 mg, 2.01 mmol) and potassium iodide (33.3 mg, 0.201 mmol) were dissolved in N,N-dimethylformamide (8 mL), potassium carbonate (555 mg, 4.02 mmol) was added and the reaction was heated to 130° C. for 4 hours. The reaction solution was cooled to room temperature, filtered, and the filtrate was concentrated under reduced pressure to deliver the crude product 1-(1,4-dioxaspiro[4.5]decan-8-ylmethyl)-3-methyl-7-(2,2,2-trifluoroethyl)-1H-purine-2,6(3H,7H)-dione (980 mg, yellow oil). MS-ESI calcd. for [M+H]$^+$ 403, found 403.

Step 2

3-Methyl-1-((4-oxocyclohexyl)methyl)-7-(2,2,2-trifluoroethyl)-1H-purine-2,6(3H,7H)-dione 1-(1,4-Dioxaspiro[4.5]decan-8-ylmethyl)-3-methyl-7-(2,2,2-trifluoroethyl)-1H-purine-2,6(3H,7H)-dione (980 mg, 1.51 mmol) was dissolved in acetone (8 mL), 4 N hydrochloric acid aqueous solution (2 mL) was added. The reaction was stirred at room temperature overnight, water (20 mL) was added and then the mixture was extracted with ethyl acetate (30 mL×3), the organic phase was dried over anhydrous sodium sulfate, filtered and the filtrate was concentrated under reduced pressure, the resulting product was purified by silica gel column chromatography (1:1 petroleum ether/ethyl acetate, Rf=0.3) to deliver the product 3-methyl-1-((4-oxocyclohexyl)methyl)-7-(2,2,2-trifluoroethyl)-1H-purine-2,6(3H,7H)-dione (78.0 mg, yellow solid), yield: 15%. MS-ESI calcd. for [M+H]$^+$ 359, found 359.

3-Methyl-1-((4-oxocyclohexyl)methyl)-7-(2,2,2-trifluoroethyl)-1H-purine-2,6(3H,7H)-dione (66.0 mg, 0.184 mmol) was dissolved in tetrahydrofuran (2 mL). Under the nitrogen gas atmosphere, methyl Grignard reagent (3 M ether solution, 0.184 mL, 0.552 mmol) was slowly added at −78° C., the resulting mixture was stirred at −78° C. for half an hour, followed by reacting at 0° C. for 2 hours. Water (10 mL) was added, then the mixture was extracted with ethyl acetate (30 mL×3), the organic phase was dried over anhydrous sodium sulfate, filtered and the filtrate was concentrated under reduced pressure to deliver the crude product, which was purified by preparative high performance liquid chromatography to deliver product 1 (8.00 mg, white solid), yield: 12%. $^1$H NMR: (400 MHz, Methanol-d$_4$) δ 8.08 (s, 1H), 5.27-5.19 (m, 2H), 3.92 (d, J=7.2 Hz, 2H), 3.58 (s, 3H), 1.71-1.62 (m, 4H), 1.46-1.38 (m, 2H), 1.32-1.18 (m, 6H). MS-ESI: calcd. for [M+H—H$_2$O]$^+$ 357, found 357.

Product 2 (12.0 mg, white solid) (isomer 2, the second peak), yield: 17%. $^1$H NMR: (400 MHz, Methanol-d$_4$) δ 8.08 (s, 1H), 5.27-5.21 (m, 2H), 3.91 (d, J=7.2 Hz, 2H), 3.57 (s, 3H), 1.69-1.66 (m, 2H), 1.49-1.44 (m, 3H), 1.37-1.28 (m, 4H), 1.17 (s, 3H). MS-ESI: calcd. for [M+H—H$_2$O]$^+$ 357, found 357.

Embodiment 47

7-Cyclopropyl-3-methyl-1-(6,6,6-trifluoro-5-hydroxy-5-methylhexyl)-1H-purine-2,6(3H,7H)-dione

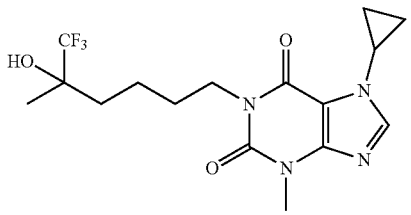

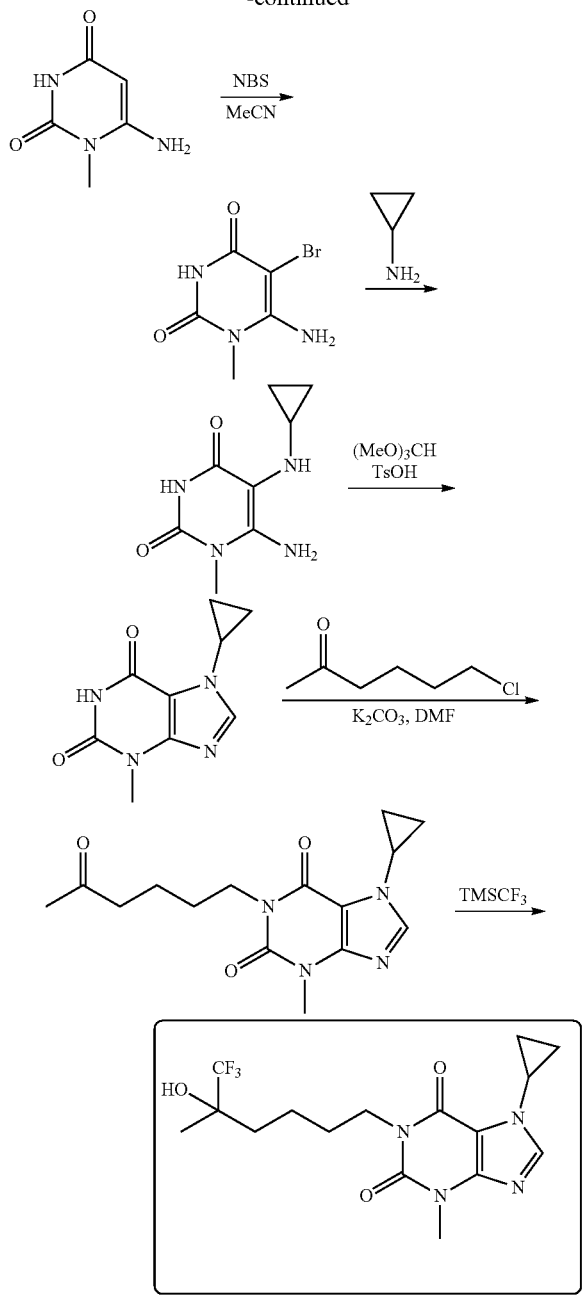

Step 1

6-Amino-5-bromo-1-methylpyrimidine-2,4(1H,3H)-dione

Under the nitrogen gas atmosphere, a solution of a mixture of 6-amino-1-methylpyrimidine-2,4(1H,3H)-dione (5.46 g, 40.0 mmol) and bromosuccinimide (7.56 g, 42.0 mmol) in acetonitrile (100 mL) was heated to reflux for 1.5 hours. The reaction solution was cooled to room temperature, filtered and the solvent was removed, and the resulting solid was washed with water (20 mL) and dried to deliver 6-amino-5-bromo-1-methylpyrimidine-2,4(1H, 3H)-dione (8.6 g, white solid), yield: 98%. $^1$H NMR: (400 MHz, DMSO-$d_6$) δ 10.90 (s, 1H), 7.04 (s, 2H), 3.28 (s, 3H).

Step 2

6-Amino-5-(cyclopropylamine)-1-methylpyrimidine-2,4(1H, 3H)-dione

6-Amino-5-bromo-1-methylpyrimidine-2,4(1H,3H)-dione (2.19 g, 10.0 mmol) was dissolved in a mixed solvent of cyclopropylamine (20 mL) and water (5 mL). The reaction solution was heated to reflux for 5 hours. The reaction solution was filtered to remove the solvent to give the crude product 6-amino-5-(cyclopropylamine)-1-methylpyrimidine-2,4(1H,3H)-dione, which was used directly for the next step.

Step 3

7-Cyclopropyl-3-methyl-1H-purine-2,6(3H,7H)-dione

Under the nitrogen gas atmosphere, 6-amino-5-(cyclopropylamine)-1-methylpyrimidine-2,4(1H,3H)-dione (1.96 g, 10.0 mmol), trimethyl orthoformate (2.12 g, 20.0 mmol) and p-toluenesulfonic acid (86.0 mg, 0.500 mmol) were dissolved in anhydrous N,N-dimethylformamide (20 mL). The reaction solution was heated to 100° C. overnight. The reaction solution was filtered and the solvent was removed to deliver the crude product 7-cyclopropyl-3-methyl-1H-purine-2,6(3H,7H)-dione, which was used directly for the next step.

Step 4

7-Cyclopropyl-3-methyl-1-(5-oxohexane)-1H-purine-2,6(3H,7H)-dione

Under the nitrogen gas atmosphere, 7-cyclopropyl-3-methyl-1H-purine-2,6(3H,7H)-dione (100 mg, 0.480 mmol), 6-chlorohexan-2-one (97.0 mg, 0.730 mmol) and potassium carbonate (132 mg, 0.960 mmol) were dissolved in N,N-dimethylformamide (5 mL). The reaction solution was heated to 120° C. for 3 hours. After cooling to room temperature, the mixture was diluted with water (20 mL) and ethyl acetate (10 mL), extracted with ethyl acetate (30 mL×2), the organic phase was dried over anhydrous sodium sulfate, filtered and concentrated to deliver the crude product 7-cyclopropyl-3-methyl-1-(5-oxohexane)-1H-purine-2,6 (3H,7H)-dione, which was used directly for the next step. MS-ESI calcd. for [M+H]$^+$ 305, found 305.

Step 5

7-Cyclopropyl-3-methyl-1-(6,6,6-trifluoro-5-hydroxy-5-methylhexyl)-1H-purine-2,6(3H,7H)-dione Under the nitrogen gas atmosphere, 7-cyclopropyl-3-methyl-1-(5-oxohexane)-1H-purine-2,6(3H,7H)-dione (200 mg, 0.660 mmol) was dissolved in anhydrous tetrahydrofuran (3 mL), trifluoromethyltrimethylsilane (0.2 mL, 0.990 mmol) and cesium fluoride (20.0 mg, 0.130 mmol) were then added successively. The resulting reaction solution was reacted at 30° C. for 2 hours. The reaction mixture was diluted with water (30 mL) and extracted with ethyl acetate (30 mL×2), the organic phase was dried over anhydrous sodium sulfate and filtered, the filtrate was concentrated under reduced pressure and the residue was purified by preparative TLC plate (1:2 petroleum ether/ethyl ester, Rf=0.3) to deliver 7-cyclopropyl-3-methyl-1-(6,6,6-trifluoro-5-hydroxy-5-methylhexyl)-1H-purine-2,6(3H,7H)-dione (150 mg, white solid), yield: 61%. $^1$H-NMR: (400 MHz, CDCl$_3$) δ 7.55 (s, 1H), 4.13-4.02 (m, 2H), 3.63-3.61 (m, 1H), 3.55 (s, 3H), 2.96 (s, 1H), 1.90-1.68 (m, 2H), 1.67-1.64 (m, 2H), 1.47-1.45 (m, 2H), 1.28 (s, 3H), 1.18-1.16 (m, 2H), 1.06-1.04 (m, 2H). MS-ESI calcd. for [M+H]$^+$ 375, found 375.

Embodiment 48

7-(Cyclopropylmethyl)-1-((4-hydroxy-4-(trifluoromethyl)cyclohexyl)methyl)-3-methyl-1H-purine-2,6 (3H,7H)-dione

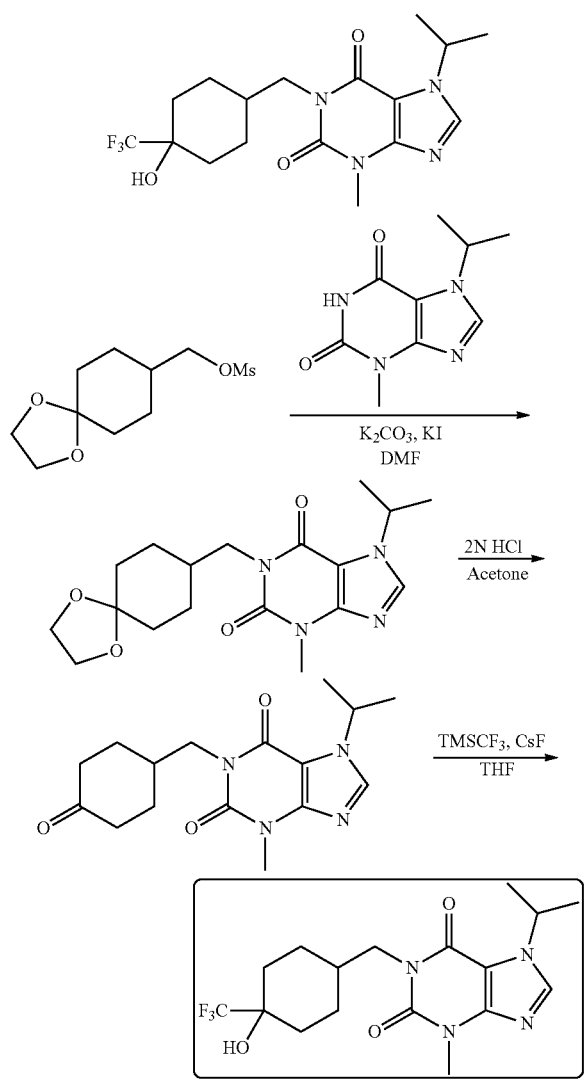

Step 1

1-(1,4-Dioxaspiro[4.5]decan-8-ylmethyl)-7-isopropyl-3-methyl-1H-purine-2,6(3H,7H)-dione 1,4-Dioxaspiro[4.5]decan-8-ylmethyl methanesulfonate (250 mg, 1.00 mmol), 7-isopropyl-3-methyl-1H-purine-2,6 (3H,7H)-dione (208 mg, 1.00 mmol), potassium iodide (15.8 mg, 0.100 mmol) and potassium carbonate (276 mg, 2.00 mmol) were dissolved in anhydrous N,N-dimethylformamide (8 mL). The reaction solution was heated to 120° C. and stirred for 3 hours. The reaction was cooled to 20° C. and the mixture was filtered and the filtrate was concentrated under reduced pressure to deliver the crude product 1-(1,4-dioxaspiro[4.5]decan-8-ylmethyl)-7-isopropyl-3-methyl-1H-purine-2,6(3H,7H)-dione (300 mg, white oil), yield: 83%. MS-ESI calcd. [M+H]$^+$ 362, found 362.

Step 2

7-Isopropyl-3-methyl-1-((4-oxocyclohexyl)methyl)-1H-purine-2,6(3H,7H)-dione 1-(1,4-Dioxaspiro[4.5]decan-8-ylmethyl)-7-isopropyl-3-methyl-1H-purine-2,6(3H,7H)-dione (300 mg, 0.828 mmol) was dissolved in acetone (10 mL), hydrochloric acid (0.5 mL) was added. The reaction solution was stirred at room temperature for 30 minutes. Water was added to the reaction solution, the pH value of which was adjusted to 7 with saturated sodium bicarbonate aqueous solution (10 mL), and the mixture was extracted with ethyl acetate (10 mL×3), the organic phases were combined, washed with saturated sodium chloride aqueous solution (20 mL×3), dried over anhydrous sodium sulfate, filtered, and the filtrate was concentrated under reduced pressure. The residue was purified by silica gel column chromatography (ethyl acetate, Rf=0.3) to deliver 7-isopropyl-3-methyl-1-((4-oxocyclohexyl)methyl)-1H-purine-2,6(3H,7H)-dione (180 mg, white oil), yield: 68%. MS-ESI calcd. for [M+H]$^+$ 319, found 319.

Step 3

7-Isopropyl-3-methyl-1-((4-hydroxy-4-(trifluoromethyl)cyclohexyl)methyl-1H-purine-2,6(3H,7H)-dione 7-Isopropyl-3-methyl-1-((4-oxocyclohexyl)methyl)-1H-purine-2,6(3H,7H)-dione (122 mg, 0.382 mmol) and cesium fluoride (11.5 mg, 0.0763 mmol) were dissolved in anhydrous tetrahydrofuran (3 mL), under the nitrogen gas atmosphere, trifluoromethyltrimethylsilane (95.0 mg, 0.640 mmol) was added. The reaction solution was heated to 30° C. and stirred for 12 hours. Then hydrochloric acid aqueous solution (1 N, 5 mL) was added and stirred for another 30 minutes. Water was added to the reaction solution, the pH value of which was adjusted to 7 with saturated sodium bicarbonate aqueous solution (10 mL) and the mixture was extracted with ethyl acetate (10 mL×3), the organic phases were combined and washed with saturated sodium chloride aqueous solution (20 mL×3), dried over anhydrous sodium sulfate, filtered, the filtrate was concentrated under reduced pressure, and the residue was purified by preparative high performance liquid chromatography to deliver 7-isopropyl-3-methyl-1-((4-hydroxy-4-(trifluoromethyl)cyclohexyl) methyl-1H-purine-2,6(3H,7H)-dione (80.0 mg, white solid), yield: 53%. $^1$H NMR: (400 MHz, Methanol-d$_4$) δ 8.10 (s, 1H), 5.06-5.00 (m, 1H), 4.08-3.91 (m, 2H), 3.55 (s, 3H), 2.17-2.00 (m, 2H), 1.88-1.84 (m, 2H), 1.61-1.40 (m, 6H), 1.59-1.57 (m, 5H). MS-ESI calcd. for [M+H]$^+$ 389, found 389.

Embodiment 49

7-(Cyclopropylmethyl)-1-((4-hydroxy-4-(trifluoromethyl)cyclohexyl)methyl)-3-methyl-1H-purine-2,6(3H,7H)-dione

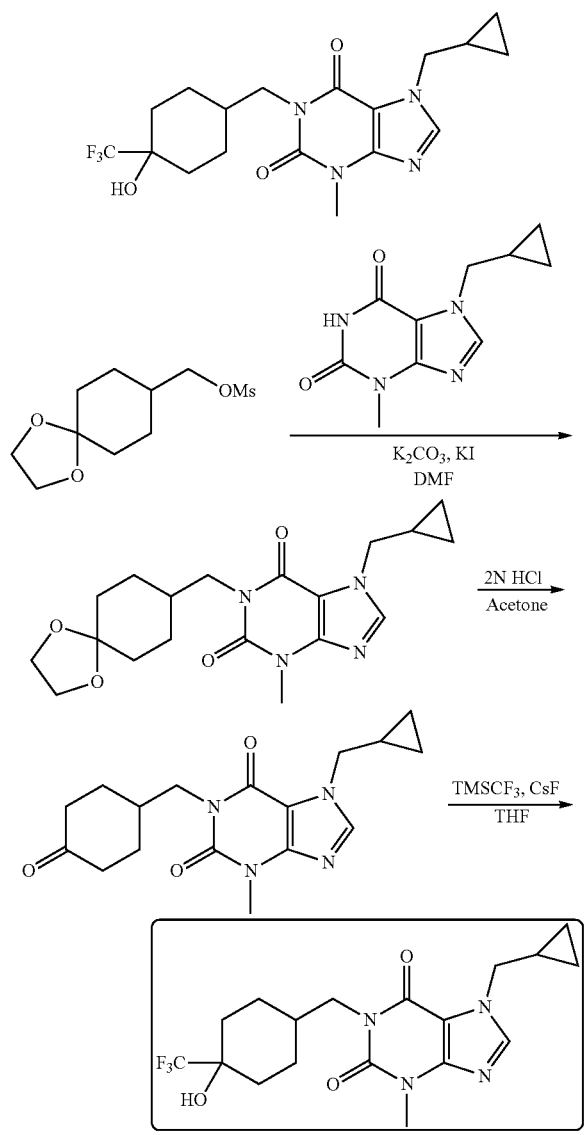

Step 1

1-(1,4-Dioxaspiro[4.5]decan-8-ylmethyl)-7-(cyclopropylmethyl)-3-methyl-1H-purine-2,6(3H,7H)-dione (Cyclopropylmethyl)-3-methyl-1H-purine-2,6(3H,7H)-dione (220 mg, 1.00 mmol), 1,4-dioxaspiro[4.5]decan-8-ylmethyl methanesulfonate (250 mg, 1.00 mmol), potassium iodide (15.8 mg, 0.100 mmol) and potassium carbonate (276 mg, 2.00 mmol) were dissolved in anhydrous N,N-dimethylformamide (8 mL), the reaction solution was heated to 120° C. and stirred for 3 hours. The reaction was cooled to 20° C. and the mixture was filtered and concentrated under reduced pressure to deliver the crude product 1-(1,4-dioxaspiro[4.5]decan-8-ylmethyl)-7-(cyclopropylmethyl)-3-methyl-1H-purine-2,6(3H,7H)-dione (300 mg, white oil), yield: 80%. MS-ESI calcd. for [M+H]$^+$ 375, found 375.

Step 2

7-(Cyclopropylmethyl)-3-methyl-1-((4-oxocyclohexyl)methyl)-1H-purine-2,6(3H,7H)-dione 1-(1,4-Dioxaspiro[4.5]decan-8-ylmethyl)-7-(cyclopropylmethyl)-3-methyl-1H-purine-2,6(3H,7H)-dione (300 mg, 0.802 mmol) was dissolved in acetone (10 mL), hydrochloric acid (0.5 mL) was added and the mixture was stirred at room temperature for 30 minutes. Water (30 mL) was added to the reaction solution, the pH value of which was adjusted to 7 with saturated sodium bicarbonate aqueous solution (10 mL), then the mixture was extracted with ethyl acetate (10 mL×3), the organic phases were combined, dried over anhydrous sodium sulfate, filtered, and the filtrate was concentrated under reduced pressure, the residue was isolated and purified by silica gel column chromatography (ethyl acetate, Rf 0.3) to deliver 7-(cyclopropylmethyl)-3-methyl-1-((4-oxocyclohexyl)methyl)-1H-purine-2,6(3H,7H)-dione (180 mg, white oil), yield: 75%. MS-ESI calcd. for [M+H]$^+$ 331, found 331.

Step 3

7-(Cyclopropylmethyl)-1-((4-hydroxy-4-(trifluoromethyl)cyclohexyl)methyl)-3-methyl-1H-purine-2,6(3H,7H)-dione 7-(Cyclopropylmethyl)-3-methyl-1-((4-oxocyclohexyl)methyl)-1H-purine-2,6(3H,7H)-dione (126 mg, 0.382 mmol) and cesium fluoride (11.5 mg, 0.0763 mmol) were dissolved in anhydrous tetrahydrofuran (3 mL), under the nitrogen gas atmosphere, trifluoromethyltrimethylsilane (95.0 mg, 0.640 mmol) was added. The mixture was stirred at 30° C. for 12 hours. Then 1 N hydrochloric acid aqueous solution (5 mL) was added and the stirring was continued for another 30 min. Water (30 mL) was added to the reaction solution, the pH value of which was adjusted to 7 with saturated sodium bicarbonate aqueous solution (10 mL) and extracted with ethyl acetate (10 mL×3), the organic phases were combined and washed with saturated sodium chloride aqueous solution (30 mL×2), dried over anhydrous sodium sulfate, filtered, the filtrate was concentrated under reduced pressure, the residue was isolated and purified by preparative high performance liquid chromatography to deliver 7-(cyclopropylmethyl)-1-((4-hydroxy-4-(trifluoromethyl)cyclohexyl)methyl)-3-methyl-1H-purine-2,6(3H,7H)-dione (80.0 mg, white solid), yield: 53%. $^1$H-NMR: (400 MHz, Methanol-d$_4$) δ 8.16-8.15 (m, 1H), 4.24-4.22 (m, 2H), 4.08-3.91 (m, 2H), 3.57 (s, 3H), 2.18-2.07 (m, 2H), 1.85-1.82 (m, 2H), 1.61-1.47 (m, 6H), 0.64-0.60 (m, 2H), 0.50-0.48 (m, 2H). MS-ESI calcd. for [M+H]$^+$ 401, found 401.

Embodiment 50

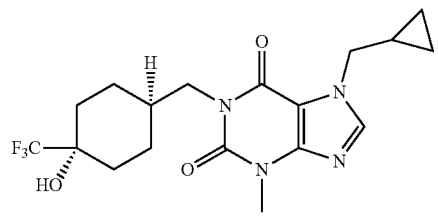
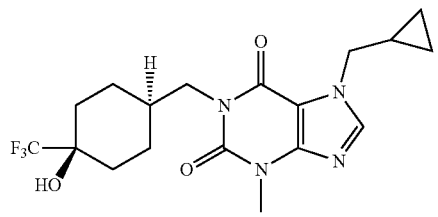

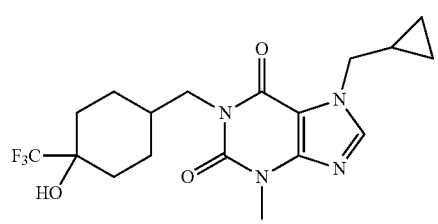
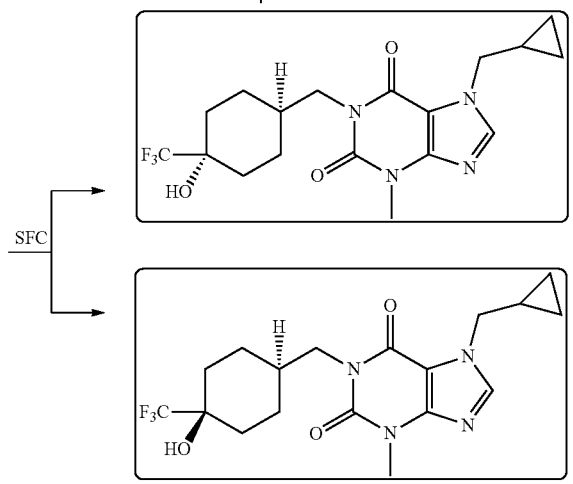

7-(Cyclopropylmethyl)-1-((4-hydroxy-4-(trifluoromethyl)cyclohexyl)methyl)-3-methyl-1H-purine-2,6(3H,7H)-dione (900 mg, 2.25 mmol) was separated by preparative SFC to deliver two isomers. Separation conditions: Column: AD 250 mm×30 mm, 5 μm; Mobile phase: A: Supercritical carbon dioxide, B: Methanol (0.05% ammonia), A:B=55:45; Flow rate: 40 mL/min; Wavelength: 220 nm. Product 1 (isomer 1, the first peak) (600 mg, white solid), yield: 100%. $^1$H NMR: (400 MHz, DMSO-$d_6$) δ 8.11 (s, 1H), 5.62 (s, 1H), 4.08 (d, J=7.6 Hz, 2H), 3.88 (d, J=7.6 Hz, 2H), 3.43 (s, 3H), 2.05-2.04 (m, 1H), 1.85-1.82 (m, 2H), 1.48-1.45 (m, 2H), 1.33-1.32 (m, 2H), 1.30-1.28 (m, 3H), 0.48-0.46 (m, 2H), 0.41-0.39 (m, 2H). MS-ESI calcd. for [M+H]$^+$ 401, found 401.

Product 2 (isomer 2, the second peak) (300 mg, white solid), yield: 100%. $^1$H NMR: (400 MHz, DMSO-$d_6$) δ 8.11 (s, 1H), 5.62 (s, 1H), 4.09 (d, J=7.6 Hz, 2H), 3.74 (d, J=7.6 Hz, 2H), 3.42 (s, 3H), 1.69-1.45 (m, 3H), 1.45-1.29 (m, 7H), 0.48-0.46 (m, 2H), 0.41-0.39 (m, 2H). MS-ESI calcd. for [M+H]$^+$ 401, found 401.

Embodiment 51

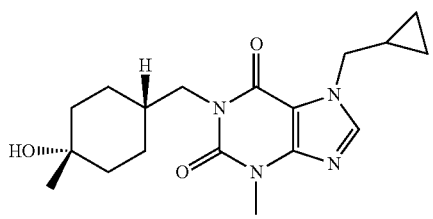

-continued

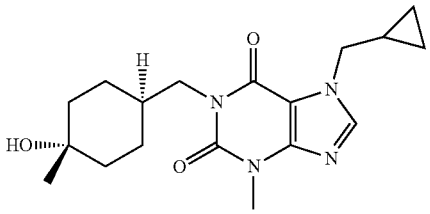

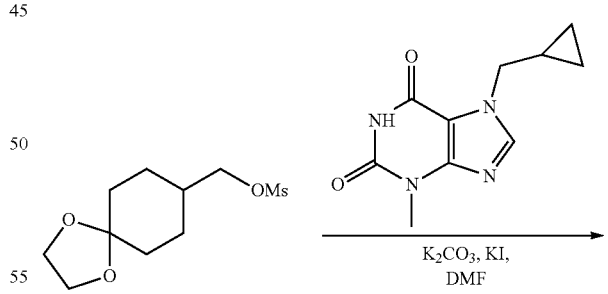

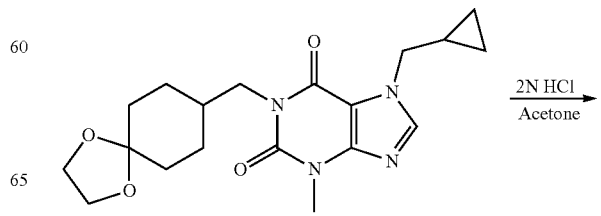

129

-continued

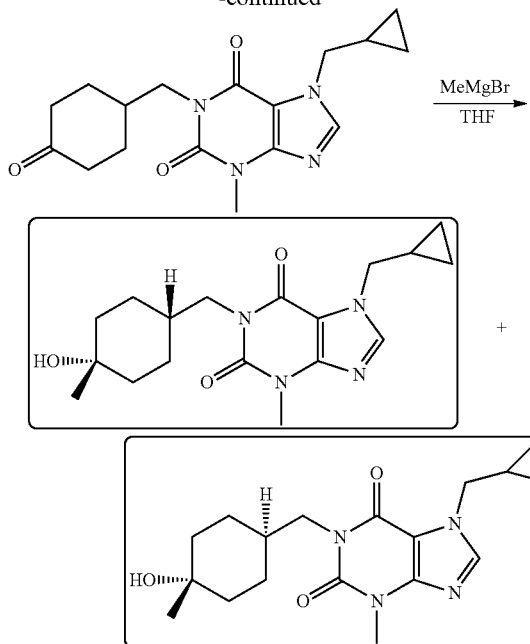

Step 1

1-(1,4-Dioxaspiro[4.5]decan-8-ylmethyl-7-(cyclopropylmethyl)-3-methyl-1H-purine-2,6-(3H,7H)-dione 1,4-Dioxaspiro[4.5]decan-8-ylmethyl methanesulfonate (682 mg, 2.72 mmol), 7-(cyclopropylmethyl)-3-methyl-1H-purine-2,6-(3H,7H)-dione (500 mg, 2.27 mmol) and potassium iodide (37.7 mg, 0.227 mmol) were dissolved in N,N-dimethylformamide (10 mL), potassium carbonate (627 mg, 4.54 mmol) was added and the reaction was heated to 130° C. for 4 hours. The reaction solution was cooled to room temperature, filtered, and the filtrate was concentrated under reduced pressure to deliver the crude product 1-(1,4-dioxaspiro[4.5]decan-8-ylmethyl-7-(cyclopropylmethyl)-3-methyl-1H-purine-2,6-(3H,7H)-dione (1.10 g, yellow oil). MS-ESI calcd. for [M+H]$^+$ 375, found 375.

Step 2

7-(Cyclopropylmethyl)-3-methyl-1-((4-oxocyclohexyl)methyl)-1H-purine-2,6-(3H,7H)-dione 1-(1,4-dioxaspiro[4.5]decan-8-ylmethyl-7-(cyclopropylmethyl)-3-methyl-1H-purine-2,6-(3H,7H)-dione (1.20 g, 2.09 mmol) was dissolved in acetone (12 mL), 4 N hydrochloric acid aqueous solution (3 mL) was added. The reaction was stirred at room temperature overnight, water (20 mL) was added and the mixture was extracted with ethyl acetate (30 mL×3), the organic phase was dried over anhydrous sodium sulfate, filtered and the filtrate was concentrated under reduced pressure, the resulting product was purified by silica gel column chromatography (1:1 petroleum ether/ethyl acetate, Rf=0.3) to deliver the product 7-(cyclopropylmethyl)-3-methyl-1-((4-oxocyclohexyl)methyl)-1H-purine-2,6-(3H,7H)-dione (52.0 mg, yellow solid), yield: 8%. MS-ESI calcd. for [M+H]$^+$ 331, found 331.

Step 3

7-(Cyclopropylmethyl)-3-methyl-1-((4-oxocyclohexyl)methyl)-1H-purine-2,6-(3H,7H)-dione (100 mg, 0.303 mmol) was dissolved in tetrahydrofuran (5 mL), under the nitrogen gas atmosphere, methyl Grignard reagent (3 M ether solution, 0.600 mL, 1.81 mmol) was slowly added at −78° C., the reaction mixture was stirred at −78° C. for half an hour, then reacted at 0° C. for 2 hours. Water (10 mL) was added, then the mixture was extracted with ethyl acetate (30 mL×3), the organic phase was dried over anhydrous sodium sulfate, filtered and the filtrate was concentrated under reduced pressure, to deliver the crude product, which was purified by preparative high performance liquid chromatography to deliver product 1 (26.0 mg, white solid) (isomer 1, the first peak), yield: 25%. $^1$H NMR: (400 MHz, Methanol-d$_4$) δ 7.99 (s, 1H), 4.19 (d, J=7.6 Hz, 2H), 3.90 (d, J=7.6 Hz, 2H), 3.54 (s, 3H), 1.90-1.79 (m, 1H), 1.70-1.61 (m, 4H), 1.45-1.36 (m, 3H), 1.27-1.16 (m, 5H), 0.65-0.55 (m, 2H), 0.49-0.42 (m, 2H). MS-ESI calcd. for [M+H—H$_2$O]$^+$ 329, found 329.

Product 2 (42.0 mg, white solid) (isomer 2, the second peak), yield: 40%. $^1$H NMR: (400 MHz, Methanol-d$_4$) δ 7.99 (s, 1H), 4.19 (d, J=7.6 Hz, 2H), 3.89 (d, J=7.6 Hz, 2H), 3.54 (s, 3H), 1.81-1.70 (m, 1H), 1.69-1.62 (m, 2H), 1.51-1.41 (m, 4H), 1.39-1.25 (m, 3H), 1.15 (s, 3H), 0.63-0.56 (m, 2H), 0.48-0.42 (m, 2H). MS-ESI calcd. for [M+H—H$_2$O]$^+$ 329, found 329.

Embodiment 52

1-((4-hydroxy-1-methyl-4-(trifluoromethyl)cyclohexyl)methyl)-3,7-dimethyl-1H-purine-2,6-(3H,7H)-dione

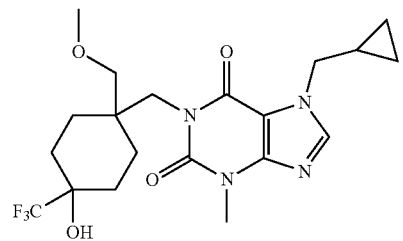

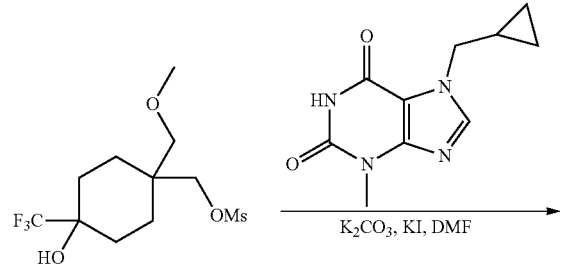

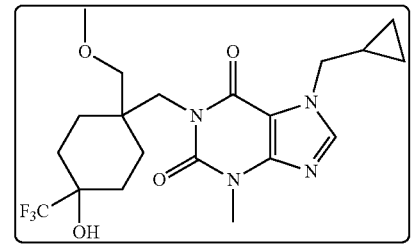

Step 1

1-((4-Hydroxy-1-methyl-4-(trifluoromethyl)cyclohexyl)methyl)-3,7-dimethyl-1H-purine-2,6(3H,7H)-dione (4-Hydroxy-1-(methoxymethyl)-4-(trifluoromethyl)cyclohexyl)methyl methanesulfonate (100 mg, 0.349 mmol), 7-(cyclopropylmethyl)-3-methyl-1H-purine-2,6-(3H,7H)-dione (76.9 mg, 0.349 mmol), potassium iodide (5.8 mg, 0.0349 mmol) and potassium carbonate (149 mg, 1.05 mmol) were dissolved in anhydrous N,N-dimethylformamide (5 mL). The reaction solution was heated to 150° C. by microwave and reacted for 2 hours. The reaction solution was cooled to 20° C., filtered, and the redidue was purified by preparative high performance liquid chromatography to deliver 1-((4-hydroxy-1-methyl-4-(trifluoromethyl)cyclohexyl)methyl)-3,7-dimethyl-1H-purine-2,6(3H,7H)-dione (10.0 mg, white solid), yield: 6%. $^1$H NMR: (400 MHz, DMSO-$d_6$) δ 8.13 (s, 1H), 4.12 (s, 2H), 3.94 (s, 1H), 3.43-3.38 (m, 4H), 3.31 (s, 3H) 3.19 (s, 3H), 1.56-1.45 (m, 8H), 1.43-1.31 (m, 1H), 0.51-0.49 (m, 2H), 0.44-0.42 (m, 2H). MS-ESI calcd. for [M+H]$^+$ 445, found 445.

Embodiment 53

7-(Cyclopropylmethyl)-1-((4-hydroxy-1-methyl-4-(trifluoromethyl)cyclohexyl)-3-methyl-1H-purine-2,6-(3H,7H)-dione

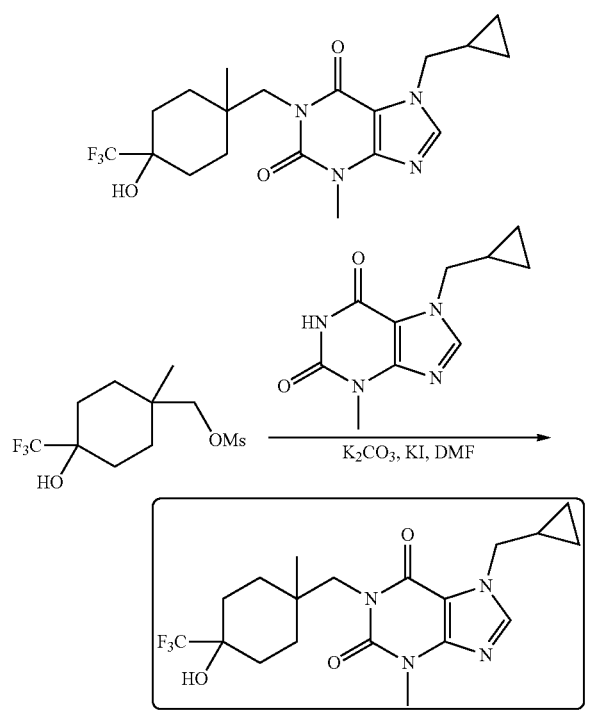

Step 1

7-(Cyclopropylmethyl)-1-((4-hydroxy-1-methyl-4-(trifluoromethyl)cyclohexyl)-3-methyl-1H-purine-2,6-(3H,7H)-dione (4-Hydroxy-1-methyl-4-(trifluoromethyl)cyclohexyl)methyl methanesulfonate (100 mg, 0.344 mmol), 7-(cyclopropylmethyl)-3-methyl-1H-purine-2,6-(3H,7H)-dione (75.9 mg, 0.344 mmol), potassium iodide (5.70 mg, 0.0344 mmol) and potassium carbonate (47.6 mg, 0.344 mmol) were dissolved in anhydrous N,N-dimethylformamide (5 mL). The reaction solution was heated to 150° C. and the microwave reaction lasted for 4 hours. The reaction solution was cooled to 20° C., filtered, concentrated and then the residue was purified by preparative high performance liquid chromatography to deliver 7-(cyclopropylmethyl)-1-((4-hydroxy-1-methyl-4-(trifluoromethyl)cyclohexyl)-3-methyl-1H-purine-2,6-(3H,7H)-dione (10.0 mg, white solid), yield: 7%. $^1$H-NMR: (400 MHz, DMSO-$d_6$) δ 8.13 (s, 1H), 4.13-4.09 (m, 2H), 3.83 (s, 1H), 3.43 (s, 3H), 3.34 (s, 2H), 1.67-1.53 (m, 6H), 1.23-1.20 (m, 3H), 0.88 (s, 3H), 0.50-0.42 (m, 4H). MS-ESI calcd. for [M+H]$^+$ 415, found 415.

Embodiment 54

7-(Cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione

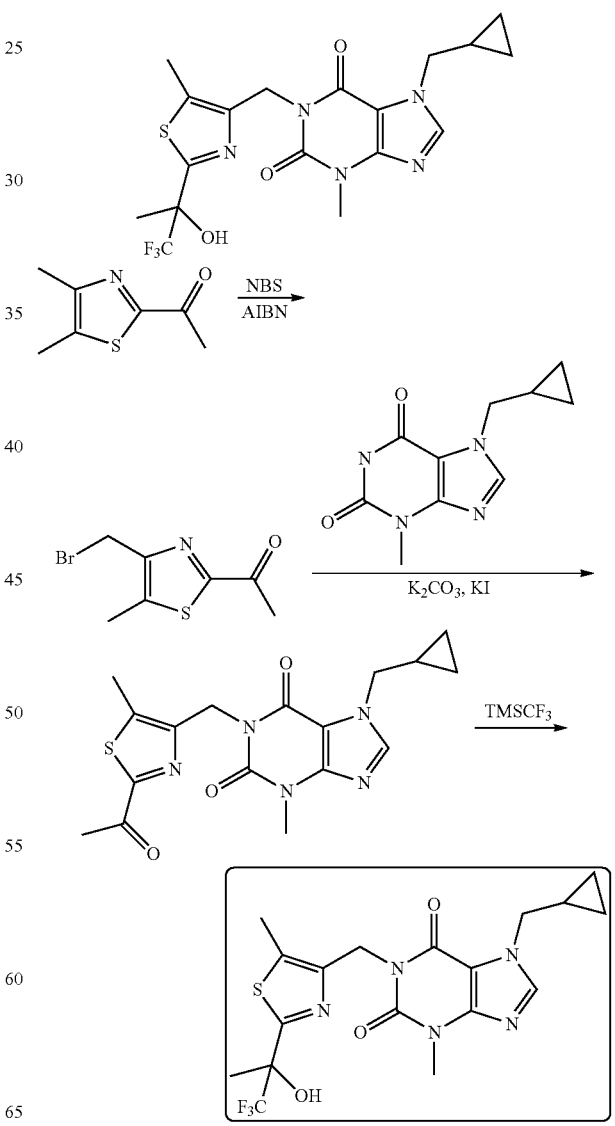

Step 1

1-(4-(Bromomethyl)-5-methylthiazol-2-yl)ethanone 1-(4,5-Dimethylpyridin-2-yl)ethanone (200 mg, 1.29 mmol), N-bromosuccinimide (229 mg, 1.29 mmol), azobisisobutyronitrile (21.2 mg, 0.129 mmol) were dissolved in carbon tetrachloride (20 mL), which was reacted at 80° C. for 12 hours. The reaction was quenched by the addition of saturated sodium thiosulfate aqueous solution (30 mL). The reaction mixture was extracted with dichloromethane (10 mL×3), dried over anhydrous sodium sulfate, filtered and the filtrate was concentrated under reduced pressure to deliver 1-(4-(bromomethyl)-5-methylthiazol-2-yl)ethanone (200 mg, yellow oil), yield: 46%. MS-ESI calcd. for [M+H]$^+$ 234, 236, found 234, 236.

Step 2

1-((2-Acetyl-5-methylthiazol-4-yl)methyl)-7-(cyclopropylmethyl)-3-methyl-1H-purine-2,6-(3H,7H)-dione 1-(4-(Bromomethyl)-5-methylthiazol-2-yl)ethanone (200 mg, 0.598 mmol), 7-(cyclopropylmethyl)-3-methyl-1H-purine-2,6-(3H,7H)-dione (132 mg, 0.598 mmol), potassium iodide (19.8 mg, 0.119 mmol) and potassium carbonate (248 mg, 1.79 mmol) were dissolved in N,N-dimethylformamide (10 mL). The reaction solution was heated to 120° C. and stirred for 3 hours. The reaction mixture was cooled to room temperature, filtered and the filtrate was concentrated under reduced pressure, the residue was isolated and purified by preparative TLC plate (1:1 petroleum ether/ethyl acetate, Rf value=0.4) to deliver 1-((2-acetyl-5-methylthiazol-4-yl)methyl)-7-(cyclopropylmethyl)-3-methyl-1H-purine-2,6-(3 H,7H)-dione (100 mg, yellow solid), yield: 45%. $^1$H NMR: (400 MHz, Methanol-d$_4$) δ 8.02 (s, 1H), 5.35 (s, 2H), 4.21 (d, J=7.6 Hz, 2H), 3.56 (s, 3H), 2.66 (s, 3H), 2.60 (s, 3H), 1.46-1.41 (m, 1H), 0.65-0.61 (m, 2H), 0.60-0.48 (m, 2H). MS-ESI calcd. for [M+H]$^+$ 374, found 374.

Step 3

7-(Cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione 1-((2-Acetyl-5-methylthiazol-4-yl)methyl)-7-(cyclopropylmethyl)-3-methyl-1H-purin e-2,6-(3H,7H)-dione (100 mg, 0.267 mmol), cesium fluoride (40.6 mg, 0.267 mmol) were dissolved in tetrahydrofuran (10 mL), trimethyl-trifluoromethyl-silane (114 mg, 0.803 mmol) was added at room temperature and stirred for 12 hours. The reaction was quenched by the addition of water (20 mL). Then the reaction mixture was extracted with ethyl acetate (10 mL×3). The organic phases were combined, washed with saturated brine, dried over anhydrous sodium sulfate, filtered and the filtrate was concentrated under reduced pressure. The residue was then purified by preparative high performance liquid chromatography to deliver 7-(cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione (50.0 mg, yellow solid), yield: 42%. $^1$H NMR: (400 MHz, Methanol-d$_4$) δ 8.11 (s, 1H), 5.33 (s, 2H), 4.23 (d, J=7.6 Hz, 2H), 3.57 (s, 3H), 2.64 (s, 3H), 1.81 (s, 3H), 1.45-1.41 (m, 1H), 0.65-0.61 (m, 2H), 0.60-0.49 (m, 2H). MS-ESI calcd. for [M+H]$^+$ 444, found 444.

Embodiment 55

7-(Cyclopropylmethyl)-3-methyl-1-((6-(1,1,1-trifluoro-2-hydroxypropan-2-yl)pyridin-3-yl)methyl)-1H-purine-2,6-(3H,7H)-dione

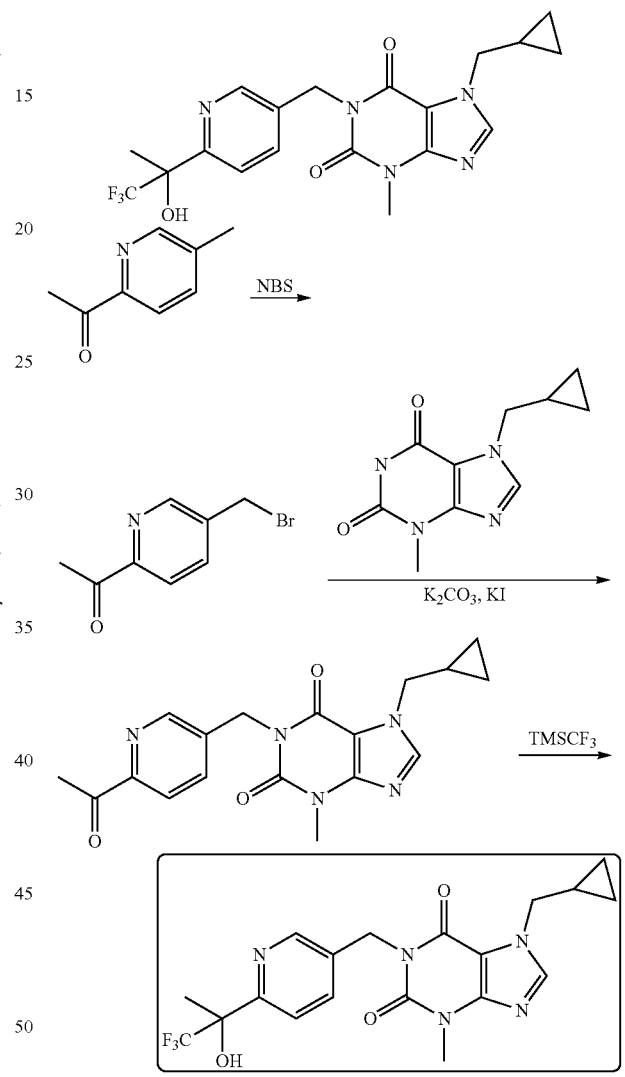

Step 1

1-[5-(Bromomethyl)-2-pyridyl]ethanone 1-(5-Methyl-2-pyridyl)ethanone (500 mg, 3.70 mmol), N-bromosuccinimide (658 mg, 3.70 mmol), azobisisobutyronitrile (182 mg, 1.11 mmol) were dissolved in carbon tetrachloride (20 mL), which was reacted at 90° C. for 12 hours. The reaction was quenched by the addition of saturated sodium thiosulfate aqueous solution (30 mL). Then the reaction mixture was extracted with dichloromethane (10 mL×3), dried over anhydrous sodium sulfate, filtered and the filtrate was concentrated under reduced pressure to deliver 1-[5-(bromomethyl)-2-pyridyl]ethanone (125 mg, yellow oil), yield: 16%. MS-ESI calcd. for [M+H]⁺ 214 and 216, found 214 and 216.

Step 2

1-[(6-Acetyl-3-pyridyl)methyl]-7-(cyclopropylmethyl)-3-methyl-1H-purine-2,6-(3H,7H)-dione 1-[5-(Bromomethyl)-2-pyridyl]ethanone (100 mg, 0.467 mmol), 7-(cyclopropylmethyl)-3-methyl-1H-purine-2,6-dione (103 mg, 0.467 mmol), potassium iodide (15.5 mg, 0.0934 mmol) and potassium carbonate (193 mg, 1.40 mmol) were dissolved in N,N-dimethylformamide (10 mL). The reaction solution was heated to 120° C. and stirred for 3 hours. Then the reaction mixture was cooled to room temperature, filtered and the filtrate was concentrated under reduced pressure, the residue was isolated and purified by preparative TLC plate (ethyl acetate, Rf=0.4) to deliver 1-[(6-acetyl-3-pyridyl)methyl-7-(cyclopropylmethyl)-3-methyl-1H-purine-2,6-(3H,7H)-dione (50.0 mg, yellow solid), yield: 30%. MS-ESI calcd. for [M+H]⁺ 354, found 354.

Step 3

7-(Cyclopropylmethyl)-3-methyl-1-((6-(1,1,1-trifluoro-2-hydroxypropan-2-yl)pyridin-3-yl)methyl)-1H-purine-2,6-(3H,7H)-dione 1-[(6-Acetyl-3-pyridyl)methyl]-7-(cyclopropylmethyl)-3-methyl-1H-purine-2,6-(3H,7 H)-dione (100 mg, 0.283 mmol), cesium fluoride (43.0 mg, 0.283 mmol) were dissolved in tetrahydrofuran (10 mL), trimethyl-trifluoromethyl-silane (60.4 mg, 0.424 mmol) was added at room temperature and stirred for 12 hours. The reaction was quenched by the addition of water (20 mL). Then the reaction mixture was extracted with ethyl acetate (10 mL×3). The organic phases were combined, washed with saturated brine, dried over anhydrous sodium sulfate, filtered and the filtrate was concentrated under reduced pressure. The residue was purified by preparative high performance liquid chromatography to deliver 7-(cyclopropylmethyl)-3-methyl-1-((6-(1,1,1-trifluoro-2-hydroxypropan-2-yl)pyridin-3-yl)methyl)-1H-purine-2,6-(3H,7H)-dione (40.0 mg, yellow solid), yield: 32%. ¹H NMR: (400 MHz, Methanol-d₄) δ 9.00 (s, 1H), 8.80-8.72 (m, 1H), 8.46 (s, 1H), 8.35-8.29 (m, 1H), 5.43 (s, 2H), 4.28 (d, J=7.6 Hz, 2H), 3.58 (s, 3H), 1.95 (s, 3H), 1.50-1.46 (m, 1H), 0.68-0.64 (m, 2H), 0.53-0.51 (m, 2H). MS-ESI calcd. for [M+H]⁺ 424, found 424.

Embodiment 56

7-(Cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione

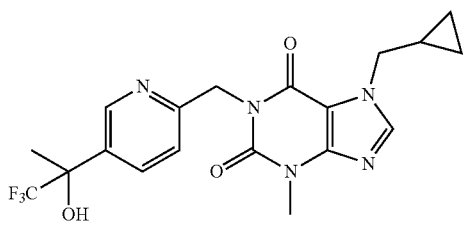

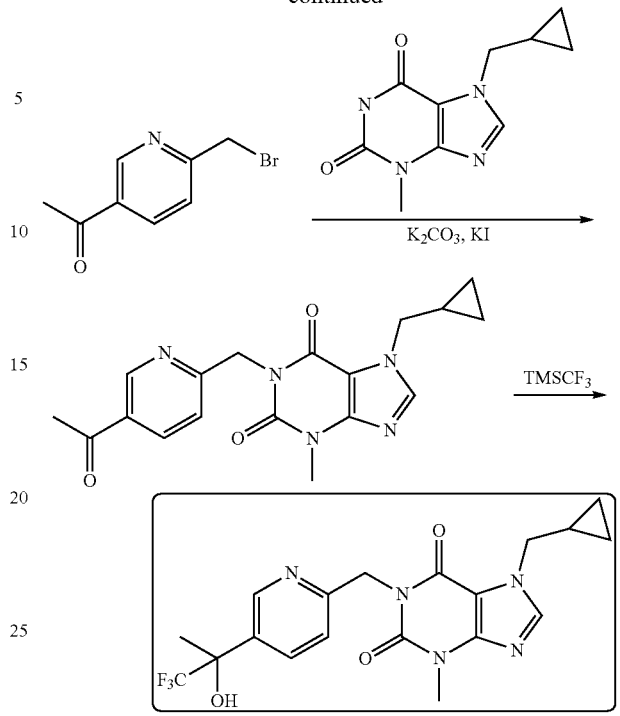

Step 1

1-[(5-Acetyl-2-pyridyl)methyl]-7-(cyclopropylmethyl)-3-methyl-1H-purine-2,6-(3H,7H)-dione 1-[6-(Bromomethyl)-3-pyridyl]ethanone (100 mg, 0.467 mmol), 7-(cyclopropylmethyl)-3-methyl-1H-purine-2,6-(3H,7H)-dione (103 mg, 0.467 mmol), potassium iodide (15.5 mg, 0.0934 mmol) and potassium carbonate (193 mg, 1.40 mmol) were dissolved in N,N-dimethylformamide (10 mL). The reaction solution was heated to 120° C. and stirred for 3 hours. The reaction mixture was cooled to room temperature, filtered, and the filtrate was concentrated under reduced pressure and purified by preparative TLC plate (ethyl acetate, Rf=0.5) to deliver 1-((5-acetyl-2-pyridyl)methyl)-7-(cyclopropylmethyl)-3-methyl-1H-purine-2,6-(3H,7H)-dione (50.0 mg, yellow solid), yield: 30%. MS-ESI calcd. for [M+H]⁺ 354, found 354.

Step 2

7-(Cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione 1-[(5-Acetyl-2-pyridyl)methyl]-7-(cyclopropylmethyl)-3-methyl-1H-purine-2,6-(3H,7 H)-dione (100 mg, 0.283 mmol), cesium fluoride (43.0 mg, 0.283 mmol) were dissolved in tetrahydrofuran (10 mL), trimethyl-trifluoromethyl-silane (60.4 mg, 0.424 mmol) was added at room temperature and stirred for 12 hours. The reaction was quenched by the addition of water (20 mL). The reaction mixture was extracted with ethyl acetate (10 mL×3). The organic phases were combined, washed with saturated brine, dried over anhydrous sodium sulfate, filtered and the filtrate was concentrated under reduced pressure. And the residue was purified by preparative high performance liquid chromatography to deliver 7-(cyclopropylmethyl)-3-methyl-1-((5-methyl-2-(1,1,1-trifluoro-2-hydroxypropan-2-yl)thiazol-4-yl)methyl)-1H-purine-2,6-(3H,7H)-dione (10.0 mg, yellow solid), yield: 8%. $^1$H NMR: (400 MHz, Methanol-d$_4$) δ 8.92 (s, 1H), 8.75 (d, J=7.6 Hz, 1H), 8.09 (d, J=7.6 Hz, 1H), 7.97 (s, 1H), 5.54 (s, 1H), 4.21 (d, J=7.6 Hz, 2H), 3.58 (s, 3H), 1.45-1.42 (m, 1H), 0.64-0.59 (m, 2H), 0.50-0.46 (m, 2H). MS-ESI calcd. for [M+H]$^+$ 424, found 424.

Embodiment 57

1-((4-Hydroxy-4-(trifluoromethyl)cyclohexyl)methyl)-7-isobutyl-3-methyl-1H-purine-2,6(3H,7H)-dione

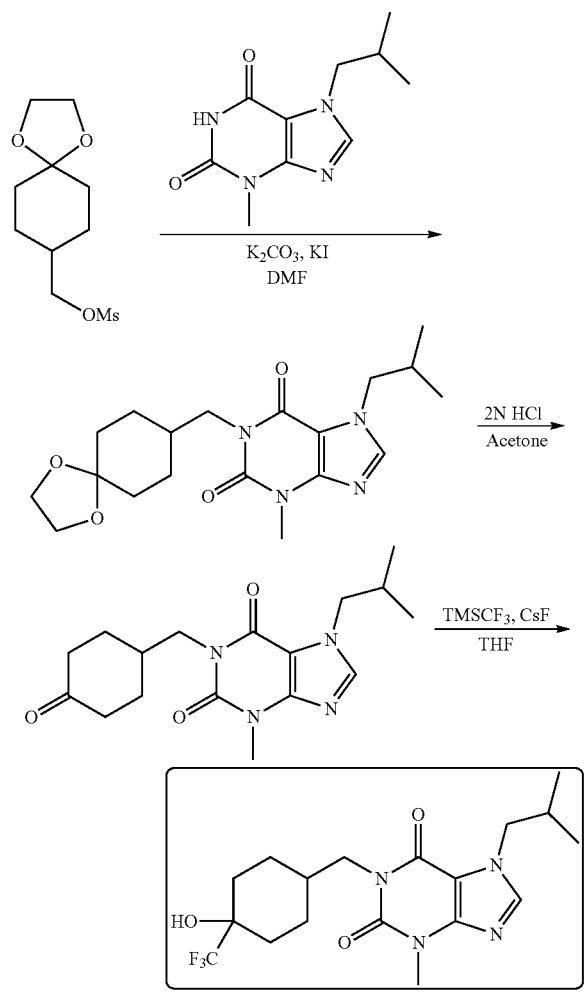

Step 1

1-(1,4-Dioxaspiro[4.5]decan-8-ylmethyl)-7-isobutyl-3-methyl-1H-purine-2,6(3H,7H)-dione 1,4-Dioxaspiro[4,5]decan-8-ylmethyl methanesulfonate (1.07 g, 4.81 mmol), 7-isobutyl-3-methyl-1H-purine-2,6 (3H,7H)-dione (1.00 g, 4.01 mmol) and potassium carbonate (647 mg, 4.81 mmol) were dissolved in N,N-dimethylformamide (14 mL), potassium iodide (66.5 mg, 0.401 mmol) was added and the reaction was heated to 130° C. and stirred at reflux for 3 hours. The reaction solution was directly filtered and the filtrate was concentrated under reduced pressure to deliver the crude product 1-(1,4-dioxaspiro[4.5]decan-8-ylmethyl)-7-isobutyl-3-methyl-1H-purine-2,6(3H,7H)-dione (crude product 2.56 g, brown oil). MS-ESI calcd. for [M+H]$^+$ 377, found 377.

Step 2

7-Isobutyl-3-methyl-1-((4-oxocyclohexyl)methyl)-1H-purine-2,6(3H,7H)-dione 1-(1,4-Dioxaspiro[4.5]decan-8-ylmethyl)-7-isobutyl-3-methyl-1H-purine-2,6(3H,7H)-dione (2.50 g, 6.00 mmol) was dissolved in acetone (12 mL), 4 N hydrochloric acid aqueous solution (2 mL) was added. The reaction was stirred at 30° C. overnight and the pH was adjusted to 7 by the addition of saturated sodium bicarbonate aqueous solution (8 mL). Water (100 mL) was added into the reaction solution, which was then extracted with ethyl acetate (150 mL×3), the organic phase was dried over anhydrous sodium sulfate, filtered and the filtrate was concentrated under reduced pressure, the resulting product was purified by silica gel column chromatography (1:2 petroleum ether/ethyl acetate, Rf=0.3) to deliver the product 7-isobutyl-3-methyl-1-((4-oxocyclohexyl)methyl)-1H-purine-2,6(3H,7H)-dione (150 mg, white solid), yield: 13%. $^1$H NMR: (400 MHz, Methanol-d$_4$) δ 7.94 (s, 1H), 4.14 (d, J=7.6 Hz, 2H), 3.99 (d, J=7.6 Hz, 2H), 3.55 (s, 3H), 2.29-2.38 (m, 5H), 2.20-2.13 (m, 1H), 2.03-1.98 (m, 2H), 1.53-1.47 (m, 2H), 0.92 (d, J=6.4 Hz, 6H). MS-ESI calcd. for [M+H]$^+$ 333, found 333.

Step 3

1-((4-Hydroxy-4-(trifluoromethyl)cyclohexyl)methyl)-7-isobutyl-3-methyl-1H-purine-2,6(3H,7H)-dione 7-Isobutyl-3-methyl-1-((4-oxocyclohexyl)methyl)-1H-purine-2,6(3H,7H)-dione (150 mg, 0.450 mmol) and cesium fluoride (8.0 mg, 0.0450 mmol) were dissolved in tetrahydrofuran (3 mL), under the nitrogen gas atmosphere, trifluoromethyltrimethylsilane (950 mg, 0.640 mmol) was added. The reaction was stirred at 30° C. for 16 hours. 4 N hydrochloric acid aqueous solution (3 mL) was added, and after stirring at 25° C. for half an hour, the pH value of the reaction mixture was added to 7 by the addition of saturated sodium bicarbonate aqueous solution (15 mL), water (50 mL) was added, and extracted with ethyl acetate (50 mL×3), the organic phase was dried over anhydrous sodium sulfate and concentrated under reduced pressure to deliver the crude product, which was purified by preparative high performance liquid chromatography to deliver the product 1-((4-hydroxy-4-(trifluoromethyl)cyclohexyl)methyl)-7-isobutyl-3-methyl-1H-purine-2,6(3H,7H)-dione (86.0 mg, white solid), yield: 48%. $^1$H NMR: (400 MHz, Methanol-d$_4$) δ 7.93 (s, 1H), 4.15-4.04 (m, 2H), 3.89 (d, J=7.6 Hz, 1H), 3.54 (s, 3H), 2.20-1.98 (m, 3H), 1.86-1.79 (m, 2H), 1.61-1.42 (m, 5H), 0.92 (d, J=6.4 Hz, 6H). MS-ESI calcd. for [M+H]$^+$ 403, found 403.

Embodiment 58

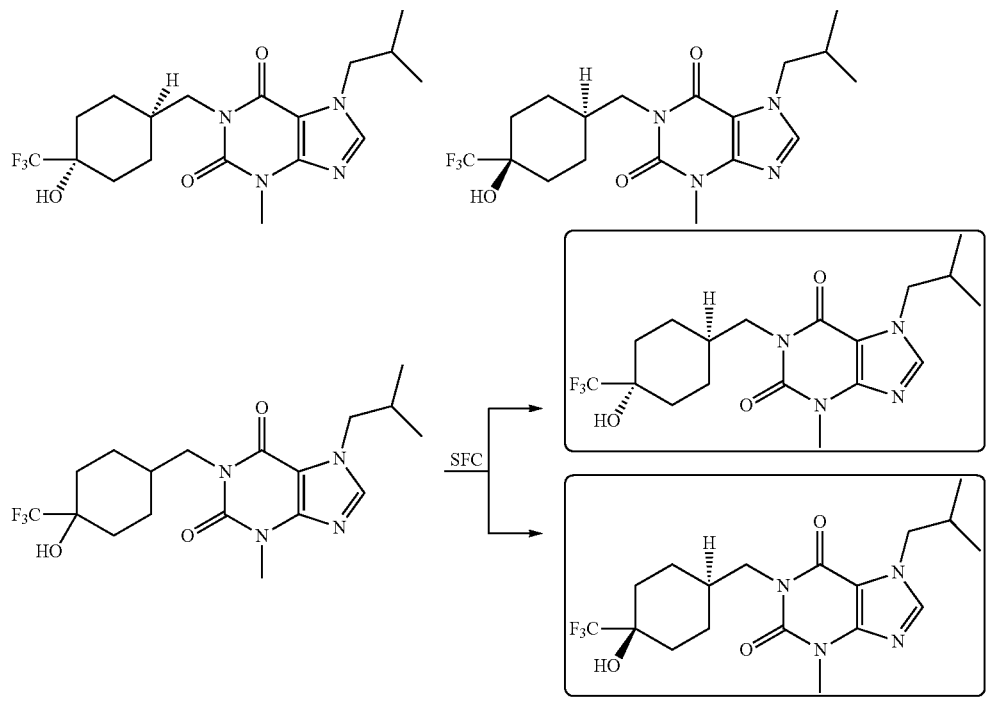

1-((4-Hydroxy-4-(trifluoromethyl)cyclohexyl)methyl)-7-isobutyl-3-methyl-1H-purine-2,6(3H,7H)-dione (900 mg, 2.24 mmol) was separated by preparative SFC to deliver two isomers. Separation conditions for isomer 1: Column: AD 250 mm×30 mm, 5 m Mobile phase: A: Supercritical carbon dioxide, B: Ethanol (0.05% ammonia), A:B=80:20 Flow rate: 50 mL/min Wavelength: 220 nm. Separation conditions for isomer 2: Column: WEEK-1 300 mm×25 mm, 5 m; Mobile phase: A: supercritical carbon dioxide, B: ethanol (0.05% ammonia), A:B=60:40, flow rate: 60 mL/min, wavelength: 220 nm.

Product 1 (isomer 1, the first peak) (216 mg, white solid), yield: 36%. $^1$H-NMR (400 MHz, DMSO-$d_6$) δ 8.09 (s, 1H), 5.65 (s, 1H), 4.07 (d, J=7.2 Hz, 2H), 3.90 (d, J=7.2 Hz, 2H), 3.43 (s, 3H), 2.14-2.00 (m, 2H), 1.92-1.80 (m, 2H), 1.77-1.66 (m, 2H), 1.52-1.44 (m, 2H), 1.37-1.30 (m, 2H), 0.84 (d, J=6.4 Hz, 6H). MS-ESI calcd. for [M+H]+ 403, found 403.

Product 2 (isomer 2, the second peak) (101 mg, white solid), yield 37%. $^1$H-NMR (400 MHz, DMSO-$d_6$) δ 8.07 (s, 1H), 5.64 (s, 1H), 4.05 (d, J=7.6 Hz, 2H), 3.75 (d, J=7.6 Hz, 2H), 3.42 (s, 3H), 2.16-2.03 (m, 1H), 1.71-1.66 (m, 3H), 1.48-1.30 (m, 6H), 0.83 (d, J=6.4 Hz, 6H). MS-ESI calcd. for [M+H]$^+$ 403, found 403.

Embodiment 59

7-(2,3-Dihydroxypropyl)-1-(5-ethyl-5-hydroxyheptyl)-3-methyl-1H-purine-2,6(3H,7H)-dione

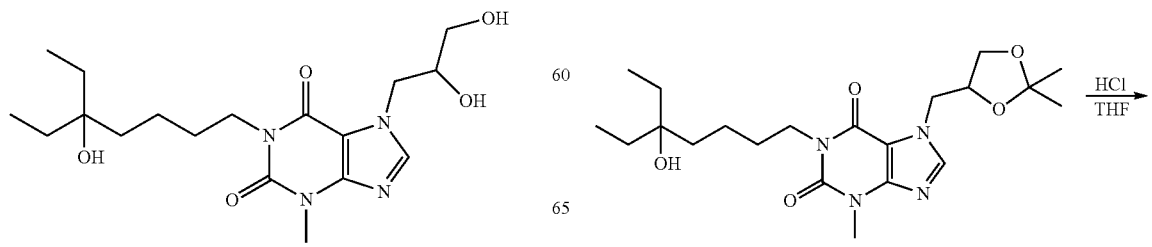

-continued

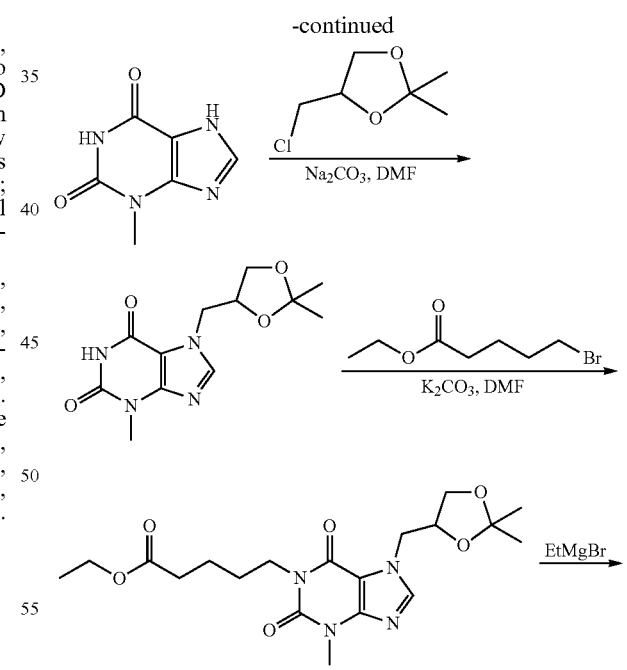

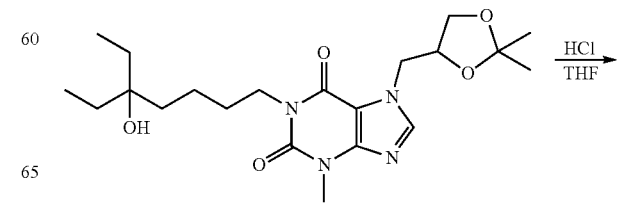

-continued

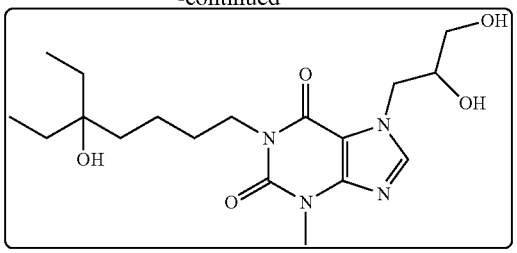

Step 1

7-((2,2-Dimethyl-1,3-dioxolan-4-yl)methyl)-3-methyl-1H-purine-2,6(3H,7H)-dione 3-Methyl-1H-purine-2,6(3H,7H)-dione (200 mg, 1.20 mmol), sodium carbonate (128 mg, 1.20 mmol), 4-(chloromethyl)-2,2-dimethyl-1,3-dioxolane (217 mg, 1.44 mmol) and potassium iodide (20.0 mg, 0.120 mmol) were dissolved in N,N-dimethylformamide (10 mL). The reaction solution was heated to 110° C. and reacted for 36 hours. The reaction was quenched by the addition of water (10 mL), then the reaction mixture was extracted with ethyl acetate (10 mL×3) and the organic phase was washed with saturated brine (5 mL), dried over anhydrous sodium sulfate, concentrated under reduced pressure and purified by preparative TLC plate (ethyl acetate, Rf=0.5) to deliver 7-((2,2-dimethyl-1, 3-dioxolan-4-yl)methyl)-3-methyl-1H-purine-2,6(3H,7H)-dione (169 mg, yellow solid), yield: 50%. MS-ESI calcd. for [M+H]$^+$ 281, found 281.

Step 2

Ethyl 5-(7-((2,2-dimethyl-1,3-dioxolan-4-yl)methyl)-3-methyl-2,6-dioxo-2,3,6,7-tetrahydro-1H-purinan-1-yl) valate 7-((2,2-Dimethyl-1,3-dioxolan-4-yl)methyl)-3-methyl-1H-purine-2,6(3H,7H)-dione (169 mg, 0.604 mmol), ethyl bromovalerate (178 mg, 0.906 mmol), potassium carbonate (167 mg, 1.21 mmol) and potassium iodide (20.0 mg, 0.0600 mmol) were dissolved in N,N-dimethylformamide (10 mL). The reaction solution was heated to 130° C., reacted for 3 hours, then the reaction mixture was filtered and concentrated, the residue was isolated and purified by preparative TLC plate (ethyl acetate, Rf=0.4) to deliver ethyl 5-(7-((2, 2-dimethyl-1,3-dioxolan-4-yl)methyl)-3-methyl-2,6-dioxo-2,3,6,7-tetrahydro-1H-purinan-1-yl)valate (124 mg, yellow solid), yield: 50%. MS-ESI calcd. for [M+H]$^+$ 409, found 409.

Step 3

7-((2,2-Dimethyl-1,3-dioxolan-4-yl)methyl)-1-(5-ethyl-5-hydroxyheptyl)-3-methyl-1H-purine-2,6(3H,7H)-dione Ethyl 5-(7-((2,2-dimethyl-1,3-dioxolan-4-yl)methyl)-3-methyl-2,6-dioxo-2,3,6,7-tetrahydro-1H-purinan-1-yl)valate (30.0 mg, 0.0750 mmol) was dissolved in anhydrous tetrahydrofuran (1 mL), ethylmagnesium bromide (3 M tetrahydrofuran solution, 0.15 mL, 0.450 mmol) was slowly added dropwise at −65° C. The reaction was reacted at −65° C. for 0.5 hour and then reacted at 0° C. for 0.5 hour. The reaction was quenched by pouring the reaction solution into water (5 mL), which was then extracted with ethyl acetate (5 mL×3), dried over anhydrous sodium sulfate, filtered, concentrated under reduced pressure and purified by preparative TLC plate (ethyl acetate, Rf=0.5) to deliver 7-((2,2-dimethyl-1,3-dioxolan-4-yl)methyl)-1-(5-ethyl-5-hydroxyheptyl)-3-methyl-1H-purine-2,6(3H,7H)-dione (20.0 mg, yellow oil), yield: 63%. MS-ESI calcd. for [M+H]$^+$ 423, found 423.

Step 4

7-(2,3-Dihydroxypropyl)-1-(5-ethyl-5-hydroxyheptyl)-3-methyl-1H-purine-2,6(3H,7H)-dione 7-((2,2-Dimethyl-1,3-dioxolan-4-yl)methyl)-1-(5-ethyl-5-hydroxyheptyl)-3-methyl-1 H-purine-2,6(3H,7H)-dione (20.0 mg, 0.0470 mmol) was dissolved in anhydrous tetrahydrofuran (1 mL) and dilute hydrochloric acid (0.3 mL), reacted at 25° C. for 36 hours. After the reaction was complete, the reaction mixture was concentrated under reduced pressure and purified by preparative TLC plate (8:1 ethyl acetate/methanol, Rf=0.3) to deliver 7-(2,3-dihydroxypropyl)-1-(5-ethyl-5-hydroxyheptyl)-3-methyl-1H-purine-2,6(3H,7H)-dione (5.0 mg, white solid), yield: 28%. $^1$H NMR: (400 MHz, Methanol-d$_4$) δ 7.90 (s, 1H), 4.57-4.53 (m, 1H), 4.26-4.22 (m, 1H), 4.03-3.96 (m, 3H), 3.58-3.55 (m, 2H), 3.54 (s, 3H), 1.66-1.61 (m, 2H), 1.48-1.44 (m, 6H), 1.34-1.29 (m, 2H), 0.85 (t, J=8.0 Hz, 6H). MS-ESI calcd. for [M+H]$^+$ 383, found 383.

Embodiment 60

1-(5-Ethyl-5-hydroxyheptyl)-7-(2-hydroxyethyl)-3-methyl-1H-purine-2,6(3H,7H)-dione

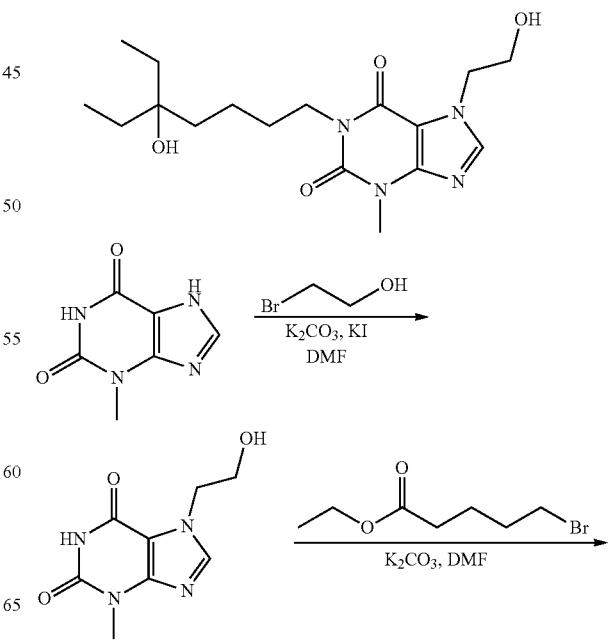

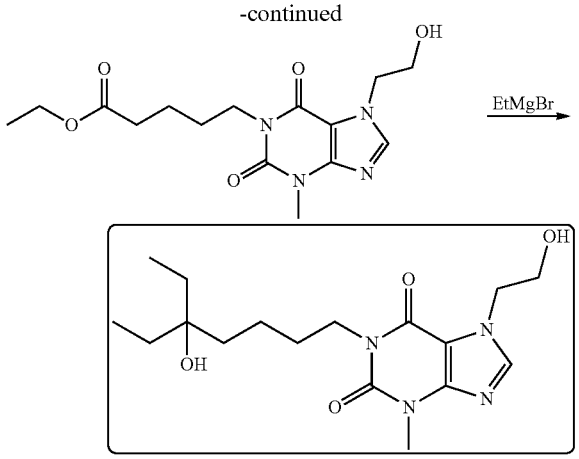

Step 1

7-(2-Hydroxyethyl)-3-methyl-1H-purine-2,6(3H,7H)-dione

3-Methyl-1H-purine-2,6(3H,7H)-dione (1.00 g, 6.00 mmol), potassium carbonate (830 mg, 6.00 mmol) were dissolved in N,N-dimethylformamide (10 mL). The reaction solution was heated to 80° C. for 0.5 hour and 2-bromoethanol (900 mg, 7.20 mmol) was added. The reaction solution was heated to 130° C. and reacted overnight. The reaction solution was concentrated to deliver the crude 7-(2-hydroxyethyl)-3-methyl-1H-purine-2,6(3H,7H)-dione, which was used directly for the next step.

Step 2

Ethyl 5-(7-(2-hydroxyethyl)-3-methyl-2,6-dioxo-2,3,6,7-tetrahydro-1H-purin-1-yl)valate 7-(2-Hydroxyethyl)-3-methyl-1H-purine-2,6(3H,7H)-dione (1.05 g, 5.00 mmol), ethyl 5-bromovalerate (1.25 g, 6.00 mmol) and potassium carbonate (1.66 g, 12.0 mmol) were dissolved in N,N-dimethylformamide (3 mL). The reaction solution was heated to 130° C. for 3 hours. The reaction was quenched by pouring the reaction solution into water (20 mL) and the mixture was then extracted with ethyl acetate (20 mL×3). The organic phases were combined, dried over anhydrous sodium sulfate, filtered, concentrated under reduced pressure, the residue was isolated and purified by preparative TLC plate to deliver ethyl 5-(7-(2-hydroxyethyl)-3-methyl-2,6-dioxo-2,3,6,7-tetrahydro-1H-purin-1-yl)valate (700 mg, yellow oil), yield: 35%. MS-ESI calcd. for [M+H]$^+$ 339, found 339.

Step 3

1-(5-Ethyl-5-hydroxyheptyl)-7-(2-hydroxyethyl)-3-methyl-1H-purine-2,6(3H,7H)-dione Ethyl 5-(7-(2-hydroxyethyl)-3-methyl-2,6-dioxo-2,3,6,7-tetrahydro-1H-purin-1-yl)valate (700 mg, 2.07 mmol) was dissolved in anhydrous tetrahydrofuran (7 mL), ethylmagnesium bromide (3 M tetrahydrofuran solution, 7 mL, 2.10 mmol) was slowly added dropwise at −78° C. The reaction solution was reacted at −78° C. for 1 hour. The reaction was quenched by pouring the reaction solution into water (20 mL) and the mixture was extracted with ethyl acetate (20 mL×3). The organic phase was dried over anhydrous sodium sulfate, filtered, concentrated under reduced pressure, the residue was isolated and purified by high performance liquid chromatography to deliver 1-(5-ethyl-5-hydroxyheptyl)-7-(2-hydroxyethyl)-3-methyl-1H-purine-2,6(3H,7H)-dione (110 mg, white solid), yield: 15%. $^1$H NMR: (400 MHz, Methanol-d$_4$): δ 7.90 (s, 1H), 4.41 (t, J=5.0 Hz, 2H), 4.00 (t, J=7.6 Hz, 2H), 3.87 (t, J=5.0 Hz, 2H), 1.68-1.59 (m, 2H), 1.50-1.42 (m, 5H), 1.39-1.29 (m, 3H), 0.95-0.77 (m, 6H). MS-ESI calcd. for [M+H—H$_2$O]$^+$ 335, found 335.

Embodiment 61

1-(5-Ethyl-5-hydroxyheptanol)-7-(2-hydroxy-3-((2-hydroxyethyl)(methyl)amino)propyl)-3-methyl-1H-2,6(3H,7H)-dione

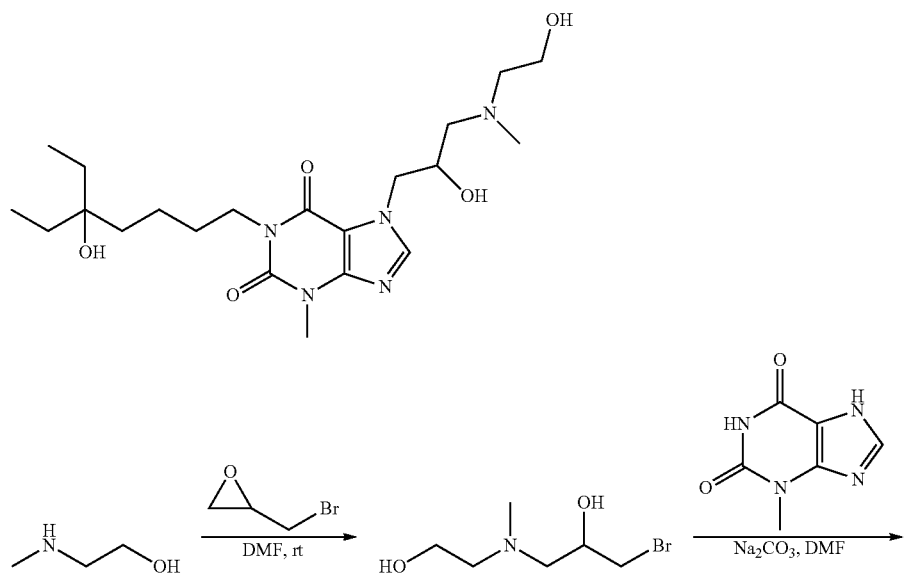

-continued

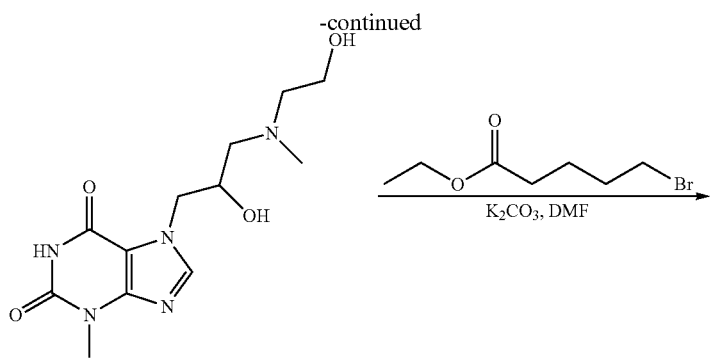

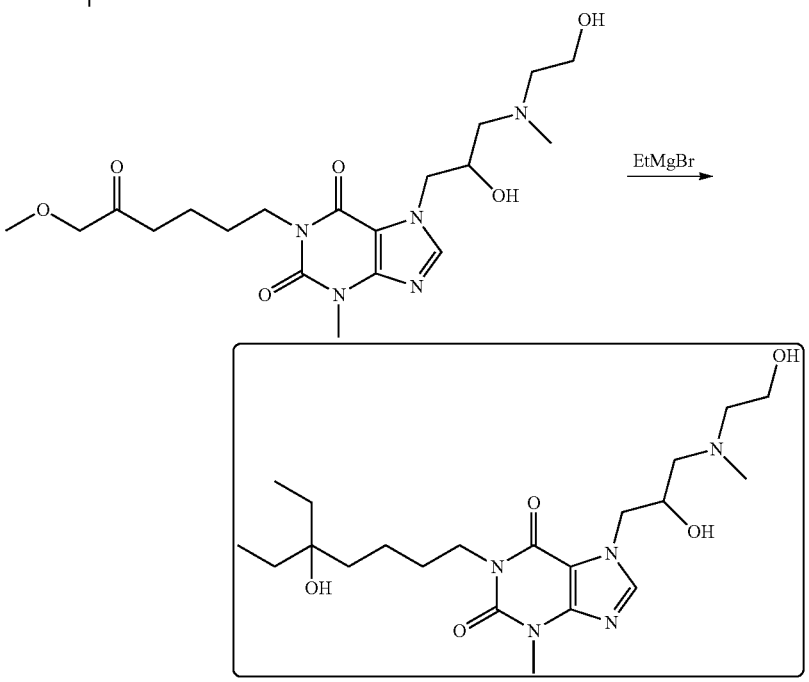

Step 1

1-Bromo-3-((2-hydroxyethyl)(methyl)amino)propan-2-ol 2-(Methylamino)ethanol (135 mg, 1.80 mmol) was dissolved in N,N-dimethylformamide (5 mL), 2-(bromomethyl)oxirane (206 mg, 1.51 mmol) was added and reacted at room temperature for 1.5 hours. After the reaction was complete, the reaction solution was directly used for the next reaction step.

Step 2

7-(2-Hydroxy-3-((2-hydroxyethyl)(methyl)amino) propyl)-3-methyl-1H-purine-2,6(3H,7H)-dione 3-Methyl-1H-purine-2,6(3H,7H)-dione (100 mg, 0.602 mmol), sodium carbonate (64.0 mg, 0.602 mmol) and potassium iodide (10.0 mg, 0.0600 mmol) were added to a solution of 1-bromo-3-((2-hydroxyethyl)(methyl)amino) propan-2-ol. The reaction solution was heated to 80° C. and reacted for 10 hours. After the reaction was complete, the reaction mixture was filtered and concentrated under reduced pressure to give the crude product 7-(2-hydroxy-3-((2-hydroxyethyl)(methyl)amino)propyl)-3-methyl-1H-purine-2,6(3H,7H)-di one, which was used directly for the next step. MS-ESI calcd. for [M+H]$^+$ 298, found 298.

Step 3

Ethyl 5-(7-(2-Hydroxy-3-((2-hydroxyethyl)(methyl) amino)propyl)-3-methyl-2,6-dioxo-2,3,6,7-tetrahydro-1H-purinan-1-yl) valate 7-(2-Hydroxy-3-((2-hydroxyethyl)(methyl)amino)propyl)-3-methyl-1H-purine-2,6(3 H,7H)-dione (170 mg, 0.572 mmol), ethyl bromovalerate (169 mg, 0.858 mmol), potassium carbonate (158 mg, 1.14 mmol) and potassium iodide (10.0 mg, 0.0570 mmol) were dissolved in N,N-dimethylformamide (5 mL). The reaction solution was heated to 130° C. and reacted for 3 hours. The reaction solution was quenched by pouring into water (5 mL), extracted with ethyl acetate (10 mL×3). The organic phases were combined, dried over anhydrous sodium sulfate, filtered and concentrated, isolated and purified by preparative TLC plate (8:1 dichloromethane/methanol, Rf=0.4) to deliver ethyl 5-(7-(2-hydroxy-3-((2-hydroxyethyl)(methyl)amino)propyl)-3-methyl-2,6-dioxo-2,3,6,7-tetrahydro-1H-purinan-1-yl) valate (118 mg, yellow oil), yield: 49%. MS-ESI calcd. for [M+H]$^+$426, found 426.

Step 4

1-(5-Ethyl-5-hydroxyheptolol)-7-(2-hydroxy-3-((2-hydroxyethyl)(methyl)amino)propyl)-3-m ethyl-1H-2,6(3H,7H)-dione Ethyl 5-(7-(2-hydroxy-3-((2-hydroxyethyl)(methyl)amino)propyl)-3-methyl-2,6-dioxo-2,3,6,7-tetrahydro-1H-purinan-1-yl)valate (100 mg, 0.235 mmol) was dissolved in anhydrous tetrahydrofuran (4 mL) and ethyl magnesium bromide (3 M tetrahydrofuran solution, 0.47 mL, 1.41 mmol) was slowly added dropwise at −65° C. The reaction was reacted at −65° C. for 0.5 hour and then reacted at 0° C. for 0.5 hour. After the reaction was complete, the reaction solution was quenched by pouring into water (5 mL), extracted with ethyl acetate (5 mL×3), which was then dried over anhydrous sodium sulfate, filtered, concentrated under reduced pressure, isolated and purified by preparative TLC plate (6:1 ethyl acetate/methanol, Rf=0.3) to deliver 1-(5-ethyl-5-hydroxyheptanol)-7-(2-hydroxy-3-((2-hydroxyethyl)(methyl)amino)propyl)-3-m ethyl-1H-2,6(3H,7H)-dione (3.0 mg, white solid), yield: 3%. $^1$H NMR: (400 MHz, Methanol-$d_4$) δ 7.92 (s, 1H), 4.91-4.59 (m, 2H), 4.52-4.39 (m, 3H), 4.30-4.25 (m, 2H), 4.03-3.99 (m, 2H), 3.88-3.84 (m, 2H), 3.55 (s, 3H), 2.90 (s, 3H), 1.68-1.59 (m, 4H), 1.48-1.45 (m, 6H), 0.88-0.84 (m, 6H). MS-ESI calcd. for $[M+H]^+$ 440, found 440.

Experimental Example 1

Evaluation of PDE2 Phosphodiesterase Inhibitory Activity in vitro

Experimental objective: The substituted Alexa Fluor 633 fluorescent dye on the AMP/GMP antibodies was detected by the fluorescence polarization analysis to determine the concentration of AMP/GMP produced in the reaction system, which was used to calculate the $IC_{50}$ values of the test compounds against PDE2 phosphodiesterase.

Experimental Materials:

The measured buffer solution: 10 mM Tris-HCl, pH 7.5, 5 mM $MgCl_2$, 0.01% Brij 35, 1 mM DTT, and 1% DMSO.

Enzyme: Expression of recombinant full-length PDE2A protein in insect Sf9 cells using N-terminal GST-tag with baculovirus.

Substrate: 1 μM cGMP.

Detection Method:

Transcreener® $AMP^2/GMP^2$ antibody, AMP2/GMP2 AlexaFluor 633 fluorescent dye.

Experimental Operations:

The enzyme solution was prepared using freshly prepared buffer solution, and then added to the reaction holes, the DMSO solutions of the test compounds were added by the Echo550 non-contact nanoliter acoustic pipetting system, and then pre-incubated at room temperature for 10 minutes, the reaction was initiated by the addition of the substrate (1 μM cGMP), and then reacted at room temperature for one hour. And then the detection system (Transcreener® $AMP^2/GMP^2$ antibody, AMP2/GMP2 AlexaFluor 633 fluorescent dye) was added, reacted at room temperature for 90 minutes, the fluorescence polarization was detected using Ex/Em 620/688.

The fluorescence polarization intensity was converted to nM concentration by AMP/GMP standard curve, The relative enzyme activity relative to DMSO blank was calculated, $IC_{50}$ values and curves were calculated using Prism software packages (GraphPad Software, San Diego Calif., USA).

Experimental Results:

TABLE 1

The test results of PDE2 phosphodiesterase inhibitory activity.

| Test sample (compound prepared by each embodiment) | PDE2 phosphodiesterase inhibitory activity |
|---|---|
| Embodiment 1 | + |
| Embodiment 2 | + + |
| Embodiment 3 | + |
| Embodiment 4 | + + |
| Embodiment 5 | + |
| Embodiment 6 | -- |
| Embodiment 7 | -- |
| Embodiment 8 isomer 1/isomer 2 | + +/+ |
| Embodiment 9 isomer 1/isomer 2 | +/+ |
| Embodiment 10 isomer 1/isomer 2 | --/-- |
| Embodiment 11 | + |
| Embodiment 12 isomer 1/isomer 2 | +/+ + |
| Embodiment 13 | -- |
| Embodiment 14 | -- |
| Embodiment 15 isomer 1/isomer 2 | + +/+ + |
| Embodiment 16 | -- |
| Embodiment 17 | -- |
| Embodiment 18 | + + |
| Embodiment 19 | + |
| Embodiment 20 | + |
| Embodiment 21 | + |
| Embodiment 22 | + + |
| Embodiment 23 isomer 1/isomer 2 | --/-- |
| Embodiment 24 | -- |
| Embodiment 25 | + + |
| Embodiment 26 | + |
| Embodiment 27 | + + |
| Embodiment 28 | + + |
| Embodiment 29 | -- |
| Embodiment 30 | -- |
| Embodiment 31 | + |
| Embodiment 32 | -- |
| Embodiment 33 | + |
| Embodiment 34 | + |
| Embodiment 35 | + |
| Embodiment 36 | + |
| Embodiment 37 | -- |
| Embodiment 38 | -- |
| Embodiment 39 | -- |
| Embodiment 40 | -- |
| Embodiment 41 isomer 1/isomer 2 | --/-- |
| Embodiment 42 | + + |
| Embodiment 43 | + |
| Embodiment 44 | + + |
| Embodiment 45/45' | --/+ + |
| Embodiment 46 isomer 1/isomer 2 | --/+ |
| Embodiment 47 | + |
| Embodiment 48 | + |
| Embodiment 49 | + + |
| Embodiment 50 isomer 1/isomer 2 | +/+ ++ |
| Embodiment 51 isomer 1/isomer 2 | +/+ + |
| Embodiment 52 | + |
| Embodiment 53 | + |
| Embodiment 54 | + + |
| Embodiment 55 | + ++ |
| Embodiment 56 | + |
| Embodiment 57 | + + |
| Embodiment 58 isomer 1/isomer 2 | --/-- |
| Embodiment 59 | -- |
| Embodiment 60 | -- |
| Embodiment 61 | -- |

Note:
10 μM ≤ "+" < 50 μM, 1 μM ≤ "+ +" < 10 μM, "+ + +" < 1 μM; -- N/A.

Conclusion: the compounds of the present invention have significant or even unexpected PDE2A protease inhibitory activity.

Experimental Example 2

Evaluation on Effect of Compounds on TNF-α in LPS-Induced Blood of Rats in vitro Experimental objective: Detect the effects of compounds on TNF-α in LPS-induced blood of rats in vitro, evaluate the inhibitory effect of the compounds on TNF-α in LPS-induced blood of rats.

Experimental Materials:
Sprague Dawley rats (male, 210-260 g, 8-10 weeks old, Shanghai Slack);
Rat TNF-alpha Quantikine ELISA Kit (R&D, #SRTA00).

Experimental Operations:
Test compounds solutions with a concentration of 1 mM were prepared, 40 μL of which (the final concentration of the compound was 100 μM) was respectively added to 48-hole cell culture plates. Rats were anesthetized with isoflurane, heart blood was collected (heparin was used to anticoagulation). The blood was added to the 48-hole plates holding the test compounds, 320 μL per hole. The 48-hole plates were placed in a cell incubator and incubated for 30 minutes, 40 μL LPS solution was added (100 μg/mL), mixed and placed in the incubator and continued to incubate. the 48-hole plates was taken out after 5 hours, the blood samples were transferred to 1.5 mL centrifuge tubes, centrifuged in a centrifuge (4,500 rpm, 4° C., 5 minutes), the upper plasma were separated, frozen after storage and stored in a refrigerator at −80° C. The levels of TNF-α in plasma samples were measured using the R & D ELISA kit according to the kit instructions the nest day.

Experimental Results:

TABLE 2

The test results of TNF-α inhibitory activity.

| Test sample (compound prepared by each embodiment) | TNF-α inhibition ratio |
|---|---|
| Embodiment 1 | + |
| Embodiment 11 | + |
| Embodiment 12 isomer 1/ isomer 2 | +/+ |
| Embodiment 27 | + |
| Embodiment 40 | + |
| Embodiment 44 | + + |
| Embodiment 49 | + + |
| Embodiment 50 isomer 1/isomer 2 | --/+ + |
| Embodiment 51 isomer 1/isomer 2 | --/+ + |
| Embodiment 55 | + + |

Note:
60% ≤ "+" < 80%; 80% ≤ " + +" < 100%; -- N/A
Conclusion: the compounds of the present invention have significant or even unexpected TNF-α inhibitory activity.

Experimental Example 3

Pharmacokinetic Evaluation of Compounds

Experimental objective: The pharmacokinetics of test compounds in SD rats.

Experimental Materials:
Sprague Dawley rats (male, 200-300 g, 7-9 weeks old, Shanghai Slack).

Experimental Operations:
The pharmacokinetic characteristics of rodents after intravenous and oral administration of the compounds were tested according to the standard protocol, in the experiment, the candidate compound was formulated into a clear solution, and the rats were given single intravenous injection and oral administration. Intravenous and oral solvents are a certain proportion of hydroxypropyl βcyclodextrin aqueous solution or physiological saline solution. Blood samples within 24 hours were collected, centrifuged (3000 g) for 15 minutes, the supernatant were separated to obtain the plasma samples, the protein was precipitated by adding a 4 times volume of acetonitrile solution that containing the internal standard, centrifuged and the supernatant was then centrifuged after adding equal volume of water, then the supernatant was injected, the plasma concentration was quantitatively analyzed by LC-MS/MS analysis, and pharmacokinetics parameters such as peak concentration, peak time, clearance rate, half-life, drug area under the curve, bioavailability etc. are calculated.

Experimental Results:

TABLE 3

The test results of pharmacokinetics.

| Test sample (compound prepared by each embodiment) | Clearance rate (mL/min/kg) | Half-life $T_{1/2}$ (h) | Concentration integration AUC (nM · hr) | Bio-availability F (%) |
|---|---|---|---|---|
| Pentoxifylline | 74.1 | 0.191 | 6622 | |
| Embodiment 1 | 54.7 | 0.659 | 1909 | 59.7 |
| Embodiment 2 | 63.6 | 0.481 | 902 | 34.2 |
| Embodiment 12 | 32.7 | 3.12 | 5863 | 41.2 |
| Embodiment 12 isomer 2 | 41.0 | 1.6 | 3853 | 34.1 |
| Embodiment 27 | 13.6 | 2.96 | 11425 | 33.8 |
| Embodiment 28 | 12.9 | 2.27 | 51155 | 149 |
| Embodiment 45 isomer 2 | 58.4 | 6.19 | 1294 | 17.1 |
| Embodiment 50 isomer 2 | 71.6 | 0.56 | 2492 | 42.6 |
| Embodiment 51 isomer 2 | 54.4 | 0.793 | 4390 | 47.9 |
| Embodiment 55 | 21.5 | 2.18 | 17782 | 95.8 |
| Embodiment 58 isomer 2 | 71.6 | 0.56 | 2492 | 42.6 |

Conclusion: the compounds of the present invention can significantly increase single or part of pharmacokinetics index of rat.

What is claimed is:
1. A compound having a structure of formula (I), a tautomer thereof or a pharmaceutically acceptable salt thereof,

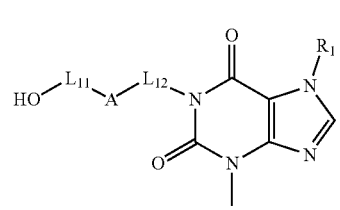

(I)

wherein,
the structural unit

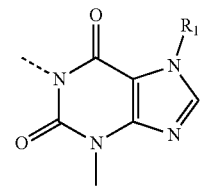

can be replaced with

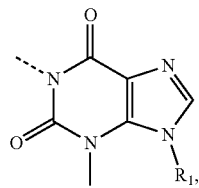

$L_{11}$ is selected from absence, or C(R)(R');
each of R and R' is independently selected from H, a halogen, OH, NH$_2$, CN, or an optionally substituted 1- to 6-membered alkyl or heteroalkyl;
or, R and R' to join together and form a 3- to 6-membered cycloalkyl or heterocycloalkyl including the carbon of $L_{11}$ by cyclization;
A is selected from

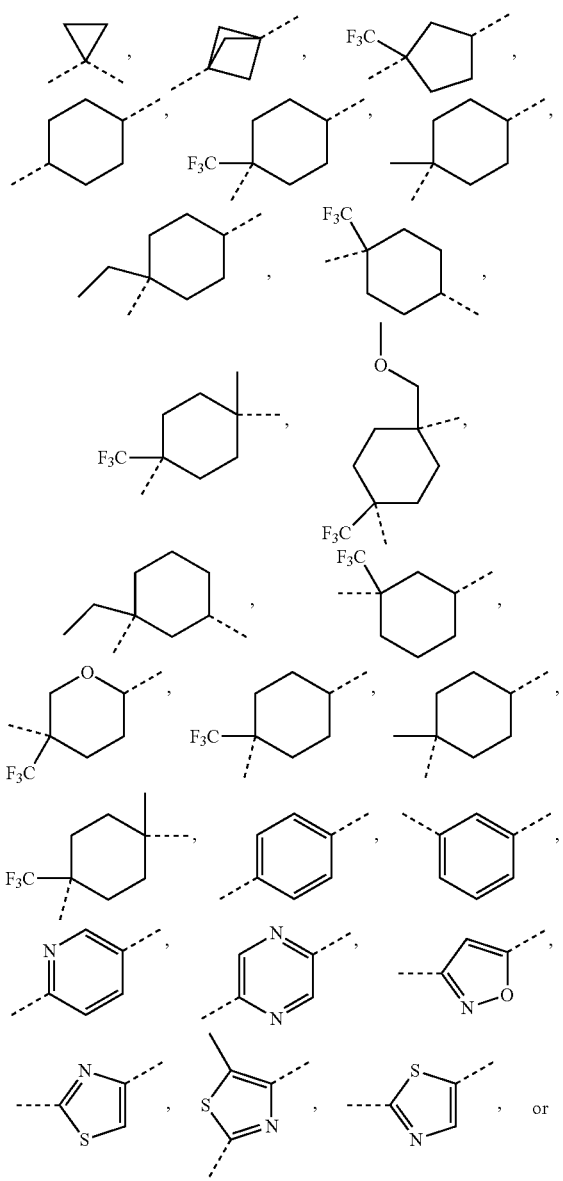

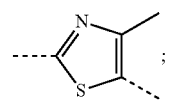

$L_{12}$ is selected from methylene,

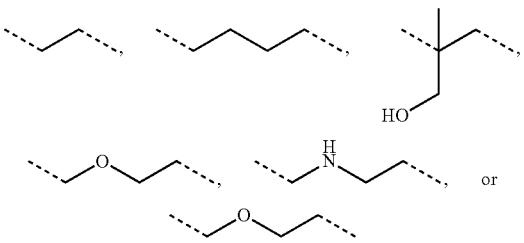

$R_1$ is selected from an optionally substituted 1- to 6-membered alkyl or heteroalkyl;
"hetero" represents N, O, S, C(=O), S(=O), or S(=O)$_2$, the number of the heteroatom on each group is selected from 1, 2, 3 or 4.

2. The compound according to claim 1, wherein the substituents in the R, R', and $R_1$ are independently selected from a halogen, OH, NH$_2$, CN, or an optionally substituted 1- to 6-membered alkyl and heteroalkyl, the number of the substituent on each group is independently selected from 1, 2 or 3.

3. The compound according to claim 1, wherein the R and R' are independently selected from H, Me, CF$_3$, or Et.

4. The compound according to claim 1, wherein the $R_1$ is selected from Me, CHF$_2$, CF$_3$, Et, CH$_2$CF$_3$, isopropyl

cyclopropyl,

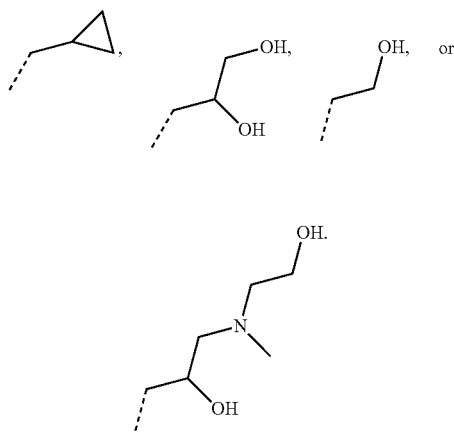

5. A compound selected from the group consisting of:
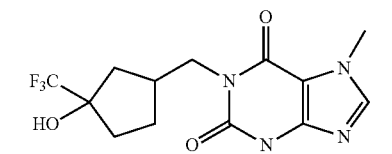
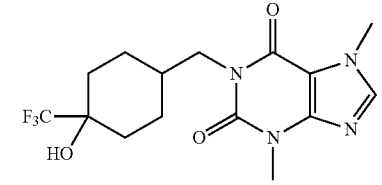 [SMILES: Cn1cnc2c1c(=O)n(CC1(C)CCC(O)(C(F)(F)F)CC1)c(=O)n2C]
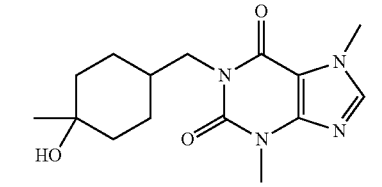
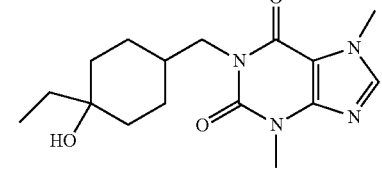
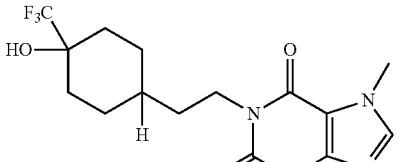
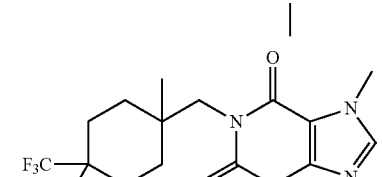
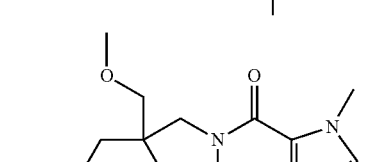
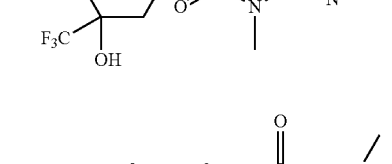
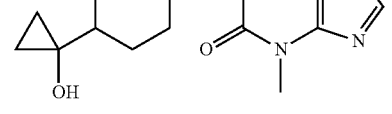
-continued
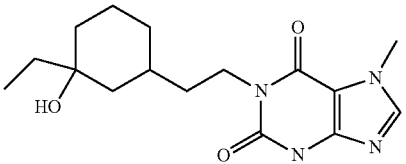
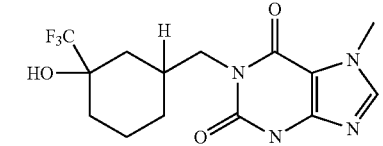
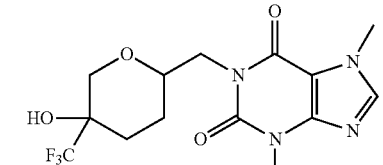
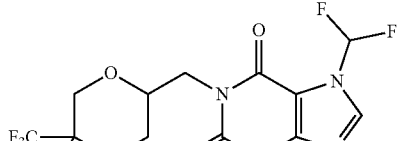
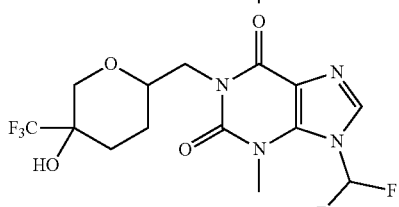
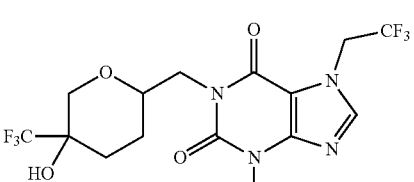
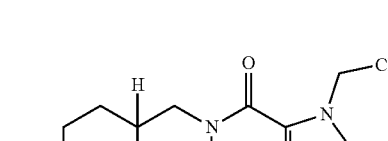
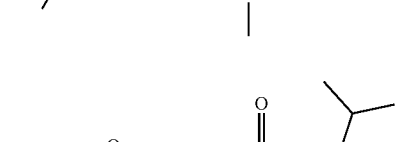
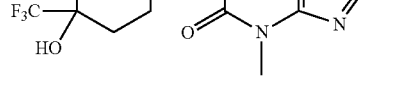

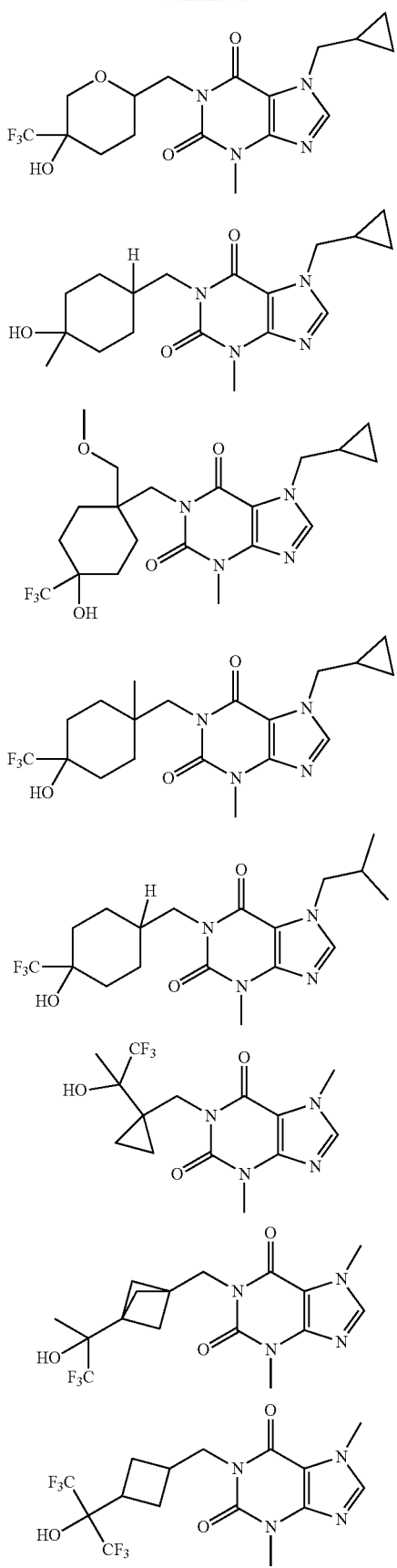
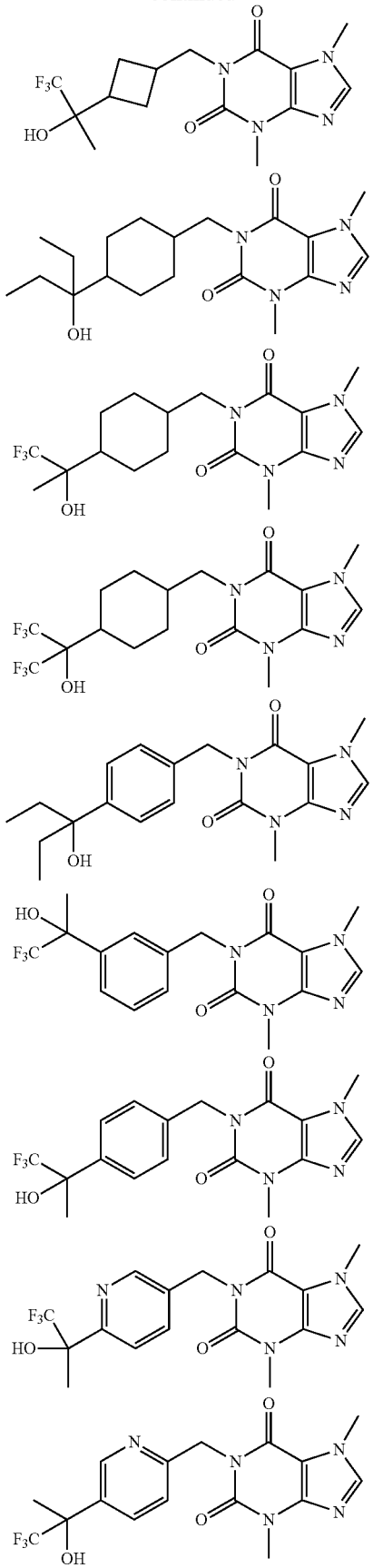

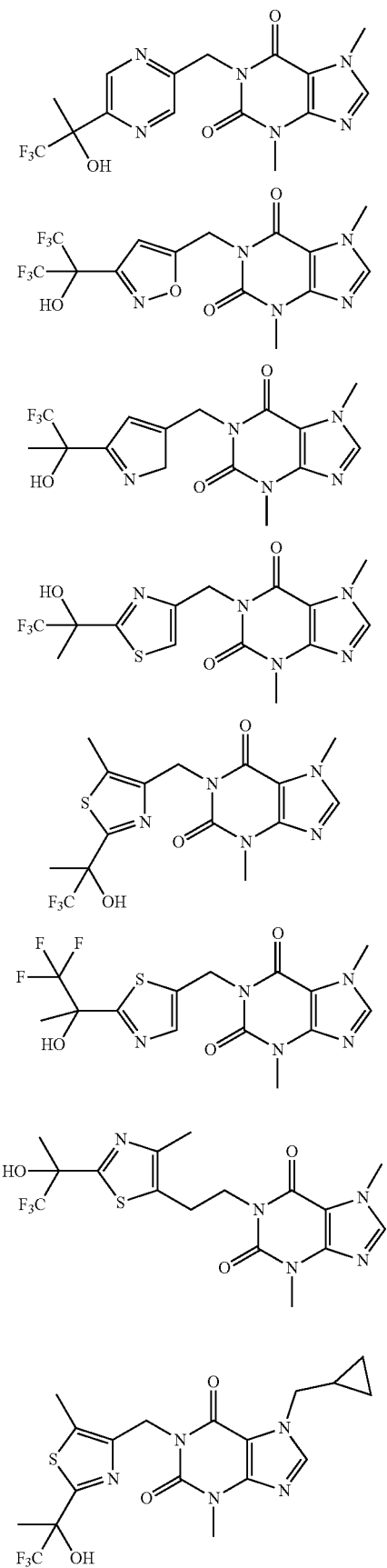
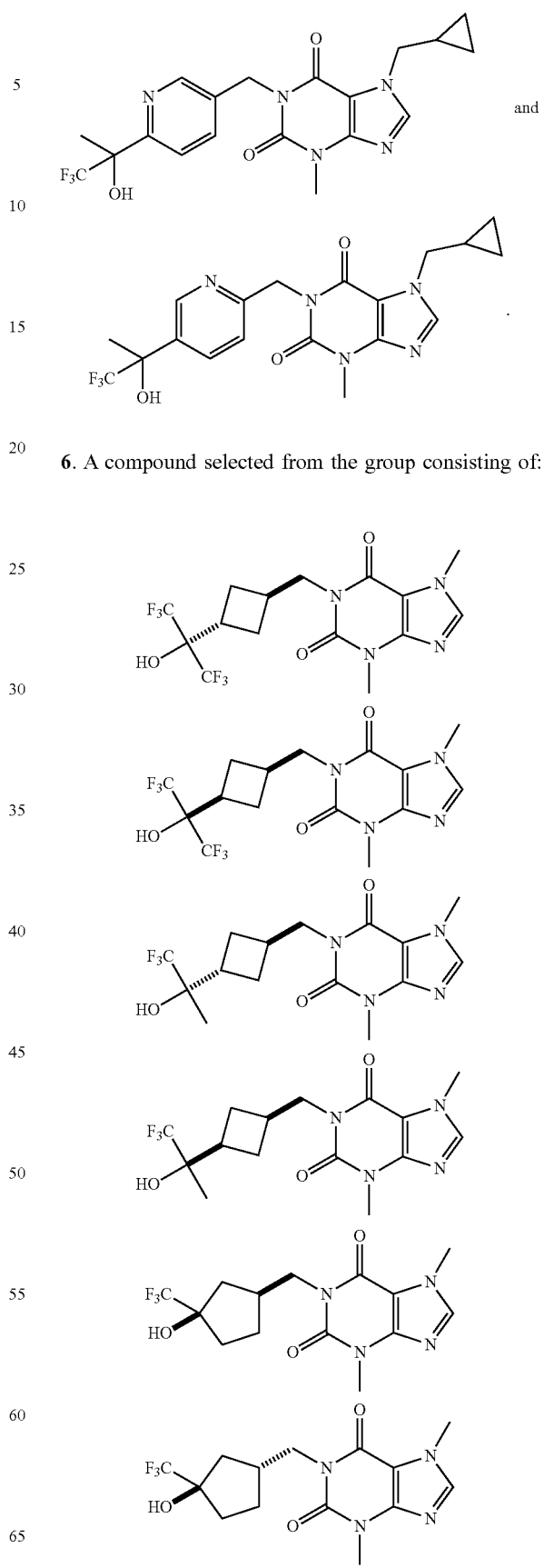
6. A compound selected from the group consisting of:

159
-continued
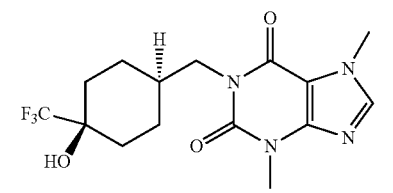
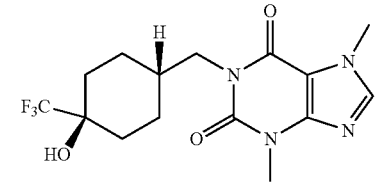
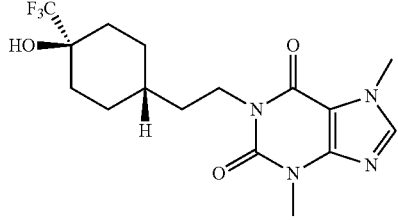
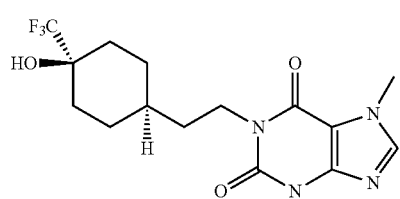
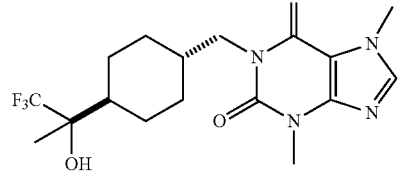
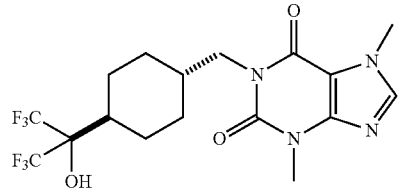 [SMILES: Cn1cnc2c1c(=O)n(C[C@H]1CC[C@H](C(C)(O)C(F)(F)F)CC1)c(=O)n2C]
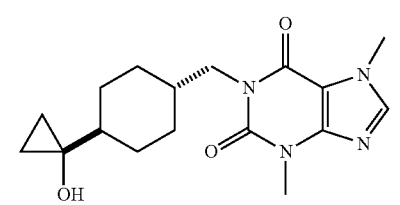
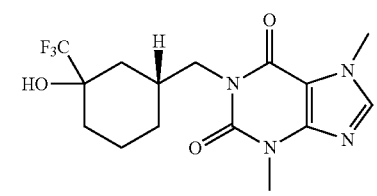
160
-continued
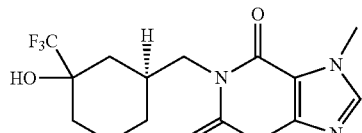
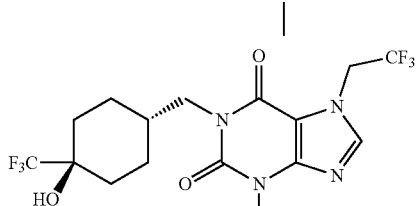
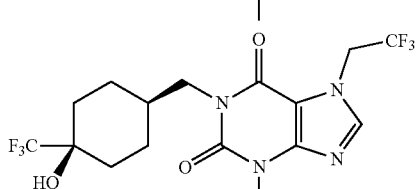
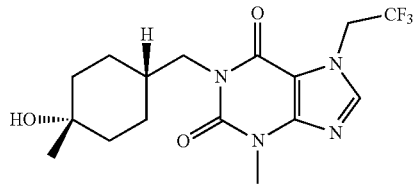
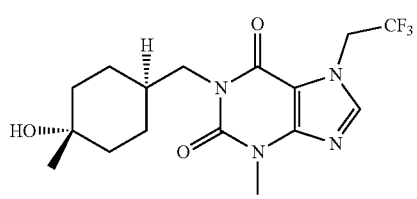
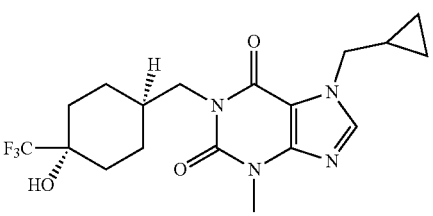
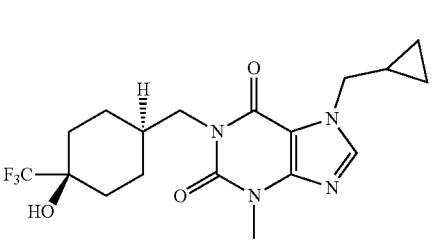
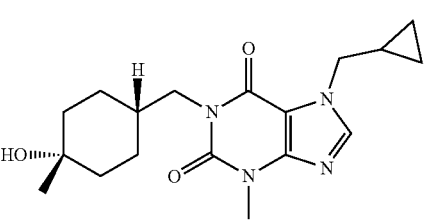

-continued

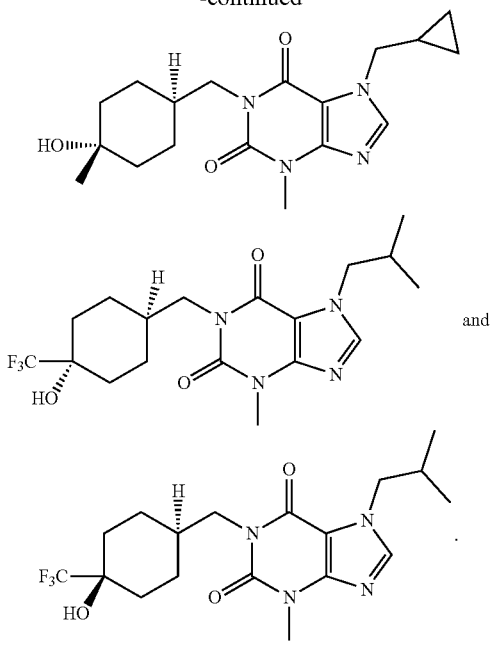

and

7. A method for inhibiting PDE2 and TNF-α in a subject in need thereof, comprising: administering to the subject an effective amount of a compound having a structure of formula (I), a tautomer thereof or a pharmaceutically acceptable salt thereof,

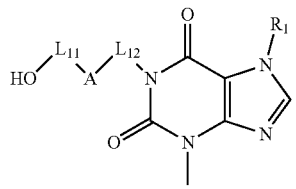
(I)

wherein
the structural unit

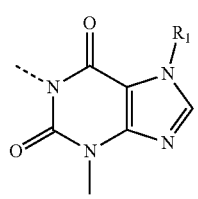

can be replaced with

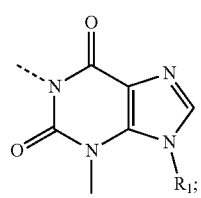

$L_{11}$ is selected from absence, or C(R)(R'),
each of R and R' is independently selected from H, a halogen, OH, $NH_2$, CN, or an optionally substituted 1- to 6-membered alkyl or heteroalkyl;
or, R and R' to join together and form a 3- to 6-membered cycloalkyl or heterocycloalkyl including the carbon of $L_{11}$ by cyclization;
A is selected from cyclopropyl, cyclopentyl, cyclohexyl, epoxypentyl, phenyl, pyridyl, pyrazinyl, oxazolyl, isoxazolyl, thiazolyl, or bicyclor[1.1.11]pentane, or a bicyclic group, a spiro group or a fused cyclic group consisting of any two of the above groups, each of which is optionally substituted;
$L_{12}$ is selected from an optionally substituted 1- to 6-membered alkyl or heteroalkyl;
$R_1$ is selected from an optionally substituted 1- to 6-membered alkyl or heteroalkyl;
"hetero" represents N, O, S, C(=O), S(=O), or S(=O)$_2$, the number of the heteroatom on each group is selected from 1, 2, 3 or 4.

8. The compound according to claim 1, wherein the structural unit

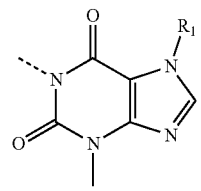

is replaced with

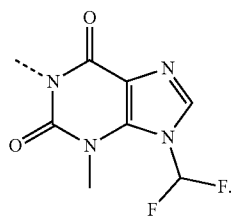

9. The compound according to claim 2, wherein the substituents in the R, R'and $R_1$ are independently selected from the halogen, $CF_3$, CN, OH, Me, Et, n-propyl, isopropyl, cyclopropyl,

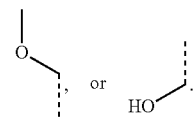, or .

10. The compound according to claim 3, wherein the $L_{11}$ is selected from

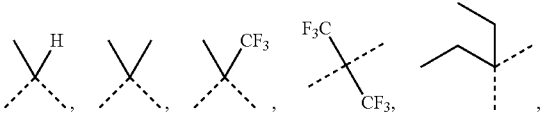

-continued

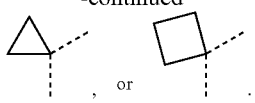

11. The method according to claim 7, wherein the substituents in the R, R', A, $L_{12}$ and $R_1$ are independently selected from a halogen, OH, $NH_2$, CN, or an optionally substituted 1- to 6-membered alkyl and heteroalkyl, the number of the substituent on each group is independently selected from 1, 2 or 3.

12. The method according to claim 7, wherein the R and R' are independently selected from H, Me, $CF_3$, or Et.

13. The method according to claim 7, wherein the $L_{12}$ is selected from methylene,

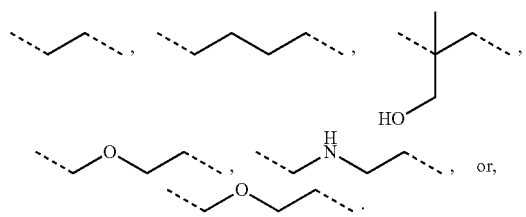

14. The method according to claim 7, wherein the $R_1$ is selected from Me, $CHF_2$, $CF_3$, Et, $CH_2CF_3$, isopropyl,

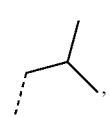

cyclopropyl,

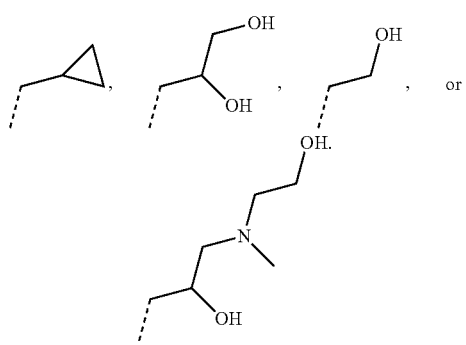

15. The method according to claim 7, wherein the structural unit

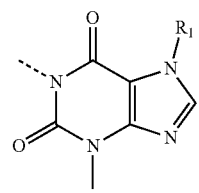

is replaced with

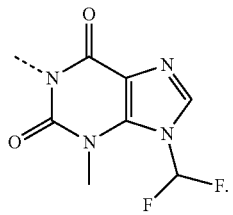

16. The method according to claim 11, wherein the substituents in the R, R', A, $L_{12}$ and $R_1$ are independently selected from the halogen, $CF_3$, CN, OH, Me, Et, n-propyl, isopropyl, cyclopropyl,

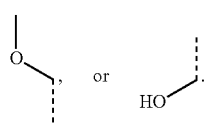

17. The method according to claim 12, wherein the $L_{11}$ is selected from

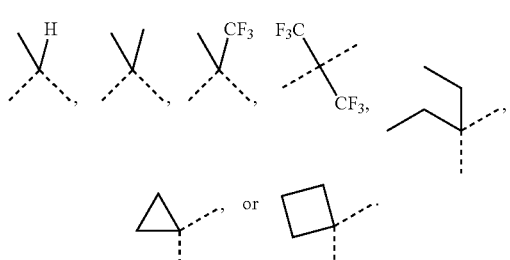

18. The method according to claim 7, wherein the A is selected from

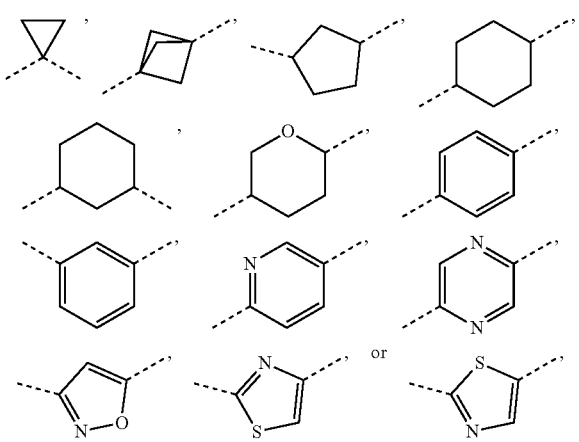

each of which is optionally substituted.

19. The method according to claim 7, wherein the A is selected from

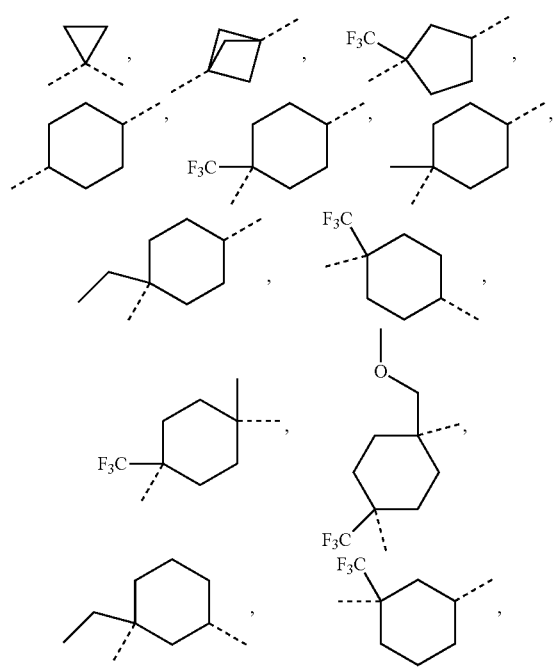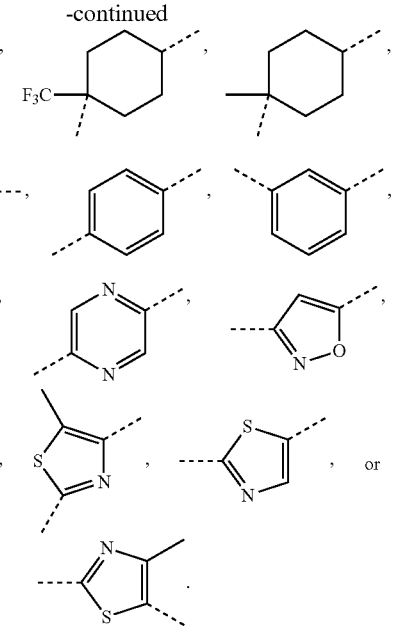

UNITED STATES PATENT AND TRADEMARK OFFICE
CERTIFICATE OF CORRECTION

PATENT NO. : 10,098,885 B2  
APPLICATION NO. : 15/517951  
DATED : October 16, 2018  
INVENTOR(S) : Lingyun Wu et al.

Page 1 of 2

It is certified that error appears in the above-identified patent and that said Letters Patent is hereby corrected as shown below:

In the Claims

At Claim 5:

Column 154, the formula beginning at Line 25, reading - 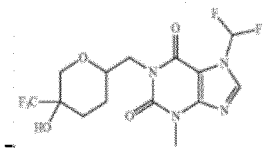 - should read as -- 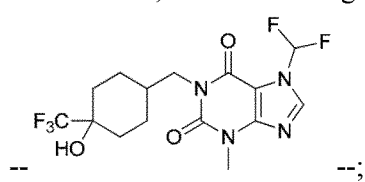 --;

The formula beginning at Line 33, reading - 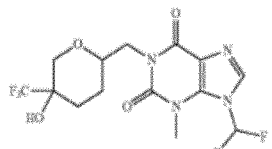 - should read as -- 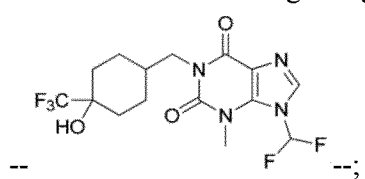 --;

The formula beginning at Line 42, reading - 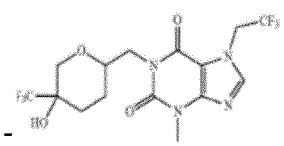 - should read as

Signed and Sealed this  
Sixteenth Day of April, 2019

Andrei Iancu  
*Director of the United States Patent and Trademark Office*

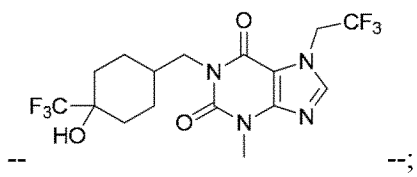 --; The formula beginning at Line 60, reading - 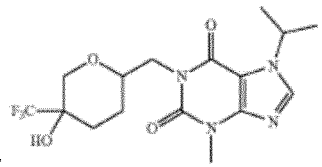 - should read as 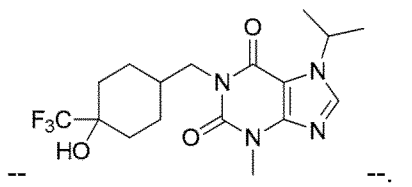 --.
Column 155, the formula beginning at Line 1, reading - 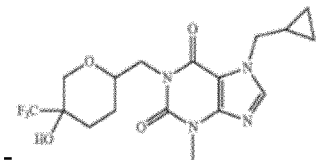 - should read as 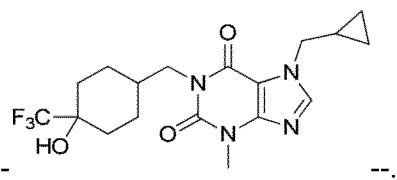 --.